(12) United States Patent
Wirtz et al.

(10) Patent No.: US 8,841,424 B2
(45) Date of Patent: *Sep. 23, 2014

(54) HUMANIZED AXL ANTIBODIES

(75) Inventors: Peter Wirtz, Gauting (DE); Jens Ruhe, Martinsried (DE); Takeshi Takizawa, Tokyo (JP); Tomoko Takayama, Tokyo (JP)

(73) Assignee: U3 Pharma GmbH, Martinsried (DE)

( * ) Notice: Subject to any disclaimer, the term of this patent is extended or adjusted under 35 U.S.C. 154(b) by 155 days.

This patent is subject to a terminal disclaimer.

(21) Appl. No.: 13/320,060

(22) PCT Filed: May 11, 2010

(86) PCT No.: PCT/EP2010/056487
§ 371 (c)(1),
(2), (4) Date: Jan. 18, 2012

(87) PCT Pub. No.: WO2010/130751
PCT Pub. Date: Nov. 18, 2010

(65) Prior Publication Data
US 2012/0117670 A1  May 10, 2012

(30) Foreign Application Priority Data

May 11, 2009 (EP) .................................... 09006355
May 13, 2009 (EP) .................................... 09006474

(51) Int. Cl.
*C07K 16/40* (2006.01)
*C07K 16/00* (2006.01)
*A61K 39/395* (2006.01)

(52) U.S. Cl.
USPC ............. 530/388.26; 530/388.15; 530/388.1; 530/387.1; 424/146.1; 424/141.1; 424/142.1

(58) Field of Classification Search
CPC . A61K 2300/00; A61K 45/06; C12Q 1/6886; C12Q 2600/158; C07D 401/14
See application file for complete search history.

(56) References Cited

U.S. PATENT DOCUMENTS

| | | | | |
|---|---|---|---|---|
| 4,931,385 A * | 6/1990 | Block et al. | ................... | 435/7.94 |
| 5,468,634 A | 11/1995 | Liu | | |
| 8,415,361 B2 * | 4/2013 | Lemke et al. | ................. | 514/257 |

| | | | |
|---|---|---|---|
| 2005/0186571 A1 | 8/2005 | Ullrich et al. | |
| 2009/0087431 A1 | 4/2009 | Yaworsky et al. | |
| 2010/0330095 A1* | 12/2010 | Hettmann et al. | ......... 424/143.1 |

FOREIGN PATENT DOCUMENTS

| | | |
|---|---|---|
| EP | 0378175 A | 7/1990 |
| EP | 1382969 A1 | 1/2004 |
| GB | 2404660 A | 2/2005 |
| WO | 97 34636 A1 | 9/1997 |
| WO | 0075333 A | 12/2000 |
| WO | 2005047327 A | 5/2005 |
| WO | 2006037604 A1 | 4/2006 |
| WO | 2006096461 A | 9/2006 |
| WO | 2006104989 A | 10/2006 |
| WO | 2006131013 A2 | 12/2006 |
| WO | 2009062690 A1 | 5/2009 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
McGuire et al. (Journal of Clinical Oncology 2005, 23:5862-5864).*
The Merck Manuals Online Medical Library, [online]. Whitehouse Station, NJ: Merck Research Laboratories, 2006-2007. [retrieved on Nov. 19, 2007]. Retrieved from the Internet: < URL: http://www.merckmanuals.com/professional/sec18/ch253/ch253e.html>. Breast Cancer. see pp. 1-8.*
Axl(149M): sc-73719 Aug. 15, 2007, Santa Cruz Biotechnology, Inc., XP002513577 Retrieved from the Internet:URL:http://datasheets.scbt.com/sc-73719.pdf [retrieved on Feb. 2, 2009].
Holland Sacha J et al: "Multiple roles for the receptor tyrosine kinase Axl in tumor formation" Cancer Research, vol. 065, No. 20, Oct. 2005, pp. 9294-9303, XP009111560 ISSN: 0008-5472.
Vajkoczy Peter et al: "Dominant-negative inhibition of the Axl receptor tyrosine kinase suppresses brain tumor cell growth and invasion and prolongs survival." Proceedings of the National Academy of Sciences of the United States of America Apr. 11, 2006, vol. 103, No. 15, Apr. 11, 2006, pp. 5799-5804, XP002505666 ISSN: 0027-8424.

* cited by examiner

*Primary Examiner* — Sharon Wen
(74) *Attorney, Agent, or Firm* — Rothwell, Figg, Ernst & Manbeck, P.C.

(57) ABSTRACT

The present invention refers to monoclonal humanized antibodies, which bind to the extracellular domain of the AXL receptor tyrosine kinase and which at least partially inhibit AXL activity.

11 Claims, 78 Drawing Sheets

Figure 1 h#11B7-T1L
DIQMTQSPSSLSASVGDRVTITCRASQDIGNYLRWYQQKPGKAPKLLI
SGATNLAAGVPSRFSGTGSGTDFTFTISSLQPEDFATYYCLQSKESPW
TFGGGTKVEIKRT h#11B7-T2L
DIQMTQSPSSLSASVGDRVTITCRASQDIGNYLRWFQQKPGKAPKLMI
SGATNLAAGVPSRFSGTGSGTDYTFTISSLQPEDFATYYCLQSKESPW
TFGGGTKVEIKRT h#11B7-T3L
DIQMTQSPSSLSASVGDRVTITCRASQDIGNYLRWFQQKPGKAPKLMI
SGATNLAAGVPSRFSGSRSGSDYTLTISSLQPEDFATYYCLQSKESPW
TFGGGTKVEIKRT h#11B7-T4L
DIQMTQSPSSLSASVGDRVTITCRASQDIGNYLRWYQQKPGKAPKLLI
SGATNLAAGVPSRFSGSGSGSDFTLTISSLQPEDFATYYCLQSKESPW
TFGQGTKLEIKRT h#11B7-T5L
DIQMTQSPSSLSASVGDRVTITCRASQDIGNYLRWFQQKPGKAPKLMI
SGATNLAAGVPSRFSGSGSGSDYTLTISSLQPEDFATYYCLQSKESPW
TFGQGTKLEIKRT h#11B7-T6L
DIQMTQSPSSLSASVGDRVTITCRASQDIGNYLRWFQQKPGKAPKLMI
SGATNLAAGVPSRFSGSGSGSDYTLTISSLQPEDFATYYCLQSKESPW
TFGQGTKVEIKRT h#11B7-T7L
DIQMTQSPSSLSASVGDRVTITCRASQDIGNYLRWYQQKPGKAPKLMI
SGATNLAAGVPSRFSGSGSGSDYTLTISSLQPEDFATYYCLQSKESPW
TFGQGTKVEIKRT

Figure 2 h#11B7-T8L
DIQMTQSPSSLSASVGDRVTITCRASQDIGNYLRWFQQKPGKAPKLLI
SGATNLAAGVPSRFSGSGSGSDYTLTISSLQPEDFATYYCLQSKESPW
TFGQGTKVEIKRT h#11B7-T9L
DIQMTQSPSSLSASVGDRVTITCRASQDIGNYLRWFQQKPGKAPKLMI
SGATNLAAGVPSRFSGSGSGSDFTLTISSLQPEDFATYYCLQSKESPW
TFGQGTKVEIKRT h#11B7-T10L
DIQMTQSPSSLSASVGDRVTITCRASQDIGNYLRWYQQKPGKAPKLLI
SGATNLAAGVPSRFSGSGSGSDYTLTISSLQPEDFATYYCLQSKESPW
TFGQGTKVEIKRT h#11B7-T11L
DIQMTQSPSSLSASVGDRVTITCRASQDIGNYLRWFQQKPGKAPKLLI
SGATNLAAGVPSRFSGSGSGSDFTLTISSLQPEDFATYYCLQSKESPW
TFGQGTKVEIKRT h#11B7-T12L
DIQMTQSPSSLSASVGDRVTITCRASQDIGNYLRWYQQKPGKAPKLMI
SGATNLAAGVPSRFSGSGSGSDFTLTISSLQPEDFATYYCLQSKESPW
TFGQGTKVEIKRT h#11B7-T13L
DIQMTQSPSSLSASVGDRVTITCRASQDIGNYLRWYQQKPGKAPKLLI
SGATNLAAGVPSRFSGSGSGSDFTLTISSLQPEDFATYYCLQSKESPW
TFGQGTKVEIKRT h#11B7-T14L
DIQMTQSPSSLSASVGDRVTITCRASQDIGNYLRWYQQKPGKAPKLMI
SGATNLAAGVPSRFSGSGSGSDYTLTISSLQPEDFATYYCLQSKESPW
TFGQGTKLEIKRT

Figure 3 h#11B7-T15L
DIQMTQSPSSLSASVGDRVTITCRASQDIGNYLRWFQQKPGKAPKLLI
SGATNLAAGVPSRFSGSGSGSDYTLTISSLQPEDFATYYCLQSKESPW
TFGQGTKLEIKRT h#11B7-T16L
DIQMTQSPSSLSASVGDRVTITCRASQDIGNYLRWFQQKPGKAPKLMI
SGATNLAAGVPSRFSGSGSGSDFTLTISSLQPEDFATYYCLQSKESPW
TFGQGTKLEIKRT h#11B7-T17L
DIQMTQSPSSLSASVGDRVTITCRASQDIGNYLRWYQQKPGKAPKLLI
SGATNLAAGVPSRFSGSGSGSDYTLTISSLQPEDFATYYCLQSKESPW
TFGQGTKLEIKRT h#11B7-T18L
DIQMTQSPSSLSASVGDRVTITCRASQDIGNYLRWFQQKPGKAPKLLI
SGATNLAAGVPSRFSGSGSGSDFTLTISSLQPEDFATYYCLQSKESPW
TFGQGTKLEIKRT h#11B7-T19L
DIQMTQSPSSLSASVGDRVTITCRASQDIGNYLRWYQQKPGKAPKLMI
SGATNLAAGVPSRFSGSGSGSDFTLTISSLQPEDFATYYCLQSKESPW
TFGQGTKLEIKRT h#11B7-T20L
DIQMTQSPSSLSASVGDRVTITCRASQDIGNYLRWYQQKPGKAPKLLI
SGATNLAAGVPSRFSGSGSGSDFTLTISSLQPEDFATYYCLQSKESPW
TFGQGTKLEIKRT

Figure 4 h#11B7-T1H
QIQLQESGPGLVKPSQTLSLTCAVSGYSITSNYWGWIRQPPGKGLEWI
GYITYSGSTSYNPSLKSRVTISVDTSKNQFSLKLSSVTAADTAVYYCA
ITTFYYWGQGTLVTVSS h#11B7-T2H
QIQLQESGPGLVKPSQTLSLTCAVSGYSITSNYWGWIRQPPGKGLEWM
GYITYSGSTSYNPSLKSRISISVDTSKNQFSLKLSSVTAADTAVYYCA
ITTFYYWGQGTLVTVSS h#11B7-T3H
QVQLQESGPGLVKPSQTLSLTCAVSGYSITSNYWGWIRKPPGDGLEWM
GYITYSGSTSYNPSLKSRISITRDTSKNQFSLKLSSVTAADTAVYYCA
ITTFYYWGQGTLVTVSS h#11B7-T4H
QVQLQQWGAGLLKPSETLSLTCTVSGYSITSNYWGWIRQPPGKGLEWI
GYITYSGSTSYNPSLKSRVTISRDTSKNQFSLKLSSVTAADTAVYYCA
ITTFYYWGQGTTVTVSS h#11B7-T5H
QVQLQQWGAGLLKPSETLSLTCTVSGYSITSNYWGWIRQPPGKGLEWM
GYITYSGSTSYNPSLKSRISISRDTSKNQFSLKLSSVTAADTAVYYCA
ITTFYYWGQGTTVTVSS h#11B7-T6H
QVQLQESGPGLVKPSETLSLTCTVSGYSITSNYWGWIRQPPGKGLEWM
GYITYSGSTSYNPSLKSRISISRDTSKNQFSLKLSSVTAADTAVYYCA
ITTFYYWGQGTLVTVSS

Figure 5 h#11B7-T7H
QVQLQESGPGLVKPSETLSLTCTVSGYSITSNYWGWIRQPPGKGLEWI
GYITYSGSTSYNPSLKSRVSISRDTSKNQFSLKLSSVTAADTAVYYCA
ITTFYYWGQGTLVTVSS h#11B7-T8H
QVQLQESGPGLVKPSETLSLTCTVSGYSITSNYWGWIRQPPGKGLEWM
GYITYSGSTSYNPSLKSRITISRDTSKNQFSLKLSSVTAADTAVYYCA
ITTFYYWGQGTLVTVSS h#11B7-T9H
QVQLQESGPGLVKPSETLSLTCTVSGYSITSNYWGWIRQPPGKGLEWI
GYITYSGSTSYNPSLKSRVTISRDTSKNQFSLKLSSVTAADTAVYYCA
ITTFYYWGQGTLVTVSS h#11B7-T10H
QVQLQQWGAGLLKPSETLSLTCTVSGYSITSNYWGWIRQPPGKGLEWI
GYITYSGSTSYNPSLKSRVSISRDTSKNQFSLKLSSVTAADTAVYYCA
ITTFYYWGQGTTVTVSS h#11B7-T11H
QVQLQQWGAGLLKPSETLSLTCTVSGYSITSNYWGWIRQPPGKGLEWM
GYITYSGSTSYNPSLKSRITISRDTSKNQFSLKLSSVTAADTAVYYCA
ITTFYYWGQGTTVTVSS h#11B7-T12H
QVQLQQWGAGLLKPSETLSLTCTVSGYSITSNYWGWIRQPPGKGLEWI
GYITYSGSTSYNPSLKSRVTISRDTSKNQFSLKLSSVTAADTAVYYCA
ITTFYYWGQGTTVTVSS

Figure 6 h#11D5-T1L
DVQMTQSPSSLSASVGDRVTITCRASQDIGNYLSWYQQKPGKAPKLLI
YGAIKLAVGVPSRFSGSGSGTDFTLTISSLQPEDFATYYCLQYIQFPL
TFGQGTKLEIKRT h#11D5-T2L
DIQMTQSPSSLSASVGDRVTITCRASQDIGNYLSWFQQKPGKAPRLMI
YGAIKLAVGVPSRFSGSGSGTDYTLTISSLQPEDFATYYCLQYIQFPL
TFGQGTKLEIKRT h#11D5-T3L
DIQMTQSPSSLSASVGDRVTITCRASQDIGNYLSWFQQKVGKSPRRMI
YGAIKLAVGVPSRFSGSRSGSDYTLTISSLQPEDFAIYYCLQYIQFPL
TFGSGTKLEIKRT h#11D5-T4L
DIQMTQSPSSLSASVGDRVTITCRASQDIGNYLSWYQQKPGKAPKRLI
YGAIKLAVGVPSRFSGSGSGTEFTLTISSLQPEDFATYYCLQYIQFPL
TFGGGTKVEIKRT h#11D5-T5L
DIQMTQSPSSLSASVGDRVTITCRASQDIGNYLSWFQQKPGKAPRRMI
YGAIKLAVGVPSRFSGSGSGTDYTLTISSLQPEDFATYYCLQYIQFPL
TFGGGTKVEIKRT h#11D5-T6L
DIQMTQSPSSLSASVGDRVTITCRASQDIGNYLSWFQQKPGKAPRRMI
YGAIKLAVGVPSRFSGSGSGTDYTLTISSLQPEDFATYYCLQYIQFPL
TFGQGTKVEIKRT h#11D5-T7L
DIQMTQSPSSLSASVGDRVTITCRASQDIGNYLSWYQQKPGKAPKRLI
YGAIKLAVGVPSRFSGSGSGTEFTLTISSLQPEDFATYYCLQYIQFPL
TFGQGTKVEIKRT

Figure 7 h#11D5-T8L
DIQMTQSPSSLSASVGDRVTITCRASQDIGNYLSWFQQKPGKAPKRLI
YGAIKLAVGVPSRFSGSGSGTEFTLTISSLQPEDFATYYCLQYIQFPL
TFGQGTKVEIKRT h#11D5-T9L
DIQMTQSPSSLSASVGDRVTITCRASQDIGNYLSWYQQKPGKAPRRLI
YGAIKLAVGVPSRFSGSGSGTEFTLTISSLQPEDFATYYCLQYIQFPL
TFGQGTKVEIKRT h#11D5-T10L
DIQMTQSPSSLSASVGDRVTITCRASQDIGNYLSWYQQKPGKAPKRMI
YGAIKLAVGVPSRFSGSGSGTEFTLTISSLQPEDFATYYCLQYIQFPL
TFGQGTKVEIKRT h#11D5-T11L
DIQMTQSPSSLSASVGDRVTITCRASQDIGNYLSWYQQKPGKAPKRLI
YGAIKLAVGVPSRFSGSGSGTDFTLTISSLQPEDFATYYCLQYIQFPL
TFGQGTKVEIKRT h#11D5-T12L
DIQMTQSPSSLSASVGDRVTITCRASQDIGNYLSWYQQKPGKAPKRLI
YGAIKLAVGVPSRFSGSGSGTEYTLTISSLQPEDFATYYCLQYIQFPL
TFGQGTKVEIKRT h#11D5-T13L
DIQMTQSPSSLSASVGDRVTITCRASQDIGNYLSWFQQKPGKAPRRLI
YGAIKLAVGVPSRFSGSGSGTEFTLTISSLQPEDFATYYCLQYIQFPL
TFGQGTKVEIKRT h#11D5-T14L
DIQMTQSPSSLSASVGDRVTITCRASQDIGNYLSWFQQKPGKAPKRMI
YGAIKLAVGVPSRFSGSGSGTEFTLTISSLQPEDFATYYCLQYIQFPL
TFGQGTKVEIKRT

Figure 8 h#11D5-T15L
DIQMTQSPSSLSASVGDRVTITCRASQDIGNYLSWFQQKPGKAPKRLI
YGAIKLAVGVPSRFSGSGSGTDFTLTISSLQPEDFATYYCLQYIQFPL
TFGQGTKVEIKRT h#11D5-T16L
DIQMTQSPSSLSASVGDRVTITCRASQDIGNYLSWFQQKPGKAPKRLI
YGAIKLAVGVPSRFSGSGSGTEYTLTISSLQPEDFATYYCLQYIQFPL
TFGQGTKVEIKRT h#11D5-T17L
DIQMTQSPSSLSASVGDRVTITCRASQDIGNYLSWYQQKPGKAPRRMI
YGAIKLAVGVPSRFSGSGSGTEFTLTISSLQPEDFATYYCLQYIQFPL
TFGQGTKVEIKRT h#11D5-T18L
DIQMTQSPSSLSASVGDRVTITCRASQDIGNYLSWYQQKPGKAPRRLI
YGAIKLAVGVPSRFSGSGSGTDFTLTISSLQPEDFATYYCLQYIQFPL
TFGQGTKVEIKRT h#11D5-T19L
DIQMTQSPSSLSASVGDRVTITCRASQDIGNYLSWYQQKPGKAPRRLI
YGAIKLAVGVPSRFSGSGSGTEYTLTISSLQPEDFATYYCLQYIQFPL
TFGQGTKVEIKRT h#11D5-T20L
DIQMTQSPSSLSASVGDRVTITCRASQDIGNYLSWYQQKPGKAPKRMI
YGAIKLAVGVPSRFSGSGSGTDFTLTISSLQPEDFATYYCLQYIQFPL
TFGQGTKVEIKRT h#11D5-T21L
DIQMTQSPSSLSASVGDRVTITCRASQDIGNYLSWYQQKPGKAPKRMI
YGAIKLAVGVPSRFSGSGSGTEYTLTISSLQPEDFATYYCLQYIQFPL
TFGQGTKVEIKRT

Figure 9 h#11D5-T22L
DIQMTQSPSSLSASVGDRVTITCRASQDIGNYLSWYQQKPGKAPKRLI
YGAIKLAVGVPSRFSGSGSGTDYTLTISSLQPEDFATYYCLQYIQFPL
TFGQGTKVEIKRT h#11D5-T23L
DIQMTQSPSSLSASVGDRVTITCRASQDIGNYLSWFQQKPGKAPRRMI
YGAIKLAVGVPSRFSGSGSGTEFTLTISSLQPEDFATYYCLQYIQFPL
TFGQGTKVEIKRT h#11D5-T24L
DIQMTQSPSSLSASVGDRVTITCRASQDIGNYLSWFQQKPGKAPRRLI
YGAIKLAVGVPSRFSGSGSGTDFTLTISSLQPEDFATYYCLQYIQFPL
TFGQGTKVEIKRT h#11D5-T25L
DIQMTQSPSSLSASVGDRVTITCRASQDIGNYLSWFQQKPGKAPRRLI
YGAIKLAVGVPSRFSGSGSGTEYTLTISSLQPEDFATYYCLQYIQFPL
TFGQGTKVEIKRT h#11D5-T26L
DIQMTQSPSSLSASVGDRVTITCRASQDIGNYLSWFQQKPGKAPKRMI
YGAIKLAVGVPSRFSGSGSGTDFTLTISSLQPEDFATYYCLQYIQFPL
TFGQGTKVEIKRT h#11D5-T27L
DIQMTQSPSSLSASVGDRVTITCRASQDIGNYLSWFQQKPGKAPKRMI
YGAIKLAVGVPSRFSGSGSGTEYTLTISSLQPEDFATYYCLQYIQFPL
TFGQGTKVEIKRT h#11D5-T28L
DIQMTQSPSSLSASVGDRVTITCRASQDIGNYLSWFQQKPGKAPKRLI
YGAIKLAVGVPSRFSGSGSGTDYTLTISSLQPEDFATYYCLQYIQFPL
TFGQGTKVEIKRT

Figure 10 h#11D5-T29L
DIQMTQSPSSLSASVGDRVTITCRASQDIGNYLSWYQQKPGKAPRRMI
YGAIKLAVGVPSRFSGSGSGTDFTLTISSLQPEDFATYYCLQYIQFPL
TFGQGTKVEIKRT h#11D5-T30L
DIQMTQSPSSLSASVGDRVTITCRASQDIGNYLSWYQQKPGKAPRRMI
YGAIKLAVGVPSRFSGSGSGTEYTLTISSLQPEDFATYYCLQYIQFPL
TFGQGTKVEIKRT h#11D5-T31L
DIQMTQSPSSLSASVGDRVTITCRASQDIGNYLSWYQQKPGKAPRRLI
YGAIKLAVGVPSRFSGSGSGTDYTLTISSLQPEDFATYYCLQYIQFPL
TFGQGTKVEIKRT h#11D5-T32L
DIQMTQSPSSLSASVGDRVTITCRASQDIGNYLSWYQQKPGKAPKRMI
YGAIKLAVGVPSRFSGSGSGTDYTLTISSLQPEDFATYYCLQYIQFPL
TFGQGTKVEIKRT h#11D5-T33L
DIQMTQSPSSLSASVGDRVTITCRASQDIGNYLSWFQQKPGKAPRRMI
YGAIKLAVGVPSRFSGSGSGTDFTLTISSLQPEDFATYYCLQYIQFPL
TFGQGTKVEIKRT h#11D5-T34L
DIQMTQSPSSLSASVGDRVTITCRASQDIGNYLSWFQQKPGKAPRRMI
YGAIKLAVGVPSRFSGSGSGTEYTLTISSLQPEDFATYYCLQYIQFPL
TFGQGTKVEIKRT h#11D5-T35L
DIQMTQSPSSLSASVGDRVTITCRASQDIGNYLSWFQQKPGKAPRRLI
YGAIKLAVGVPSRFSGSGSGTDYTLTISSLQPEDFATYYCLQYIQFPL
TFGQGTKVEIKRT

Figure 11 h#11D5-T36L
DIQMTQSPSSLSASVGDRVTITCRASQDIGNYLSWFQQKPGKAPKRMI
YGAIKLAVGVPSRFSGSGSGTDYTLTISSLQPEDFATYYCLQYIQFPL
TFGQGTKVEIKRT h#11D5-T37L
DIQMTQSPSSLSASVGDRVTITCRASQDIGNYLSWYQQKPGKAPRRMI
YGAIKLAVGVPSRFSGSGSGTDYTLTISSLQPEDFATYYCLQYIQFPL
TFGQGTKVEIKRT

Figure 12 h#11D5-T1H
QVQLQESGPGLVKPSQTLSLTCTVSGYSITSNYWGWIRQPPGMGLEWI
GHITNSGNTTYNPSLKSRVTISVDTSENQFSLKLSSVTPADTAVYYCA
KGAFDYWGQGTLVTVSS h#11D5-T2H
EVQLQESGPGLVKPSQTLSLTCTVSGYSITSNYWGWIRQPPGMGLEWI
GHITNSGNTTYNPSLKSRISISVDTSENQFSLKLSSVTPADTAVYYCA
KGAFDYWGQGTLVTVSS h#11D5-T3H
EVQLQESGPGLVKPSQTLSLTCTVSGYSITSNYWGWIRKFPGNKMEWI
GHITNSGNTTYNPSLKSRISISRDTSKNQFSLKLSSVTPADTAVYYCA
KGAFDYWGQGTLVTVSS h#11D5-T4H
QVQLQQWGAGLLKPSETLSLTCTVSGYSITSNYWGWIRQPPGKGLEWI
GHITNSGNTTYNPSLKSRVTISRDTSKNQFSLKLSSVTAADTAVYYCA
KGAFDYWGQGTLVTVSS h#11D5-T5H
EVQLQQWGAGLLKPSETLSLTCTVSGYSITSNYWGWIRQPPGKGLEWI
GHITNSGNTTYNPSLKSRISISRDTSKNQFSLKLSSVTAADTAVYYCA
KGAFDYWGQGTLVTVSS h#11D5-T6H
EVQLQESGPGLVKPSETLSLTCTVSGYSITSNYWGWIRQPPGKGLEWI
GHITNSGNTTYNPSLKSRISISRDTSKNQFSLKLSSVTAADTAVYYCA
KGAFDYWGQGTLVTVSS h#11D5-T7H
QVQLQESGPGLVKPSETLSLTCTVSGYSITSNYWGWIRQPPGKGLEWI
GHITNSGNTTYNPSLKSRVTISRDTSKNQFSLKLSSVTAADTAVYYCA
KGAFDYWGQGTLVTVSS

Figure 13 h#11D5-T8H
EVQLQESGPGLVKPSETLSLTCTVSGYSITSNYWGWIRQPPGKGLEWI
GHITNSGNTTYNPSLKSRVTISRDTSKNQFSLKLSSVTAADTAVYYCA
KGAFDYWGQGTLVTVSS h#11D5-T9H
QVQLQESGPGLVKPSETLSLTCTVSGYSITSNYWGWIRQPPGKGLEWI
GHITNSGNTTYNPSLKSRITISRDTSKNQFSLKLSSVTAADTAVYYCA
KGAFDYWGQGTLVTVSS h#11D5-T10H
QVQLQESGPGLVKPSETLSLTCTVSGYSITSNYWGWIRQPPGKGLEWI
GHITNSGNTTYNPSLKSRVSISRDTSKNQFSLKLSSVTAADTAVYYCA
KGAFDYWGQGTLVTVSS h#11D5-T11H
EVQLQESGPGLVKPSETLSLTCTVSGYSITSNYWGWIRQPPGKGLEWI
GHITNSGNTTYNPSLKSRITISRDTSKNQFSLKLSSVTAADTAVYYCA
KGAFDYWGQGTLVTVSS h#11D5-T12H
EVQLQESGPGLVKPSETLSLTCTVSGYSITSNYWGWIRQPPGKGLEWI
GHITNSGNTTYNPSLKSRVSISRDTSKNQFSLKLSSVTAADTAVYYCA
KGAFDYWGQGTLVTVSS h#11D5-T13H
QVQLQESGPGLVKPSETLSLTCTVSGYSITSNYWGWIRQPPGKGLEWI
GHITNSGNTTYNPSLKSRISISRDTSKNQFSLKLSSVTAADTAVYYCA
KGAFDYWGQGTLVTVSS

Figure 14 A

Primer EFF1
ccacgcgccctgtagcggcgcattaagc

Primer EFsmaR
aaacccgggagcttttttgcaaaagcctagg

Fragment B
ggtaccacccaagctggctaggtaagcttgctagcgccaccatggtgctgcagacccaggtgttcatc
tccctgctgctgtggatctccggcgcatatggcgatatcgtgatgattaaacgtacggtggccgcccc
ctccgtgttcatcttccccccctccgacgagcagctgaagtccggcaccgcctccgtggtgtgcctgc
tgaataacttctaccccagagaggccaaggtgcagtggaaggtggacaacgccctgcagtccgggaac
tcccaggagagcgtgaccgagcaggacagcaaggacagcacctacagcctgagcagcaccctgaccct
gagcaaagccgactacgagaagcacaaggtgtacgcctgcgaggtgacccaccagggcctgagctccc
ccgtcaccaagagcttcaacagggggagtgttaggggcccgtttaaacgggtggcatccctgtgacc
cctccccagtgcctctcctggccctggaagttgccactccagtgcccaccagccttgtcctaataaaa
ttaagttgcatcatttttgtctgactaggtgtccttctataatattatggggtggaggggggtggtatg
gagcaaggggcaagttgggaagacaacctgtagggcctgcggggtctattgggaaccaagctggagtg
cagtggcacaatcttggctcactgcaatctccgcctcctgggttcaagcgattctcctgcctcagcct
cccgagttgttgggattccaggcatgcatgaccaggctcacctaattttgttttttttggtagagacg
gggtttcaccatattggccaggctggtctccaactcctaatctcaggtgatctacccaccttggcctc
ccaaattgctgggattacaggcgtgaaccactgctccacgcgccctgtagcggcgcattaagcgcggc
gggtgtggtggttacgcgcagcgtgaccgctacacttgccagcgccctagcgcccgctcctttcgctt
tcttcccttcctttctcgccacgttcgccggctttccccgtcaagctctaaatcgggggctcccttta
gggttccgatttagtgctttacggcacctcgaccccaaaaaacttgattagggtgatggttcacgtag
tgggccatcgccctgatagacggtttttcgccctttgacgttggagtccacgttctttaatagtggac
tcttgttccaaactggaacaacactcaaccctatctcggtctattcttttgattataagggattttg
ccgatttcggcctattggttaaaaaatgagctgatttaacaaaaatttaacgcgaattaattctgtgg
aatgtgtgtcagttagggtgtggaaagtccccaggctccccagcaggcagaagtatgcaaagcatgca
tctcaattagtcagcaaccaggtgtggaaagtccccaggctccccagcaggcagaagtatgcaaagca
tgcatctcaattagtcagcaaccatagtcccgcccctaactccgcccatcccgcccctaactccgccc
agttccgcccattctccgccccatggctgactaattttttttatttatgcagaggccgaggccgcctc
tgcctctgagctattccagaagtagtgaggaggcttttttggaggcctaggcttttgcaaaaagctcc
cggg human IgG1 signal + human IgG1 constant
tgctagcgccaccatgaaacacctgtggttcttcctcctgctggtggcagctcccagatgggtgctga
gccaggtgcaattgtgcaggcggttagctcagcctccaccaagggcccaagcgtcttcccctggcac
cctcctccaagagcacctctggcggcacagccgccctgggctgcctggtcaaggactacttcccccgaa
cccgtgaccgtgagctggaactcaggcgccctgaccagcggcgtgcacaccttcccggctgtcctgca
gtcctcaggactctactccctcagcagcgtggtgaccgtgccctccagcagcttgggcacccagacct
acatctgcaacgtgaatcacaagcccagcaacaccaaggtggacaagagagttgagcccaaatcttgt
gacaaaactcacacatgcccaccctgcccagcacctgaactcctgggggaccctcagtcttcctctt
cccccaaaacccaaggacaccctcatgatctcccggacccctgaggtcacatgcgtggtggtggacg
tgagccacgaagaccctgaggtcaagttcaactggtacgtggacggcgtggaggtgcataatgccaag
acaaagccgcgggaggagcagtacaacagcacgtaccgggtggtcagcgtcctcaccgtcctgcacca
ggactggctgaatggcaaggagtacaagtgcaaggtctccaacaaagccctcccagcccccatcgaga
aaaccatctccaaagccaaaggccagccccgggaaccacaggtgtacaccctgcccccatcccgggag
gagatgaccaagaaccaggtcagcctgacctgcctggtcaaaggcttctatcccagcgacatcgcgt
ggagtgggagagcaatggccagccgagaacaactacaagaccacccctcccgtgctggactccgacg
gctccttcttcctctacagcaagctcaccgtggacaagagcaggtggcagcagggcaacgtcttctca
tgctccgtgatgcatgaggctctgcacaaccactacacccagaagagcctctccctgtctccggcaa
atgagatatcgggcccgtttaaacgggtggca Figure 14B (Continued)

| Antibody | CDR | Sequence |
|---|---|---|
| 11B7 Light chain | L4 | RASQDIGNYLR |
| 11B7 Light chain | L5 | GATNLAA |
| 11B7 Light chain | L6 | LQSKESPWT |
| 11B7 Heavy Chain | H1 | SNYWG |
| 11B7 Heavy Chain | H2 | YITYSGSTSYNPSLKS |
| 11B7 Heavy Chain | H3 | ----TTFYY |
| 11D5 Light Chain | L4 | RASQDIGNYLS |
| 11D5 Light Chain | L5 | GAIKLAV |
| 11D5 Light Chain | L6 | LQYIQFPLT |
| 11D5 Heavy Chain | H1 | SNYWG |
| 11D5 Heavy Chain | H2 | HITNSGNTTYNPSLKS |
| 11D5 Heavy Chain | H3 | ----GAFDY |

Leader Sequence

Nucleotide Sequence

1 ATGGGTGACAATGACATCCACTTTGCCTTTCTCTCCACAGG TGTGCATTCC 52

Amino Acid Sequence

11B7-chimer light chain

D I Q M T Q A P S S L P A S L G D R V T I T C R A S Q D I
G N Y L R W F Q Q K P G K S P R L M I S G A T N L A A G V
P S R F S G S R S G S D Y S L T I S S L E S E D M A D Y Y
C L Q S K E S P W T F G G G T K L E L K R T V A A P S V F
I F P P S D E Q L K S G T A S V V C L L N N F Y P R E A K
V Q W K V D N A L Q S G N S Q E S V T E Q D S K D S T Y S
L S S T L T L S K A D Y E K H K V Y A C E V T H Q G L S S
P V T K S F N R G E C

11B7-chimer heavy chain

E V Q L Q E S G P G L V K P S Q S L S L T C S V T G Y S I
T S N Y W G W I R K F P G D K M E W M G Y I T Y S G S T S
Y N P S L K S R I S I T R D T S K N Q F F L Q L N S V T S
E D T A T Y Y C A I T T F Y Y W G Q G V M V T V S S A S T
K G P S V F P L A P S S K S T S G G T A A L G C L V K D Y
F P E P V T V S W N S G A L T S G V H T F P A V L Q S S G
L Y S L S S V V T V P S S S L G T Q T Y I C N V N H K P S
N T K V D K K V E P K S C D K T H T C P P C P A P E L L G
G P S V F L F P P K P K D T L M I S R T P E V T C V V V D
V S H E D P E V K F N W Y V D G V E V H N A K T K P R E E
Q Y N S T Y R V V S V L T V L H Q D W L N G K E Y K C K V
S N K A L P A P I E K T I S K A K G Q P R E P Q V Y T L P
P S R D E L T K N Q V S L T C L V K G F Y P S D I A V E W
E S N G Q P E N N Y K T T P P V L D S D G S F F L Y S K L
T V D K S R W Q Q G N V F S C S V M H E A L H N H Y T Q K
S L S L S P G K

11D5-chimer light chain

D I Q M T Q S P S S M S T S L G D R V T I T C R A S Q D I
G N Y L S W F Q Q K V G K S P R R M I Y G A I K L A V G V
P S R F S G S R S G S D Y S L T I S S L E S E D M A I Y Y
C L Q Y I Q F P L T F G S G T K L E L K R T V A A P S V F
I F P P S D E Q L K S G T A S V V C L L N N F Y P R E A K
V Q W K V D N A L Q S G N S Q E S V T E Q D S K D S T Y S
L S S T L T L S K A D Y E K H K V Y A C E V T H Q G L S S
P V T K S F N R G E C

11D5-chimer heavy chain

RAT-11B7 LIGHT CHAIN VARAIBLE REGION

DIQMTQAPSSLPASLGDRVTITCRASQDIGNYLRWFQQKPGKSPRLMISGA
TNLAAGVPSRFSGSRSGSDYSLTISSLESEDMADYYCLQSKESPWTFGGG
TKLELKR

RAT-11B7 HEAVY CHAIN VARAIBLE REGION

EVQLQESGPGLVKPSQSLSLTCSVTGYSITSNYWGWIRKFPGDKMEWMG
YITYSGSTSYNPSLKSRISITRDTSKNQFFLQLNSVTSEDTATYYCAITTFYY
WGQGVMVTVSS

RAT-11D5 LIGHT CHAIN VARAIBLE REGION

DIQMTQSPSSMSTSLGDRVTITCRASQDIGNYLSWFQQKVGKSPRRMIYG
AIKLAVGVPSRFSGSRSGSDYSLTISSLESEDMAIYYCLQYIQFPLTFGSGT
KLELKR

RAT-11D5 HEAVY CHAIN VARAIBLE REGION

EVQLQESGPGLVKPSQSLSLTCSVTGYSITSNYWGWIRKFPGNKMEWIGH
ITNSGNTTYNPSLKSRISISRDTSRNQFFLQLNSVTTEDTATYYCAKGAFDY
WGQGVMVTVSS

Figure 24 A upper panel

| | Ab280 | Dilution | Protein conc. (mg/mL) | Absorption coefficient (Ab280/mg/mL) |
|---|---|---|---|---|
| T1 | 0.30 | 1 | 0.20 | 1.538 |
| T2 | 0.41 | 2.5 | 0.66 | 1.537 |
| T3 | 0.68 | 1 | 0.44 | 1.535 |
| T4 | 0.50 | 2 | 0.62 | 1.611 |
| T5 | 0.36 | 2.9 | 0.65 | 1.61 |
| T6 | 0.51 | 2 | 0.67 | 1.535 |
| T7 | 0.98 | 11 | 6.9 | 1.556 |
| T8 | 0.78 | 10.1 | 5.1 | 1.556 |
| T9 | 0.62 | 22.5 | 9.5 | 1.516 |
| T10 | 1.17 | 10.2 | 7.7 | 1.557 |
| T11 | 0.71 | 20.4 | 0.6 | 1.516 |
| T12 | 0.59 | 10.0 | 3.9 | 1.536 |
| T13 | 0.22 | 26.4 | 3.8 | 1.536 |
| T14 | 0.80 | 10.6 | 5.5 | 1.555 |

Figure 24 B (Continued)

lower panel

| | Ab280 | Dilution | Protein conc. (mg/mL) | Absorption coefficient (Ab280/mg/mL) |
|---|---|---|---|---|
| T15 | 0.66 | 11.0 | 4.7 | 1.535 |
| T16 | 0.56 | 20.9 | 7.8 | 1.515 |
| T17 | 0.99 | 10.7 | 7.0 | 1.515 |
| T18 | 0.46 | 24.3 | 7.4 | 1.515 |
| T19 | 0.68 | 10.8 | 4.8 | 1.535 |
| T20 | 0.64 | 10.4 | 4.3 | 1.535 |
| T21 | 0.60 | 11.5 | 4.4 | 1.556 |
| T22 | 0.45 | 11.5 | 3.4 | 1.536 |
| T23 | 0.98 | 10.6 | 6.8 | 1.515 |
| T24 | 0.62 | 10.8 | 4.3 | 1.556 |
| T25 | 0.93 | 10.7 | 6.6 | 1.516 |
| T26 | 0.65 | 10.5 | 4.4 | 1.536 |
| T27 | 0.73 | 10.8 | 5.2 | 1.536 |

Figure 25

| | Ab280 | Dilution | Protein Conc. (mg/mL) | Absorption coefficient (Ab280/mg/mL) |
|---|---|---|---|---|
| T1 | 0.55 | 14.4 | 5.5 | 1.437 |
| T2 | 0.70 | 10.3 | 5.0 | 1.438 |
| T3 | 0.56 | 3.9 | 1.5 | 1.432 |
| T4 | 0.60 | 4.0 | 1.6 | 1.514 |
| T5 | 0.43 | 4.1 | 1.2 | 1.513 |
| T6 | 0.83 | 5.0 | 2.9 | 1.437 |

Figure 27
Hs578T:
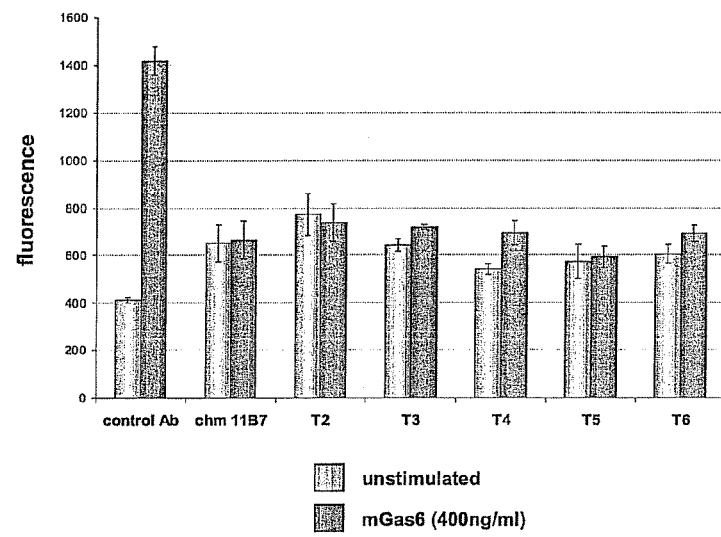
NCI-H292:
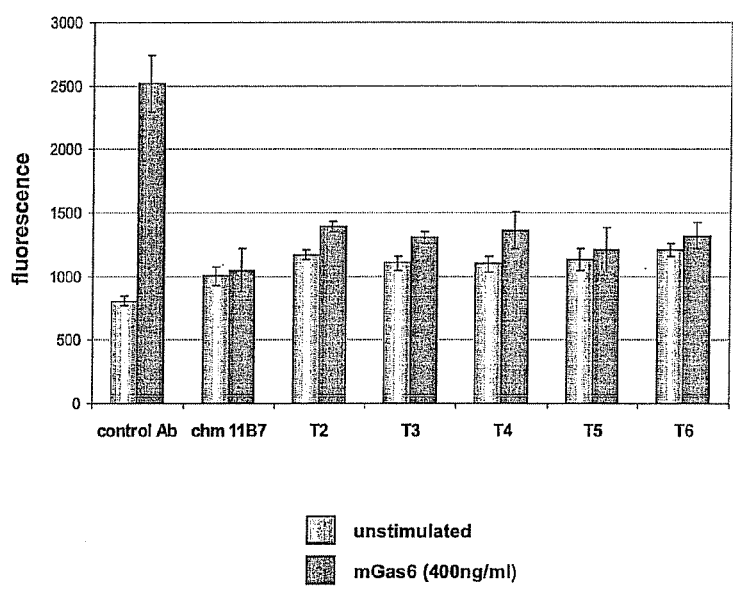

Figure 28
A:
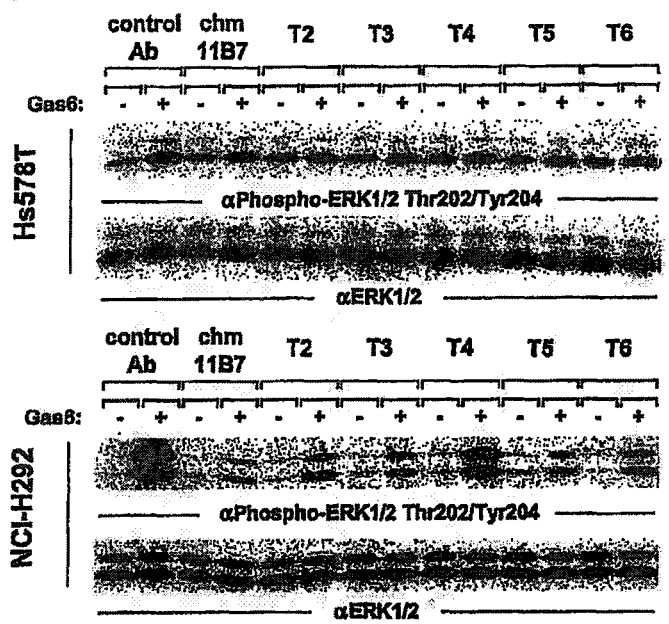
B:
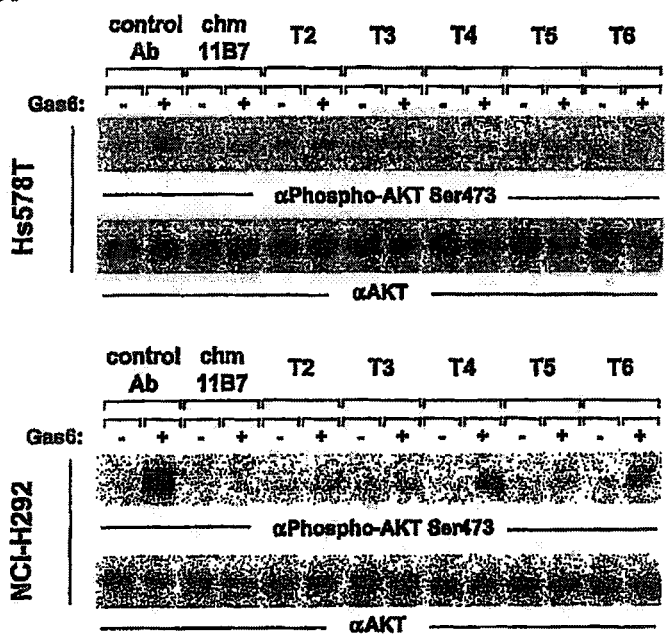

Figure 28 (continued)
C:
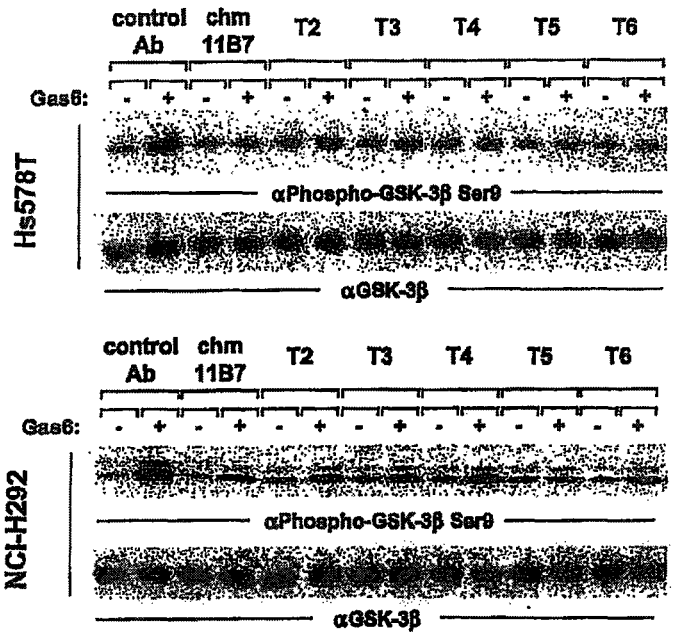
D:
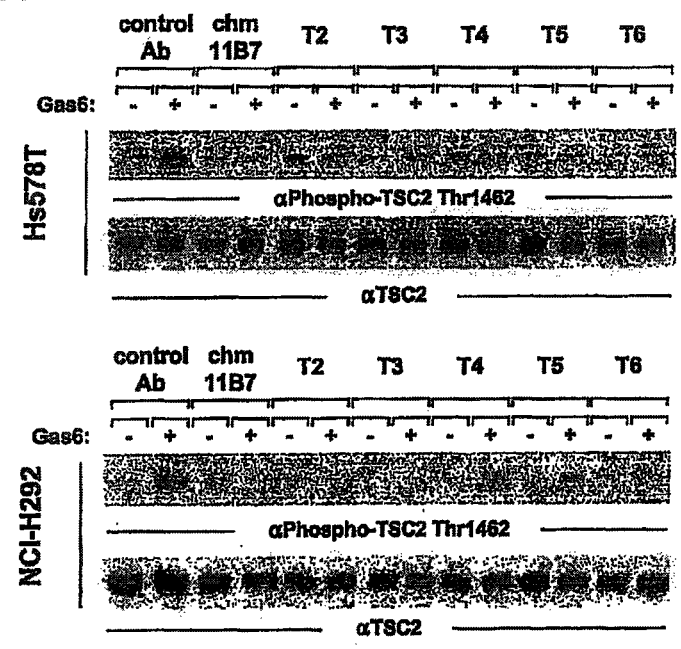

Figure 28 (continued)
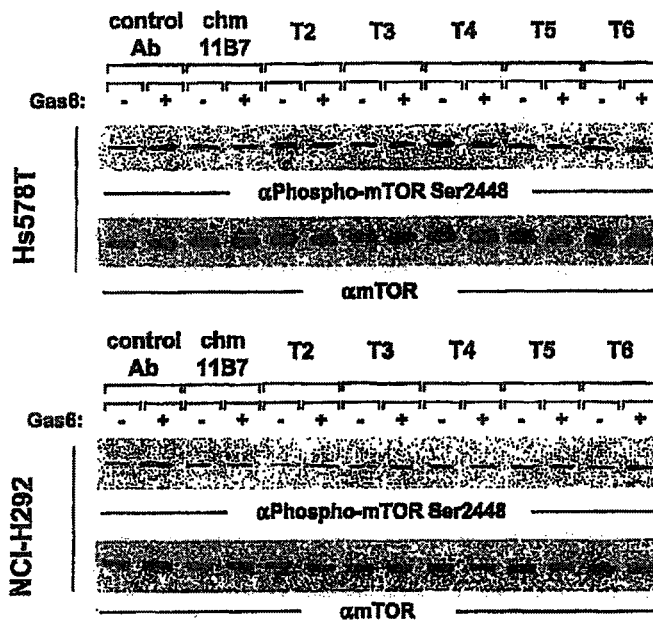
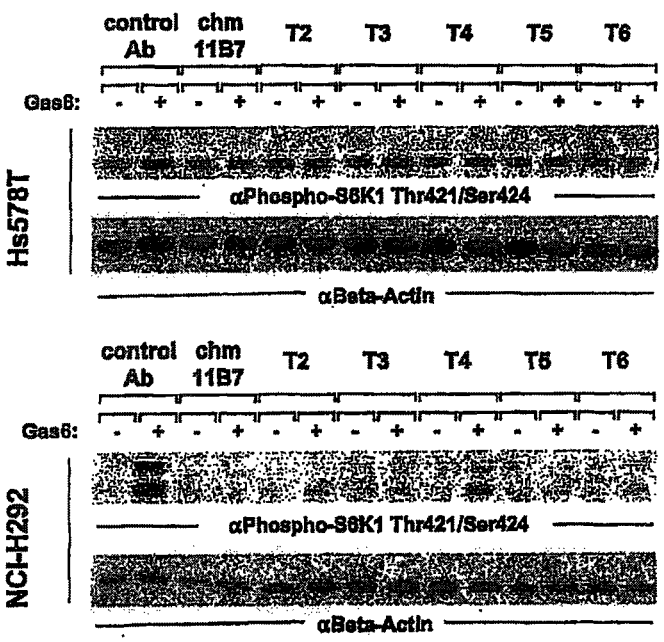

Figure 30A (Accession No.P_30530 of NCBI protein database)
MGRVPLAWCLALCGWACMAPRGTQAEESPFVGNPGNITGARGLTGTLRCQLQVQGEPPEVHW
LRDGQILELADSTQTQVPLGEDEQDDWIVVSQLRITSLQLSDTGQYQCLVFLGHQTFVSQPG
YVGLEGLPYFLEEPEDRTVAANTPFNLSCQAQGPPEPVDLLWLQDAVPLATAPGHGPQRSLH
VPGLNKTSSFSCEAHNAKGVTTSRTATITVLPQQPRNLHLVSRQPTELEVAWTPGLSGIYPL
THCTLQAVLSDDGMGIQAGEPDPPEEPLTSQASVPPHQLRLGSLHPHTPYHIRVACTSSQGP
SSWTHWLPVETPEGVPLGPPENISATRNGSQAFVHWQEPRAPLQGTLLGYRLAYQGQDTPEV
LMDIGLRQEVTLELQGDGSVSNLTVCVAAYTAAGDGPWSLPVPLEAWRPGEAQPVHQLVKEP
STPAFSWPWWYVLLGAVVAAACVLILALFLVHRRKKETRYGEVFEPTVERGELVVRYRVRKS
YSRRTTEATLNSLGISEELKEKLRDVMVDRHKVALGKTLGEGEFGAVMEGQLNQDDSILKVA
VKTMKIAICTRSELEDFLSEAVCMKEFDHPNVMRLIGVCFQGSERESFPAPVVILPFMKHGD
LHSFLLYSRLGDQPVYLPTQMLVKFMADIASGMEYLSTKRFIHRDLAARNCMLNENMSVCVA
DFGLSKKIYNGDYYRQGRIAKMPVKWIAIESLADRVYTSKSDVWSFGVTMWEIATRGQTPYP
GVENSEIYDYLRQGNRLKQPADCLDGLYALMSRCWELNPQDRPSFTELREDLENTLKALPPA
QEPDEILYVNMDEGGGYPEPPGAAGGADPPTQPDPKDSCSCLTAAEVHPAGRYVLCPSTTPS
PAQPADRGSPAAPGQEDGA Figure 30B (SEQ ID NO: 140)
DIQMTQAPSSLPASLGDRVTITCRASQDIGNYLRWFQQKPGKSPRLMISGATNLAAGVPSRF
SGSRSGSDYSLTISSLESEDMADYYCLQSKESPWTFGGGTKLELKR Figure 30C (SEQ ID No: 141)
EVQLQESGPGLVKPSQSLSLTCSVTGYSITSNYWGWIRKFPGDKMEWMGYITYSGSTSYNPS
LKSRISITRDTSKNQFFLQLNSVTSEDTATYYCAITTFYYWGQGVMVTVSS Figure 30D (SEQ ID NO: 142)
DIQMTQSPSSMSTSLGDRVTITCRASQDIGNYLSWFQQKVGKSPRRMIYGAIKLAVGVPSRF
SGSRSGSDYSLTISSLESEDMAIYYCLQYIQFPLTFGSGTKLELKR Figure 30E (SEQ ID NO: 143)
EVQLQESGPGLVKPSQSLSLTCSVTGYSITSNYWGWIRKFPGNKMEWIGHITNSGNTTYNPS
LKSRISISRDTSRNQFFLQLNSVTTEDTATYYCAKGAFDYWGQGVMVTVSS Figure 31
A   11B7 (rIgG1)
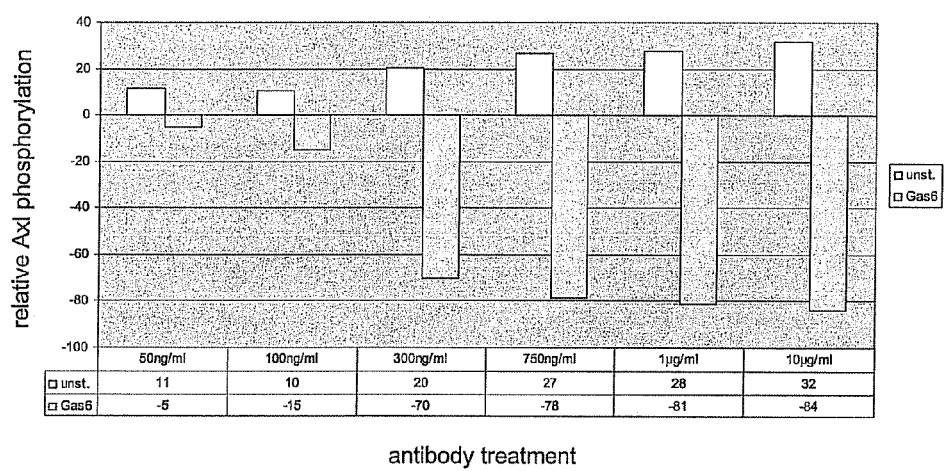
antibody treatment
B   ch11B7 (hIgG1)
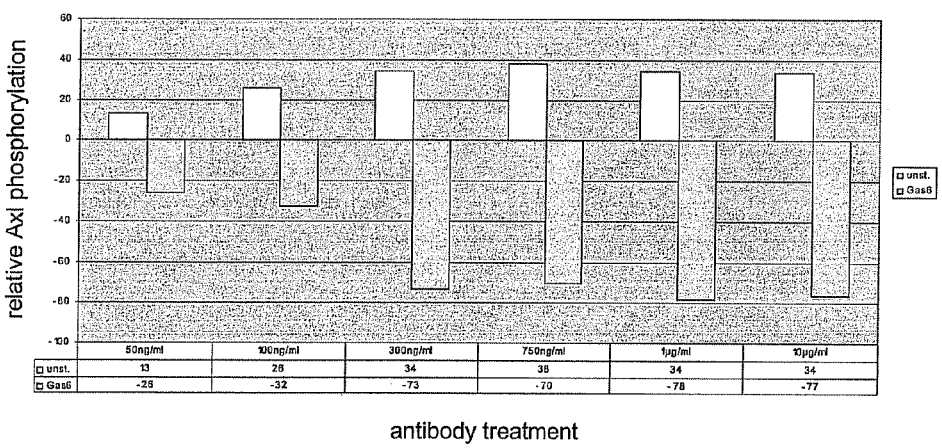
antibody treatment

Figure 32A h#11B7-T15L (also shown in Figure 3)

DIQMTQSPSSLSASVGDRVTITCRASQDIGNYLRWFQQKPGKAPKLLI
SGATNLAAGVPSRFSGSGSGSDYTLTISSLQPEDFATYYCLQSKESPW
TFGQGTKLEIKRT h#11B7-T18L (also shown in Figure 3)

DIQMTQSPSSLSASVGDRVTITCRASQDIGNYLRWFQQKPGKAPKLLI
SGATNLAAGVPSRFSGSGSGSDFTLTISSLQPEDFATYYCLQSKESPW
TFGQGTKLEIKRT

Figure 32B h#11B7-T11H (also shown in Figure 5)

QVQLQQWGAGLLKPSETLSLTCTVSGYSITSNYWGWIRQPPGKGLEWM
GYITYSGSTSYNPSLKSRITISRDTSKNQFSLKLSSVTAADTAVYYCA
ITTFYYWGQGTTVTVSS h#11B7-T12H (also shown in Figure 5)

QVQLQQWGAGLLKPSETLSLTCTVSGYSITSNYWGWIRQPPGKGLEWI
GYITYSGSTSYNPSLKSRVTISRDTSKNQFSLKLSSVTAADTAVYYCA
ITTFYYWGQGTTVTVSS

Figure 34

| | Absorption coefficient (Ab280/mg/mL) | Protein conc. (mg/mL) |
|---|---|---|
| h#11B7-T28 | 1.610 | 0.9 |
| h#11B7-T29 | 1.590 | 2.5 |
| h#11B7-T30 | 1.611 | 0.5 |
| h#11B7-T31 | 1.590 | 1.3 |

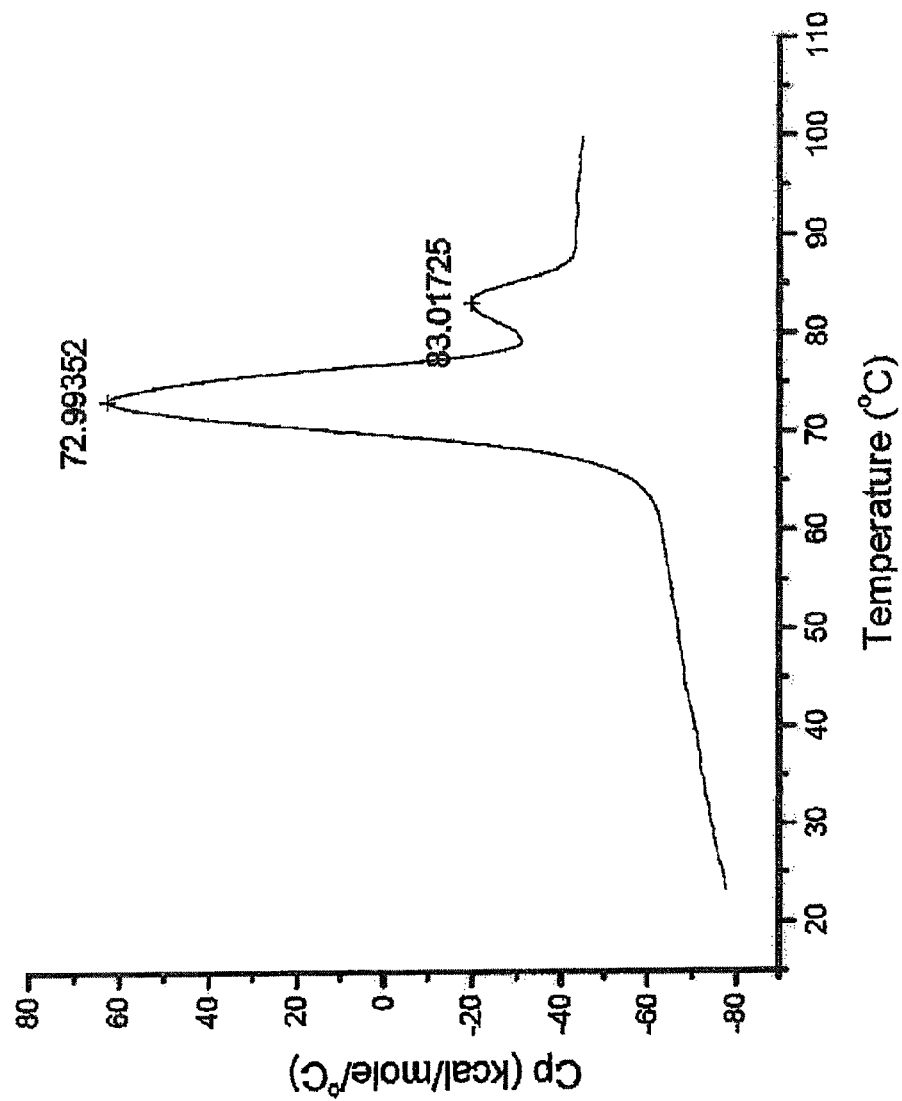
Figure 35 C  h#11B7-T3

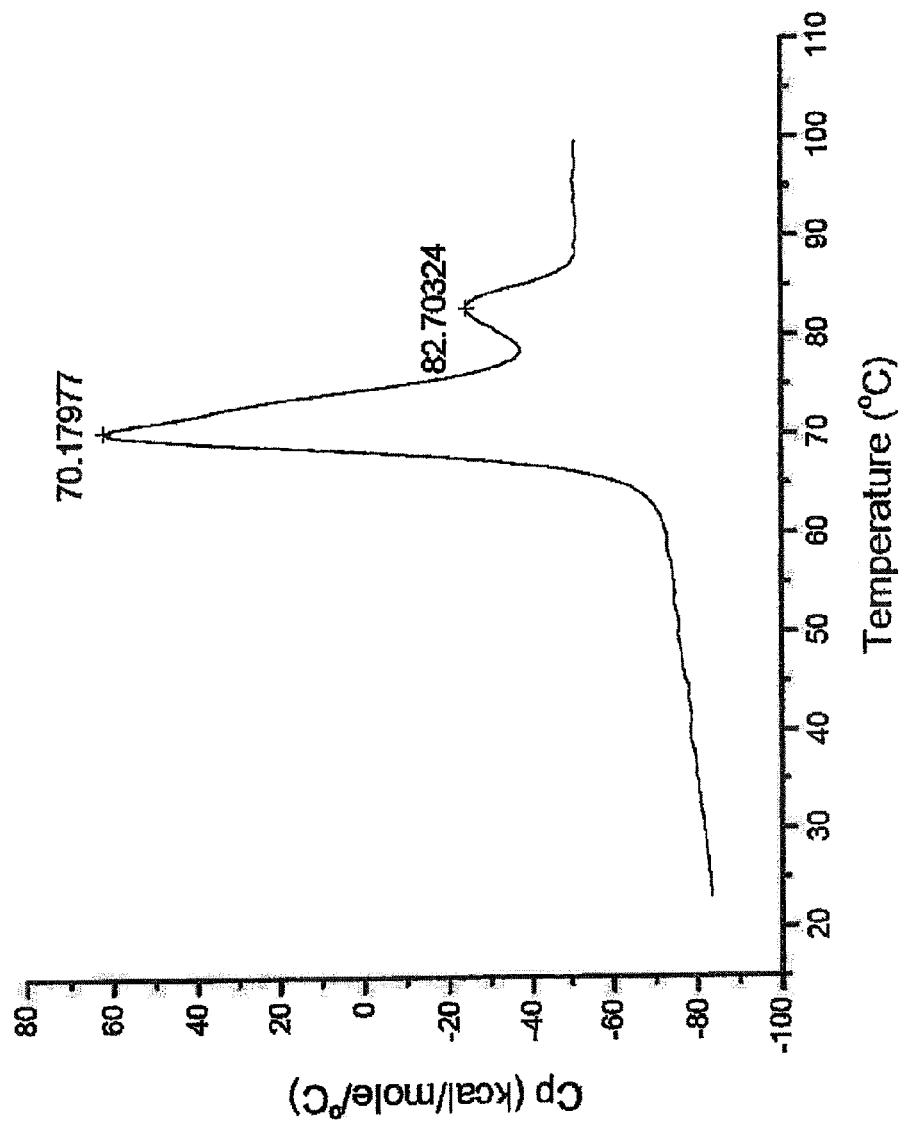
Figure 35 D    h#11B7-T4

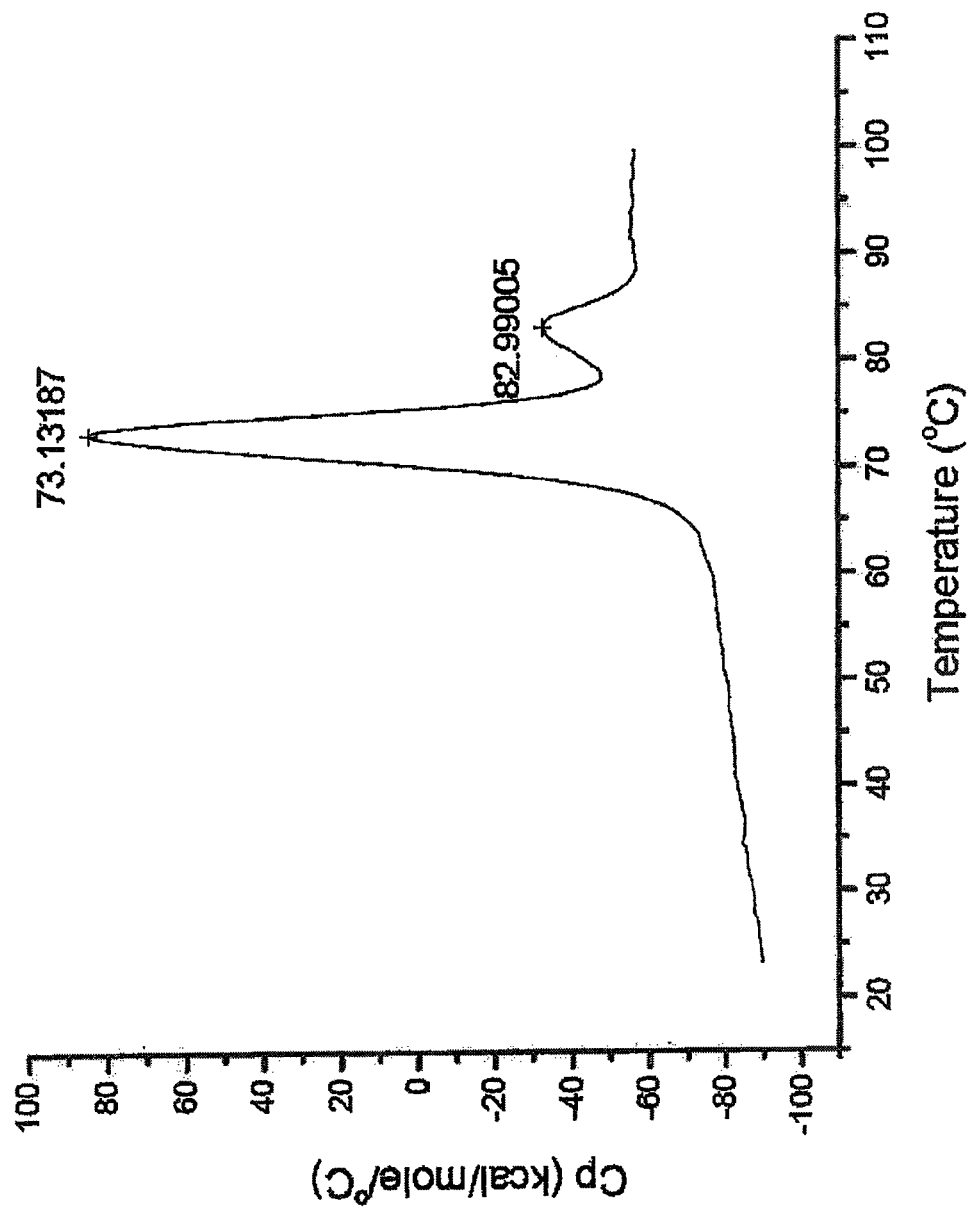
Figure 35 E    h#11B7-T5

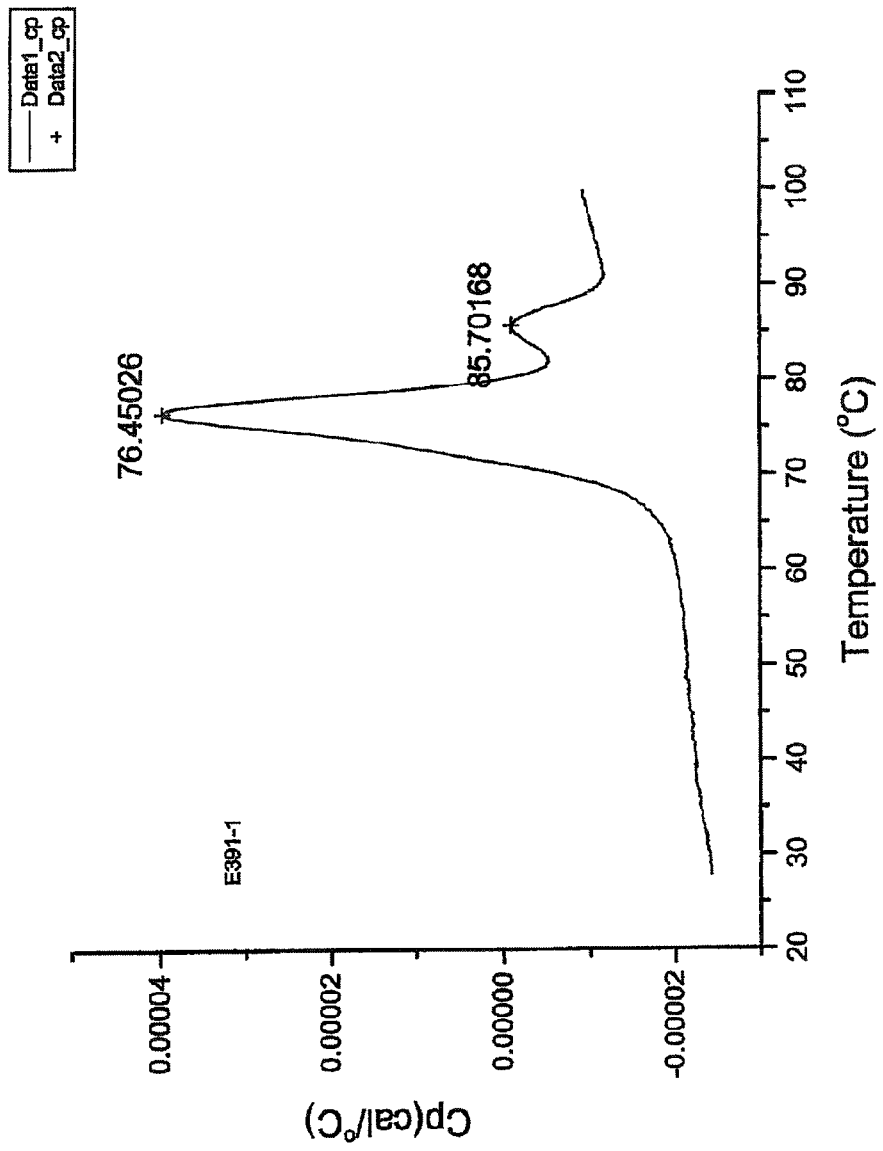
Figure 35G h#11B7-T7

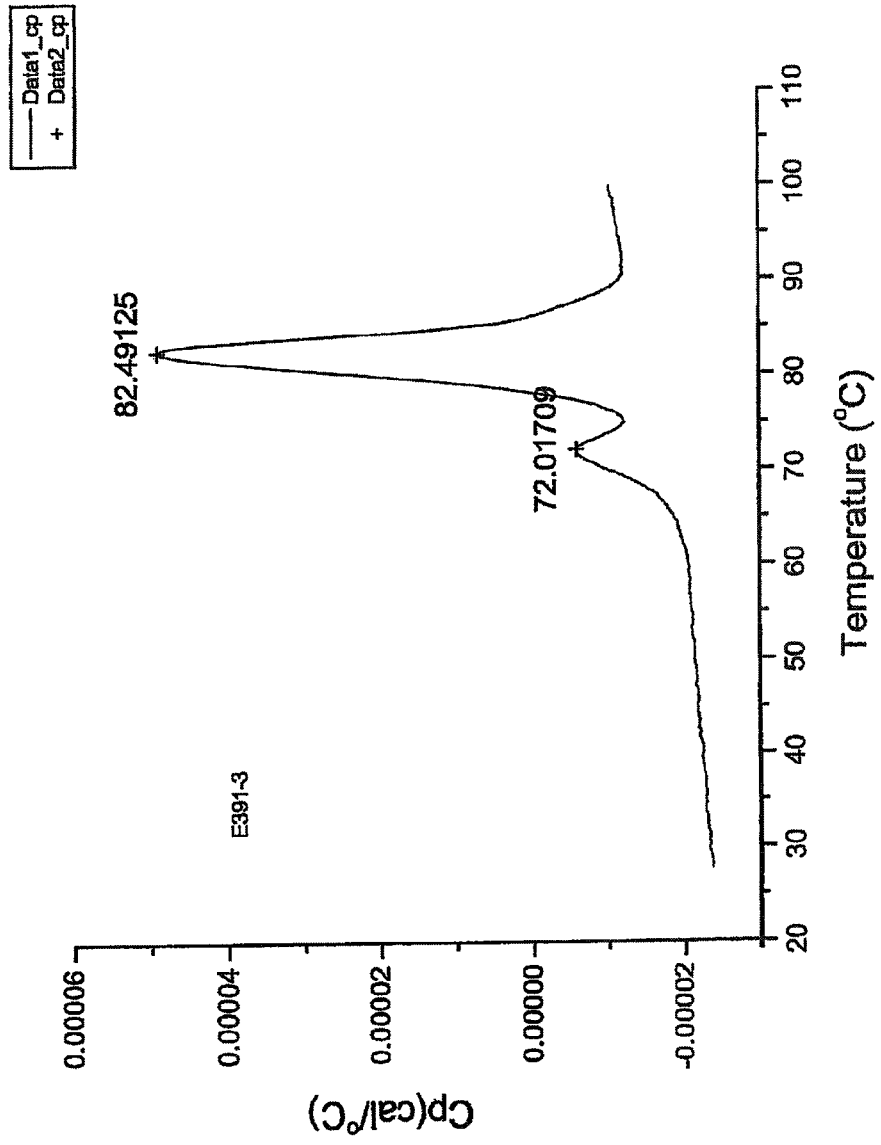
Figure 35 I  h#11B7-T9

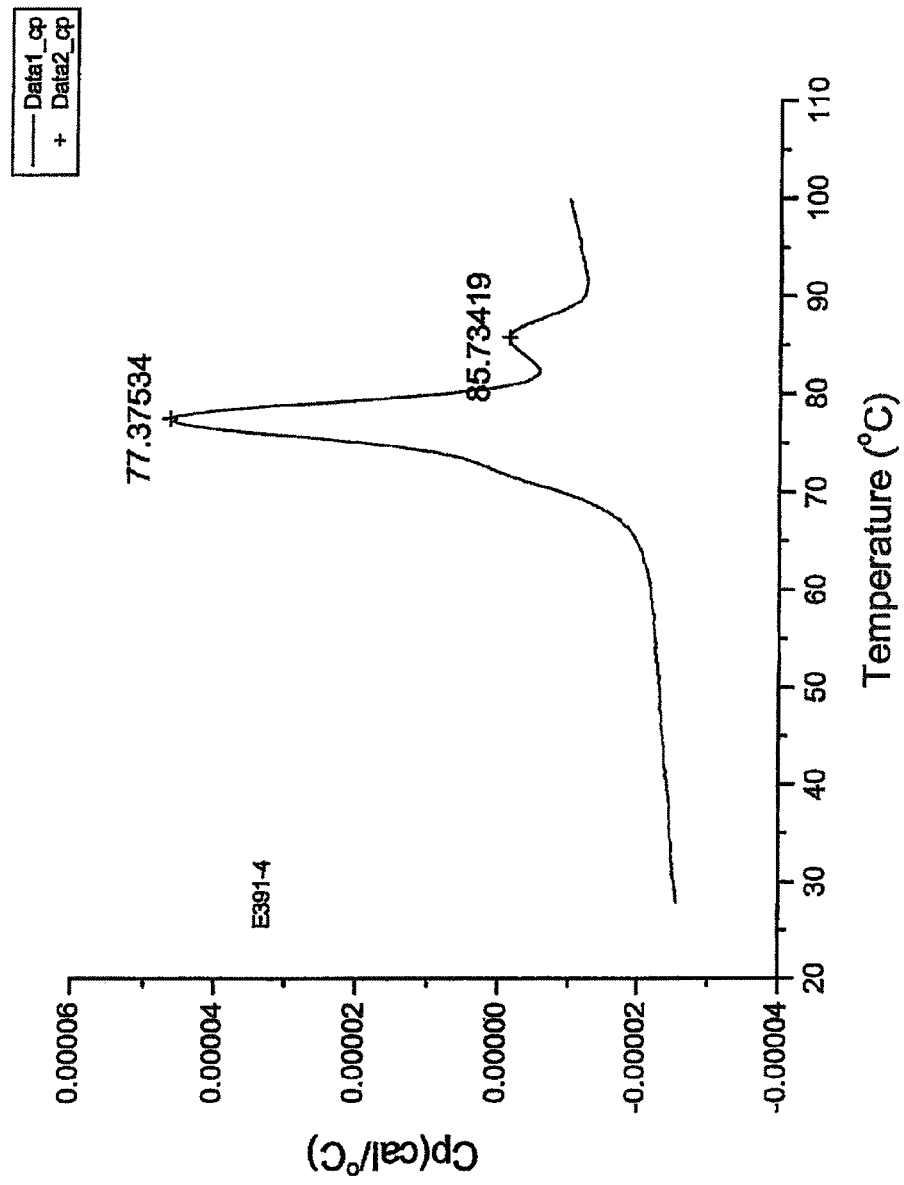
Figure 35 J        h#11B7-T10

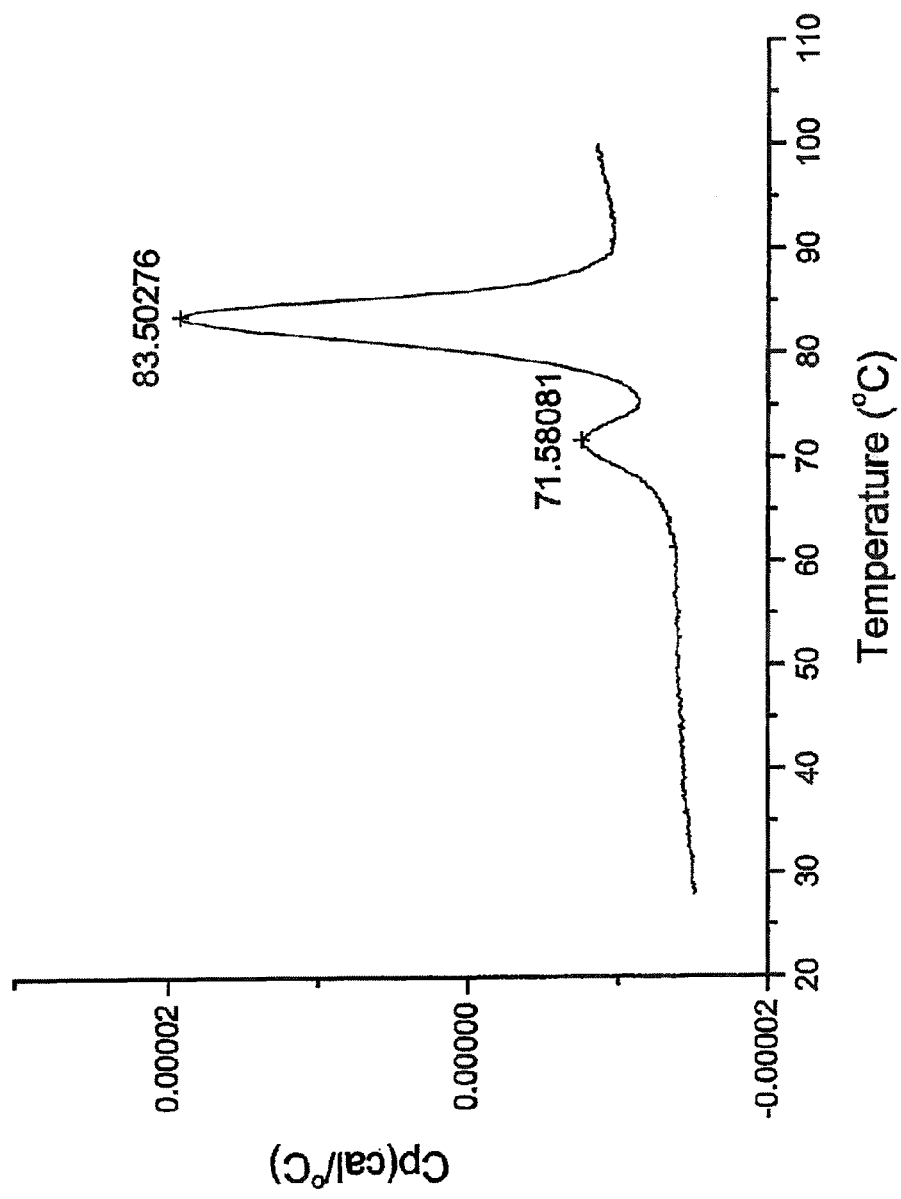

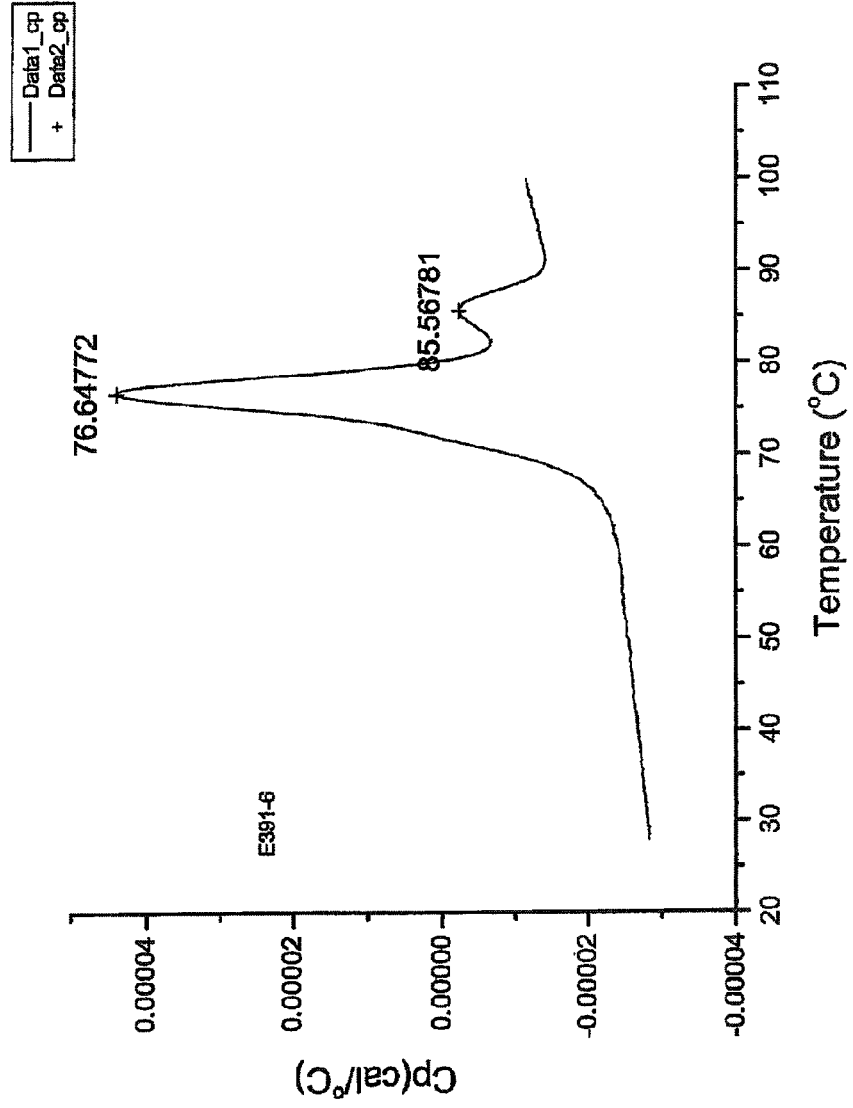
Figure 35 L   h#11B7-T12

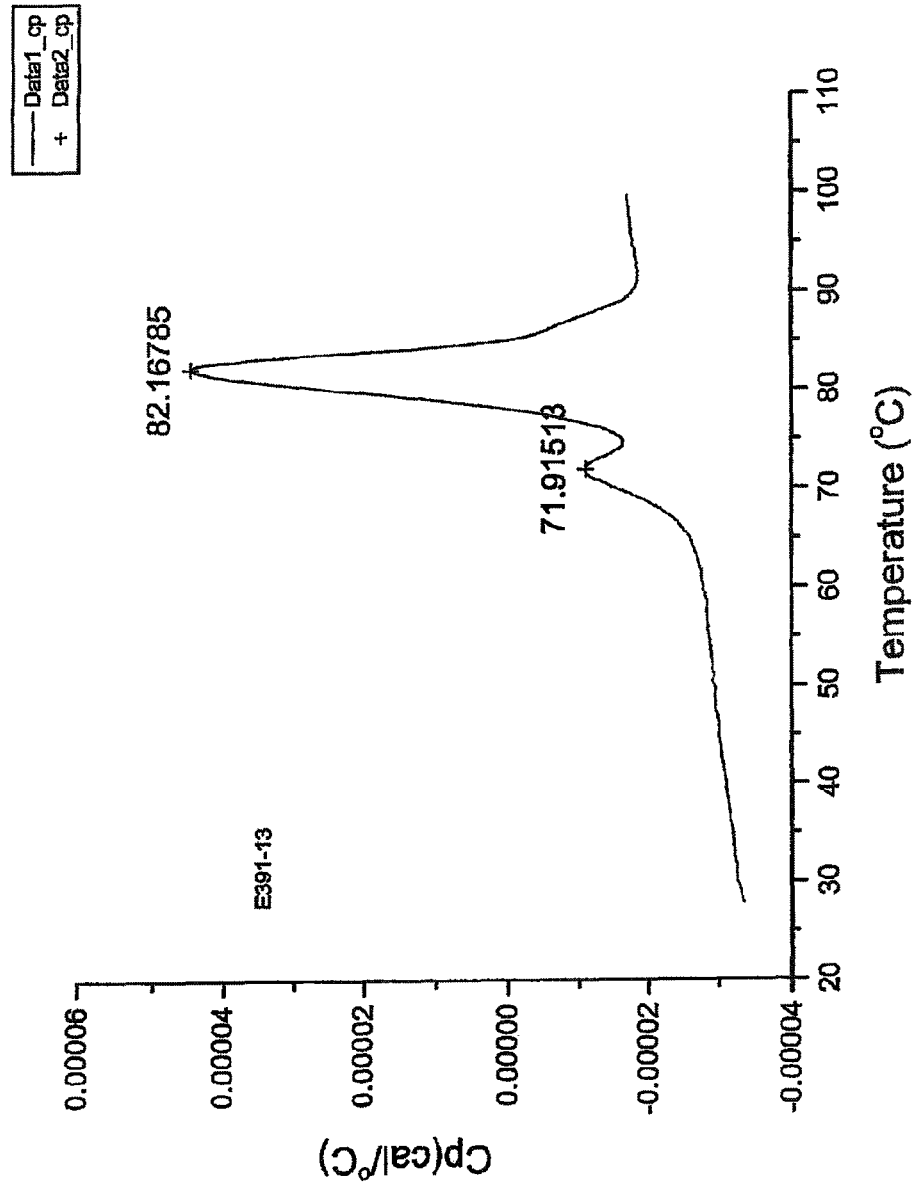
Figure 35 P  h#11B7-T16

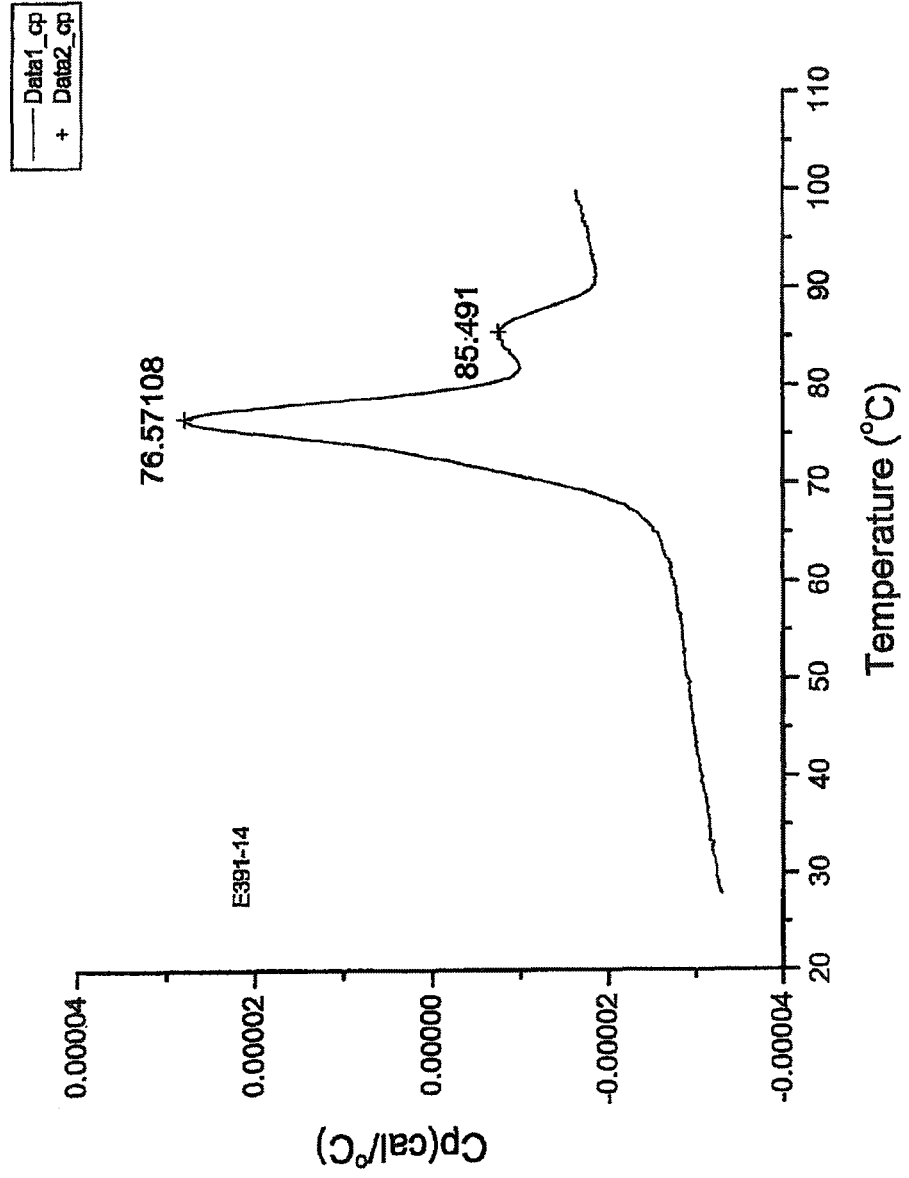
Figure 35 Q    h#11B7-T17

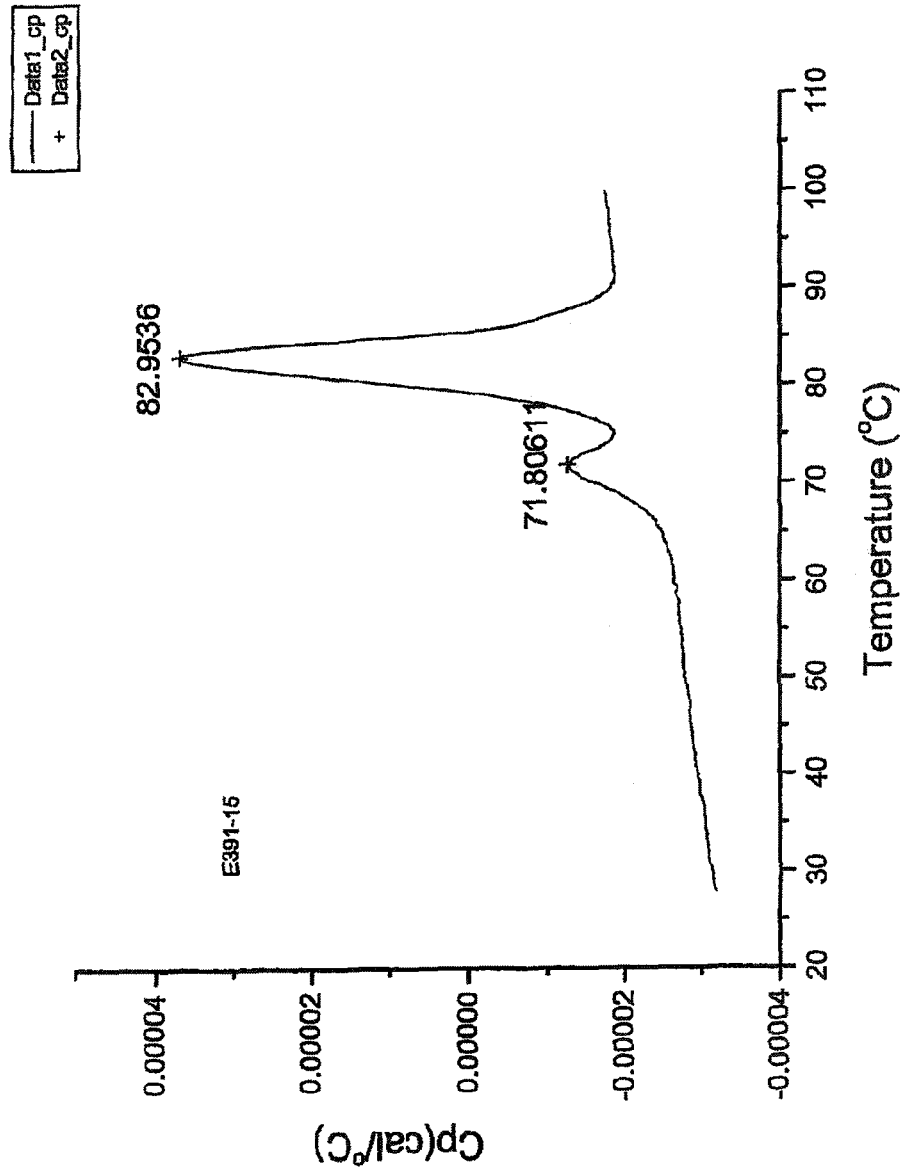
Figure 35 R    h#11B7-T18

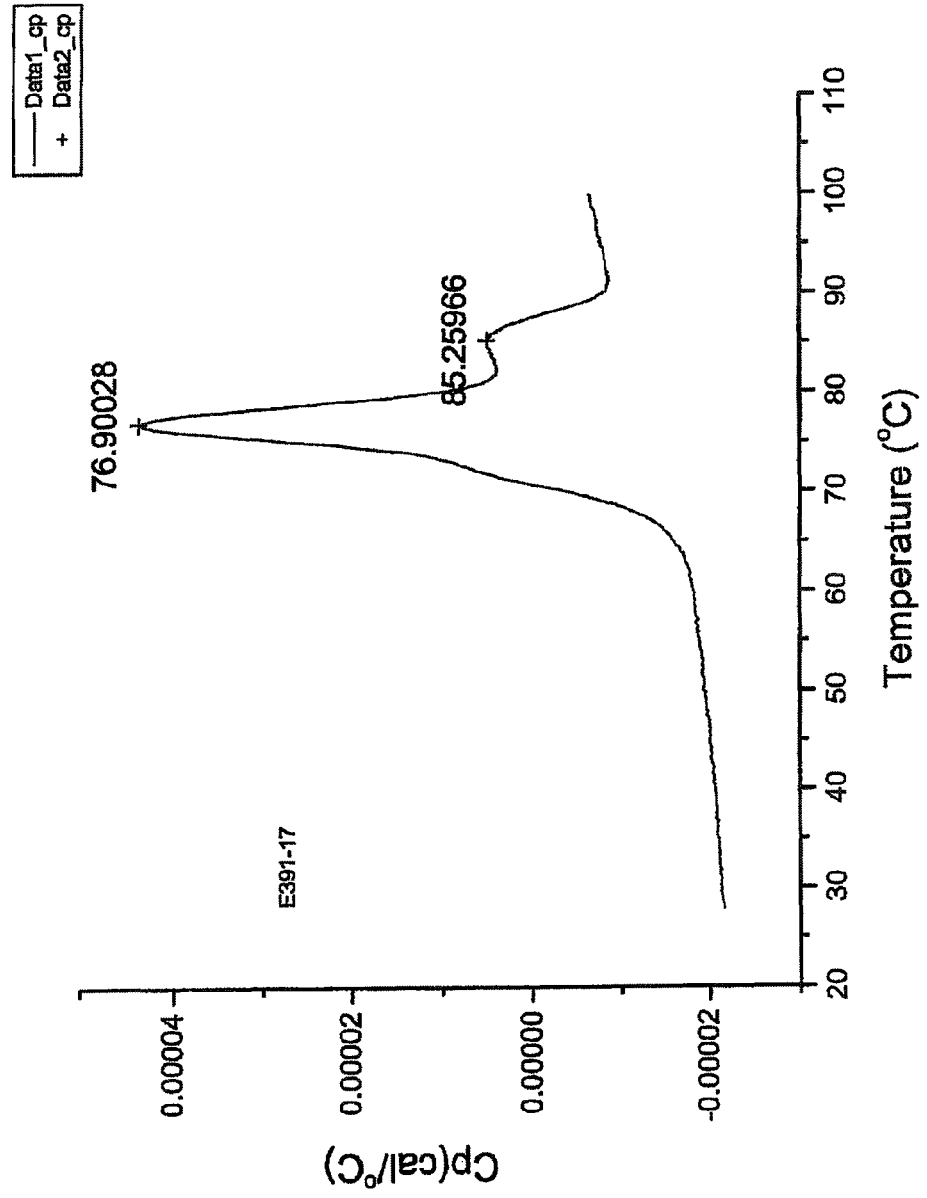
Figure 35  h#11B7-T20

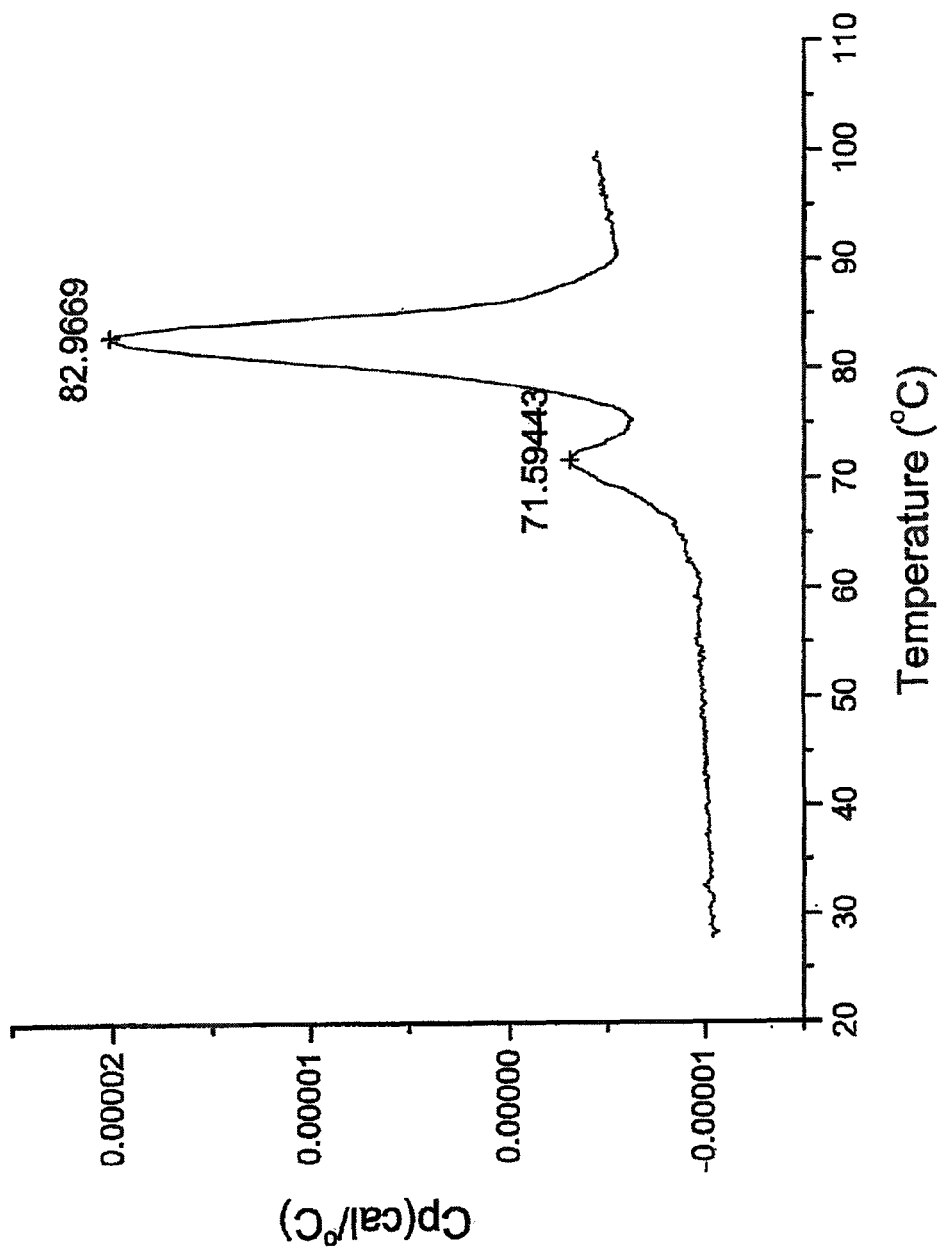
Figure 35 W    h#11B7-T23

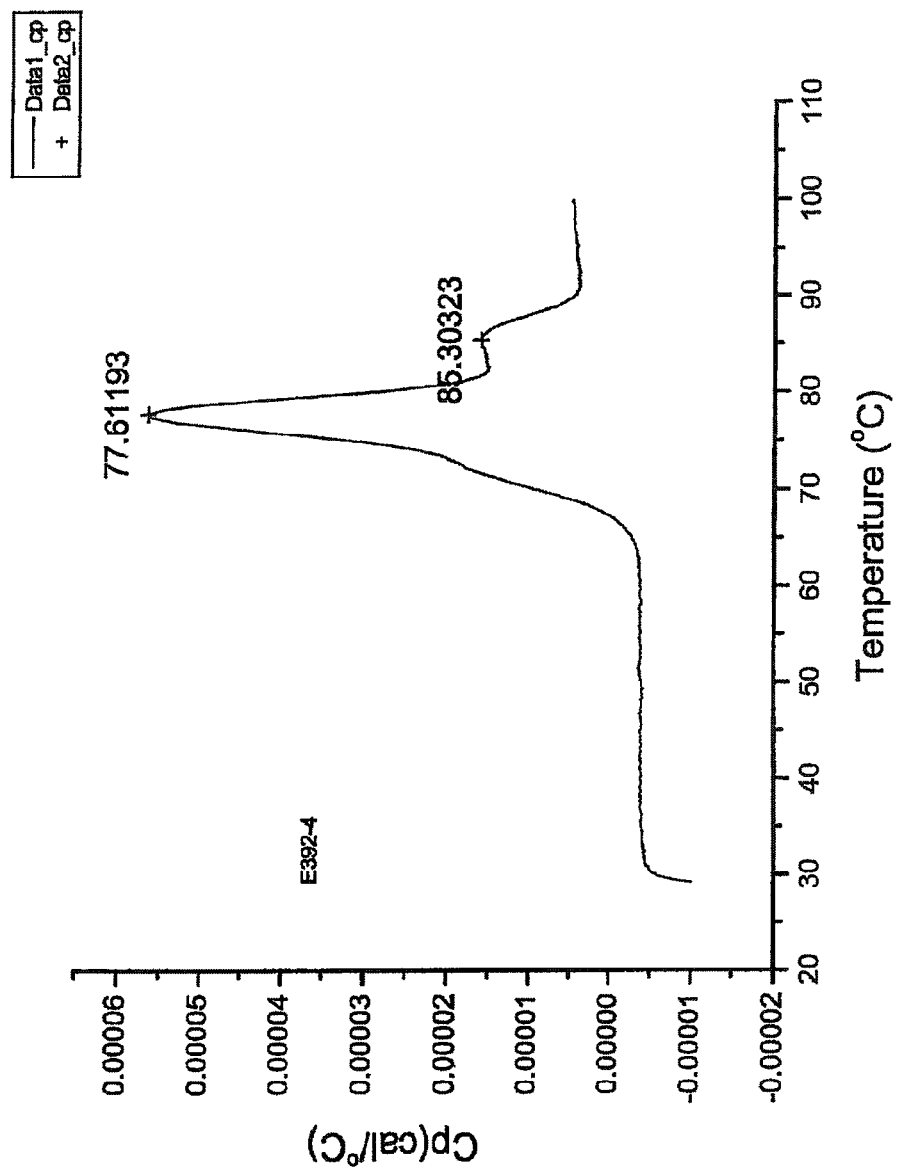
Figure 35 X    h#11B7-T24

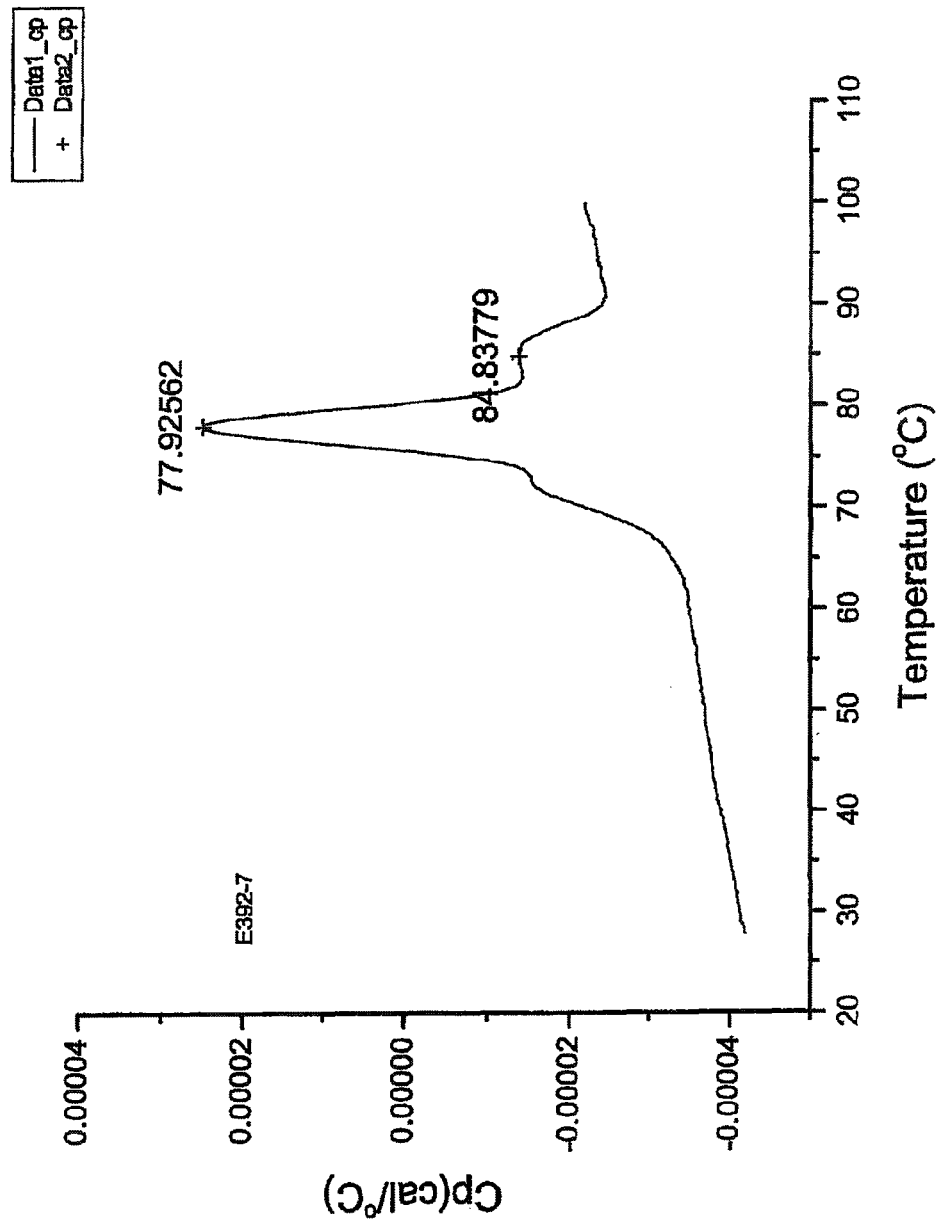
Figure 35 AA    h#11B7-T27

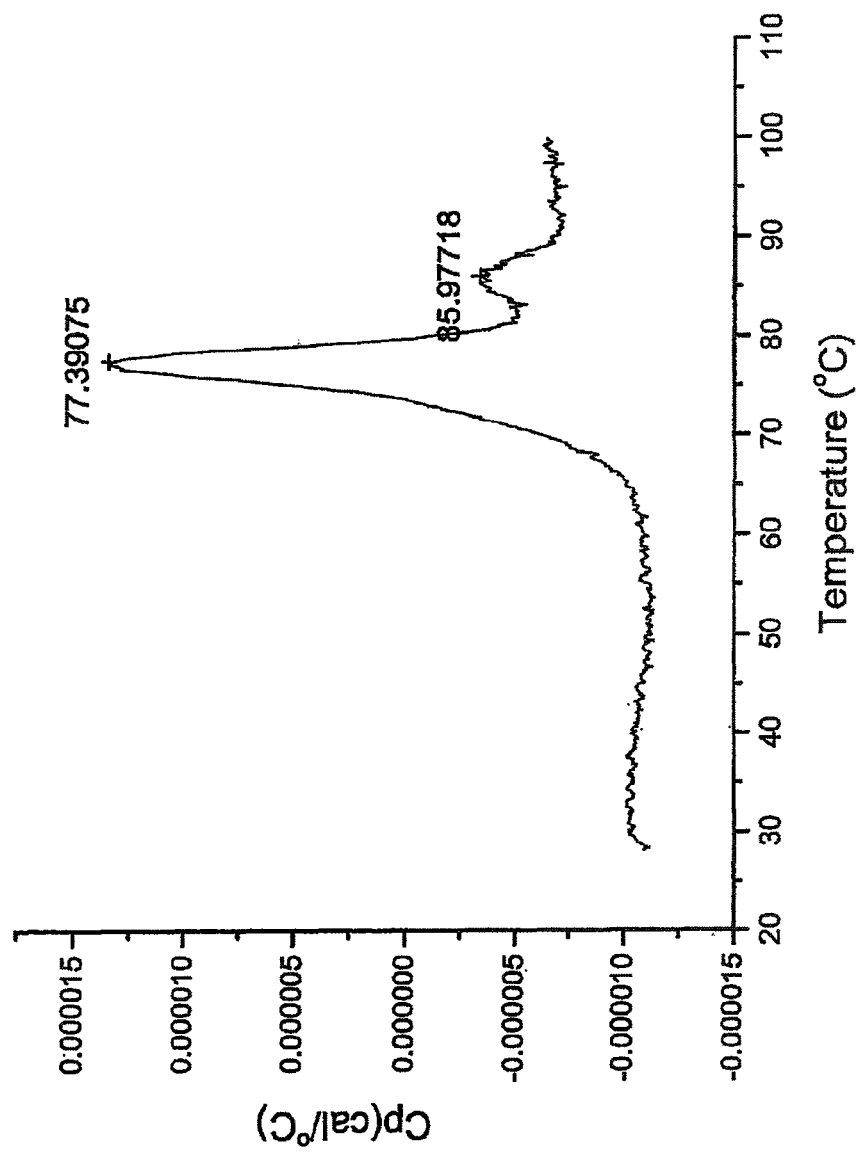
Figure 35 AB  h#11B7-T28

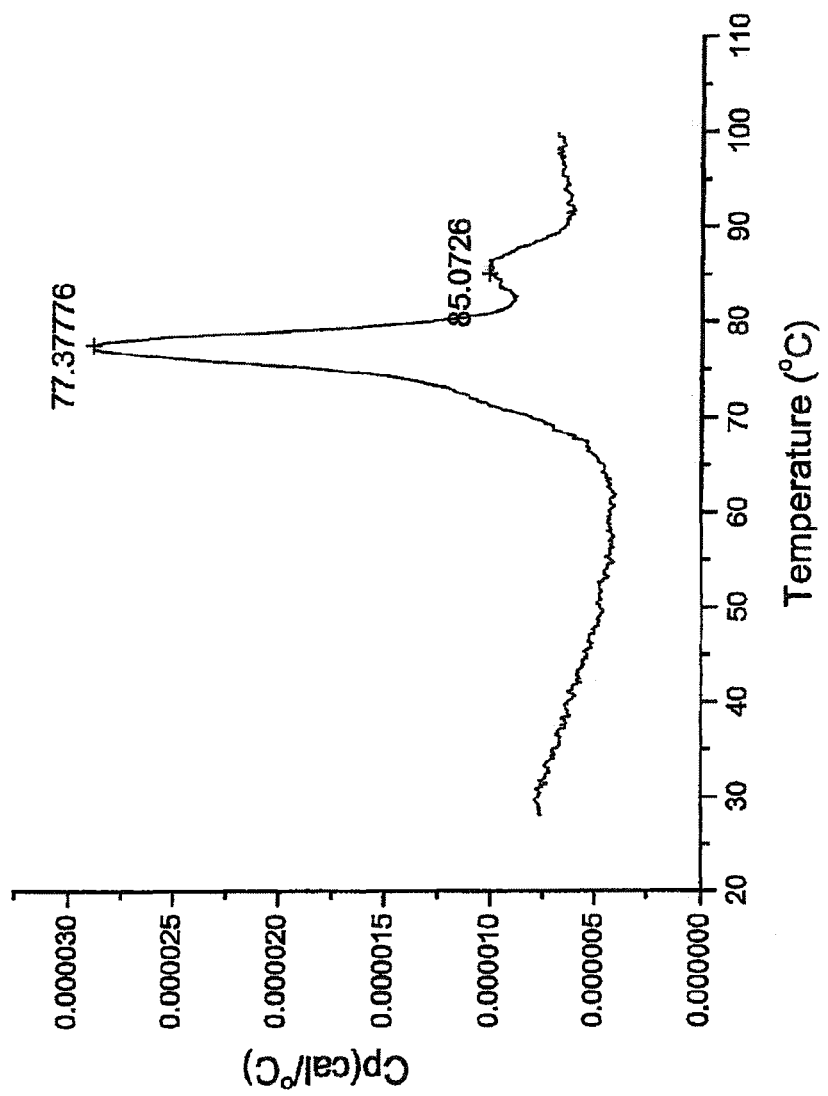
Figure 35 AC h#11B7-T29

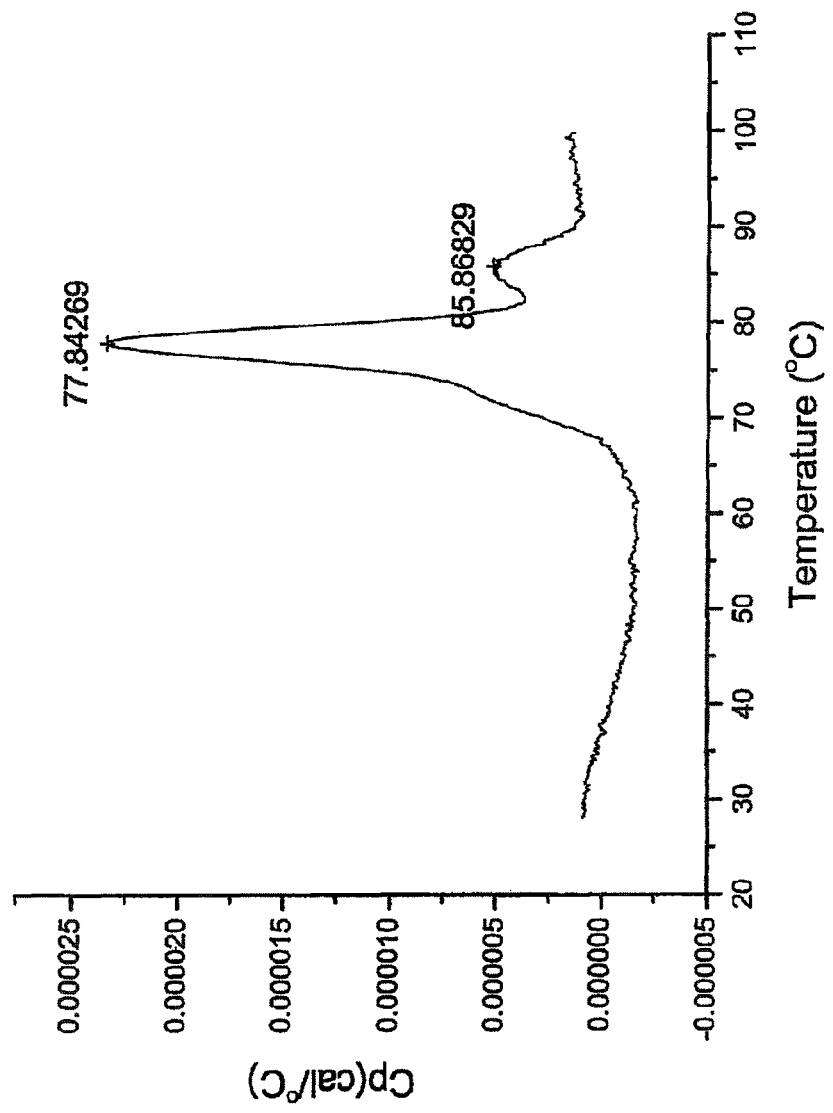
Figure 35 AD h#11B7-T30

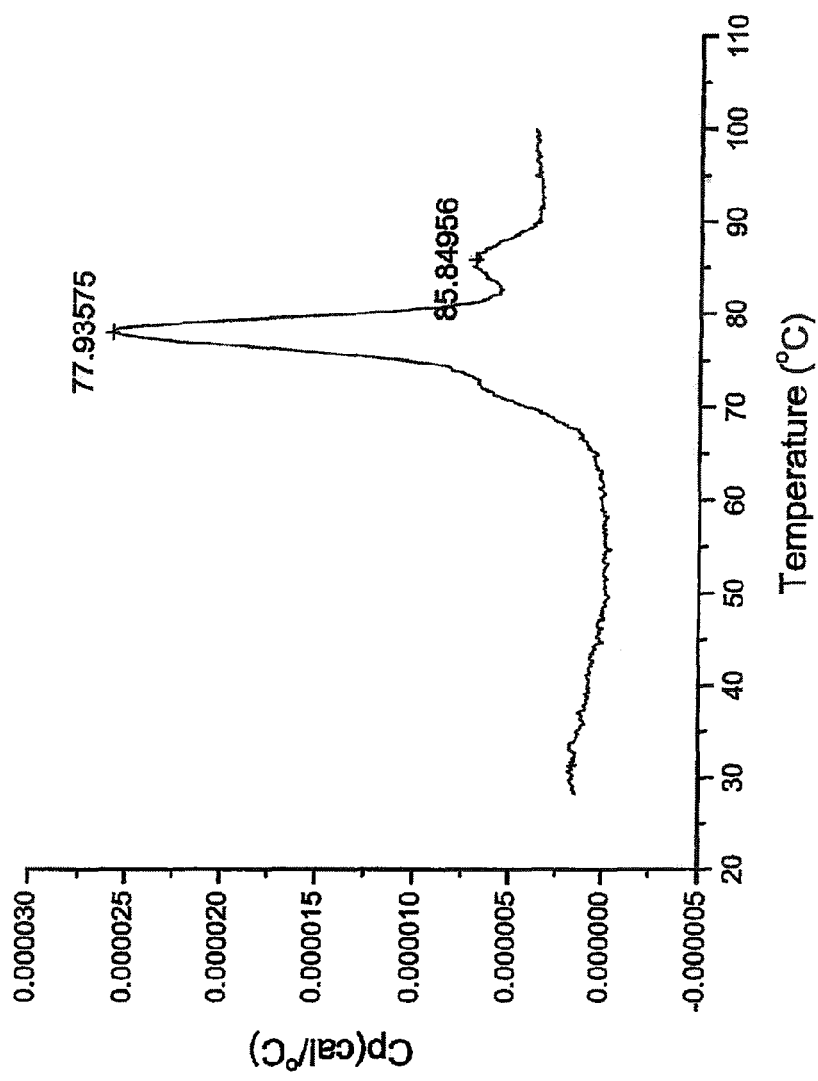
Figure 35AE  h#11B7-T31

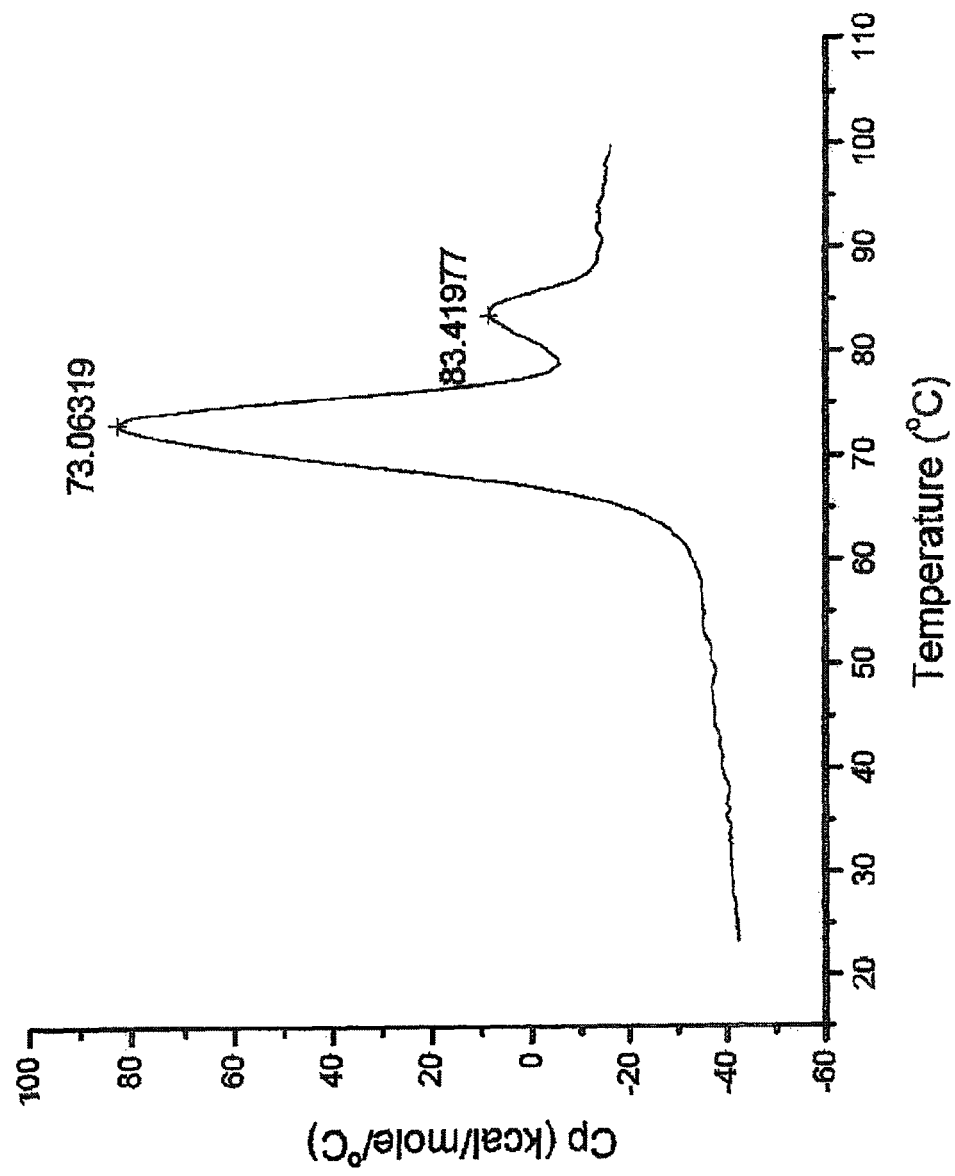
Figure 35 AF    chimeric h#11B7

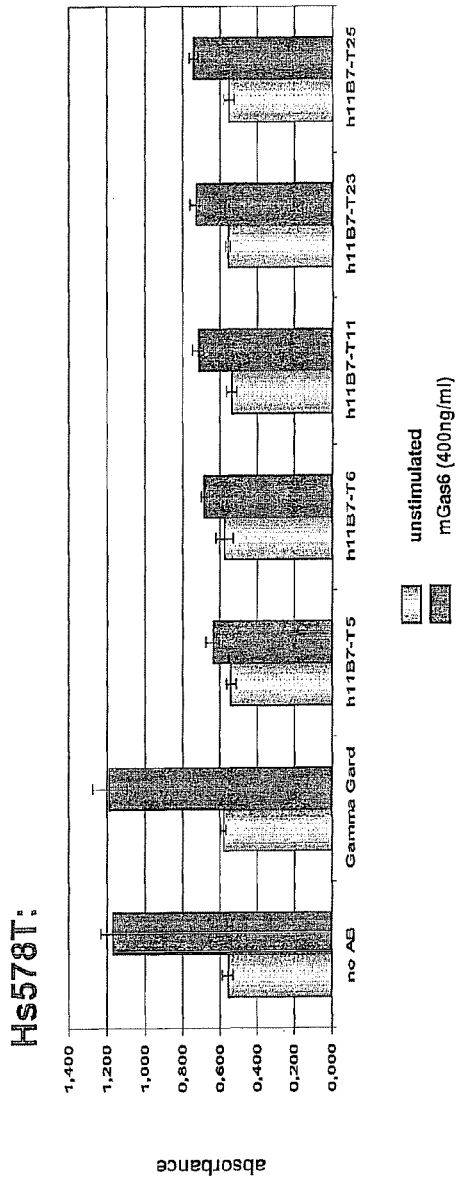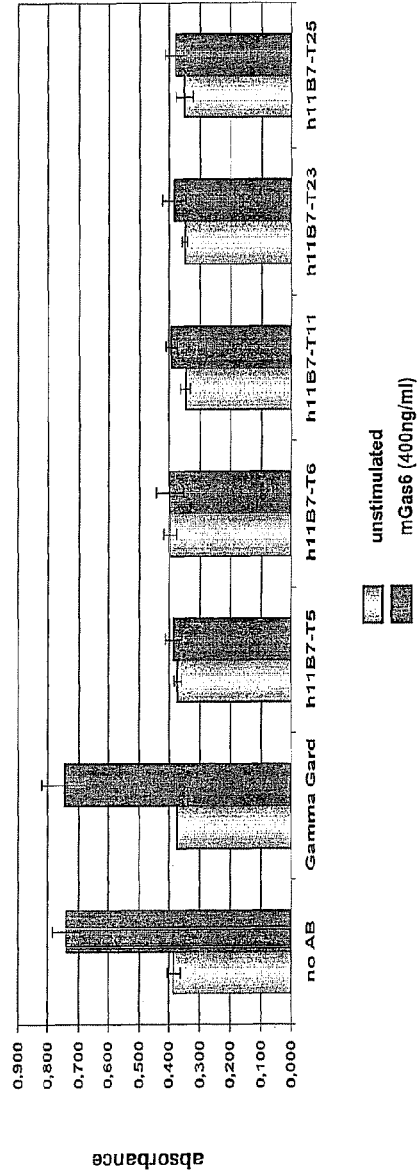
Figure 37

Figure 39 A
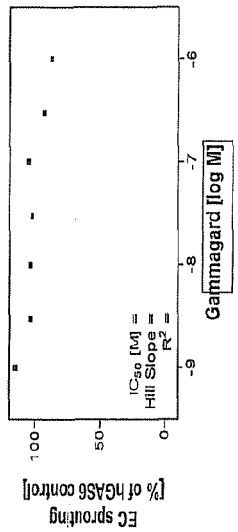
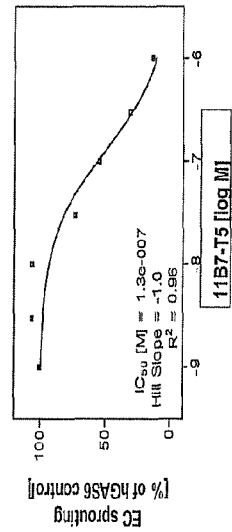
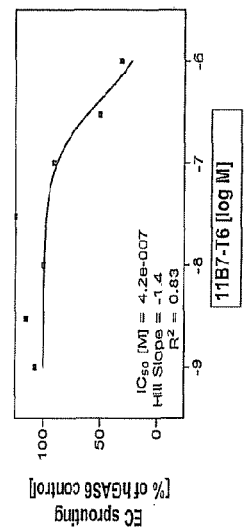
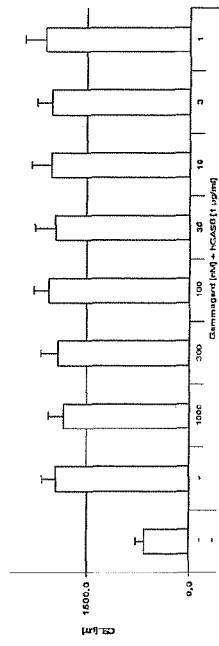
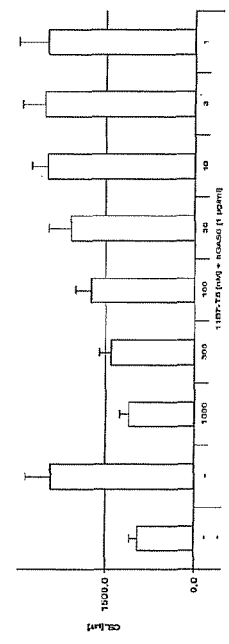
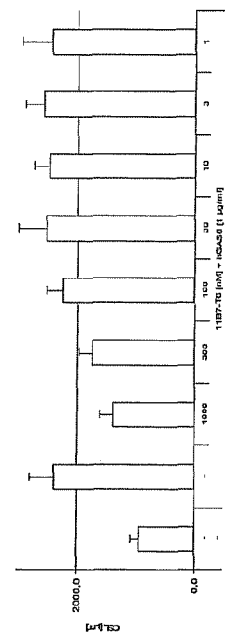

HUMANIZED AXL ANTIBODIES

CROSS REFERENCE TO RELATED APPLICATION

This application is a 35 U.S.C 371 National Phase Entry Application from PCT/EP2010/056487, filed May 11, 2010, which claims the benefit of European Patent Application Nos. 09006355.3 filed on May 11, 2009 and 09006474.2 filed on May 13, 2009, the disclosures of which are incorporated herein in their entirety by reference.

The present invention refers to monoclonal humanized antibodies, which bind to the extracellular domain of the AXL receptor tyrosine kinase and which at least partially inhibit AXL activity.

BACKGROUND

The AXL (Ark, UFO, Tyro-7) receptor tyrosine kinase is a member of the Tyro-3 family of kinases with the other members being Mer (Eyk, Nyk, Tyro-12) and Sky (Rse, Tyro-3, Dtk, Etk, Brt, Tif). It is activated by binding of the heterophilic ligand Gas6, a 70-kDa protein homologous to the anticoagulation factor protein S. In contrast to other receptor tyrosine kinases, AXL tyrosine phosphorylation can also be induced by homophilic binding. AXL activation leads to signalling through PI-3-kinase/Akt (Franke et al., Oncogene 22: 8983-8998, 2003) and other major pathways like Ras/Erk and β-catening/TCF (Goruppi et al., Mol. Cell. Biol. 21: 902-915, 2001).

AXL is weakly expressed in a range of normal tissues, including brain, heart, skeletal muscle, the organ capsules and connective tissues of several other organs, and in monocytes, but not lymphocytes. Akt phosphorylation induced by AXL has been described in survival of fibroblasts (Goruppi et al., Mol Cell Biol 17: 4442-4453 1997), endothelial cells (Hasanbasic et al., Am J Physiol Heart Circ Physiol, 2004), vascular smooth muscle cells (Melaragno et al., J. Mol. Cell. Cardiol. 37: 881-887, 2004) and neurons (Allen et al., Mol. Endocrinol. 13: 191-201 1999). Furthermore, AXL plays a role in cell-adhesion and chemotaxis. AXL knockouts display impaired platelet aggregate stabilization and thrombus formation as a result of reduced activation of the platelet integrin IIb3.

AXL overexpression has been demonstrated in various cancer types, e.g. breast (Meric et al., Clin. Cancer Res. 8: 361-367, 2002; Berclaz et al., Ann. Oncol. 12: 819-824, 2001), colon (Chen et al., Int. J. Cancer 83: 579-584, 1999; Craven et al., Int. J. Cancer 60: 791-797, 1995), prostate (Jacob et al., Cancer Detect. Prev. 23: 325-332, 1999), lung (Wimmel et al., Eur J Cancer 37: 2264-2274, 2001), gastric (Wu et al., Anticancer Res 22: 1071-1078, 2002), ovarian (Sun et al., Oncology 66: 450-457, 2004), endometrial (Sun et al., Ann. Oncol. 14: 898-906, 2003), renal (Chung et al., DNA Cell Biol. 22: 533-540, 2003), hepatocellular (Tsou et al., Genomics 50:331-340, 1998), thyroid (Ito et al., Thyroid 12:971-975, 2002; Ito et al., Thyroid 9: 563-567, 1999), and esophageal carcinoma (Nemoto et al., 1997), furthermore in CML (Janssen et al., A novel putative tyrosine kinase receptor with oncogenic potential. Oncogene, 6: 2113-2120, 1991; Braunger et al., Oncogene 14:2619-2631 1997; O'Bryan et al., Mol Cell Biol 11:5016-5031, 1991), AML (Rochlitz et al., Leukemia 13: 1352-1358, 1999), osteosarcoma (Nakano et al., J. Biol. Chem. 270:5702-5705, 2003) melanoma (van Ginkel et al., Cancer Res 64:128-134, 2004) and in head and neck squamous cell carcinoma (Green et al., Br J. Cancer. 2006 94:1446-5, 2006).

Moreover AXL has been identified as a metastasis-associated gene that is upregulated in aggressive breast cancer cell lines compared to non-invasive cells. In vitro, AXL activity was found to be required for migration and invasion, and this activity could be inhibited by antibody treatment (WO04008147). Similarly, abrogation of AXL activity in vivo, either via expression of a dominant negative version of AXL (Vajkoczy, P., et al., Proc. Natl. Acad. Science U.S.A. 103: 5799-5804. 2005) or by siRNA mediated downregulation of AXL (Holland et al., Cancer Res. 65: 9294-9303, 2005) prevented subcutaneous and orthotopic cell growth in murine xenograft experiments.

So far antibodies that bind to AXL and posses biological activity have been described. For example, one known antibody is capable of reducing AXL mediated cell invasion (WO04008147) whereas an other antibody has been reported to reduce AXL/Ligand interaction. However, all known antibodies are polyclonal or non-humanized monoclonal antibodies. Non-humanized antibodies, polyclonal or monoclonal, are rapidly removed from circulation and usually cause systemic inflammatory effects, rendering them unsuitable for therapeutic administration.

Thus in light of the therapeutic potential of AXL there is a high need for monoclonal humanized AXL antibodies, antibody fragments or derivatives thereof that effectively and specifically block AXL mediated signal transduction and which are suitable for therapeutic treatment.

Accordingly a first aspect of the present invention relates to a monoclonal humanized antibody including a fragment or derivative thereof that binds to the extracellular domain of AXL, particularly of human AXL, and at least partially inhibits AXL activity.

Preferably the humanized antibody of the present invention possesses at least one or more of the following properties: the ability to reduce or block AXL-mediated signal transduction, the ability to reduce or block AXL phosphorylation, the ability to reduce or block cell proliferation, the ability to reduce or block angiogenesis, the ability to reduce or block cell migration, the ability to reduce or block tumor metastasis, and the ability to reduce or block AXL mediated anti-apoptosis, thereby increasing for example the sensitivity of a cell against treatment with an antineoplastic agent.

According to an especially preferred embodiment of the invention the humanized antibodies described herein show the ability to reduce and/or block ligand induced phosphorylation of AXL downstream signaling molecules such as ERK1/2, AKT, GSK-3β, TSC2, mTOR and/or S6K1.

Moreover the humanized antibodies of the present invention may exhibit high specificity for AXL, particularly human AXL and do not significantly recognize other Tyro-3 family members, e.g. MER and/or SKY and/or mammalian non-primate AXL, such as murine AXL.

The term "activity" as used herein refers to the biological function of AXL, which influences the phenotype of a cell, in particular but not limited to cancer phenotypes such as evasion of apoptosis, self sufficiency in growth signals, cell proliferation, tissue invasion and/or metastasis, insensitivity to anti-growth signals (anti-apoptosis) and/or sustained angiogenesis.

The term "AXL mediated signal transduction" means the activation of second messenger pathways, such as downstream signaling, triggered by direct or indirect interaction of AXL with second messenger molecules.

The term "AXL phosphorylation" refers to the phosphorylation of amino acid residues, preferably tyrosine residues, either by a second AXL protein (transphosphorylation) or by another protein having protein kinase activity.

The term "cell proliferation" refers to all AXL-involving processes underlying the reproduction of human cells, in particular but not limited to human cancer cells. They contribute to or result in the replication of cellular DNA, separation of the duplicated DNA into two equally sized groups of chromosomes, and the physical division (called cytokinesis) of entire cells, and shall be stimulated or mediated by non-catalytic or catalytic activities of AXL, preferably including AXL phosphorylation and/or AXL-mediated signal transduction.

The term "angiogenesis" refers to all AXL-involving processes that contribute to the growth of new blood vessels from pre-existing vessels, in particular but not limited to new tumor supplying blood vessels. These processes include multiple cellular events such as proliferation, survival, migration and sprouting of vascular endothelial cells, attraction and migration of pericytes as well as basal membrane formation for vessel stabilization, vessel perfusion, or secretion of angiogenic factors by stromal or neoplastic cells, and shall be stimulated or mediated by non-catalytic or catalytic activities of AXL, preferably including AXL phosphorylation and/or AXL-mediated signal transduction.

The term "metastasis" refers to all AXL-involving processes that support cancer cells to disperse from a primary tumor, penetrate into lymphatic and/or blood vessels, circulate through the bloodstream, and grow in a distant focus (metastasis) in normal tissues elsewhere in the body. In particular, it refers to cellular events of tumor cells such as proliferation, migration, anchorage independence, evasion of apoptosis, or secretion of angiogenic factors, that underlay metastasis and are stimulated or mediated by non-catalytic or catalytic activities of AXL, preferably including AXL phosphorylation and/or AXL-mediated signal transduction.

The term "AXL mediated anti-apoptosis" refers to all AXL-involving processes that prevent human cells, preferably but not limited to human cancer cells from programmed cell death (apoptosis). In particular, it refers to processes that prevent human cells, preferably but not limited to human cancer cells from induction of apoptosis through growth factor withdrawal, hypoxia, exposure to chemotherapeutic agents or radiation, or initiation of the Fas/Apo-1 receptor-mediated signaling, and are stimulated or mediated by non-catalytic or catalytic activities of AXL, preferably including AXL phosphorylation and/or AXL-mediated signal transduction.

The terms "region" and "domain" are compatible with each other in the invention.

The antibodies designated as "11B7" and "11D5" may be also designated as "#11B7" and "#11D5", respectively, in the invention.

According to a second aspect of the invention the humanized antibodies described herein are derived from one of the chimeric (rat/human) anti-AXL antibodies 11B7 (the amino acid sequence of its light and heavy chain are represented by SEQ ID NO: 135 and 136, respectively), 11D5 (the amino acid sequence of its light and heavy chain are represented by SEQ ID NO: 137 and 138, respectively) or 10D12 or an antibody recognizing the same epitope on the extracellular domain of AXL. Particular preferred, the humanized antibodies are derived from 11B7 and 11D5. Preferably the humanized antibody contains at least one mutation in the frame work region of at least one variable domain. Such mutations may be introduced by any method known to the person skilled in the art to alter amino acid sequences. The mutation replaces preferably an amino acid in an frame work region of 11B7 or 11D5 by an amino acid which is conserved in human frame work regions. Methods for determining conserved or consensus amino acids in human frame work regions, such for example homology modelling using programs such as IgBLAST are known to the person skilled in the art. According to another preferred embodiment, the humanized antibodies of the invention are derived from anti-AXL antibodies, preferably from anti-AXL antibodies 11B7 or 11D5, wherein the frame work regions of at least one variable domain of the antibody, preferably 11B7 or 11D5, been replaced by a human or humanized frame work region.

The binding activity of an antibody of the present invention to AXL can be determined by methods known to those skilled in the art. For example, the activity can be determined using surface plasmon resonance with Biacore, and/or by ELISA (enzyme-linked immunosorbent assays), EIA (enzyme immunoassays), RIA (radioimmunoassays), or fluorescent antibody techniques, e.g. FACS.

Preferably the humanized antibodies of the invention are less immunogenic if compared with polyclonal or monoclonal non-humanized anti-AXL antibodies such as rat 11B7 or 11D5. Beside other methods known to those skilled in the art reduced immunogenicity may be determined by ELISA based HAHA or HAMA assays (IBL-America, Minnesota/LiSrarFish, Italy). Moreover, preferably the inventive antibodies are not rapidly removed from blood circulation and do not cause systemic inflammatory effects if administered to a patient.

The antibodies of the invention may have at least one antigen binding site, e.g. one or two antigen binding sites. Further, the antibody preferably comprises at least one heavy immunoglobulin chain and at least one light immunoglobulin chain. An immunoglobulin chain comprises a variable domain and optionally a constant domain. A variable domain may comprise complementary determining regions (CDRs), e.g. a CDR1, CDR2 and/or CDR3 region, and framework regions. The term "complementary determining region" (CDR) is well-defined in the art (see, for example, Harlow and Lane, "Antibodies, a Laboratory Manual", CSH Press, Cold Spring Harbour, 1988) and refers to the stretches of amino acids within the variable region of an antibody that primarily makes contact with the antigen.

According to a further embodiment the humanized antibodies of the invention are derived from the anti-AXL antibody 11B7 and may comprise a heavy chain amino acid sequence selected from the group consisting of SEQ ID NO:40 to SEQ ID NO:48, or at least the variable domain thereof, or an amino acid sequence having a sequence identity of at least 90% thereto and represents a variable region having binding activity to AxI which is equivalent to that of one having a sequence identity of 100% or a variable domain of a heavy chain amino acid sequence selected from the group consisting of SEQ ID NO:80 to SEQ ID NO:82 or an amino acid sequence having a sequence identity of at least 90% thereto and represents a variable region having binding activity to AxI which is equivalent to that of one having a sequence identity of 100% and/or a light chain amino acid sequence selected from the group consisting of SEQ ID NO: 18 to SEQ ID NO:30, or at least the variable domain thereof or an amino acid sequence having a sequence identity of at least 90% thereto and represents a variable region having binding activity to Axl which is equivalent to that of one having a sequence identity of 100%, or a variable domain of a light chain amino acid sequence selected from the group consisting of SEQ ID NO: 73 to SEQ ID NO:79 or an amino acid sequence having a sequence identity of at least 90% thereto and represents a variable region having binding activity to Axl which is equivalent to that of one having a sequence identity of 100%, or a fragment thereof recognizing the same epitope on the extracellular domain of AXL. A description of the sequences according to the invention is presented below under "Description of the Sequences" and in the Sequence Listing.

According to another further embodiment the humanized antibodies of the invention are derived from the anti-AXL antibody 11B7 and may comprise a heavy chain amino acid sequence selected from the group consisting of SEQ ID NO:150 and SEQ ID NO:151, or at least the variable domain thereof, or an amino acid sequence having a sequence identity of at least 90% thereto and represents a variable region having binding activity to Axl which is equivalent to that of one having a sequence identity of 100%, and/or a light chain amino acid sequence selected from the group consisting of SEQ ID NO: 146 and SEQ ID NO:147, or at least the variable domain thereof or an amino acid sequence having a sequence identity of at least 90% thereto and represents a variable region having binding activity to Axl which is equivalent to that of one having a sequence identity of 100%.

In particular preferred embodiment the humanized h#11B7 antibodies are selected from the group consisting of h#11B7-T1, h#11B7-T2, h#11B7-T3, h#11B7-T4, h#11B7-T5, h#11B7-T6, h#11B7-T7, h#11B7-T8, h#11B7-T9, h#11B7-T10, h#11B7-T11, h#11B7-T12, h#11B7-T13, h#11B7-T14, h#11B7-T15, h#11B7-T16, h#11B17-T17, h#11B7-T18, h#11B7-T19, h#11B7-T20, h#11B7-T21, h#11B7-T22, h#11B7-T23, h#11B7-T24, h#11B7-T25, h#11B7-T26, and h#11B7-T27 antibodies. Table 1 (Example 10) summarizes by which combinations of specific humanized heavy and light chain amino acid sequences, respectively by which combination of corresponding expression vectors, the above humanized h#11B7 antibodies are characterized in the invention.

In another particular preferred embodiment the humanized h#11B7 antibodies are selected from the group consisting of h#11B7-T28, h#11B7-T29, h#11B7-T30 and h#11B7-T31 antibodies. Table 2 (Example 22) summarizes by which combinations of specific humanized heavy and light chain amino acid sequences, respectively by which combination of corresponding expression vectors, the above humanized h#11B7 antibodies are characterized.

A humanized antibody derived from rat anti-human Axl monoclonal antibody #11B7 is not limited to the specific antibodies exemplified in the previous paragraphs, as far as said humanized antibody retains all of six CDRs and binding activity to the Axl antigen. Said humanized antibody retains CDRH1 (SNYWG; SEQ ID NO: 124), CDRH2 (YITYSGSTSYNPSLKS; SEQ ID NO: 125) and CDRH3 (TTFYY; SEQ ID NO: 126) in its heavy chain, and, CDRL4 (RASQDIGNYLR; SEQ ID NO: 121), CDRL5 (GATNLAA; SEQ ID NO: 122) and CDRL6 (LQSKESPWT; SEQ ID NO:123) in its light chain, respectively.

According to a further embodiment the humanized antibodies of the invention are derived from 11D5 and comprise a heavy chain amino acid sequence selected from the group consisting of SEQ ID NO:67 to SEQ ID NO:72, or at least the variable domain thereof or an amino acid sequence having a sequence identity of at least 90% thereto and represents a variable region having binding activity to Axl which is equivalent to that of one having a sequence identity of 100%, or a variable domain of a heavy chain amino acid sequence selected from the group consisting of SEQ ID NO:114 to SEQ ID NO:120 or an amino acid sequence having a sequence identity of at least 90% thereto and represents a variable region having binding activity to Axl which is equivalent to that of one having a sequence identity of 100% and/or a light chain amino acid sequence selected from the group consisting of SEQ ID NO:55 to SEQ ID NO:60, or at least the variable domain thereof or an amino acid sequence having a sequence identity of at least 90% thereto and represents a variable region having binding activity to Axl which is equivalent to that of one having a sequence identity of 100%, or a variable domain of a light chain amino acid sequence selected from the group consisting of SEQ ID NO:83 to SEQ ID NO:113 or an amino acid sequence having a sequence identity of at least 90% thereto and represents a variable region having binding activity to Axl which is equivalent to that of one having a sequence identity of 100%, or a fragment thereof recognizing the same epitope on the extracellular domain of AXL.

In particular preferred embodiment the humanized h#11D5 antibodies are selected from the group consisting of h#11D5-T1, h#11D5-T2, h#11D5-T3, h#11D5-T4, h#11D5-T5 or h#11D5-T6 antibodies. Examples 11, 12 and 14 show by which combinations of specific humanized heavy and light chain amino acid sequences, respectively by which combination of corresponding expression vectors, the above humanized h#11D5 antibodies are characterized.

One of the preferred embodiments of the present invention is a humanized antibody having a relatively high thermal denaturation midpoint (Tm). In this invention, a humanized antibody has a Tm of at least 70° C., preferably, a Tm of at least 75° C., more preferably, a Tm of at least 78° C., moreover preferably, a Tm of at least 80° C., further moreover preferably, 82° C. Or, in the present invention, a humanized antibody has a Tm equivalent to the Tm of its ancestor rat or chimeric antibody, but, preferably, a Tm of at least 3° C. higher, more preferably, a Tm of at least 6° C. higher, moreover preferably, a Tm of at least 8° C. higher, further moreover preferably, a Tm of at least 10° C. higher, than the Tm of its ancestor rat or chimeric antibody. Such a preferred, more preferred, moreover preferred or further moreover preferred humanized antibody is less prone to be denatured (unfolded) or inactivated, and is suitable to be prepared into solution formulations that can be stored stably for a long time.

A humanized antibody derived from rat anti-human Axl monoclonal antibody #11D5 is not limited to the specific antibodies exemplified in the previous paragraphs, as far as said humanized antibody retains all of six CDRs and binding activity to the Axl antigen. Said humanized antibody retains CDRH1 (SNYWG, SEQ ID NO: 130), CDRH2 (HITNSGNTTYNPSLKS; SEQ ID NO: 131) and CDRH3 (GAFDY; SEQ ID NO: 132) in its heavy chain, and, CDRL4 (RASQDIGNYLS; SEQ ID NO: 127), CDRL5 (GAIKLAV; SEQ ID NO: 128) and CDRL6 (LQYIQFPLT; SEQ ID NO: 129) in its light chain, respectively.

Another preferred embodiment of the invention is an antibody which (specifically) binds or recognizes one of IG domains closer to the carboxy terminus (the domain comprising amino acid residues of amino acid Nos. 129-220 in NCBI protein database ACCESSION No. P_30530: SEQ ID NO: 139; FIG. 30A). Such a preferred antibody is not limited to a humanized antibody, but can be a human antibody or a functional fragment of one of them. More preferably, such a preferred antibody inhibits at least one of the biological activities that Axl has.

A (full) antibody of the present invention can be produced, for example, by carrying out the following steps: constructing a heavy chain expression vector and light chain expression vector, wherein each of said vector has an insert comprising a variable region and constant region; introducing said vectors into a host cell; culturing said cell; recovering antibody polypeptides from the culture supernatant (the conditioned medium), as exemplified in Examples 9 to 12.

As used herein, "sequence identity" between two polypeptide sequences, indicates the percentage of amino acids that are identical between the sequences. Methods how to determine the "sequence identity" between two given polypeptide sequences are known to the person skilled in the art. Preferred polypeptide sequences of the invention have a sequence identity of at least 90%, more preferably of al least 95% and even more preferably of at least 98%. The sequence identity can be determined, for example, by BLAST, an algorithm by Karlin and Altschul (Proc. Natl. Acad. Sci. USA, 90, pp 5873 (1993)) or FASTA (Methods in Enzymol., 183, pp 63 (1990)). A program designated BLASTN or BLASTX is available (J. Mol. Biol., 215, pp 403 (1990)).

The antibody of the invention may be of the IgA-, IgD-, IgE, IgG- or IgM-type, preferably of the IgG- or IgM-type including, but not limited to, the IgG2-, IgG3-, IgM1- and IgM2-type.

Inventive antibodies may be preferably designed by homology modeling using any suitable procedure known to the person skilled in the art Moreover, humanized forms of given antibodies, such as 11B7 or 11D5, may be generated according to the methods known in the art such as chimerization or CDR grafting. Alternative methods for the production of humanized antibodies are well known in the art and are described in, e.g., EP-A1 0 239 400 and WO9007861. Generally, a humanized antibody has one or more amino acid residues introduced into it from a source which is non-human. These non-human amino acid residues are often referred to as "import" residues, which are typically taken from an "import" variable domain. Humanization can be for example performed following the method of Winter and co-workers (Jones et al., Nature, 321:522-525 (1986); Riechmann et al., Nature, 332:323-327 (1988); Verhoeyen et al., Science, 239: 1534-1536 (1988)), by substituting CDRs or CDR sequences of non human origin for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in non human antibodies.

A human antibody can be derived from a phage-display library of human antibodies (Wormstone, I. M. et. al, Investigative Ophthalmology & Visual Science. (2002) 43 (7), p. 2301-2308; Carmen, S. et. al., Briefings in Functional Genomics and Proteomics (2002), 1 (2), p. 189-203; Siriwardena, D. et. al., Opthalmology (2002) 109 (3), p. 427-431), which is well-known to the skilled person.

For example, a phage display method, which comprises having a variable region of human antibody expressing on the surface of phage as a single chain antibody, scFv, and selecting a phage which binds to an antigen, can be used (Nature Biotechnology (2005), 23, (9), p. 1105-1116).

By analyzing the gene of the selected phage, the DNA sequence encoding the variable region of a human antibody binding to the antigen can be determined.

After the DNA sequence of the scFv is determined, a human antibody can be produced by constructing an expression vector comprising said sequence and introducing said vector into a suitable host cell to express said antibody (WO92001047, WO92020791, WO93006213, WO93011236, WO93019172, WO95001438, WO95015388 and Annu. Rev. Immunol (1994) 12, p. 433-455 and Nature Biotechnology (2005) 23 (9), p. 1105-1116).

Any human antibody, regardless of a method for the production thereof, can be an embodiment of the present invention, as far as said human antibody has binding activity to human Axl antigen, and all of the following six CDRs: CDRH1 (SNYWG; SEQ ID NO: 130), CDRH2 (HITNSGNTTYNPSLKS; SEQ ID NO: 131) and CDRH3 (GAFDY; SEQ ID NO: 132) in its heavy chain, and, CDRL4 (RASQDIGNYLS; SEQ ID NO: 127), CDRL5 (GAIKLAV; SEQ ID NO: 128) and CDRL6 (LQYIQFPLT; SEQ ID NO: 129) in its light chain, respectively, alternatively, as far as said human antibody has binding activity to human Axl antigen, and all of the following six CRDs: CDRH1 (SNYWG; SEQ ID NO: 124), CDRH2 (YITYSGSTSYNPSLKS; SEQ ID NO: 125) and CDRH3 (TTFYY; SEQ ID NO: 126) in its heavy chain, and, CDRL4 (RASQDIGNYLR; SEQ ID NO: 121), CDRL5 (GATNLAA; SEQ ID NO: 122) and CDRL6 (LQSKESPWT; SEQ ID NO:123) in its light chain, respectively.

For therapeutic purposes, the antibody may be conjugated with a therapeutic effector group, e.g. a radioactive group or a cytotoxic group.

For diagnostic purposes, the antibody may be labeled. Suitable labels include radioactive labels, fluorescent labels, or enzyme labels.

As discussed above, the antibody of the invention may exist in a variety of forms besides complete antibodies; including, for example, Fv, Fab, Fab' and F(ab')$_2$, diabody, minibody, divalent or multivalent antibody comprising a fragment of more than one antibody, as well as in single chains (scFV); see e.g. WO8809344.

An antibody of the present invention can be a bi-specific antibody or mutli-specific antibody which is specific for more than one antigen or epitope.

A scFv can be obtained by fusing a variable region of an immunoglobulin heavy chain to the variable region of an immunoglobulin light chain through a polypeptide linker (Pluckthun, The Pharmacology of Monoclonal Antibodies, 113, edited by Rosenburg and Moore, Springer Verlag, New York, p. 269-315 (1994) and Nature Biotechnology (2005), 23, p. 1126-1136). A BiscFv can be obtained by fusing two different scFV through a polypeptide linker.

Methods for generating scFv are well-know to the person skilled in the art (U.S. Pat. Nos. 4,946,778, 5,260,203, 5,091, 513, 5,455,030 etc). Preferably, a linker between two variable regions does not produce a conjugate (Huston, J. S. et al., Proc. Natl. Acad. Sci. U.S.A. (1988) 85, p. 5879-5883). A scFV immunoglobulin heavy chain variable region and a scFV immunoglobulin light chain variable region can be derived from an identical antibody or two antibodies, one of which is different from the other. A polypeptide linker can be a single chain peptide consisting of, for example, 12 to 19 amino acid residues.

A DNA encoding a scFV can be generated by PCR which comprises amplifying a DNA fragment using a DNA encoding a full length or portion of an immunoglobulin heavy chain variable region or light chain variable region and two oligonucleotides corresponding to each of both terminuses as a template as a pair of primers, respectively, and then amplifying using a pair of primers which are designed so that a heavy chain variable region and light chain variable region are connected to one terminus and the other terminus of a polypeptide linker, respectively.

A functional fragment of an antibody including scFv can be produced by introducing a DNA encoding said scFv into a host cell and culturing said cell, as described elsewhere in the description.

One of the embodiments of the invention is a multimeric antibody that has higher binding affinity to an antigen than a monomeric antibody. The Unit of said multimeric antibody can be the same, or different from each other when a unit binds to an epitope of an antigen and another unit binds to a different epitope of the same antigen. Binding of IgG CH3 domain and two scFv, binding with streptoavidin and introduction of a helix-turn-helix motif can be applied for producing multimeric antibody.

If desired, the antibodies of the invention may be mutated in the variable domains of the heavy and/or light chains to alter a binding property of the antibody. For example, a mutation may be made in one or more of the CDR regions to increase or decrease the Kd of the antibody for AXL, or to alter the binding specificity of the antibody. Techniques in site directed mutagenesis are well-known in the art. See, e.g., Sambrook et al. and Ausubel et al., supra. Furthermore, mutations may be made at an amino acid residue that is known to be changed compared to germline in a variable region of an AXL antibody.

In another aspect, beside mutations with respect to humanization, further mutations may be introduced into one or more of the framework regions. A mutation may be made in a framework region or constant domain to increase the half-life of the AXL antibody. See, e.g., WO0009560. A mutation in a framework region or constant domain may also be made to alter the immunogenicity of the antibody, to provide a site for covalent or non-covalent binding to another molecule, or to alter such properties as complement fixation. Mutations may be made in each of the framework regions, the constant domain and the variable regions in a single mutated antibody. Alternatively, mutations may be made in only one of the framework regions, the variable regions or the constant domain in a single mutated antibody.

One of the embodiments of the invention is a polyclonal antibody comprising more than one antibody of the present invention.

One of the embodiments of the invention is a chemical modification of an antibody or its functional fragment of the present invention. Molecules such as polymer (polyethylene glycol or the like) can be used to generate a modified antibody or modified functional fragment.

In a further aspect, the humanized antibody according to the invention may have a constant domain with effector functions, whereby AXL expressing cells which have bound the antibody, antibody fragment or derivative thereof on the cell surface may be attacked by immune system functions. For example, the antibody may be capable of fixing complement and participating in complement-dependent cytotoxicity (CDC). Moreover, the antibody may be capable of binding to Fc receptors on effector cells, such as monocytes and natural killer (NK) cells, and participate in antibody-dependent cellular cytotoxicity (ADCC).

In yet a further aspect the antibodies described herein are applicable for therapeutic treatment, preferably for treatment of hyperproliferative diseases, cardiovascular diseases, in particular artherosclerosis and thrombosis, diabetes related diseases, in particular glomerular hypertrophy or diabetic nephropathy, and particularly of disorders associated with, accompanied by or caused by AXL expression, overexpression or hyperactivity. The hyperproliferative diseases are preferably selected from disorders associated with, accompanied by or caused by AXL expression, overexpression or hyperactivity, such as cancer, e.g. breast cancer, colon cancer, lung cancer, kidney cancer, follicular lymphoma, myeloid leukemia, skin cancer/melanoma, glioblastoma, ovarian cancer, prostate cancer, pancreatic cancer, Barrett's esophagus and esophageal cancer, stomach cancer, bladder cancer, cervical cancer, liver cancer, thyroid cancer, and head and neck cancer, or hyperplastic and neoplastic diseases or other AXL expressing or overexpressing hyperproliferative diseases.

The applicability of the antibodies of the present invention for the treatment of any Axl-related diseases such as hyperproliferative diseases can be demonstrated, indicated or suggested by in vitro, in vivo or ex vivo experiments, including those on ligand-induced autophosphorylation of Axl, effect on Axl-mediated downstream signal tranceduction such as ligand-induced Akt and p42/44 MAP-kinase phosphorylation, cancer cell migration or proliferation, ligand-induced migration or proliferation of a cell expressing Axl, angiogenesis of tissues or cells, and growth or metastasis of human cancer or cancer cell transplanted onto non-human animals such as xenograft mice, as well as any other pre-clinical/non-clinical experiments and clinical trials.

In another aspect the antibodies of the present invention can be used for the co-administration with an antineoplastic agent for the treatment of one of the above mentioned disorders.

Co-administration as used herein includes the administration of an antibody of the present invention with an antineoplastic agent, preferably an apoptosis inducing antineoplastic agent. The term co-administration further includes the administration of the antibody of the present invention and the antineoplastic agent, preferably an apoptosis inducing antineoplastic agent, in the form of a single composition or in the form of two or more distinct compositions. Co-administration includes the administration of an antibody of the present invention with an antineoplastic agent, preferably an apoptosis inducing antineoplastic agent simultaneously (i.e. at the same time) or sequentially, (i.e. at intervals).

The invention further relates to a nucleic acid molecule encoding the antibody, antibody fragment or derivative thereof of the invention. The nucleic acid molecule of the invention encoding the above-described antibody, antibody fragment or derivative thereof may be, e.g. DNA, cDNA, RNA or synthetically produced DNA or RNA or recombinantly produced chimeric nucleic acid molecule comprising any of those nucleic acid molecules either alone or in combination. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions or additions. In a particular preferred embodiment of the present invention, the nucleic acid molecule is a cDNA molecule.

According to a further aspect, the present invention relates to an isolated nucleic acid molecule selected from the group consisting of:
  (a) a nucleic acid sequence encoding a monoclonal antibody according to the present invention, antibody fragment or a derivative thereof,
  (b) a nucleic acid sequence as shown in one of the SEQ ID NOs. selected from the group consisting of SEQ ID NO:5 to SEQ ID NO:17, SEQ ID NO:31 to SEQ ID NO:39, SEQ ID NO:49 to SEQ ID NO:54 and SEQ ID NO:60 to SEQ ID NO:66

(c) a nucleic acid sequence encoding a polypeptide selected from the group consisting of SEQ ID NO:18 to SEQ ID NO:30, SEQ ID NO:40 to SEQ ID NO:48, SEQ ID NO:55 to SEQ ID NO:60, SEQ ID NO:67 to SEQ ID NO:72, SEQ ID NO:73 to SEQ ID NO:120 and SEQ ID NO:121 to 132, (d) a nucleic acid complementary to any of the sequences in (a) to (c), or (e) a nucleic acid sequence capable of hybridizing to (a), (b), (c) or (d) under stringent conditions and encoding a polypeptide, wherein an antibody or functional fragment thereof comprising said polypeptide binds to the extracellular domain of AXL, (f) a nucleic acid sequence as shown in one of the SEQ ID NOs. selected from the group consisting of SEQ ID NO:144 and SEQ ID 145 and SEQ ID NO:148 and SEQ ID NO:149, (g) a nucleic acid sequence encoding a polypeptide selected from the group consisting of SEQ ID NO: 146 and SEQ ID NO: 147 and SEQ ID NO: 150 and SEQ ID NO:151, (h) a nucleic acid complementary to any of the sequences in (f) or (g), or (i) a nucleic acid sequence capable of hybridizing to (f), (g), or (h) under stringent conditions, and encoding a polypeptide, wherein antibody or functional fragment thereof comprising said polypeptide binds to the extracellular domain of AXL.

The term "hybridizing under stringent conditions" means that two nucleic acid fragments hybridize with one another under standardized hybridization conditions as described for example in Sambrook et al., "Expression of cloned genes in *E. coli*" in Molecular Cloning: A laboratory manual (1989), Cold Spring Harbor Laboratory Press, New York, USA. Such conditions are for example hybridization in 6.0×SSC at about 45° C. followed by a washing step with 2.0×SSC at 50° C., preferably 2.0×SSC at 65° C., or 0.2×SSC at 50° C., preferably 0.2×SSC at 65° C.

The invention also relates to a vector comprising a nucleic acid molecule of the invention. Said vector may be, for example, a phage, plasmid, viral or retroviral vector. Retroviral vectors may be replication competent or replication defective. In the latter case, viral propagation generally will occur only in complementing host cells.

The nucleic acid molecules of the invention may be joined to a vector containing selectable markers for propagation in a host. Generally, a plasmid vector is introduced in a precipitate such as a calcium phosphate precipitate or rubidium chloride precipitate, or in a complex with a charged lipid or in carbon-based clusters, such as fullerens. Should the vector be a virus, it may be packaged in vitro using an appropriate packaging cell line prior to application to host cells.

Preferably, the vector of the invention is an expression vector wherein the nucleic acid molecule is operatively linked to one or more control sequences allowing the transcription and optionally expression in prokaryotic and/or eukaryotic host cells. Expression of said nucleic acid molecule comprises transcription of the nucleic acid molecule, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (Invitrogen) or pSPORTI (GIBCO BRL). Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (2001, Third Edition) N.Y. and Ausubel, Current Protocols in Molecular Biology, Green Publishing Associates and Wiley Interscience, N.Y. (1994). Alternatively, the nucleic acid molecules of the invention can be reconstituted into liposomes for delivery to target cells.

The invention further relates to a host comprising the vector of the invention. Said host may be a prokaryotic or eukaryotic cell or a non-human transgenic animal. The polynucleotide or vector of the invention which is present in the host may either be integrated into the genome of the host or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press.

The host can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*. The term "prokaryotic" is meant to include all bacteria which can be transformed or transfected with a polynucleotide for the expression of a variant polypeptide of the invention. Prokaryotic hosts may include gram negative as well as gram positive bacteria such as, for example, *E. coli*, *S. typhimurium*, *Serratia marcescens* and *Bacillus subtilis*. A polynucleotide coding for a mutant form of variant polypeptides of the invention can be used to transform or transfect the host using any of the techniques commonly known to those of ordinary skill in the art. Methods for preparing fused, operably linked genes and expressing them in bacteria or animal cells are well-known in the art (Sambrook, Molecular Cloning A Laboratory Manual, Cold Spring Harbor Laboratory (2001, Third Edition). The genetic constructs and methods described therein can be utilized for expression of variant antibodies, antibody fragments or derivatives thereof of the invention in, e.g., prokaryotic hosts. In general, expression vectors containing promoter sequences which facilitate the efficient transcription of the inserted nucleic acid molecule are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The antibodies, antibody fragments or derivatives thereof of the invention can then be isolated from the growth medium, cellular lysates, or cellular membrane fractions. The isolation and purification of the microbially or otherwise expressed antibodies, antibody fragments or derivatives thereof of the invention may be by any conventional means such as, for example, preparative chromatographic separations and immunological separations such as those involving the use of monoclonal or polyclonal antibodies.

In a preferred embodiment of the invention, the host is a bacterium, fungal, plant, amphibian or animal cell. Preferred animal cells include but are not limited to Chinese hamster ovary (CHO) cells (CHO cell, ATCC CCL-61) or a dihydrofolate reductaase-deficient strain thereof (Urlaub, G. and Chasin, L. A. Proc. Natl. Acad. Sci. U.S.A. (1980) 77, p. 4126-4220), baby hamster kidney (BHK) cells, monkey kidney cells (COS) (Gluzman, Y. Cell (1981) 23, p. 175-182 and ATCC CRL-1650), 3T3 cells or NIH3T3 cells derived from a mouse fibroblast (ATCC No. CRL-1658), NSO cells and a number of other cell lines including human cells, for example Per.C6. In another preferred embodiment, said animal cell is an insect cell. Preferred insect cells include but are not limited to cells of the SF9 cell lines.

In a more preferred embodiment of the invention, said host is a human cell or human cell line. Said human cells include, but are not limited to Human embryonic kidney cells (HEK293, 293T, 293 freestyle). Furthermore, said human cell lines include, but are not limited to HeLa cells, human hepatocellular carcinoma cells (e.g., Hep G2), A549 cells.

The invention also provides transgenic non-human animals comprising one or more nucleic acid molecules of the invention that may be used to produce antibodies of the invention. Antibodies can be produced in and recovered from tissue or body fluids, such as milk, blood or urine, of goats, cows, horses, pigs, rats, mice, rabbits, hamsters or other mammals. See, e.g., U.S. Pat. Nos. 5,827,690; 5,756,687; 5,750,172; and 5,741,957. As described above, non-human transgenic animals that comprise human immunoglobulin loci can be produced by immunizing with AXL or a portion thereof.

The invention additionally relates to a method for the preparation of an antibody, comprising culturing the host of the invention under conditions that allow synthesis of said antibody and recovering said antibody from said culture.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer-Verlag, N.Y. (1982). The antibody or its corresponding immunoglobulin chain(s) of the invention can then be isolated from the growth medium, cellular lysates, or cellular membrane fractions. The isolation and purification of the, e.g., microbially expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention.

It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

In a preferred embodiment of the present invention, the antibody is coupled to an effector, such as a radioisotope or a toxic chemotherapeutic agent. Preferably, these antibody conjugates are useful in targeting cells, e.g. cancer cells, expressing AXL, for elimination. The linking of antibodies/antibody fragments of the invention to radioisotopes e.g. provides advantages to tumor treatments. Unlike chemotherapy and other forms of cancer treatment, radioimmunotherapy or the administration of a radioisotope-antibody combination directly targets the cancer cells with minimal damage to surrounding normal, healthy tissue. Preferred radioisotopes include e.g. $^{3}H$, $^{14}C$, $^{15}N$, $^{35}S$, $^{90}Y$, $^{99}Tc$, $^{111}In$, $^{125}I$, $^{131}I$.

Furthermore, the antibodies of the invention can be used to treat cancer when being conjugated with toxic chemotherapeutic drugs such as geldanamycin (Mandler et al., J. Natl. Cancer Inst., 92(19), 1549-51 (2000>> and maytansin, for example, the maytansinoid drug, DM1 (Liu et al., Proc. Natl. Acad. Sci. U.S.A. 93:8618-8623 (1996) and auristatin-E or monomethylauristatin-E (Doronina et al., Nat. Biotechnol. 21:778-784 (2003) or calicheamicit). Different linkers that release the drugs under acidic or reducing conditions or upon exposure to specific proteases are employed with this technology. The antibodies of the invention may be conjugated as described in the art.

One of the embodiments of the invention is a chemical modification of an antibody or its functional fragment of the present invention. Molecules such as polymer (polyethylene glycol or the like) can be used to generate a modified antibody or modified functional fragment.

The invention further relates to a pharmaceutical composition comprising the antibody, the nucleic acid molecule, the vector, the host of the invention or an antibody obtained by the method of the invention.

The term "composition" as employed herein comprises at least one compound of the invention. Preferably, such a composition is a pharmaceutical or a diagnostic composition.

It is preferred that said pharmaceutical composition comprises a pharmaceutically acceptable carrier and/or diluent. The herein disclosed pharmaceutical composition may be partially useful for the treatment of disorders associated with, accompanied by or caused by AXL expression, overexpression or hyperactivity, e.g. hyperproliferative diseases, cardiovascular diseases, in particular artherosclerosis and thrombosis, diabetes related diseases, in particular glomerular hypertrophy or diabetic nephropathy. Said disorders comprise, but are not limited to cancer, e.g. breast cancer, colon cancer, lung cancer, kidney cancer, follicular lymphoma, myeloid leukemia, skin cancer/melanoma, glioblastoma, ovarian cancer, prostate cancer, pancreatic cancer, Barrett's esophagus and esophageal cancer, stomach cancer, bladder cancer, cervical cancer, liver cancer, thyroid cancer, and head and neck cancer, or other hyperplastic or neoplastic diseases or other AXL expressing or overexpressing diseases.

The term "hyperactivity" herein refers to uncontrolled AXL signaling which may be caused by a lack and/or dysfunction of negative regulation. By way of example negative regulation comprises protein dephosphorylation, degradation and/or endocytosis. Moreover uncontrolled AXL signaling may be the result of genetic alterations, either somatic or germline, which result in changes of the AXL amino acid sequence.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The compositions of the invention may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 μg and 100 mg/kg body weight per dose; however, doses below or above this exemplary range are envisioned, especially considering the aforementioned factors. If the regimen is a continuous infusion, it should also be in the range of 1 pg to 100 mg per kilogram of body weight per minute.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition.

It is particularly preferred that the pharmaceutical composition comprises at least one further active agent like, e.g. an additional antineoplastic agent, small molecule inhibitor, anti-tumor agent, chemotherapeutic agent or a combination of those agents.

The invention also relates to a pharmaceutical composition comprising an humanized anti-AXL-antibody of the invention in combination with at least one further antineoplastic agent. Said combination is effective, for example, in inhibiting abnormal cell growth.

Many antineoplastic agents are presently known in the art. In general the term includes all agents that are capable of prevention, alleviation and/or treatment of hyperproliferative disorders. In one embodiment, the antineoplastic agent is selected from the group of therapeutic proteins including but not limited to antibodies or immunomodulatory proteins. In another embodiment the antineoplastic agent is selected from the group of small molecule inhibitors or chemotherapeutic agents consisting of mitotic inhibitors, kinase inhibitors, alkylating agents, anti-metabolites, intercalating antibiotics, growth factor inhibitors, cell cycle inhibitors, enzymes, topoisomerase inhibitors, histone deacetylase inhibitors, anti-survival agents, biological response modifiers, anti-hormones, e.g. anti-androgens, and antiangiogenesis agents.

Specific examples of antineoplastic agents which can be used in combination with the antibodies provided herein include, for example, gefitinib, lapatinib, sunitinib, pemetrexed, bevacisumab, cetuximab, imatinib, trastuzumab, alemtuzumab, rituximab, erlotinib, bortezomib and the like. Other specific antineoplastic agents to be used in the compositions as described and claimed herein include for example, chemotherapeutic agents such as capecitabine, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. In particular preferred are such antineoplastic agents that induce apoptosis.

The invention relates also to a polyclonal antibody comprising more than one antibody of the present invention.

When used with the described AXL antibodies, such antineoplastic agents may be used individually (e.g., 5-FU and an antibody), sequentially (e.g., 5-EU and an antibody for a period of time followed by MTX and an antibody), or in combination with one or more other such antineoplastic agents (e.g., 5-FU, MTX and an antibody, or 5-FU, radiotherapy and an antibody).

The term "antineoplastic agent" may also include therapeutic procedures, as for example irradiation or radiotherapy.

The pharmaceutical composition of the invention are preferably used in human medicine but may be used also for veterinary purposes.

Additionally, the invention relates to the use of the antibody of the invention, the nucleic acid molecule, the vector, the host of the invention or an antibody obtained by the method of the invention for the preparation of a pharmaceutical composition for diagnosis, prevention or treatment of hyperproliferative diseases, cardiovascular diseases, in particular artherosclerosis and thrombosis; diabetes related diseases, in particular glomerular hypertrophy or diabetic nephropathy, and particularly of disorders associated with, accompanied by or caused by AXL expression, overexpression or hyperactivity.

A hyperproliferative disease as mentioned above includes any neoplasia, i.e. any abnormal and/or uncontrolled new growth of tissue. The term "uncontrolled new growth of tissue" as used herein may depend upon a dysfunction and/or loss of growth regulation. A hyperproliferative disease includes tumor diseases and/or cancer, such as metastatic or invasive cancers.

In a preferred embodiment of the use of the invention, said hyperproliferative disease is in particular breast cancer, colon cancer, lung cancer, kidney cancer, follicular lymphoma, myeloid leukemia, skin cancer/melanoma, glioblastoma, ovarian cancer, prostate cancer, pancreatic cancer, Barrett's esophagus and esophageal cancer, stomach cancer, bladder cancer, cervical cancer, liver cancer, thyroid cancer, and head and neck cancer, or hyperplastic or neoplastic diseases or other AXL expressing or overexpressing hyperproliferative diseases.

In yet another embodiment the present invention refers to the use of an humanized anti-AXL-antibody of the present invention for the manufacture of a medicament for the co-administration with an antineoplastic agent for the treatment of one of the above mentioned disorders.

According to a further preferred embodiment the present invention is directed to the use of an humanized anti-AXL antibody of the invention for the manufacture of a pharmaceutical composition for the treatment of drug resistant cancer.

Further the present invention relates to a diagnostic composition comprising the antibody of the invention, the nucleic acid molecule, the vector, the host of the invention or an antibody obtained by the method of the invention and optionally a pharmaceutically acceptable carrier.

The diagnostic composition of the invention is useful in the detection of an undesired expression, overexpression or hyperactivity of the mammalian AXL in different cells, tissues or another suitable sample, comprising contacting a sample with an antibody of the invention, and detecting the presence of AXL in the sample. Accordingly, the diagnostic composition of the invention may be used for assessing the onset or the disease status of a hyperproliferative disease.

Furthermore, malignant cells, such as cancer cells expressing AXL, can be targeted with the antibody of the invention. The cells which have bound the antibody of the invention might thus be attacked by immune system functions such as the complement system or by cell-mediated cytotoxicity, thereby reducing the number of or eradicating cancer cells. These considerations equally apply to the treatment of metastases and re-current tumors.

In another aspect of the present invention, the antibody of the invention is coupled to a labelling group. As already outlined above, such antibodies are particularly suitable for diagnostic applications. As used herein, the term "labelling group" refers to a detectable marker, e.g. a radiolabelled amino acid or biotinyl moieties that can be detected by marked avidin. Various methods for labelling polypeptides and glycoproteins, such as antibodies, are known in the art and may be used in performing the present invention. Examples of suitable labelling groups include, but are not limited to, the following: radioisotopes or radionuclides (e.g. $^3$H, $^{14}$C, $^{15}$N, $^{35}$S, $^{90}$Y, $^{99}$Tc, $^{111}$In, $^{125}$I, $^{131}$I), fluorescent groups (e.g. FITC, rhodamine, lanthanide phosphors), enzymatic groups (e.g. horseradish peroxidase, β-galactosidase, luciferase, alkaline phosphatase), chemiluminescent groups, biotinyl groups, or predetermined polypeptide epitopes recognized by a secondary reporter (e.g. leucine zipper pair sequences, binding sites for secondary antibodies, metal binding domains, epitope tags).

In certain aspects, it may be desirable, that the labelling groups are attached by spacer arms of various lengths to reduce potential steric hindrance.

In another embodiment the present invention relates to a method of assessing for the presence of AXL expressing cells comprising contacting the antibody of the invention with cells or a tissue suspected of carrying AXL on their/its surface. Suitable methods for detection of AXL expression in a sample may be an Enzyme-Linked Immunosorbent Assay (ELISA) or Immunohistochemistry (IHC).

An ELISA assay may be carried out in a microtiter plate format, wherein e.g. wells of a microtiter plate, are adsorbed with an AXL antibody. The wells are rinsed and treated with a blocking agent such as milk protein or albumin to prevent nonspecific adsorption of the analyte. Subsequently the wells are treated with a test sample. After rinsing away the test sample or standard, the wells are treated with a second AXL antibody that is labelled, e.g. by conjugation with biotin. After washing away excess secondary antibody, the label is detected, e.g. with avidin-conjugated horseradish peroxidase (HRP) and a suitable chromogenic substrate. The concentration of the AXL antigen in the test samples is determined by comparison with a standard curve developed from standard samples.

For IHC, paraffin-embedded tissues may be used, wherein the tissues are, e.g. first deparaffinized in xylene and then dehydrated, e.g. with ethanol and rinsed in distilled water. Antigenic epitopes masked by formalin-fixation and paraffin-embedding may be exposed by epitope unmasking, enzymatic digestion or saponin. For epitope unmasking paraffin sections may be heated in a steamer, water bath or microwave oven for 20-40 min in an epitope retrieval solution as for example 2N HCl solution (pH 1.0). In the case of an enzyme digestion, tissue sections may be incubated at 37° C. for 10-30 minutes in different enzyme solutions such as proteinase K, trypsin, pronase, pepsin etc. After rinsing away the epitope retrieval solution or excess enzyme, tissue sections are treated with a blocking buffer to prevent unspecific interactions. The primary AXL antibody is added at appropriate concentrations. Excess primary antibody is rinsed away and sections are incubated in peroxidase blocking solution for 10 min at room temperature. After another washing step, tissue sections are incubated with a secondary labeled antibody, e.g. labeled with a group that might serve as an anchor for an enzyme. Examples therefore are biotin labeled secondary antibodies that are recognized by streptavidin coupled horseradish peroxidase. Detection of the antibody/enzyme complex is achieved by incubating with a suitable chromogenic substrate.

In an additional embodiment the present invention relates to a method of blocking AXL function comprising contacting the antibody of the invention with cells, or a tissue suspected of carrying AXL on their/its surface under conditions, wherein the antibody is capable of blocking AXL function. The contacting may be in vitro or in vivo.

The invention also relates to a method of treating a hyperproliferative disease, cardiovascular diseases, in particular artherosclerosis and thrombosis, diabetes related diseases, in particular glomerular hypertrophy or diabetic nephropathy, comprising, administering to a patient in need thereof a suitable dose of the antibody or antibody fragment or derivative thereof of the present invention. The hyperproliferative disease is preferably selected from disorders associated with, accompanied by or caused by AXL expression, overexpression or hyperactivity, such as cancer, e.g. breast cancer, colon cancer, lung cancer, kidney cancer, follicular lymphoma, myeloid leukemia, skin cancer/melanoma, glioblastoma, ovarian cancer, prostate cancer, pancreatic cancer, Barrett's esophagus and esophageal cancer, stomach cancer, bladder cancer, cervical cancer, liver cancer, thyroid cancer, and head and neck cancer, or hyperplastic and neoplastic diseases or other AXL expressing or overexpressing hyperproliferative diseases.

According to another preferred embodiment of the invention the cancer to be treated is a drug resistant cancer, preferably selected from the group of cancers cited above.

The invention further relates to a method of treating a disease wherein the antibody of the invention is administered to a mammal and wherein said disease is correlated directly or indirectly with the abnormal level of expression or activity of AXL.

Finally, the invention relates to a kit comprising an anti-AXL-antibody, preferably the antibody, antibody fragment or derivative thereof of the invention, the nucleic acid molecule encoding said components and/or the vector of the invention.

All embodiments covering the compounds disclosed herein can be used as single compounds or in combination for the preparation of a medicament.

BRIEF DESCRIPTION OF THE FIGURES

FIG. 1: This figure describes the amino acid sequence of the humanized variable regions of the light chain of the rat anti-human AXL monoclonal antibody #11B7, designated as h#11B7-T1L to h#11B7-T7L.

FIG. 2: This figure describes the amino acid sequence of the humanized variable regions of the light chain of the rat anti-human AXL monoclonal antibody #11B7, designated as h#11B7-T8L to h#11B7-T14L.

FIG. 3: This figure describes the amino acid sequence of the humanized variable regions of the light chain of the rat anti-human AXL monoclonal antibody #11B7, designated as h#11B7-T15L to h#11B7-T20L.

FIG. 4: This figure describes the amino acid sequence of the humanized variable regions of the heavy chain of the rat anti-human AXL monoclonal antibody #11B7, designated as h#11B7-T1H to h#11B7-T6H.

FIG. 5: This figure describes the amino acid sequence of the humanized variable regions of the heavy chain of the rat anti-human AXL monoclonal antibody #11B7, designated as h#11B7-T7H to h#11B7-T12H.

FIG. 6: This figure describes the amino acid sequence of the humanized variable regions of the light chain of the rat anti-human AXL monoclonal antibody #11D5, designated as h#11D5-T1L to h#11D5-T7L.

FIG. 7: This figure describes the amino acid sequence of the humanized variable regions of the light chain of the rat anti-human AXL monoclonal antibody #11D5, designated as h#11D5-T8L to h#11D5-T14L.

FIG. 8: This figure describes the amino acid sequence of the humanized variable regions of the light chain of the rat anti-human AXL monoclonal antibody #11D5, designated as h#11D5-T15L to h#11D5-T21L.

FIG. 9: This figure describes the amino acid sequence of the humanized variable regions of the light chain of the rat anti-human AXL monoclonal antibody #11D5, designated as h#11D5-T22L to h#11D5-T28L.

FIG. 10: This figure describes the amino acid sequence of the humanized variable regions of the light chain of the rat anti-human AXL monoclonal antibody #11D5, designated as h#11D5-T29L to h#11D5-T35L.

FIG. 11: This figure describes the amino acid sequence of the humanized variable regions of the light chain of the rat anti-human AXL monoclonal antibody #11D5, designated as h#11D5-T36L and h#11D5-T37L.

FIG. 12: This figure describes the amino acid sequence of the humanized variable regions of the heavy chain of the rat anti-human AXL monoclonal antibody #11D5, designated as h#11D5-T1H to h#11D5-T7H.

FIG. 13: This figure describes the amino acid sequence of the humanized variable regions of the heavy chain of the rat anti-human AXL monoclonal antibody #11D5, designated as h#11D5-T8H to h#11D5-T13H.

FIGS. 14A-D: These figures describe nucleotide sequences of Primers EFF1 and EfsmR, Fragment B comprising the secretion signal and constant region of human kappa chain and poly (A) addition signal, a DNA fragment encoding a polypeptide which comprises a human IgG1 signal and constant domain, and Leader sequence, and, amino acid sequence of CDRs of the rat anti-human Axl monoclonal antibodies 11B7 and 11D5, chimeric #11B7 antibody heavy and light chain (IgG1/kappa), chimeric #11D5 antibody heavy and light chain (IgG1/Kappa) and Leader sequence FIG. 15. A Flow cytometry analysis of cell surface AXL in RatI-Mock and RatI-AXL cI.2 fibroblasts. Polyclonal RatI-Mock and clonal RatI-AXL cI.2 cells, generated by infection of RatI fibroblasts with pLXSN and pLXSN-hAXL ecotrophic virus, respectively, were collected and stained with mouse control antibody 72A1 (left panel) or mouse anti-AXL MAB154 primary antibody (right panel) at 3 μg/ml and PE-conjugated anti-mouse secondary antibody. See text for details. Staining of RatI-AXL cI.2 cells results in a shift by three orders of magnitude and demonstrates AXL overexpression on the surface of these cells.

B. Flow cytometry analysis of cell surface AXL in NIH3T3-Mock and NIH3T3-AXL cI.7 fibroblasts. Polyclonal NIH3T3-Mock and clonal NIH3T3-AXL cI.7 cells, generated by infection of NIH3T3 fibroblasts with pLXSN and pLXSN-AXL ecotrophic virus, respectively, were collected and stained with mouse control antibody 72A1 (left panel) or mouse anti-AXL MAB154 primary antibody (right panel) at 3 μg/ml and PE-conjugated anti-mouse secondary antibody. See text for details. Staining of NIH3T3-AXL cI.7 cells results in a shift by two orders of magnitude and demonstrates AXL overexpression on the surface of these cells.

Figure 16:
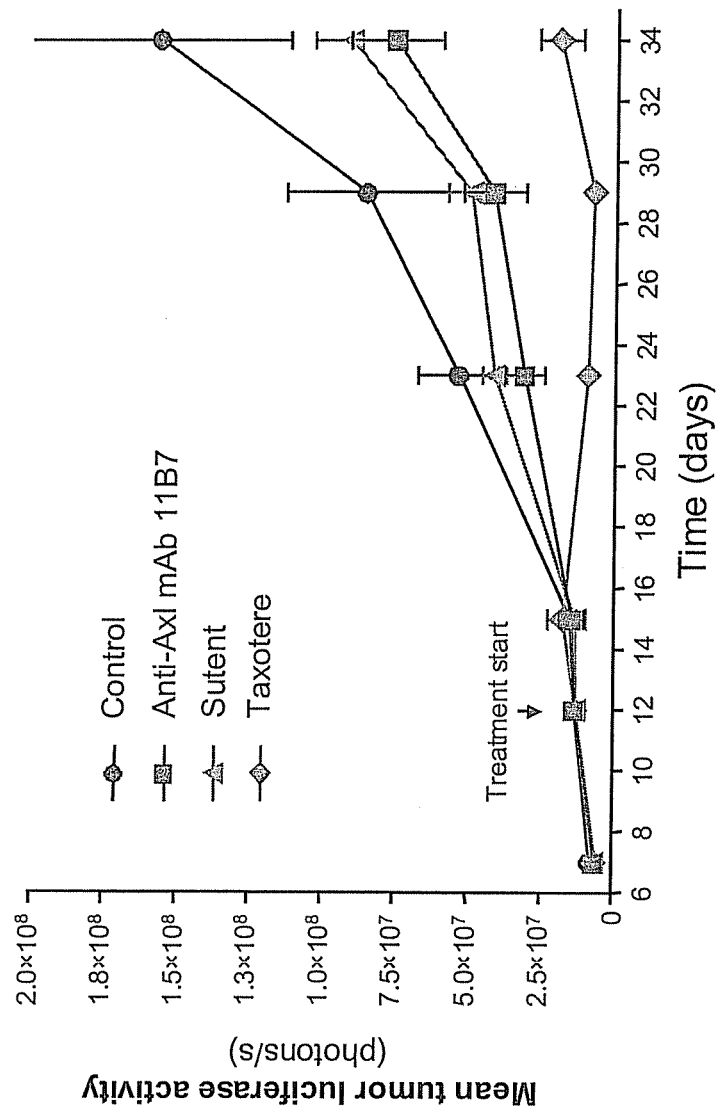

FIG. 16. Orthotopic xenograft model to investigate the effects of rat anti-AXL antibodies on human prostate carcinoma growth in nude mice. PC-3-LN prostate carcinoma cells were orthotopically implanted into the prostate of NMRI-nu/nu mice. Animals were randomized into 4 groups and received 25 mg/kg of the isotypic control antibody 1D5 or the antagonistic rat anti-AXL antibody 11B7, as well as 40 mg/kg Sutent or 12.5 mg/kg Taxotere. During the treatment period, the growth of orthotopically growing PC-3-LN tumors as well as peripheral metastases was monitored once weekly via in vivo bioluminescence imaging on day 15, day 23, day 29, and day 34. See text for details. Compared to the isotypic control antibody 1D5, the antagonistic rat anti-AXL antibody 11B7 reduced the overall growth of PC-3-LN prostate tumors in nude mice.

Figure 17:
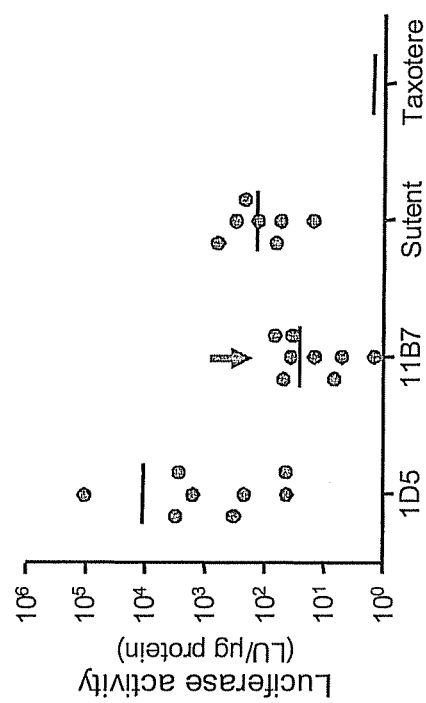

FIG. 17. Orthotopic xenograft model to investigate the effects of rat anti-AXL antibodies on human prostate carcinoma metastasis in nude mice. PC-3-LN prostate carcinoma cells were orthotopically implanted into the prostate of NMRI-nu/nu mice. Animals were randomized into 4 groups and received 25 mg/kg of the isotypic control antibody 1D5 or the antagonistic rat anti-AXL antibody 11B7, as well as 40 mg/kg Sutent or 12.5 mg/kg Taxotere. Post necropsy, selected organs (liver, spleen, lung, femur, and a part of the lumbar spine) were collected and analyzed for the presence of metastases via bioluminescence imaging. See text for details. Compared to the isotypic control antibody 1D5, the antagonistic rat anti-AXL antibody 11B7 of the invention reduced the occurrence of spleen metastases. Noteworthy, the antimetastatic effect of 11B7 in this experiment was stronger than that of Sutent.

Figure 18:
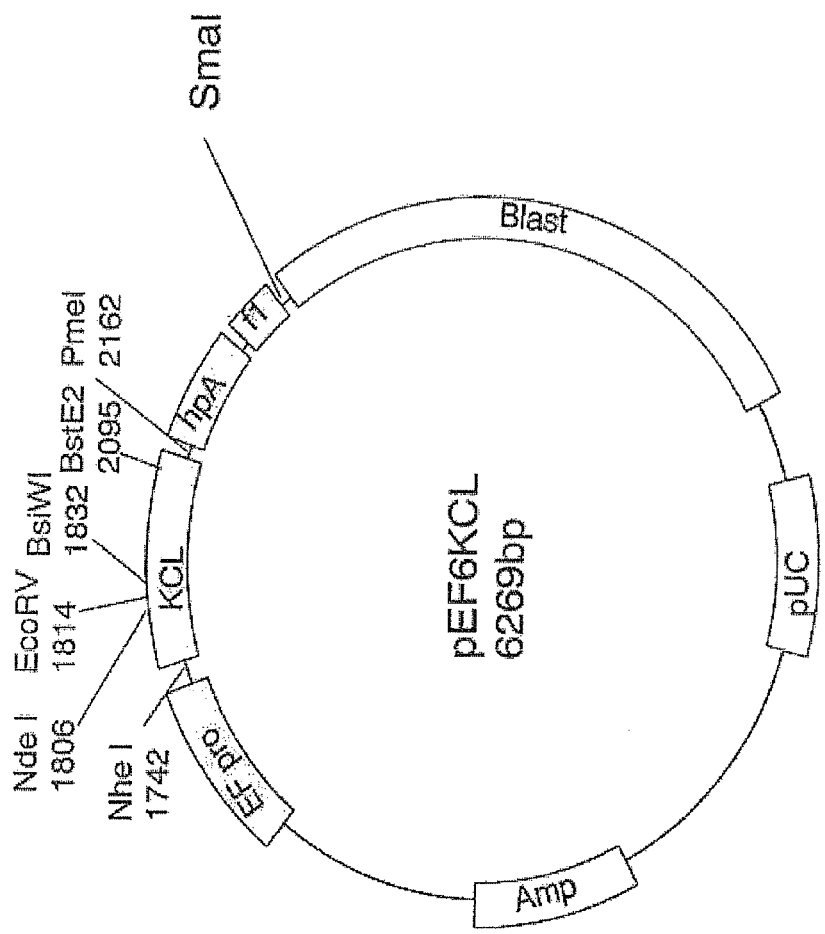

FIG. 18: This figure describes the construct of the vector pEF6KCL.

Figure 19:
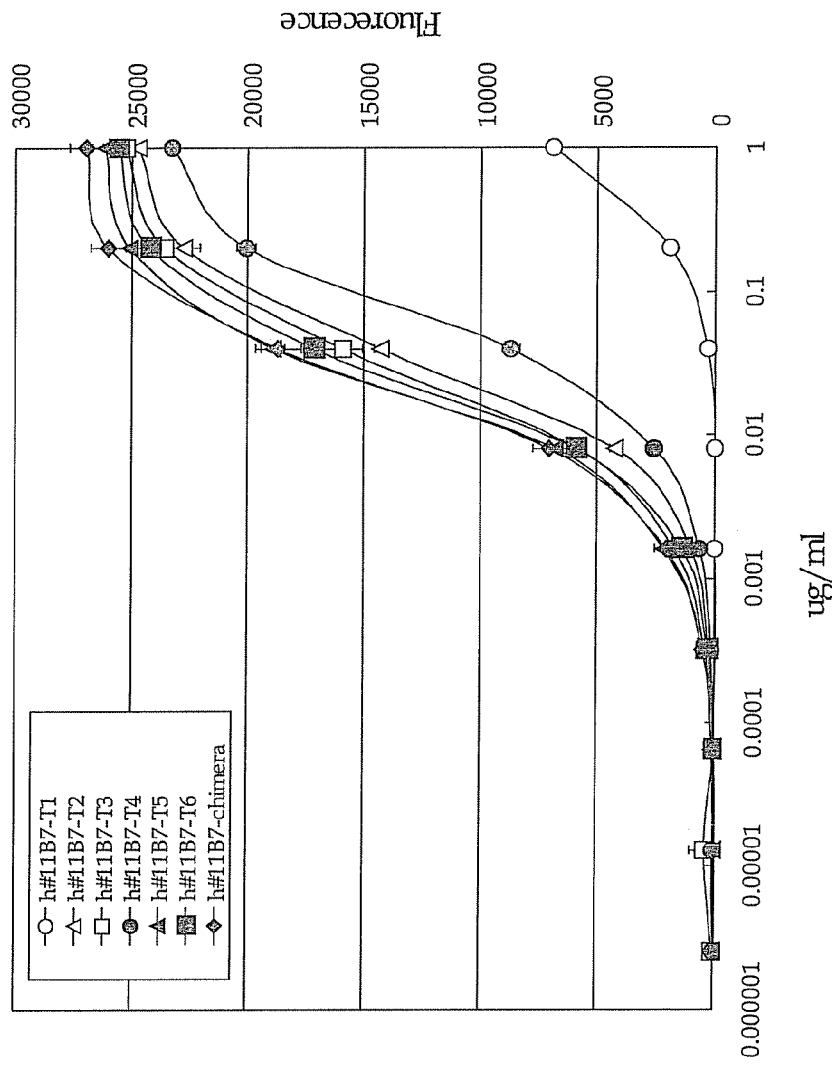

FIG. 19: This figure describes binding activity of the rat anti-human AXL humanized antibodies h#11B7-T1 to h#11B7-T6 determined by ELISA using human AXL-Fc coated plate.

Figure 20:
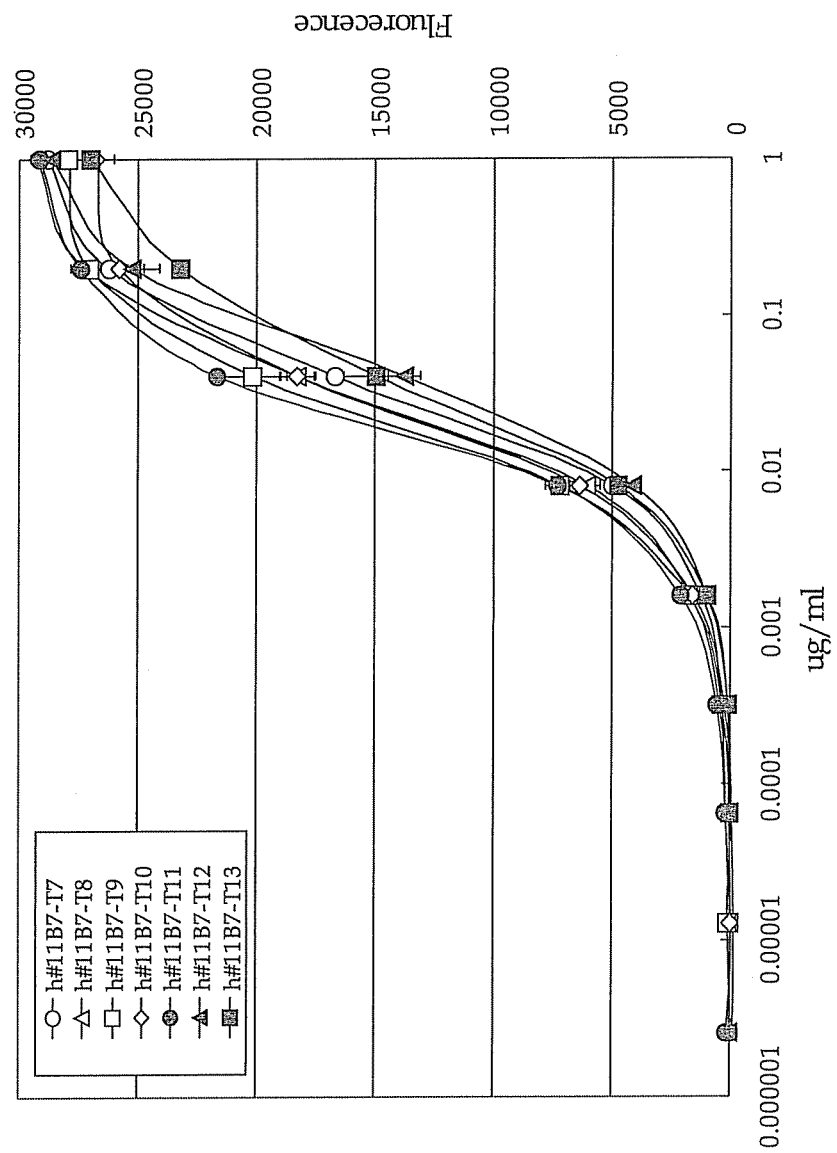

FIG. 20: This figure describes binding activity of the rat anti-human AXL humanized antibodies h#11B7-T7 to h#11B7-T13 determined by ELISA using human AXL-Fc coated plate.

Figure 21:
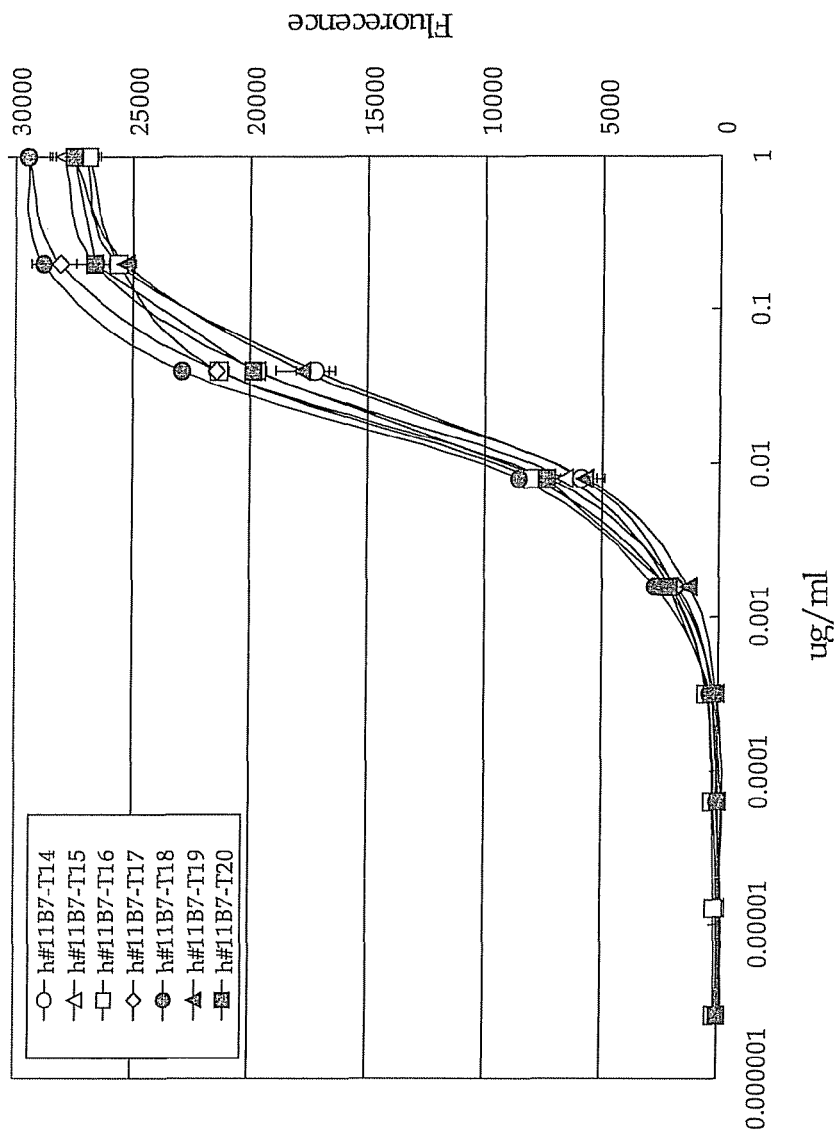

FIG. 21: This figure describes binding activity of the rat anti-human AXL humanized antibodies h#11B7-T14 to h#11B7-T20 determined by ELISA using human AXL-Fc coated plate.

Figure 22:
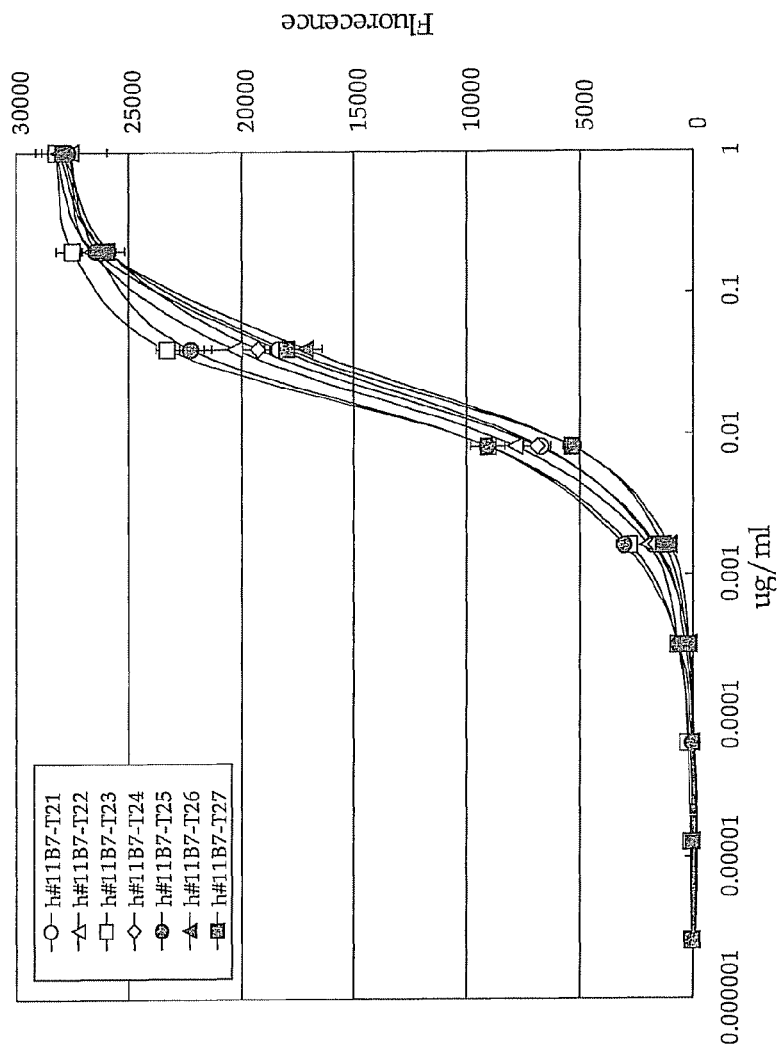

FIG. 22: This figure describes binding activity of the rat anti-human AXL humanized antibodies h#11B7-T21 to h#11B7-T27 determined by ELISA using human AXL-Fc coated plate.

Figure 23:
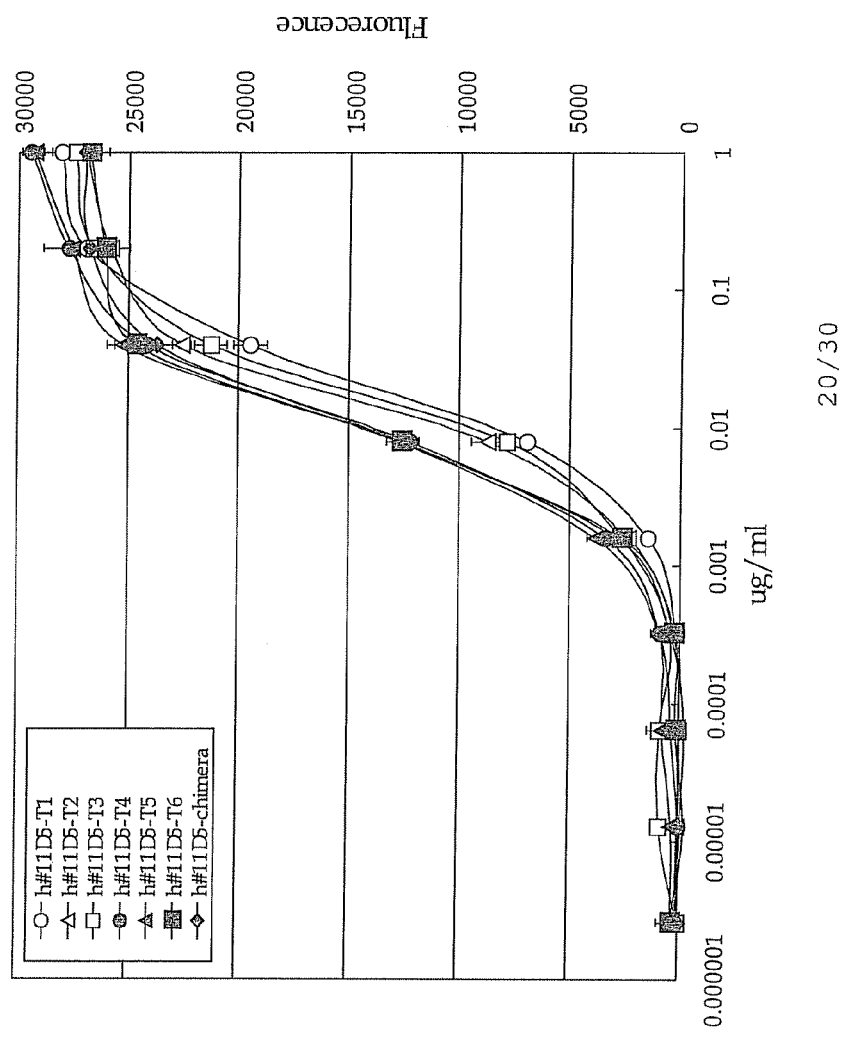

FIG. 23: This figure describes binding activity of the rat anti-human AXL humanized antibodies h#11D5-T1 to h#11D5-T6 determined by ELISA using human AXL-Fc coated plate.

FIGS. 24A-B (upper and lower panels): These figures describe protein concentration of the rat anti-human AXL humanized antibodies h#11B7-T1 to h#11B7-T27 determined by direct protein absorbance assay.

FIG. 25: This figure describes protein concentration of the rat anti-human AXL humanized antibodies h#11D5-T1 to h#11D5-T6 determined by direct protein absorbance assay.

Figure 26:
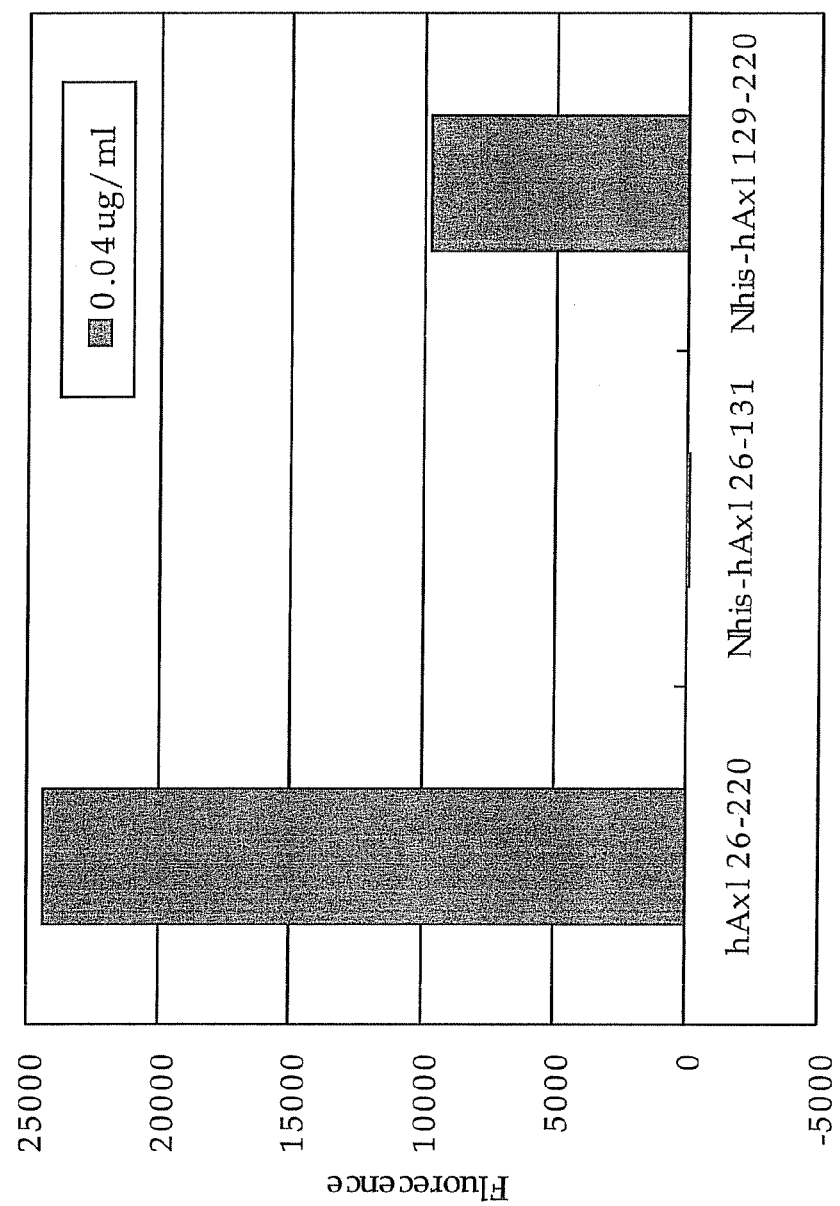

FIG. 26: This figure describes a determination of the domain to which the rat anti-human AXL monoclonal antibody #11B7 binds on the human AXL antigen.

FIG. 27. ELISA experiments to investigate the effects of humanized 11B7 anti-Axl antibodies on Axl receptor phosphorylation. Hs578T breast cancer cells (top) and NCI-H292 lung cancer cells (bottom) were starved, pre-incubated with 10 μg/ml of Gammagard control antibody, the chimeric anti-Axl mAb chm11B7 (IgG1/Kappa) as well as the humanized anti-Axl antibodies h#11B7-T2, h#11B7-T3, h#11B7-T4, h#11B7-T5, and h#11B7-T6 (T2-T6) of the invention, treated with or without 400 ng/ml mGas6, and lysed. Lysates were transferred to anti-phospho-tyrosine antibody 4G10-coated Maxi-Sorp 96 well plates, which then were washed and incubated with 0.125 μg/ml biotinylated rat anti-Axl antibody 12B7, AP-conjugated streptavidin and AttoPhos substrate solution in order to collect fluorescence intensities. See text for details. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention were able to block or significantly reduce Gas6-mediated Axl activation in both cell lines as indicated by decreased Axl tyrosine phosphorylation levels in Gas6-stimulated versus corresponding non-stimulated cells.

FIG. 28A. Western Blot experiments to investigate the effects of humanized 11B7 anti-Axl antibodies on ERK1/2 phosphorylation. Hs578T breast cancer cells (top) and NCI-H292 lung cancer cells (bottom) were starved, pre-incubated with 10 μg/ml of Gammagard control antibody, the chimeric anti-Axl mAb chm11B7 (IgG1/Kappa) or the humanized anti-Axl antibodies h#11B7-T2, h#11B7-T3, h#11B7-T4, h#11B7-T5, and h#11B7-T6 of the invention prior to treatment with or without 400 ng/ml mGas6, and lysed. Whole cell lysates were separated by SDS-PAGE and analyzed by Western Blotting using anti-phospho-p44/42 MAP kinase (Thr202/Tyr204) antibody. Subsequently, the same filters were re-probed with anti-p44/42 MAP kinase antibody antibody. See text for details. Compared with Gammagard control antibody, the chimeric anti-Axl antibody chm 11B7 as well as the humanized anti-Axl antibodies h#11B7-T2, h#11B7-T3, h#11B7-T4, h#11B7-T5, and h#11B7-T6 of the invention interfered with the weak, Gas6-induced increase of ERK1/2 activation in Hs578T breast cancer cells. Due to the high basal activity of ERK1/2 in this cell line, however, these effects which are indicated by decreased ERK1/2 Thr202/Tyr204 phosphorylation levels in Gas6-stimulated versus corresponding non-stimulated cells appear relatively moderate only. In contrast, the inhibitory effects of the chimeric anti-Axl antibody chm11B7 as well as the humanized anti-Axl antibodies h#11B7-T2, h#11B7-T3, h#11B7-T4, h#11B7-T5, or h#11B7-T6 on ERK1/2 Thr202/Tyr204 phosphorylation are much clearer reflected in NCI-H292 lung cancer cells.

FIG. 28B. Western Blot experiments to investigate the effects of humanized 11B7 anti-Axl antibodies on AKT phosphorylation. Hs578T breast cancer cells (top) and NCI-H292 lung cancer cells (bottom) were starved, pre-incubated with 10 μg/ml of Gammagard control antibody, the chimeric anti-Axl mAb chm11B7 (IgG1/Kappa) or the humanized anti-Axl antibodies h#11B7-T2, h#11B7-T3, h#11B7-T4, h#11B7-T5, and h#11B7-T6 of the invention prior to treatment with or without 400 ng/ml mGas6, and lysed. Whole cell lysates were separated by SDS-PAGE and analyzed by Western Blotting using anti-AKT1/2/3 antibody. Subsequently, the same filter was re-probed with anti-phospho-AKT (Ser473) antibody. See text for details. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention were able to significantly reduce Gas6-induced AKT activation in Hs578T breast cancer cells (top) and NCI-H292 lung cancer cells (bottom) as indicated by decreased AKT Ser473 phosphorylation levels in Gas6-stimulated versus corresponding non-stimulated cells.

FIG. 28C. Western Blot experiments to investigate the effects of humanized 11B7 anti-Axl antibodies on GSK-3β phosphorylation. Hs578T breast cancer cells (top) and NCI-H292 lung cancer cells (bottom) were starved, pre-incubated with 10 μg/ml of Gammagard control antibody, the chimeric anti-Axl mAb chm11B7 (IgG1/kappa) or the humanized anti-Axl antibodies h#11B7-T2, h#11B7-T3, h#11B7-T4, h#11B7-T5, and h#11B7-T6 of the invention prior to treatment with or without 400 ng/ml mGas6, and lysed. Whole cell lysates were separated by SDS-PAGE and analyzed by Western Blotting using anti-phospho-GSK-3β (Ser9) antibody. Subsequently, the same filter was re-probed with anti-GSK-3β antibody. See text for details. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention were able to significantly reduce Gas6-induced GSK-3β activation in Hs578T breast cancer cells (top) and NCI-H292 lung cancer cells (bottom) as indicated by decreased GSK-3β Ser9 phosphorylation levels in Gas6-stimulated versus corresponding non-stimulated cells.

FIG. 28D. Western Blot experiments to investigate the effects of humanized 11B7 anti-Axl antibodies on TCS2 phosphorylation. Hs578T breast cancer cells (top) and NCI-H292 lung cancer cells (bottom) were starved, pre-incubated with 10 μg/ml of Gammagard control antibody, the chimeric anti-Axl mAb chm11B7 (IgG1/kappa) or the humanized anti-Axl antibodies h#11B7-T2, h#11B7-T3, h#11B7-T4, h#11B7-T5, and h#11B7-T6 of the invention prior to treatment with or without 400 ng/ml mGas6, and lysed. Whole cell lysates were separated by SDS-PAGE and analyzed by Western Blotting using anti-TSC2 antibody. Subsequently, the same filter was re-probed with anti-phospho-TSC2 (Thr1462). See text for details. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention were able to significantly reduce Gas6-induced phosphorylation of TCS2 on Thr1462 in Hs578T breast cancer cells (top) and NCI-H292 lung cancer cells (bottom) as indicated by decreased phosphorylation levels of this amino acid residue in Gas6-stimulated versus corresponding non-stimulated cells.

FIG. 28E. Western Blot experiments to investigate the effects of humanized 11B7 anti-Axl antibodies on mTOR phosphorylation. Hs578T breast cancer cells (top) and NCI-H292 lung cancer cells (bottom) were starved, pre-incubated with 10 μg/ml of Gammagard control antibody, the chimeric anti-Axl mAb chm11B7 (IgG1/Kappa) or the humanized anti-Axl antibodies h#11B7-T2, h#11B7-T3, h#11B7-T4, h#11B7-T5, and h#11B7-T6 of the invention prior to treatment with or without 400 ng/ml mGas6, and lysed. Whole cell lysates were separated by SDS-PAGE and analyzed by Western Blotting using anti-phospho-mTOR (Ser2448) antibody. Subsequently, the same filter was re-probed with anti-mTOR antibody. See text for details. The inhibitory effects of the anti-Axl antibodies were relatively weak in Hs578T breast cancer cells (top). However, compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention were able to interfere with the Gas6-induced mTOR activation in NCI-H292 lung cancer cells as indicated by decreased mTOR Ser2448 phosphorylation levels in Gas6-stimulated versus corresponding non-stimulated cells (bottom).

FIG. 28F. Western Blot experiments to investigate the effects of humanized 11B7 anti-Axl antibodies on S6K1 phosphorylation. Hs578T breast cancer cells (top) and NCI-H292 lung cancer cells (bottom) were starved, pre-incubated with 10 μg/ml of Gammagard control antibody, the chimeric anti-Axl mAb chm11B7 (IgG1/Kappa) or the humanized anti-Axl antibodies h#11B7-T2, h#11B7-T3, h#11B7-T4, h#11B7-T5, and h#11B7-T6 of the invention prior to treatment with or without 400 ng/ml mGas6, and lysed. Whole cell lysates were separated by SDS-PAGE and analyzed by Western Blotting using anti-phospho-p70 S6 Kinase 1 (Thr421/Ser424) antibody. Subsequently, the same filter was re-probed with anti-β-actin antibody. See text for details. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention showed some inhibitory effects on Gas6-induced S6K1 activation in Hs578T breast cancer cells as indicated by decreased S6K1 Thr421/Ser424 phosphorylation levels in Gas6-stimulated versus corresponding non-stimulated cells (top). However, a much stronger decrease of Gas6-induced S6K1 Thr421/Ser424 phosphorylation and thus activation upon pre-treatment with the chimeric anti-Axl antibody chm11B7 as well as the humanized anti-Axl antibodies h#11B7-T2, h#11B7-T3, h#11B7-T4, h#11B7-T5, or h#11B7-T6 of the invention could be observed in NCI-H292 lung cancer cells (bottom).

Figure 29:
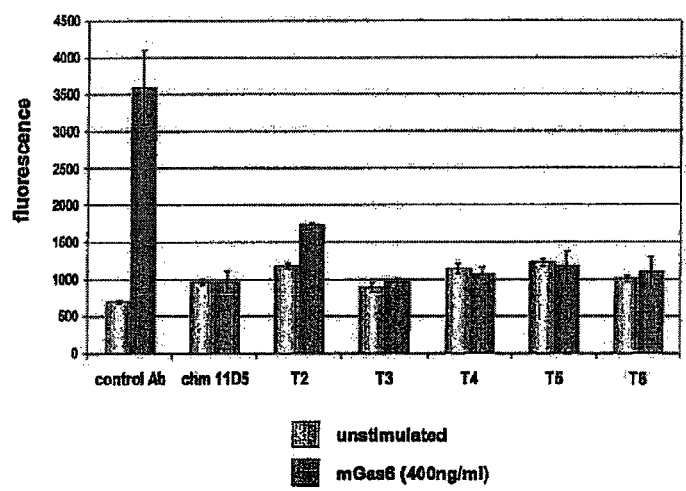

FIG. 29. ELISA experiments to investigate the effects of humanized 11D5 anti-Axl antibodies on Axl receptor phosphorylation. Hs578T breast cancer cells were starved, pre-incubated with 10 μg/ml of Gammagard control antibody, the chimeric anti-Axl mAb chm11D5 (IgG1/Kappa) as well as the humanized anti-Axl antibodies h#11D5-T2, h#11D5-T3, h#11D5-T4, h#11D5-T5, and h#11D5-T6 of the invention, treated with or without 400 ng/ml mGas6, and lysed. Lysates were transferred to anti-phospho-tyrosine antibody 4G10-coated Maxi-Sorp 96 well plates, which then were washed and incubated with 0.125 μg/ml biotinylated rat anti-Axl antibody 12B7, AP-conjugated streptavidin and AttoPhos substrate solution in order to collect fluorescence intensities. See text for details. Compared with Gammagard control antibody, the chimeric anti-Axl antibody chm11D5 as well as the humanized anti-Axl antibodies h#11D5-T2, h#11D5-T3, h#11D5-T4, h#11D5-T5, and h#11D5-T6 of the invention were able to block or significantly reduce Gas6-mediated Axl activation as indicated by decreased Axl tyrosine phosphorylation levels in Gas6-stimulated versus corresponding non-stimulated cells.

FIG. 30A: The amino acid sequence of human Axl, Accession No. P_30530 of NCBI protein database FIG. 30B: The amino acid sequence of the variable region of the light chain of the rat anti-human Axl monoclonal antibody 11B7

FIG. 30C: The amino acid sequence of the variable region of the heavy chain of the rat anti-human Axl monoclonal antibody 11B7

FIG. 30D: The amino acid sequence of the variable region of the light chain of the rat anti-human Axl monoclonal antibody 11D5

FIG. 30E: The amino acid sequence of the variable region of the heavy chain of the rat anti-human Axl monoclonal antibody 11D5

FIG. 31. ELISA experiments to compare the effects of rat and chimeric anti-Axl antibodies on Axl phosphorylation. CaSki cervical cancer cells were starved, pre-incubated with 50 ng/ml, 100 ng/ml, 300 ng/ml, 750 ng/ml, 1 jJg/ml, and 10 jJg/ml of rat anti-Axl antibody 11B7 (A) or chimeric anti Axl antibody ch11B7 (B), treated with or without 400 ng/ml mGas6, and lysed. Lysates were transferred to anti-phospho-tyrosine antibody 4G10-coated Maxi-Sorp 96 well plates. Afterwards, plates were washed and incubated with 0.5 IJg/ml of biotinylated rat anti-Axl antibody 12B7, AP-conjugated streptavidin, and AttoPhos substrate solution in order to collect fluorescence intensities. See text for details. As demonstrated by concentration-dependent decrease of the relative Axl phosphorylation in the cervical cancer cell line CaSki, the rat anti-Axi antibody 11B7 (A) and the chimeric anti-Axl antibody ch11B7 (B) of the invention were able to block ligand-induced activation of the receptor tyrosine kinase Axl to similar extent.

FIG. 32A: This figure describes the amino acid sequence of the humanized variable regions of the light chain of the rat anti-human AXL monoclonal antibody #11B7, designated as h#11B7-T15L and h#11B7-T18L, respectively.

FIG. 32B: This figure describes the amino acid sequence of the humanized variable regions of the heavy chain of the rat anti-human AXL monoclonal antibody #11B7, designated as h#11B7-T11H and h#11B7-T12H, respectively.

Figure 33:
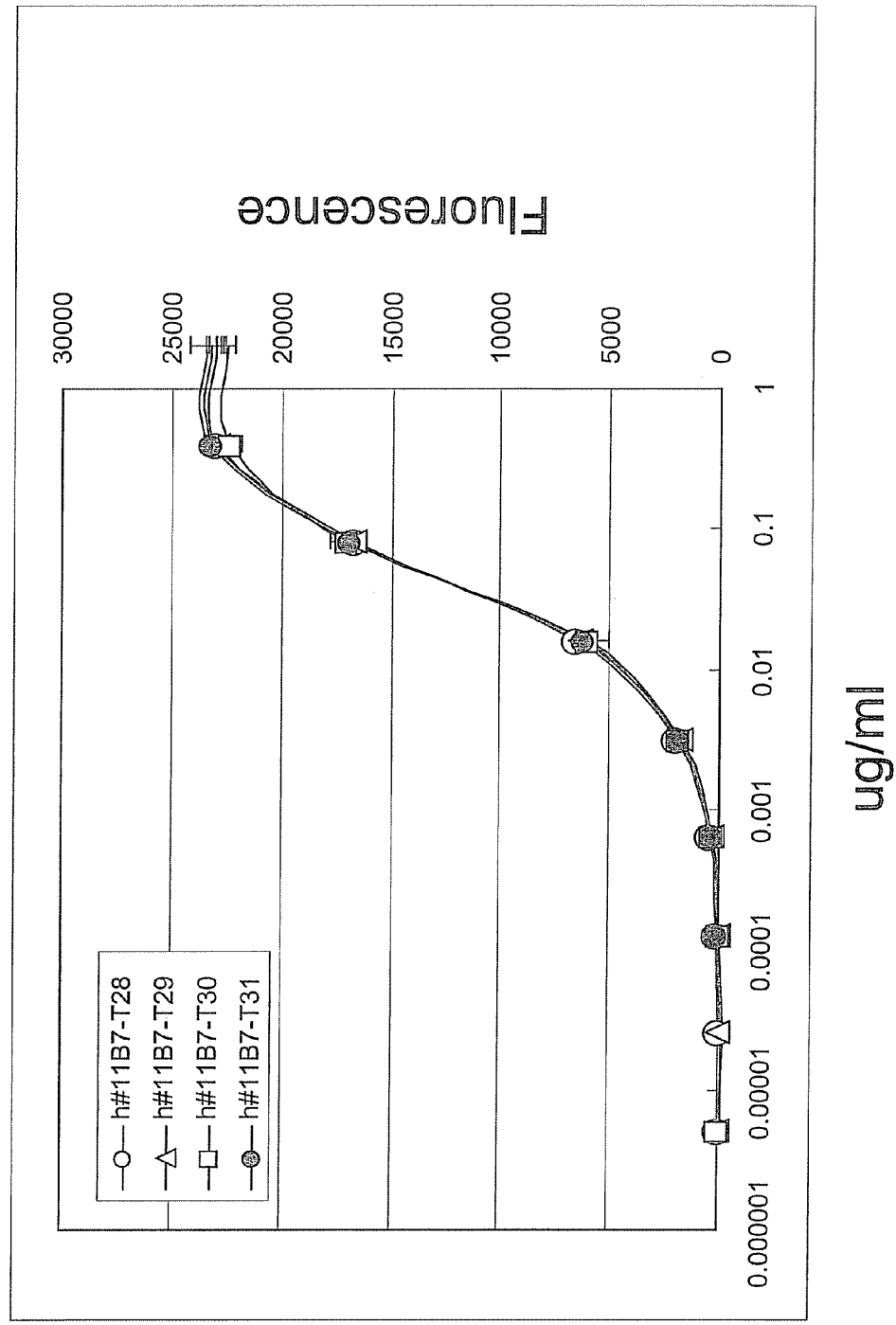

FIG. 33: This figure describes binding activity of the rat anti-human AXL humanized antibodies h#11B7-T28 to h#11B7-T31 determined by ELISA using human AXL-Fc coated plate (ELISA).

FIG. 34: This figure describes protein concentration of the rat anti-human AXL humanized antibodies h#11B7-T28 to h#11B7-T31 determined by the HPLC assay (See Example 24).

FIGS. 35A-35AF: These figures describe determination of Tm of the rat anti-human AXL humanized antibodies h#11B7-T1 to h#11B7-T31 and Chimeric h#11B7 antibody determined by differential scanning calorimetry (DSC).

Figure 36:
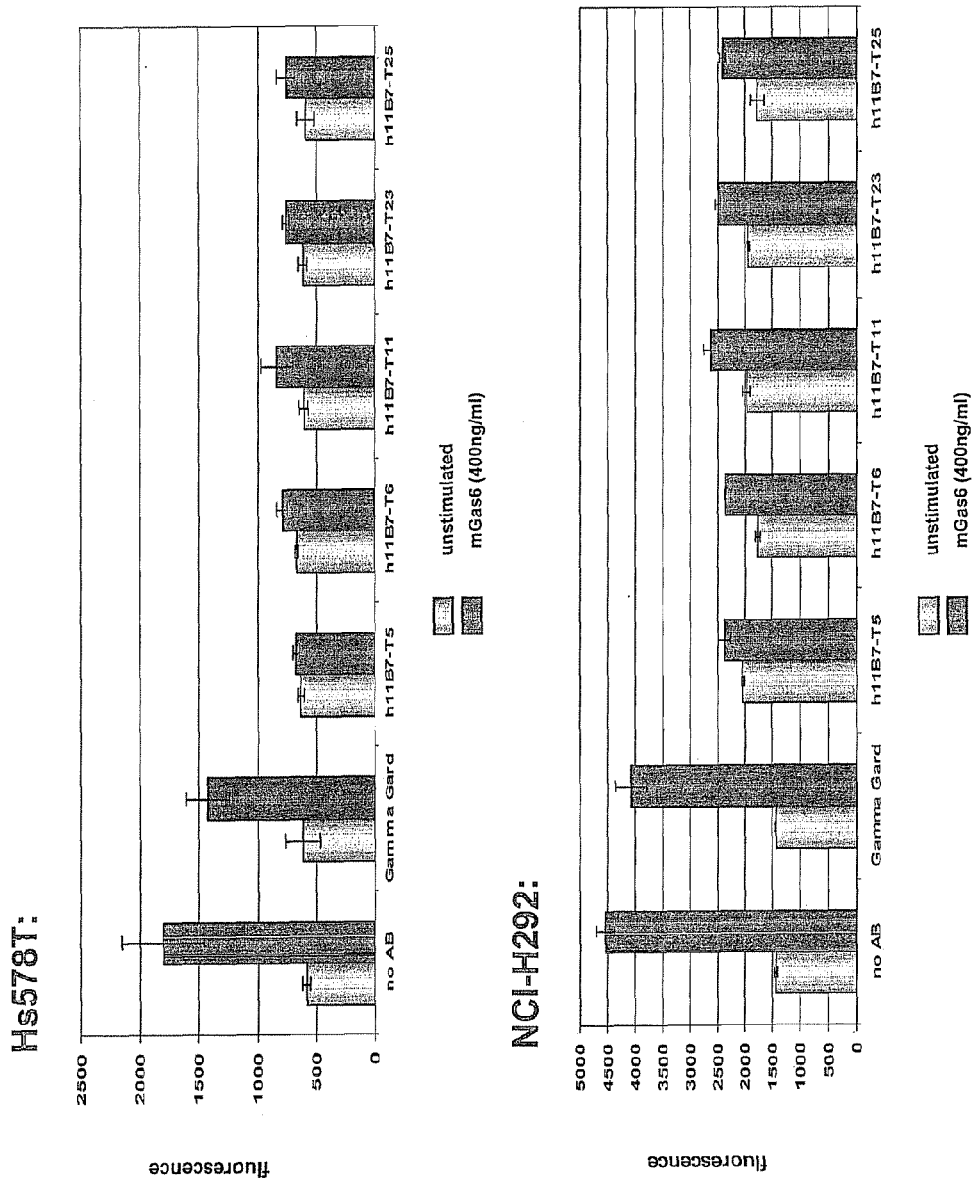

FIG. 36. ELISA experiments to investigate the effects of humanized 11B7 anti-Axl antibodies on Axl receptor phosphorylation. Hs578T breast cancer cells (top) and NCI-H292 lung cancer cells (bottom) were starved, pre-incubated with no antibody or 10 μg/ml of Gammagard control antibody as well as the humanized anti-Axl antibodies 11B7-T5, 11B7-T6, 11B7-T11, 11B7-T23, and 11B7-T25 of the invention, treated with or without 400 ng/ml mGas6, and lysed. Lysates were transferred to anti-phospho-tyrosine antibody 4G10-coated Maxi-Sorp 96 well plates, which then were washed and incubated with 0.125 μg/ml biotinylated rat anti-Axl antibody 12B7, AP-conjugated streptavidin and AttoPhos substrate solution in order to collect fluorescence intensities. See text for details. Compared with Gammagard control antibody, the humanized anti-Axl antibodies 11B7-T5, 11B7-T6, 11B7-T11, 11B7-T23, and 11B7-T25 of the invention significantly reduced Gas6-mediated Axl activation in both cell lines as indicated by decreased Axl tyrosine phosphorylation levels in Gas6-stimulated versus corresponding non-stimulated cells.

FIG. 37. ELISA experiments to investigate the effects of humanized 11B7 anti-Axl antibodies on Akt-Kinase phosphorylation. Hs578T breast cancer cells (top) and NCI-H292 lung cancer cells (bottom) were starved, pre-incubated with no antibody or 10 μg/ml of Gammagard control antibody as well as the humanized anti-Axl antibodies 11B7-T5, 11B7-T6, 11B7-T11, 11B7-T23, and 11B7-T25 of the invention, treated with or without 400 ng/ml mGas6, and fixed with formaldehyde. Cells were washed, quenched and incubated with anti-phospho-Akt (Ser473) primary antibody, HRP-conjugated anti-rabbit secondary antibody and Tetramethylbenzidine solution in order to measure absorbance intensities. See text for details. Compared with Gammagard control antibody, the humanized anti-Axl antibodies 11B7-T5, 11B7-T6, 11B7-T11, 11B7-T23, and 11B7-T25 of the invention were able to block or reduce Gas6-mediated Akt-kinase activation in both cell lines as indicated by decreased Akt (Ser473) phosphorylation levels in Gas6-stimulated versus corresponding non-stimulated cells.

Figure 38:
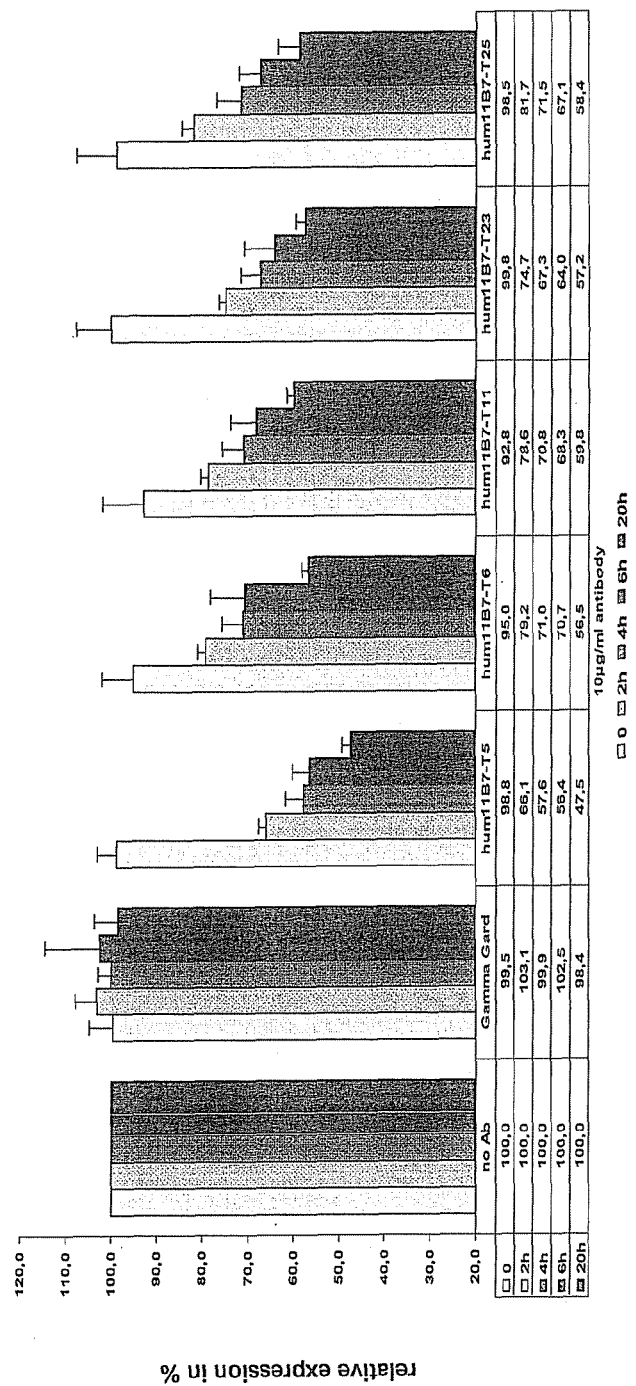

FIG. 38. FACS analysis to investigate the effects of humanized 11B7 anti-Axl antibodies on Axl receptor internalization. Hs578T breast cancer cells were starved, incubated with no antibody or 10 μg/ml of Gammagard control antibody as well as the humanized anti-Axl antibodies 11B7-T5, 11B7-T6, 11B7-T11, 11B7-T23, and 11B7-T25 of the invention for the indicated periods of time, and fixed with formaldehyde. Cells were stained with rat anti-Axl mAb 2A1 primary antibody and PE-conjugated donkey-anti-rat IgG secondary antibody, and subjected to FACS analysis. See text for details. In contrast to Gammagard control antibody, treatment of Hs578 breast cancer cells with the humanized anti-Axl antibodies 11B7-T5, 11B7-T6, 11B7-T11, 11B7-T23, and 11B7-T25 leads to internalization of the Axl receptor. Relative Axl expression levels in %, defined as mean fluorescence intensity of anti-Axl mAb treated samples relative to untreated samples of the respective treatment period is shown.

Figure 39:
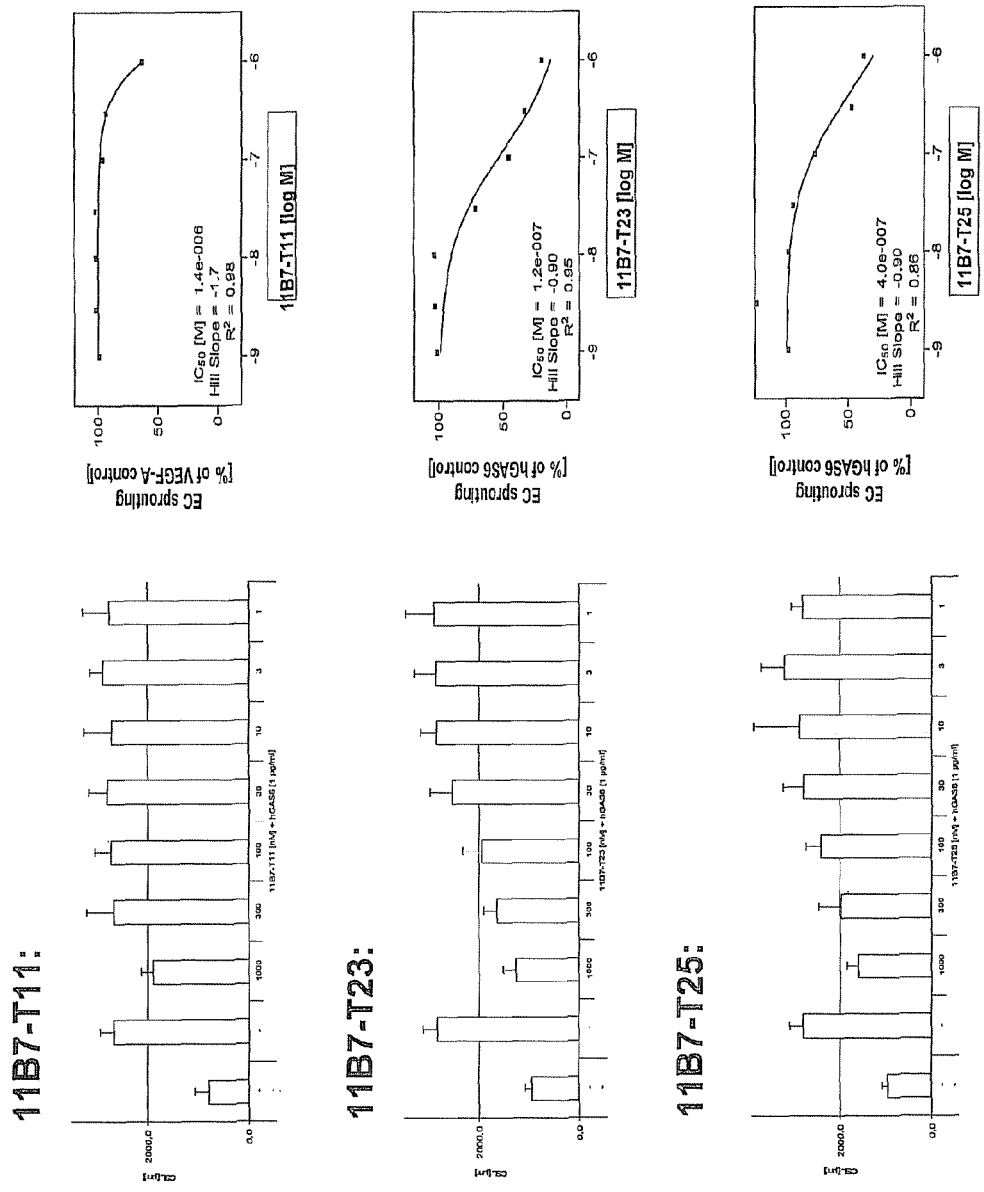

FIG. 39 A+B. Spheroid-based cellular angiogenesis assay to investigate the effects of humanized 11B7 anti-Axl antibodies on Gas6-induced endothelial cell sprouting. VEGF-A pre-treated HUVEC spheroids were embedded in a 3D collagen gel, stimulated with 1 μg/ml human Gas6 and treated with indicated concentrations of Gammagard control antibody as well as the humanized anti-Axl antibodies 11B7-T5, 11B7-T6, 11B7-T11, 11B7-T23, and 11B7-T25 of the invention for 24 h. The mean±SEM of the cumulative sprout length of 10 randomly selected spheroids per data point was analyzed (left panel) and the relative inhibition by the antibody was determined (right panel). Fitting of $IC_{50}$ curves and calculation of $IC_{50}$ values was performed with Graph Pad Prism 4.03. See text for details.

DESCRIPTION OF THE SEQUENCES

[SEQ ID NO:1] the nucleotide sequence of a primer for amplifying Fragment A, designated as Primer EFF1

[SEQ ID NO:2] the nucleotide sequence of a primer for amplifying Fragment A, designated as Primer EFsmaR

[SEQ ID NO:3] the nucleotide sequence of Fragment B comprising the secretion signal and constant region of human kappa chain, and the signal for addition of poly (A)

[SEQ ID NO:4] the nucleotide sequence of a DNA fragment comprising the nucleotide sequence encoding the amino acid sequence of the signal sequence and constant region of human IgG1

[SEQ ID NO:5] the nucleotide sequence encoding the amino acid sequence of the h#11B7-T1L, signal sequence (1-60), variable region (61-387), constant region (388-702)

[SEQ ID NO:6] the nucleotide sequence encoding the amino acid sequence of the h#11B7-T2L, signal sequence (1-60), variable region (61-387), constant region (388-702)

[SEQ ID NO:7] the nucleotide sequence encoding the amino acid sequence of the h#11B7-T3L, signal sequence (1-60), variable region (61-387), constant region (388-702)

[SEQ ID NO:8] the nucleotide sequence encoding the amino acid sequence of the h#11B7-T4L, signal sequence (1-60), variable region (61-387), constant region (388-702)

[SEQ ID NO:9] the nucleotide sequence encoding the amino acid sequence of the h#11B7-T5L, signal sequence (1-60), variable region (61-387), constant region (388-702)

[SEQ ID NO:10] the nucleotide sequence encoding the amino acid sequence of the h#11B7-T6L, signal sequence (1-60), variable region (61-387), constant region (388-702)

[SEQ ID NO:11] the nucleotide sequence encoding the amino acid sequence of the h#11B7-T7L, signal sequence (1-60), variable region (61-387), constant region (388-702)

[SEQ ID NO:12] the nucleotide sequence encoding the amino acid sequence of the h#11B7-T8L, signal sequence (1-60), variable region (61-387), constant region (388-702)

[SEQ ID NO:13] the nucleotide sequence encoding the amino acid sequence of the h#11B7-T9L, signal sequence (1-60), variable region (61-387), constant region (388-702)

[SEQ ID NO:14] the nucleotide sequence encoding the amino acid sequence of the h#11B7-T10L, signal sequence (1-60), variable region (61-387), constant region (388-702)

[SEQ ID NO:15] the nucleotide sequence encoding the amino acid sequence of the h#11B7-T11L, signal sequence (1-60), variable region (61-387), constant region (388-702)

[SEQ ID NO:16] the nucleotide sequence encoding the amino acid sequence of the h#11B7-T12L, signal sequence (1-60), variable region (61-387), constant region (388-702)

[SEQ ID NO:17] the nucleotide sequence encoding the amino acid sequence of the h#11B7-T13L, signal sequence (1-60), variable region (61-387), constant region (388-702)

[SEQ ID NO:18] the amino acid sequence of the h#11B7-T1L, signal sequence (1-20), variable region (21-129), constant region (130-234)

[SEQ ID NO:19] the amino acid sequence of the h#11B7-T2L, signal sequence (1-20), variable region (21-129), constant region (130-234)

[SEQ ID NO:20] the amino acid sequence of the h#11B7-T3L, signal sequence (1-20), variable region (21-129), constant region (130-234)

[SEQ ID NO:21] the amino acid sequence of the h#11B7-T4L, signal sequence (1-20), variable region (21-129), constant region (130-234)

[SEQ ID NO:22] the amino acid sequence of the h#11B7-T5L, signal sequence (1-20), variable region (21-129), constant region (130-234)

[SEQ ID NO:23] the amino acid sequence of the h#11B7-T6L, signal sequence (1-20), variable region (21-129), constant region (130-234)

[SEQ ID NO:24] the amino acid sequence of the h#11B7-T7L, signal sequence (1-20), variable region (21-129), constant region (130-234)

[SEQ ID NO:25] the amino acid sequence of the h#11B7-T8L, signal sequence (1-20), variable region (21-129), constant region (130-234)

[SEQ ID NO:26] the amino acid sequence of the h#11B7-T9L, signal sequence (1-20), variable region (21-129), constant region (130-234)

[SEQ ID NO:27] the amino acid sequence of the h#11B7-T10L, signal sequence (1-20), variable region (21-129), constant region (130-234)

[SEQ ID NO:28] the amino acid sequence of the h#11B7-T11L, signal sequence (1-20), variable region (21-129), constant region (130-234)

[SEQ ID NO:29] the amino acid sequence of the h#11B7-T12L, signal sequence (1-20), variable region (21-129), constant region (130-234)

[SEQ ID NO:30] the amino acid sequence of the h#11B7-T13L, signal sequence (1-20), variable region (21-129), constant region (130-234)

[SEQ ID NO:31] the nucleotide sequence encoding the amino acid sequence of the h#11B7-T1H, signal sequence (1-57), variable region (58-396), constant region (397-1386)

[SEQ ID NO:32] the nucleotide sequence encoding the amino acid sequence of the h#11B7-T2H, signal sequence (1-57), variable region (58-396), constant region (397-1386)

[SEQ ID NO:33] the nucleotide sequence encoding the amino acid sequence of the h#11B7-T3H, signal sequence (1-57), variable region (58-396), constant region (397-1386)

[SEQ ID NO:34] the nucleotide sequence encoding the amino acid sequence of the h#11B7-T4H, signal sequence (1-57), variable region (58-396), constant region (397-1386)

[SEQ ID NO:35] the nucleotide sequence encoding the amino acid sequence of the h#11B7-T5H, signal sequence (1-57), variable region (58-396), constant region (397-1386)

[SEQ ID NO:362] the nucleotide sequence encoding the amino acid sequence of the h#11B7-T6H, signal sequence (1-57), variable region (58-396), constant region (397-1386)

[SEQ ID NO:37] the nucleotide sequence encoding the amino acid sequence of the h#11B7-T7H, signal sequence (1-57), variable region (58-396), constant region (397-1386)

[SEQ ID NO:38] the nucleotide sequence encoding the amino acid sequence of the h#11B7-T8H, signal sequence (1-57), variable region (58-396), constant region (397-1386)

[SEQ ID NO:39] the nucleotide sequence encoding the amino acid sequence of the h#11B7-T9H, signal sequence (1-57), variable region (58-396), constant region (397-1386)

[SEQ ID NO:40] the amino acid sequence of the h#11B7-T1H, signal sequence (1-19), variable region (20-132), constant region (133-462)

[SEQ ID NO:41] the amino acid sequence of the h#11B7-T2H, signal sequence (1-19), variable region (20-132), constant region (133-462)

[SEQ ID NO:42] the amino acid sequence of the h#11B7-T3H, signal sequence (1-19), variable region (20-132), constant region (133-462)

[SEQ ID NO:43] the amino acid sequence of the h#11B7-T4H, signal sequence (1-19), variable region (20-132), constant region (133-462)

[SEQ ID NO:44] the amino acid sequence of the h#11B7-T5H, signal sequence (1-19), variable region (20-132), constant region (133-462)

[SEQ ID NO:45] the amino acid sequence of the h#11B7-T6H, signal sequence (1-19), variable region (20-132), constant region (133-462)

[SEQ ID NO:46] the amino acid sequence of the h#11B7-T7H, signal sequence (1-19), variable region (20-132), constant region (133-462)

[SEQ ID NO:47] the amino acid sequence of the h#11B7-T8H, signal sequence (1-19), variable region (20-132), constant region (133-462)

[SEQ ID NO:48] the amino acid sequence of the h#11B7-T9H, signal sequence (1-19), variable region (20-132), constant region (133-462)

[SEQ ID NO:49] the nucleotide sequence encoding the amino acid sequence of the h#11D5-T1L, signal sequence (1-60), variable region (61-387), constant region (388-702)

[SEQ ID NO:50] the nucleotide sequence encoding the amino acid sequence of the h#11D5-T2L, signal sequence (1-60), variable region (61-387), constant region (388-702)

[SEQ ID NO:51] the nucleotide sequence encoding the amino acid sequence of the h#11D5-T3L, signal sequence (1-60), variable region (61-387), constant region (388-702)

[SEQ ID NO:52] the nucleotide sequence encoding the amino acid sequence of the h#11D5-T4L, signal sequence (1-60), variable region (61-387), constant region (388-702)

[SEQ ID NO:53] the nucleotide sequence encoding the amino acid sequence of the h#11D5-T5L, signal sequence (1-60), variable region (61-387), constant region (388-702)

[SEQ ID NO:54] the nucleotide sequence encoding the amino acid sequence of the h#11D5-T6L, signal sequence (1-60), variable region (61-387), constant region (388-702)

[SEQ ID NO:55] the amino acid sequence of h#11D5-T1L, signal sequence (1-20), variable region (21-129), constant region (130-234)

[SEQ ID NO:56] the amino acid sequence of h#11D5-T2L, signal sequence (1-20), variable region (21-129), constant region (130-234)

[SEQ ID NO:57] the amino acid sequence of h#11D5-T3L, signal sequence (1-20), variable region (21-129), constant region (130-234)

[SEQ ID NO:58] the amino acid sequence of h#11D5-T4L, signal sequence (1-20), variable region (21-129), constant region (130-234)

[SEQ ID NO:59] the amino acid sequence of h#11D5-T5L, signal sequence (1-20), variable region (21-129), constant region (130-234)

[SEQ ID NO:60] the amino acid sequence of h#11D5-T6L, signal sequence (1-20), variable region (21-129), constant region (130-234)

[SEQ ID NO:61] the nucleotide sequence encoding the amino acid sequence of the h#11D5-T1H, signal sequence (1-57), variable region (58-396), constant region (297-1386)

[SEQ ID NO:62] the nucleotide sequence encoding the amino acid sequence of the h#11D5-T2H, signal sequence (1-57), variable region (58-396), constant region (297-1386)

[SEQ ID NO:63] the nucleotide sequence encoding the amino acid sequence of the h#11D5-T3H, signal sequence (1-57), variable region (58-396), constant region (297-1386)

[SEQ ID NO:64] the nucleotide sequence encoding the amino acid sequence of the h#11D5-T4H, signal sequence (1-57), variable region (58-396), constant region (297-1386)

[SEQ ID NO:65] the nucleotide sequence encoding the amino acid sequence of the h#11D5-T5H, signal sequence (1-57), variable region (58-396), constant region (297-1386)

[SEQ ID NO:66] the nucleotide sequence encoding the amino acid sequence of the h#11D5-T6H, signal sequence (1-57), variable region (58-396), constant region (297-1386)

[SEQ ID NO:67] the amino acid sequence of h#11D5-T1H, signal sequence (1-19), variable region (20-132), constant region (133-462)

[SEQ ID NO:68] the amino acid sequence of h#11D5-T2H, signal sequence (1-19), variable region (20-132), constant region (133-462)

[SEQ ID NO:69] the amino acid sequence of h#11D5-13H, signal sequence (1-19), variable region (20-132), constant region (133-462)

[SEQ ID NO:70] the amino acid sequence of h#11D5-T4H, signal sequence (1-19), variable region (20-132), constant region (133-462)

[SEQ ID NO:71] the amino acid sequence of h#11D5-T5H, signal sequence (1-19), variable region (20-132), constant region (133-462)

[SEQ ID NO:72] the amino acid sequence of h#11D5-T6H, signal sequence (1-19), variable region (20-132), constant region (133-462)

[SEQ ID NO:73] the amino acid sequence of h#11B7-T14L, variable region

[SEQ ID NO:74] the amino acid sequence of h#11B7-T15L, variable region

[SEQ ID NO:75] the amino acid sequence of h#11B7-T16L, variable region

[SEQ ID NO:76] the amino acid sequence of h#11B7-T17L, variable region

[SEQ ID NO:77] the amino acid sequence of h#11B7-T18L, variable region

[SEQ ID NO:78] the amino acid sequence of h#11B7-T19L, variable region

[SEQ ID NO:79] the amino acid sequence of h#11B7-T20L, variable region

[SEQ ID NO:80] the amino acid sequence of h#11B7-T10H, variable region

[SEQ ID NO:81] the amino acid sequence of h#11B7-T11H, variable region

[SEQ ID NO:82] the amino acid sequence of h#11B7-T12H, variable region

[SEQ ID NO:83] the amino acid sequence of h#11D5-T7L, variable region

[SEQ ID NO:84] the amino acid sequence of h#11D5-T8L, variable region

[SEQ ID NO:85] the amino acid sequence of h#11D5-T9L, variable region

[SEQ ID NO:86] the amino acid sequence of h#11D5-T10L, variable region

[SEQ ID NO:87] the amino acid sequence of h#11D5-T11L, variable region

[SEQ ID NO:88] the amino acid sequence of h#11D5-T12L, variable region

[SEQ ID NO:89] the amino acid sequence of h#11D5-T13L, variable region

[SEQ ID NO:90] the amino acid sequence of h#11D5-T14L, variable region

[SEQ ID NO:91] the amino acid sequence of h#11D5-T15L, variable region

[SEQ ID NO:92] the amino acid sequence of h#11D5-T16L, variable region

[SEQ ID NO:93] the amino acid sequence of h#11D5-T17L, variable region

[SEQ ID NO:94] the amino acid sequence of h#11D5-T18L, variable region

[SEQ ID NO:95] the amino acid sequence of h#11D5-T19L, variable region

[SEQ ID NO:96] the amino acid sequence of h#11D5-T20L, variable region

[SEQ ID NO:97] the amino acid sequence of h#11D5-T21L, variable region

[SEQ ID NO:98] the amino acid sequence of h#11D5-T22L, variable region

[SEQ ID NO:99] the amino acid sequence of h#11D5-T23L, variable region

[SEQ ID NO:100] the amino acid sequence of h#11D5-T24L, variable region

[SEQ ID NO:101] the amino acid sequence of h#11D5-T25L, variable region

[SEQ ID NO:102] the amino acid sequence of h#11D5-T26L, variable region

[SEQ ID NO:103] the amino acid sequence of h#11D5-T27L, variable region

[SEQ ID NO:104] the amino acid sequence of h#11D5-T28L, variable region

[SEQ ID NO:105] the amino acid sequence of h#11D5-T29L, variable region

[SEQ ID NO:106] the amino acid sequence of h#11D5-T30L, variable region

[SEQ ID NO:107] the amino acid sequence of h#11D5-T31L, variable region

[SEQ ID NO:108] the amino acid sequence of h#11D5-T32L, variable region

[SEQ ID NO:109] the amino acid sequence of h#11D5-T33L, variable region

[SEQ ID NO:110] the amino acid sequence of h#11D5-T34L, variable region

[SEQ ID NO:111] the amino acid sequence of h#11D5-T35L, variable region

[SEQ ID NO:112] the amino acid sequence of h#11D5-T36L, variable region

[SEQ ID NO:113] the amino acid sequence of h#11D5-T37L, variable region

[SEQ ID NO:114] the amino acid sequence of h#11D5-T7H, variable region

[SEQ ID NO:115] the amino acid sequence of h#11D5-T8H, variable region

[SEQ ID NO:116] the amino acid sequence of h#11D5-T9H, variable region

[SEQ ID NO:117] the amino acid sequence of h#11D5-T10H, variable region

[SEQ ID NO:118 the amino acid sequence of h#11D5-T11H, variable region

[SEQ ID NO:119] the amino acid sequence of h#11D5-T12H, variable region

[SEQ ID NO:120] the amino acid sequence of h#11D5-T13H, variable region

[SEQ ID NO:121] the amino acid sequence of 11B7 Light chain CDRL4

[SEQ ID NO:122] the amino acid sequence of 11B7 Light chain CDRL5

[SEQ ID NO:123] the amino acid sequence of 11B7 Light chain CDRL6

[SEQ ID NO:124] the amino acid sequence of 11B7 Heavy chain CDRH1

[SEQ ID NO:125] the amino acid sequence of 11B7 Heavy chain CDRH2

[SEQ ID NO:126] the amino acid sequence of 11B7 Heavy chain CDRH3

[SEQ ID NO:127] the amino acid sequence of 11D5 Light chain CDRL4

[SEQ ID NO:128] the amino acid sequence of 11D5 Light chain CDRL5

[SEQ ID NO:129] the amino acid sequence of 11D5 Light chain CDRL6

[SEQ ID NO:130] the amino acid sequence of 11D5 Heavy chain CDRH1

[SEQ ID NO:131] the amino acid sequence of 11D5 Heavy chain CDRH2

[SEQ ID NO:132] the amino acid sequence of 11D5 Heavy chain CDRH3

[SEQ ID NO:133] nucleotide sequence of the Leader sequence

[SEQ ID NO:134] the amino acid sequence of the Leader sequence

[SEQ ID NO:135] the amino acid sequence of #11B7-chimeric light chain

[SEQ ID NO:136] the amino acid sequence of #11B7-chimeric heavy chain

[SEQ ID NO:137] the amino acid sequence of #11D5-chimeric light chain

[SEQ ID NO:138] the amino acid sequence of #11D5-chimeric heavy chain

[SEQ ID NO: 139] the amino acid sequence of human Axl, Accession No. P_30530 of NCBI protein database, which is also described FIG. 30A

[SEQ ID NO: 140] the amino acid sequence of the variable region of the light chain of the rat anti-human Axl monoclonal antibody 11B7, which is also described in FIG. 30B, and which is identical to the amino acid sequence consisting of the amino acids No. 1 to 108 of the #11B7-chimeric light chain (SEQ ID NO: 135)

[SEQ ID NO: 141] the amino acid sequence of the variable region of the heavy chain of the rat anti-human Axl monoclonal antibody 11B7, which is also described in FIG. 30C, and which is identical to the amino acid sequence consisting of the amino acids No. 1 to 113 of the #11B7-chimeric heavy chain (SEQ ID NO: 136)

[SEQ ID NO: 142] the amino acid sequence of the variable region of the light chain of the rat anti-human Axl monoclonal antibody 11D5, which is also described in FIG. 30D, and which is identical to the amino acid sequence consisting of the amino acid No. 1 to 108 of the #11D5-chimeric light chain (SEQ ID NO: 137)

[SEQ ID NO: 143] the amino acid sequence of the variable region of the heavy chain of the rat anti-human Axl monoclonal antibody 11D5, which is also described in FIG. 30E, and which is identical to the amino acid sequence consisting of the amino acid No. 1 to 113 of the #11D5-chimeric heavy chain (SEQ ID NO: 138)

[SEQ ID NO: 144] the nucleotide sequence encoding the amino acid sequence of the h#11B7-T15L, signal sequence (1-60), variable region (61-387), constant region (388-702)

[SEQ ID NO: 145] the nucleotide sequence encoding the amino acid sequence of the h#11B7-T18L, signal sequence (1-60), variable region (61-387), constant region (388-702)

[SEQ ID NO: 146] the amino acid sequence of the h#11B7-T15L, signal sequence (1-20), variable region (21-129), constant region (130-234)

[SEQ ID NO: 147] the amino acid sequence of the h#11B7-T18L, signal sequence (1-20), variable region (21-129), constant region (130-234)

[SEQ ID NO: 148] the nucleotide sequence encoding the amino acid sequence of the h#11B7-T11H, signal sequence (1-57), variable region (58-396), constant region (397-1386)

[SEQ ID NO: 149] the nucleotide sequence encoding the amino acid sequence of the h#11B7-T12H, signal sequence (1-57), variable region (58-396), constant region (397-1386)

[SEQ ID NO: 150] the amino acid sequence of the h#11B7-T11H, signal sequence (1-19), variable region (20-132), constant region (133-462)

[SEQ ID NO: 151] the amino acid sequence of the h#11B7-T12H, signal sequence (1-19), variable region (20-132), constant region (133-462)

EXAMPLES

Example 1

Generation of AXL Overexpressing RatI Fibroblasts as Immunogen

The full length coding sequence for the human receptor tyrosine kinase AXL transcript variant 1 according to the National Center for Biotechnology Information (NCBI) reference sequence (NM_021913) was subcloned into pLXSN via flanking recognition elements for the restriction endonucleases EcoRI and BamHI, thereby resulting in the retroviral expression vector pLXSN-hAXL.

For the generation of antibodies that specifically bind to human receptor tyrosine kinase AXL, RatI fibroblasts stably overexpressing human AXL were generated by retroviral gene transfer. In brief, 3×105 Phoenix-E cells were seeded on 60 mm culture dishes and transfected with 2 µg/ml pLXSN vector or pLXSN-hAXL using the calcium phosphate method. After 24 h, medium was replaced by fresh medium in which Phoenix-E cells were incubated for 4 h. The supernatants of Phoenix-E cells releasing pLXSN or pLXSN-hAXL ecotrophic virus were harvested and used for the incubation of subconfluent RatI cells (2×105 cells per 6 cm dish) for 3 h in the presence of Polybrene (4 mg/ml; Aldrich). Simultaneously, Phoenix-E cells were re-incubated with fresh medium, which after another 3 h was used for a second infection of the RatI fibroblasts in the presence of Polybrene (4 mg/ml; Aldrich). Likewise, a third infection cycle was performed. After changing the medium, selection of RatI cells with G418 was started. Usually, stable clones were picked after selection for 21 days.

A panel of stable clones was propagated and quantified for membrane-localized human AXL expression by FACS analysis. In detail, 1×105 cells were harvested with 10 mM EDTA in PBS, washed once with FACS buffer (PBS, 3% FCS, 0.4% azide) and seeded on a 96 well round bottom plate. The cells were spun for 3 min at 1,000 rpm to remove supernatant and were resuspended with mouse anti-AXL primary antibody MAB154 (R&D Systems, 3 µg/ml). Cell suspensions were incubated on ice for 1 h, washed twice with FACS buffer and resuspended in 100 µl/well of PE-conjugated donkey anti-mouse secondary antibody (Jackson) diluted 1:50 in FACS buffer. The cell suspensions were incubated on ice and in the dark for 30 min, washed twice with FACS buffer and analyzed using an Epics XL-MCL flow cytometer (Beckman Coulter).

Figure 15:
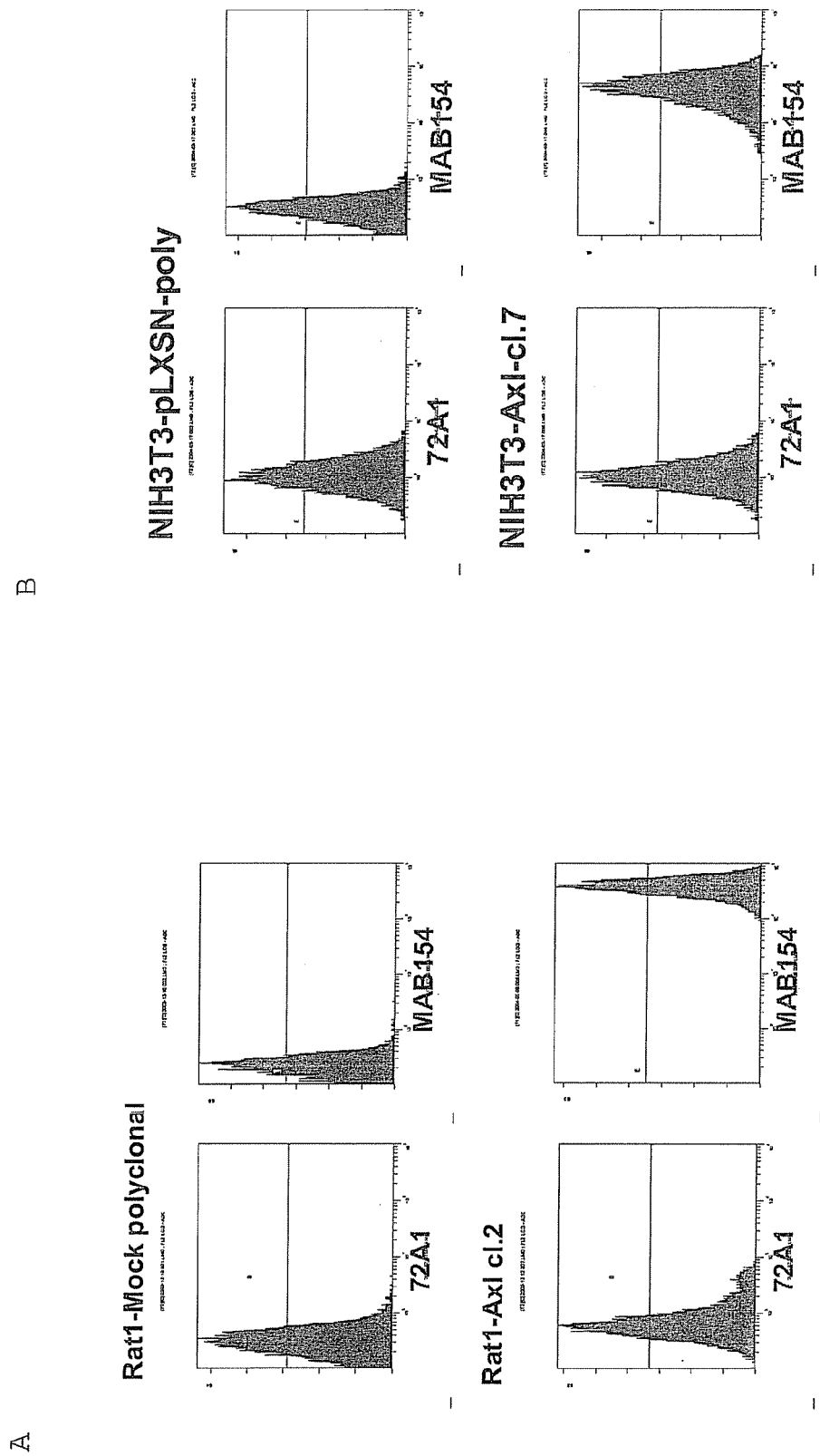

FIG. 15A shows the FACS analysis of the polyclonal RatI-Mock population stably infected with pLXSN empty vector and RatI-AXL cl.2 stably infected with pLXSN-hAXL, and demonstrates AXL overexpression on the cell surface of this representative clone.

Additionally, in order to generate a suitable cellular model system for experimental purposes, NIH3T3 fibroblasts stably overexpressing AXL were generated in analogy to procedures described for RatI. In brief 3×105 Phoenix-E cells were seeded on 60 mm culture dishes and transfected with 2 µg/ml pLXSN vector or pLXSN-AXL cDNA using the calcium phosphate method. After 24 h, medium was replaced by fresh medium in which Phoenix-E cells were incubated for 4 h. The supernatants of Phoenix-E cells releasing pLXSN or pLXSN-hAXL ecotrophic virus were harvested and used for the incubation of subconfluent NIH3T3 cells (2×105 cells per 6 cm dish) for 3 h in the presence of Polybrene (4 mg/ml; Aldrich). Simultaneously, Phoenix-E cells were re-incubated with fresh medium, which after another 3 h was used for a second infection of the NIH3T3 fibroblasts in the presence of Polybrene (4 mg/ml; Aldrich). Likewise, a third infection cycle was performed. After changing the medium, selection of NIH3T3 cells with G418 was started. Usually, stable clones were picked after selection for 21 days. A panel of stable clones was propagated and quantified for membrane-localized AXL expression by FACS analysis. In detail, 1×105 cells were harvested with 10 mM EDTA in PBS, washed once with FACS buffer (PBS, 3% FCS, 0.4% azide) and seeded on a 96 well round bottom plate. The cells were spun for 3 min at 1000 rpm to remove supernatant and were resuspended with mouse anti-AXL primary antibody MAB154 (R&D Systems, 3 µg/ml). Cell suspensions were incubated on ice for 1 h, washed twice with FACS buffer and resuspended in 100 µl/well of PE-conjugated donkey anti-mouse secondary antibody (Jackson) diluted 1:50 in FACS buffer. The cell suspensions were incubated on ice and in the dark for 30 min, washed twice with FACS buffer and analyzed using an Epics XL-MCL flow cytometer (Beckman Coulter).

FIG. 15B shows the FACS analysis of the polyclonal NIH3T3-Mock population stably infected with pLXSN empty vector and NIH3T3-AXL cI.7 stably infected with pLXSN-hAXL, and demonstrates AXL overexpression on the cell surface of this representative clone.

Example 2

Generation of Rat Anti-AXL Monoclonal Antibodies

Monoclonal rat anti-AXL antibodies were raised by injection of approximately 10×106 frozen cells of RatI-AXL cI.2 both i.p. and subcutaneously into Lou/C or Long Evans rats. After an 8-week interval, a final boost was given i.p and subcutaneously 3 d before fusion. Fusion of the myeloma cell line P3X63-Ag8.653 with the rat immune spleen cells was performed according to standard procedures and yielded 105 hybridomas. After 2 weeks, first supernatants from hybridomas were collected and tested in a primary FACS screen for binding to NIH3T3-AXL cI.7 fibroblasts versus NIH3T3-Mock control cells. Clones positive for AXL binding were further cultivated. From 50 ml supernatant of these clones, antibodies were purified and re-analyzed for specific binding to AXL on NIH3T3-AXL cI.7 fibroblasts versus NIH3T3-Mock control cells. Purified antibodies specifically binding to NIH3T3-AXL cI.7 fibroblasts but not NIH3T3-Mock control cells were furthermore tested in Akt-Kinase phosphorylation ELISAs, and ELISAs to determine the isotype were performed. For purification of rat antibodies, supernatants were spun for 20 minutes at 5,000 g and subsequently sterile filtered. 500 µl of protein G sepharose FF were added and incubated at 4° C. for at least 1 h on a spinning wheel. Sepharose was spun down, supernatant discarded and protein G matrix was washed twice with PBS prior to protein elution utilizing citrate buffer (100 mM) pH 2.1. Elution fractions were immediately rebuffered to neutral pH by adding 1M Tris pH 8.0 and dialyzed against PBS. Of the oligoclonal antibodies tested, 91 specifically bound to NIH3T3-AXL cI.7 fibroblasts but not NIH3T3-Mock control cells, 9 inhibited Gas6-induced Akt phosphorylation in the same cells, whereas 71 stimulated Akt phosphorylation. Four antagonistic antibodies (I11B7, I10D12, I6E7, and III11D5, in the following examples referred to as 11B7, 10D12, 6E7 and 11D5, respectively), two agonistic antibodies (I11D7 and III2A1; in the following examples referred to as 11D7 and 2A1) and one control antibody (III1D5; in the following examples referred to as 1D5) were kryoconserved and subcloned.

Example 3

Structure and Characteristics of Anti-AXL Antibodies 3.1. Nucleotide Sequences of Rat Antibody Variable Domains Rat anti-AXL antibody variable domains were cloned from hybridoma cells. RNA was prepared utilizing the RNA-Extraction kit RNeasy (RNeasy midi-kit, Qiagen). cDNA encoding for the antibody genes was prepared using the 5'RACE kit (Invitrogen) according to manufacturer's instructions. Briefly, first strand cDNA was synthesized from total or RNA using the gene-specific GSP1-primers and SuperScript™ II Reverse Transcriptase. After first strand cDNA synthesis, the original mRNA template is removed by treatment with the RNase Mix. A homopolymeric tail is then added to the 3'-end of the cDNA. PCR amplification is accomplished using Taq DNA polymerase, a nested, gene-specific primer (GSP2) that anneals to a site located within the cDNA molecule and an anchor primer provided with the kit. Following amplification 5' RACE products were cloned into the pLXSN-ESK vector for sequencing. To facilitate cloning the Anchor Primer (AP) included a recognition sequence for Sal I, GSP2 primers contained a XhoI site.

```
GSP1 primer:
kappa_GSP1:  GATGGATGCATTGGTGCAGC new_kappa_GSP1:  atagatacagttggtgcagc heavy_GSP1:  CAGGGTCACCATGGAGTTA GSP2 primer:
XhoI-hGSP2:  CCGCTCGAGCGGGCCAGTGGATAGACAGATGG XhoI-kGSP2:  CCGCTCGAGCGGCCGTTTCAGCTCCAGCTTGG
```

Utilization of GSP primers for rat anti-AXL Mab cloning:
11B7: kappa GSP1; XhoI-kGSP2
  heavy GSP1; XhoI-hGSP2
10D12: kappa_GSP1, new_kappa_GSP1; XhoI-kGSP2
  heavy GSP1; XhoI-hGSP2
11D5: new_kappa_GSP1, XhoI-kGSP2
  heavy GSP1; XhoI-hGSP2

3.2. Aminoacid Sequence Rat Anti-AXL Antibody Variable Domains

Rat antibody variable domain sequences were translated from sequenced genes cloned into the pLXSN-ESK vectors. The given amino acid sequences start at position one of the variable domain. The complementarity determining regions (CDRs) required for the specific binding of the antibody to its target are defined according to Kabat (Kabat et al. Sequences of Proteins of Immunological Interest, Fifth Edition. NIH Publication No. 91-3242, 1991). The Kabat definition is based on the sequence variability within the variable domains. Anti-AXL specific CDR regions of the antibodies are listed in FIG. 14 and SEQ ID NO: 121 to SEQ ID NO: 132.

The individual CDRs include the following positions:
CDR-L1: 24-34
CDR-L2: 50-56
CDR-L3: 89-97
CDR-H1: 31-35b
CDR-H2: 50-65
CDR-H3: 95-102

The amino acid sequence of the rat 11B7 antibody light and heavy chain variable regions are represented by SEQ ID NOs: 140 and 141, respectively. The subclasses of the light and heavy chains of the rat 11B7 antibody are kappa and IgG1, respectively.

The amino acid sequence of the rat 11D5 antibody light and heavy chain variable regions are represented by SEQ ID NOs: 142 and 143, respectively. The subclasses of the light and heavy chains of the rat 11D5 antibody are kappa and IgG2a, respectively.

3.3 Rat Antibody Expression and Purification:

Hybridomas were cultured in Celline CL 1000 bioreactors (Integra Biosciences) at 37° C., 5-7% CO2 using DMEM including 4.5 g/L glucose; 1% Glutamine, 1% Pyrovate 1% Pen/Strep. FCS supplementation is 1 FCS for the nutrient compartment and 5% low IgG FCS for the cell compartment. Harvest and media exchange is performed twice a week. Cell splitting 1/1->1/3 depending on cell growth. Productivity is tested once a week via SDS-PAGE analysis. Supernatants are stored at −20° C. until purification. Mycoplasma test of running cultures is done once a week.

Antibodies are purified using Protein A or G Sepharose FF (GE-Healthcare) via an Äkta Explorer 100 System (GE-Healthcare). Columns are individually packed for each purification. The column size is adjusted to the expected productivity and size of each batch (usually 50-500 mg). Protein containing solutions are kept on ice or at 4° C. wherever possible. Sterile buffers and double destined water are used for the entire process.

Supernatants are thawed, buffered with 50 mM TRIS pH 8.5, centrifuged, filtered through a 0.22 µm membrane and loaded onto the column. After washing with 8 column volumes (CV) 50 mM PO4, pH8.5 the antibody is eluted within 10 CV 100 mM Glycin, pH 3.3. Eluate fractions are rebuffered immediately to neutral pH by adding 1/5 µM Tris pH 8.0 (1 ml Tris per 4 ml eluate fraction) and analysed by rSDS-PAGE subsequently. Fractions containing pure antibody are pooled, dialysed against PBS at 4° C. and sterile filtered.

Buffer system requirements are adjusted according to the individual properties of each antibody. In particular, rat IgG2a antibody 11D5 was bound to ProteinG 4 FF matrix (GE-Healthcare) and washed under high salt conditions (2M NaCl). Rat antibody IgG1 11B7 was purified via rProteinA (GE-Healthcare) under high salt conditions according to 11D5. Antibody elution was performed at pH 5.5. Flow rate for rat antibody purification has to be kept low for increased binding efficiency.

As a second purification step either ion exchange chromatography (under individual, suitable conditions) or preparative size exclusion chromatography (PBS, pH 7.4) can be implemented.

The standard protocol for quality control of the purified antibodies includes:
rSDS-PAGE gel analysis; Coommassie or silver stained
BCA test (Pierce #23227 BCA Protein Assay Kit; rat IgG standard #31233)
Analytical size exclusion (Superdex 200 Tricorn 10/300 GL, ~250 mg in 250 µl; 0.5 ml/min, Akta Explorer 100)
Endotoxin test (LAL, Cambrex QCL-1000® Chromogenic LAL Endpoint Assay #US50-648U)
Cell based activity assays (FACS binding; pAkt; pAXL)

Purified antibodies are stored in PBS, pH 7.4 under steril conditions at 4° C. or −20° C. depending on their stability.

One of the obtained rat antibodies, 11B7, was applied to Examples 5, 6 and 16.

3.4. Antibody Affinity Determination by FACS Scatchard

Human AXL overexpression NIH3T3 cells were harvested by incubation with 10 mM EDTA in PBS and resuspended at 6 million cells per ml in FACS buffer (PBS pH 7.4, 3% FCS, 0.1% NaN3). In a round-bottom microtiter plate, 100 µl of cell suspension were added to 100 µl of antibody solution containing antibodies 11B7, 11D5, ch11B7-IgG1, ch11B7-IgG2, ch11D5-IgG1 or ch11D5-IgG2 at concentrations between 40 and 0.002 µg/ml (266 and 0.01 nM) in FACS buffer. Antibody binding was allowed to proceed for 2 hours on ice. Then, cells were washed twice with 250 µl FACS buffer per well, and resuspended in 200 µl of secondary antibody (anti-rat-PE; Jackson) diluted 1:50 in FACS buffer. After 45 minutes of incubation, cells were again washed twice in FACS buffer and resuspended in 500 ml PBS for FACS analysis. Analysis was carried out on a Beckman-Coulter FACS FC500. To determine the apparent affinity constant KDapp, mean fluorescence values were plotted against the ratio of mean fluorescence and the corresponding antibody concentration ([M]). The calculated KDapp resulted from the inverse slope of the straight line are listed below:

| Clone | KD value (nM) |
|---|---|
| 11B7 | 0.38 |
| ch11B7-IgG1 | 0.6 |
| 11D5 | 0.81 |
| Ch11D5-IgG1 | 0.4 |

The KD values listed above include those of chimeric antibodies obtained in Example 4.

Example 4

Chimerization of Rat Anti-AXL Antibodies

Human kappa light chain and heavy chain IgG1/2 genes were cloned from peripheral blood mononuclear cells (PBMC) of a human volunteer as described below:

PBMCs were prepared from whole blood. Blood was diluted 1/2, 5 in PBS/2 mM EDTA with 10 U/ml heparin at RT, layered over 15 ml Biocoll solution covered by a diaphragm (35 ml/tube) [Biocoll from Biochrom #L6115]. Samples were centrifuged at RT for 30 min at 400×g and serum (~15 ml) was discarded. Interface containing PBMCs was carefully recovered using a Pasteur pipette. PBMCs were washed 2× in PBS/2 mM EDTA (first wash 100 ml, second wash 50 ml) and spun down at 300×g for 10 min. Cell pellet was resuspended in RPM/10% FCS (25 ml) and yielded 5.5× 10"7 PBMCs. RNA was prepared from PBMCs using RNeasy kit from Qiagen (#75142) according to manufacturer's instructions. Purified RNA (30 µg) was stored in aliquots at −80° C.

cDNA for antibody IgG gamma 1 and 2 as well as kappa chains were prepared from isolated RNA by RT-PCR using Superskript III Reverse Transkriptase (invitrogen #18080-93) according to manufacturers instructions using the following primers:

```
1) RT-gamma:
GCG TGT AGT GGT TGT GCA GAG

2) RT-gamma2:
ggg ctt gcc ggc cgt g

3) RT-kappa:
TGG AAC TGA GGA GCA GGT GG 4) 5'Blp:
AGA TAA GCT TTG CTC AGC GTC CAC CAA GGG CCC ATC

GGT 5) 3'Bam(GAG):
AGA TGG ATC CTC ATT TAC CCG GAG ACA GGG AGA G 6) 5'Bsi:
AGA TAA GCT TCG TAC GGT GGC TGC ACC ATC TGT CTT

CAT 7) 3'Bam(CTT):
AGA TGG ATC CCT AAC ACT CTC CCC TGT TGA AGC TCT
```

Primers were dissolved at 100 μM. RT-PCR reactions were performed using 2 pmol oligo RTγ and RTκ respectively, adding 1 μg RNA, 10 mM dNTP mix and heat for 5 min to 65° C. 4 μl first strand buffer, 1 μl 0.1M DTT, 1 μl RNase inhibitor (40 U/μl Fermentas #E00311) and 2 μl Superscript III RT were added, mixed and incubated at 50° C. for 1 h followed by a heat inactivation step for 15 min at 70° C.

2 μl of first strand reaction were used for second step PCR using Taq polymerase (Eurochrom #EME010001) to yield double stranded DNA of antibody constant domains. The primer 5'Blp and 3'Bam(GAG) were used to amplify γ̃ chain, and 5'Bsi and 3'Bam(CTT) were used to amplify κ-chain constant regions using the following PCR settings.

κ-chain amplification:

| 94° C. | 120 sec |
| 94° C. | 30 sec |
| 55° C. | 30 sec |
| 72° C. | 45 sec cycle 35 times |
| 72° C. | 10 min |

γ̃-chain amplification:

| 94° C. | 120 sec |
| 94° C. | 30 sec |
| 45° C. | 30 sec |
| 72° C. | 60 sec cycle 5 times |
| 94° C. | 30 sec |
| 50° C. | 30 sec |
| 72° C. | 60 sec cycle 35 times |
| 72° C. | 10 min |

The PCR products were analysed on a TAE buffered 2% agarose gel. A single band of ~350 bp for kappa light chain and a single band of ~1000 bp for the heavy chains γ1 and γ2 were found. The PCR products were purified by Qiagen gel extraction kit, (QIAGEN, #28784) according to the manufacturer's instructions. To clone the PCR fragments into the multiple cloning site of the pcDNA3 vector (Invitrogen), pcDNA3 vector and PCR fragments were digested with HindIII (5') and BamHI (3') restriction endonucleases. Restriction sites were encoded within the PCR primers. Digested fragments were purified using the Qiagen PCR purification kit (QIAGEN, 28104), and DNA encoding the γ1, γ2̃, and κ chains were ligated into the pcDNA3 vector facilitating T4 DNA ligase at 16° C. overnight. Ligase was inactivated for 10 min. at 65° C. Ligated DNA plasmids were directly transformed into CaCl2 competent *E. coli* using standard protocol and plated onto Ampicillin containing LB-plates. After incubation at 37° C. overnight single colonies were picked, suspended in 10 μl H2O and proofed for containing the respective antibody chain carrying plasmid by PCR (5 μl suspended cells, Taq polymerase, primer 5Blp and 3Bam(GAG) γ1/γ2̃ and 5Bsi and 3Bam(CTT) for κ colonies:

| 94° C. | 120 sec |
| 94° C. | 30 sec |
| 55° C. | 30 sec |
| 72° C. | 60 sec cycle 35 times |
| 72° C. | 10 min |

Samples were analysed on 1.5% agarose gel for PCR products. Antibody gene containing colonies were selected to inoculate 5 ml LB/Ampicillin medium. After incubation at 37° C. overnight *E. coli* were harvested and DNA was prepared using Qiagen miniprep kit (QIAGEN, #12123). A control digest (HindIII, BamHI) showed all κ and γ chain gene inserts at the expected size; sequences were verified by DNA sequencing at Medigenomix.

Rat variable domains were amplified by PCR from pLXSN-ESK vector and cloned into g1/g2 and k pcDNA3 vectors to yield the chimeric full length antibodies. Variable VL domains were amplified with the following primers, containing a HindIII and BsmI site at the 5' end and a BsiWI site at the 3' end:

```
VL-11B7-5':
AGA TAA GCT TGT GCA TTC CGA CAT CCA GAT GAC CCA

GGC TCC

VL-11B7-3':
AGA TCG TAC GTT TCA GCT CCA GCT TGG TGC CTC

VL-11D5-5':
AGA TAA GCT TGT GCA TTC CGA CAT CCA GAT GAC CCA

GTC TCC ATC

VL-11D5-3':
AGA TCG TAC GTT TCA GCT TGG TCC CAG
```

Variable VH domains were amplified with the following primers, containing a HindIII and BsmI site at the 5' end and a BlpI site at the 3' end:

```
VH-11 B7/11 D5-5':
AGA TAA GCT TGT GCA TTC CGA GGT GCA GCT TCA GGA

GTC AGG

VH-11 B7/11 D5-3':
AGA TGC TGA GCT GAC AGT GAC CAT GAC TCC TTG GCC
```

BsiWI for the light chain and the BlpI for the heavy chain are single sites at the 5' end of the constant regions to enable the direct fusion with the 3' end of the variable domain genes.

Fused to the Leader sequence SEQ ID No.: 133 derived from pLNOH2 vector (Norderhaug et. al. J. Immunol. Methods 204, 1997; Neuberger EMBO J. 1983; 2 (8): 1373-8, 1983) genes encoding the chimeric antibody chains were cloned into pCEP vector system for recombinant expression. Light chain genes were cloned NheI (5') and XhoI (3') into pCEP4 (Invitrogen) heavy chain genes KpnI (5') and XhoI (3') into pCEP-Pu (Kohfeld FEBS Vol 414; (3) 557ff, 1997).

HEK 293 cells seeded on 20×20 cm plates were co-transfected with 1 µg/ml of each plasmid coding for light and heavy chain genes using standard CaPO4 transfection method for transient expression. Culture conditions were 37° C., 5% CO2 in DMEM/F12 high glucose medium containing 5% low IgG FCS, 1% pyrovate, 1% glutamine, 1% penicillin/streptomycin. 24 h after transfection medium was exchanged by fresh medium. Supernatants were collected every 2-3 days for approximately 3 weeks. Chimeric antibodies were purified from approximately 600 ml supernatant utilizing 1 ml Hitrap rProtein A columns (GE-Healthcare) under standard buffer conditions (loading: 50 mM Tris; pH=8.5, wash: 50 mM PO4; pH=8.5, elution: 100 mM Glycin; pH 3.3) as described for rat antibody purification.

One of the obtained chimeric molecules derived from rat 11B7 antibody consists of a human IgG1 heavy chain represented by the amino acid sequence of SEQ ID NO: 136 (FIG. 14) and a human kappa light chain represented by the amino acid sequence of SEQ ID NO: 135 (FIG. 14).

One of the obtained chimeric molecules derived from rat 11D5 antibody consists of a human IgG1 heavy chain represented by the amino acid sequence of SEQ ID NO: 138 (FIG. 14) and a human kappa light chain represented by the amino acid sequence of SEQ ID NO: 137 (FIG. 14).

These chimeric 11B7 and 11D5 antibodies, designated as ch11B7-IgG1 and ch11D5-IgG1, respectively, were applied to Examples 3, 13, 14 and 17 to 20.

Example 5

Rat Anti-AXL Antibodies of the Invention Reduce Human Prostate Carcinoma Growth in Nude Mice The anti-tumor efficacy of therapeutic antibodies is often evaluated in human xenograft tumor studies. In these model systems, human tumors grow as xenografts in immunocompromised mice and therapeutic efficacy is measured by the degree of tumor growth inhibition. The aim of this study was to evaluate whether the antagonistic rat anti-AXL antibody 11B7 of the invention interferes with tumor growth of human prostate cancer cells in nude mice. In brief, on day 0, 7-8 weeks old male NMR$^{-nu/nu}$ mice (approximate weight: 30 g after acclimatization) were anesthesized with 1.5-2.0 volume percent isoflurane at an oxygen flow rate of 2 l/min, and 1×10$^6$ PC-3-LN cells in 25 µl PBS were orthotopically implanted into the prostate. PC-3-LN cells are derived from the PC-3 prostate carcinoma cell line which was infected with a retrovirus coding for a luciferase-neomycin fusion protein. The onset of tumor growth and tumor growth progression was therefore measurable via in vivo bioluminescence imaging. For this purpose, luciferin was injected intraperitoneally (i.p.) into the mice and light emission was measured 10 min post injection using a NightOWL LB 981 bioluminescence imaging system (Berthold Technologies, Germany). Prior to first treatment, mice were randomized and statistical tests performed to assure uniformity in starting tumor volumes (mean, median and standard deviation) across the treatment groups of 10 animals each. On day 8, all treatments started and were continued until day 34, followed by necropsy on day 35. 25 mg/kg of the isotypic control antibody 1D5 and the antagonistic rat anti-AXL antibody 11B7 were intraperitoneally (i.p.) administered 3× a week (Mo, Wed, Fr) into animals of group 1 and 2, respectively. Animals of group 3 orally (p.o.) received 40 mg/kg of Sutent once a day. Animals of Group 4 received three intraveneous (i.v.) injections with 12.5 mg/kg of Taxotere 4 days apart of each other. An overview of the treatment groups is given below.

FIG. 16 shows the results of this experiment. Compared to the isotypic control antibody 1D5, the antagonistic rat anti-AXL antibody 11B7 of the invention reduced the overall growth of PC-3-LN prostate tumors in nude mice.

Example 6

Rat Anti-AXL Antibodies of the Invention Inhibit Metastasis of Human Prostate Carcinoma In the same experiment as described under "Rat anti-AXL antibodies of the invention reduce human prostate carcinoma growth in nude mice", relocalization of PC-3-LN tumor cells into other organs (metastasis) was analyzed post necropsy to evaluate anti-metastatic effects of the antagonistic rat anti-AXL antibody 11B7 of the invention. For this purpose, selected organs (liver, spleen, lungs, femur, part of the lumbar spine) were collected post necropsy, homogenized, and supplemented with luciferin. Subsequently, light emission was measured using a NightOWL LB 981 bioluminescence imaging system (Berthold Technologies, Germany).

FIG. 17 shows the results of this experiment for the analysis of spleens. Compared to the isotypic control antibody 1D5, the antagonistic rat anti-AXL antibody 11B7 of the invention reduced the occurrence of spleen metastases. Noteworthy, the anti-metastatic effect of 11B7 in this experiment was stronger than that of Sutent. Similar observations were obtained for liver, lung, femur, and lumbar spine metastasis.

Example 7

Design of Humanized Antibody 7.1 Design of Humanized Version of #11B7
7.1.1 Molecular Modeling of #11B7 Variable Domains The molecular modeling of #11B7 variable domains was practised according to the method generally known in the art as homology modeling (Methods in Enzymology, 203, 121-153, (1991)). The primary sequences (three-dimensional structures derived from X-ray crystal structures are available) of human immunoglobulin variable domains registered in Protein Data Bank (Nuc. Acid Res. 35, D301-D303 (2007)) were compared with the #11B7 variable domains thus determined. As a result, 1JPT was selected as having the highest sequence homology to the #11B7 light chain variable domain. Moreover, 1F8T was selected as having the highest sequence homology to the #11B7 heavy chain variable domain. The three-dimensional structures of framework domains were prepared based on a "framework model" obtained by combining the coordinates of 1JPT and 1F8T corresponding to the #11B7 light and heavy chains. For #11B7 CDRs, CDRL$_1$, CDRL$_2$, CDRL$_3$, CDRH$_1$, and CDRH$_2$ were assigned to clusters 11A, 7A, 9A, 10A, and 9A, respectively, according to the classification of Thornton et al. (J. Mol. Biol., 263, 800-815, (1996)). CDRH$_3$ was classified in k (3)-according to the H3-rules (FEBS letters 399, 1-8 (1996)). Subsequently, the typical conformation of each CDR was incorporated in the framework model.

Finally, to obtain possible molecular models of the #11B7 variable domains in terms of energy, energy calculation was conducted for excluding disadvantageous interatomic contact. These procedures were performed using a commercially available three-dimensional protein structure prediction program Prime and coordinate search program MacroModel (Schrödinger, LLC).

7.1.2 Design of Amino Acid Sequence of Humanized #11B7

Humanized #11B7 antibodies were constructed according to the method generally known in the art as CDR grafting (Proc. Natl. Acad. Sci. USA 86, 10029-10033 (1989)). Acceptor antibodies were selected in two ways based on amino acid homology within the framework domains.

The sequences of the #11B7 framework domains were compared with those of all human frameworks registered in the Kabat Database (Nuc. Acid Res. 29, 205-206 (2001)) involving antibody amino acid sequences. As a result, a GM4672'CL antibody was selected as an acceptor due to 72% sequence homology between their framework domains. The amino acid residues of the framework domains in GM4672'CL were aligned with the corresponding amino acid residues in #11B7 to identify positions where different amino acids there between were used. The positions of these residues were analysed using the three-dimensional model of #11B7 thus constructed. Then, donor residues to be grafted on the acceptor were selected according to the criteria provided by Queen et al. (Proc. Natl. Acad. Sci. USA 86, 10029-10033 (1989)).

The sequences of the #11B7 framework domains were compared with those of all human frameworks registered in IgBLAST (Nuc. Acid Res. 36, D25-D30 (2007)). As a result, BAC01582 was selected as an L chain acceptor due to 76% sequence homology between their framework domains. AAF80028 was selected as an H chain acceptor due to 66% sequence homology between their framework domains. The amino acid residues of the framework domains in the BAC01582 L chain and in the AAF80028 H chain were aligned with the corresponding amino acid residues in #11B7 to identify positions where different amino acids therebetween were used. The positions of these residues were analysed using the three-dimensional model of #11B7 thus constructed. Then, donor residues to be grafted on the acceptor were selected according to the criteria provided by Queen et al. (Proc. Natl. Acad. Sci. USA 86, 10029-10033 (1989)).

In all methods, humanized #11B7 sequences were constructed as described in Examples below by transferring some selected donor residues to the acceptor antibodies.

7.1.3 Humanization of #11B7 light chain (FIGS. 1, 2 and 3)

7.1.3.1 h#11B7-T1L-Type Light Chain:

A humanized #11B7 light chain variable region designed by substituting amino acid Nos. 7 (alanine), 12 (proline), 15 (leucine), 36 (phenylalanine), 43 (serine), 45 (arginine), 47 (methionine), 65 (serine), 66 (arginine), 69 (serine), 71 (tyrosine), 72 (serine), 73 (leucine), 79 (glutamic acid), 80 (serine), 83 (methionine), 85 (aspartic acid), 104 (leucine), 106 (leucine), and 109 (proline) of #11B7 light chain variable region represented by SEQ ID NO: 140 of Sequence Listing (FIG. 30B) by serine, serine, valine, tyrosine, alanine, lysine, leucine, threonine, glycine, threonine, phenylalanine, threonine, phenylalanine, glutamine, proline, phenylalanine, threonine, valine, isoleucine, and threonine, respectively, was designated as "h#11B7-T1L"-type light chain variable region.

7.1.3.2 h#11B7-T2L-Type Light Chain:

A humanized #11B7 light chain variable region designed by substituting amino acid Nos. 7 (alanine), 12 (proline), 15 (leucine), 43 (serine), 45 (arginine), 65 (serine), 66 (arginine), 69 (serine), 72 (serine), 73 (leucine), 79 (glutamic acid), 80 (serine), 83 (methionine), 85 (aspartic acid), 104 (leucine), 106 (leucine), and 109 (proline) of #11B7 light chain variable region represented by SEQ ID NO: 140 of Sequence Listing (FIG. 30B) by serine, serine, valine, alanine, lysine, threonine, glycine, threonine, threonine, phenylalanine, glutamine, proline, phenylalanine, threonine, valine, isoleucine, and threonine, respectively, was designated as "h#11B7-T2L"-type light chain variable region.

7.1.3.3 h#11B7-T3L-Type Light Chain:

A humanized #11B7 light chain variable region designed by substituting amino acid Nos. 7 (alanine), 12 (proline), 15 (leucine), 43 (serine), 45 (arginine), 72 (serine), 79 (glutamic acid), 80 (serine), 83 (methionine), 85 (aspartic acid), 104 (leucine), 106 (leucine), and 109 (proline) of #11B7 light chain variable region represented by SEQ ID NO: 140 of Sequence Listing (FIG. 30B) by serine, serine, valine, alanine, lysine, threonine, glutamine, proline, phenylalanine, threonine, valine, isoleucine, and threonine, respectively, was designated as "h#11B7-T3L"-type light chain variable region.

7.1.3.4 h#11B7-T4L-Type Light Chain:

A humanized #11B7 light chain variable region designed by substituting amino acid Nos. 7 (alanine), 12 (proline), 15 (leucine), 36 (phenylalanine), 43 (serine), 45 (arginine), 47 (methionine), 66 (arginine), 71 (tyrosine), 72 (serine), 79 (glutamic acid), 80 (serine), 83 (methionine), 85 (aspartic acid), 100 (glycine), 106 (leucine), and 109 (proline) of #11B7 light chain variable region represented by SEQ ID NO: 140 of Sequence Listing (FIG. 30B) by serine, serine, valine, tyrosine, alanine, lysine, leucine, glycine, phenylalanine, threonine, glutamine, proline, phenylalanine, threonine, glutamine, isoleucine, and threonine, respectively, was designated as "h#11B7-T4L"-type light chain variable region.

7.1.3.5 h#11B7-T5L-Type Light Chain:

A humanized #11B7 light chain variable region designed by substituting amino acid Nos. 7 (alanine), 12 (proline), 15 (leucine), 43 (serine), 45 (arginine), 66 (arginine), 72 (serine), 79 (glutamic acid), 80 (serine), 83 (methionine), 85 (aspartic acid), 100 (glycine), 106 (leucine), and 109 (proline) of #11B7 light chain variable region represented by SEQ ID NO: 140 of Sequence Listing (FIG. 30B) by serine, serine, valine, alanine, lysine, glycine, threonine, glutamine, proline, phenylalanine, threonine, glutamine, isoleucine, and threonine, respectively, was designated as "h#11B7-T5L"-type light chain variable region.

7.1.3.6 h#11B7-T6L-Type Light Chain:

A humanized #11B7 light chain variable region designed by substituting amino acid Nos. 7 (alanine), 12 (proline), 15 (leucine), 43 (serine), 45 (arginine), 66 (arginine), 72 (serine), 79 (glutamic acid), 80 (serine), 83 (methionine), 85 (aspartic acid), 100 (glycine), 104 (leucine), 106 (leucine), and 109 (proline) of #11B7 light chain variable region represented by SEQ ID NO: 140 of Sequence Listing (FIG. 30B) by serine, serine, valine, alanine, lysine, glycine, threonine, glutamine, proline, phenylalanine, threonine, glutamine, valine, isoleucine, and threonine, respectively, was designated as "h#11B7-T6L"-type light chain variable region.

7.1.3.7 h#11B7-T7L-Type Light Chain:

A humanized #11B7 light chain variable region designed by substituting amino acid Nos. 7 (alanine), 12 (proline), 15 (leucine), 36 (phenylalanine), 43 (serine), 45 (arginine), 66 (arginine), 72 (serine), 79 (glutamic acid), 80 (serine), 83 (methionine), 85 (aspartic acid), 100 (glycine), 104 (leucine), 106 (leucine), and 109 (proline) of #11B7 light chain variable region represented by SEQ ID NO: 140 of Sequence Listing (FIG. 30B) by serine, serine, valine, tyrosine, alanine, lysine, glycine, threonine, glutamine, proline, phenylalanine, threonine, glutamine, valine, isoleucine, and threonine, respectively, was designated as "h#11B7-T7L"-type light chain variable region.

7.1.3.8 h#11B7-T8L-Type Light Chain:

A humanized #11B7 light chain variable region designed by substituting amino acid Nos. 7 (alanine), 12 (proline), 15

(leucine), 43 (serine), 45 (arginine), 47 (methionine), 66 (arginine), 72 (serine), 79 (glutamic acid), 80 (serine), 83 (methionine), 85 (aspartic acid), 100 (glycine), 104 (leucine), 106 (leucine), and 109 (proline) of #11B7 light chain variable region represented by SEQ ID NO: 140 of Sequence Listing (FIG. 30B) by serine, serine, valine, alanine, lysine, leucine, glycine, threonine, glutamine, proline, phenylalanine, threonine, glutamine, valine, isoleucine, and threonine, respectively, was designated as "h#11B7-T8L"-type light chain variable region.

7.1.3.9 h#11B7-T9L-Type Light Chain:

A humanized #11B7 light chain variable region designed by substituting amino acid Nos. 7 (alanine), 12 (proline), 15 (leucine), 43 (serine), 45 (arginine), 66 (arginine), 71 (tyrosine), 72 (serine), 79 (glutamic acid), 80 (serine), 83 (methionine), 85 (aspartic acid), 100 (glycine), 104 (leucine), 106 (leucine), and 109 (proline) of #11B7 light chain variable region represented by SEQ ID NO: 140 of Sequence Listing (FIG. 30B) by serine, serine, valine, alanine, lysine, glycine, phenylalanine, threonine, glutamine, proline, phenylalanine, threonine, glutamine, valine, isoleucine, and threonine, respectively, was designated as "h#11B7-T9L"-type light chain variable region.

7.1.3.10 h#11B7-T10L-Type Light Chain:

A humanized #11B7 light chain variable region designed by substituting amino acid Nos. 7 (alanine), 12 (proline), 15 (leucine), 36 (phenylalanine), 43 (serine), 45 (arginine), 47 (methionine), 66 (arginine), 72 (serine), 79 (glutamic acid), 80 (serine), 83 (methionine), 85 (aspartic acid), 100 (glycine), 104 (leucine), 106 (leucine), and 109 (proline) of #11B7 light chain variable region represented by SEQ ID NO: 140 of Sequence Listing (FIG. 30B) by serine, serine, valine, tyrosine, alanine, lysine, leucine, glycine, threonine, glutamine, proline, phenylalanine, threonine, glutamine, valine, isoleucine, and threonine, respectively, was designated as "h#11B7-T10L"-type light chain variable region.

7.1.3.11 h#11B7-T11L-Type Light Chain:

A humanized #11B7 light chain variable region designed by substituting amino acid Nos. 7 (alanine), 12 (proline), 15 (leucine), 43 (serine), 45 (arginine), 47 (methionine), 66 (arginine), 71 (tyrosine), 72 (serine), 79 (glutamic acid), 80 (serine), 83 (methionine), 85 (aspartic acid), 100 (glycine), 104 (leucine), 106 (leucine), and 109 (proline) of #11B7 light chain variable region represented by SEQ ID NO: 140 of Sequence Listing (FIG. 30B) by serine, serine, valine, alanine, lysine, leucine, glycine, phenylalanine, threonine, glutamine, proline, phenylalanine, threonine, glutamine, valine, isoleucine, and threonine, respectively, was designated as "h#11B7-T11L"-type light chain variable region.

7.1.3.12 h#11B7-T12L-Type Light Chain:

A humanized #11B7 light chain variable region designed by substituting amino acid Nos. 7 (alanine), 12 (proline), 15 (leucine), 36 (phenylalanine), 43 (serine), 45 (arginine), 66 (arginine), 71 (tyrosine), 72 (serine), 79 (glutamic acid), 80 (serine), 83 (methionine), 85 (aspartic acid), 100 (glycine), 104 (leucine), 106 (leucine), and 109 (proline) of #11B7 light chain variable region represented by in SEQ ID NO: 140 of Sequence Listing (FIG. 30B) by serine, serine, valine, tyrosine, alanine, lysine, glycine, phenylalanine, threonine, glutamine, proline, phenylalanine, threonine, glutamine, valine, isoleucine, and threonine, respectively, was designated as "h#11B7-T12L"-type light chain variable region.

7.1.3.13 h#11B7-T13L-Type Light Chain:

A humanized #11B7 light chain variable region designed by substituting amino acid Nos. 7 (alanine), 12 (proline), 15 (leucine), 36 (phenylalanine), 43 (serine), 45 (arginine), 47 (methionine), 66 (arginine), 71 (tyrosine), 72 (serine), 79 (glutamic acid), 80 (serine), 83 (methionine), 85 (aspartic acid), 100 (glycine), 104 (leucine), 106 (leucine), and 109 (proline) of #11B7 light chain variable region represented by SEQ ID NO: 140 of Sequence Listing (FIG. 30B) by serine, serine, valine, tyrosine, alanine, lysine, leucine, glycine, phenylalanine, threonine, glutamine, proline, phenylalanine, threonine, glutamine, valine, isoleucine, and threonine, respectively, was designated as "h#11B7-T13L"-type light chain variable region.

7.1.3.14 h#11B7-T14L-Type Light Chain:

A humanized #11B7 light chain variable region designed by substituting amino acid Nos. 7 (alanine), 12 (proline), 15 (leucine), 36 (phenylalanine), 43 (serine), 45 (arginine), 66 (arginine), 72 (serine), 79 (glutamic acid), 80 (serine), 83 (methionine), 85 (aspartic acid), 100 (glycine), 106 (leucine), and 109 (proline) of #11B7 light chain variable region represented by SEQ ID NO: 140 of Sequence Listing (FIG. 30B) by serine, serine, valine, tyrosine, alanine, lysine, glycine, threonine, glutamine, proline, phenylalanine, threonine, glutamine, isoleucine, and threonine, respectively, was designated as "h#11B7-T14L"-type light chain variable region.

7.1.3.15 h#11B7-T15L-Type Light Chain:

A humanized #11B7 light chain variable region designed by substituting amino acid Nos. 7 (alanine), 12 (proline), 15 (leucine), 43 (serine), 45 (arginine), 47 (methionine), 66 (arginine), 72 (serine), 79 (glutamic acid), 80 (serine), 83 (methionine), 85 (aspartic acid), 100 (glycine), 106 (leucine), and 109 (proline) of #11B7 light chain variable region represented by SEQ ID NO: 140 of Sequence Listing (FIG. 30B) by serine, serine, valine, alanine, lysine, leucine, glycine, threonine, glutamine, proline, phenylalanine, threonine, glutamine, isoleucine, and threonine, respectively, was designated as "h#11B7-T15L"-type light chain variable region.

7.1.3.16 h#11B7-T16L-Type Light Chain:

A humanized #11B7 light chain variable region designed by substituting amino acid Nos. 7 (alanine), 12 (proline), 15 (leucine), 43 (serine), 45 (arginine), 66 (arginine), 71 (tyrosine), 72 (serine), 79 (glutamic acid), 80 (serine), 83 (methionine), 85 (aspartic acid), 100 (glycine), 106 (leucine), and 109 (proline) of #11B7 light chain variable region represented by SEQ ID NO: 140 of Sequence Listing (FIG. 30B) by serine, serine, valine, alanine, lysine, glycine, phenylalanine, threonine, glutamine, proline, phenylalanine, threonine, glutamine, isoleucine, and threonine, respectively, was designated as "h#11B7-T16L"-type light chain variable region.

7.1.3.17 h#11B7-T17L-Type Light Chain:

A humanized #11B7 light chain variable region designed by substituting amino acid Nos. 7 (alanine), 12 (proline), 15 (leucine), 36 (phenylalanine), 43 (serine), 45 (arginine), 47 (methionine), 66 (arginine), 72 (serine), 79 (glutamic acid), 80 (serine), 83 (methionine), 85 (aspartic acid), 100 (glycine), 106 (leucine), and 109 (proline) of #11B7 light chain variable region represented by SEQ ID NO: 140 of Sequence Listing (FIG. 30B) by serine, serine, valine, tyrosine, alanine, lysine, leucine, glycine, threonine, glutamine, proline, phenylalanine, threonine, glutamine, isoleucine, and threonine, respectively, was designated as "h#11B7-T17L"-type light chain variable region.

7.1.3.18 h#11B7-T18L-Type Light Chain:

A humanized #11B7 light chain variable region designed by substituting amino acid Nos. 7 (alanine), 12 (proline), 15 (leucine), 43 (serine), 45 (arginine), 47 (methionine), 66 (arginine), 71 (tyrosine), 72 (serine), 79 (glutamic acid), 80 (serine), 83 (methionine), 85 (aspartic acid), 100 (glycine), 106 (leucine), and 109 (proline) of #11B7 light chain variable region represented by SEQ ID NO: 140 of Sequence Listing (FIG. 30B) by serine, serine, valine, alanine, lysine, leucine, glycine, phenylalanine, threonine, glutamine, proline, phenylalanine, threonine, glutamine, isoleucine, and threonine, respectively, was designated as "h#11B7-T18L"-type light chain variable region.

7.1.3.19 h#11B7-T19L-Type Light Chain:

A humanized #11B7 light chain variable region designed by substituting amino acid Nos. 7 (alanine), 12 (proline), 15 (leucine), 36 (phenylalanine), 43 (serine), 45 (arginine), 66 (arginine), 71 (tyrosine), 72 (serine), 79 (glutamic acid), 80 (serine), 83 (methionine), 85 (aspartic acid), 100 (glycine), 106 (leucine), and 109 (proline) of #11B7 light chain variable region represented by SEQ ID NO: 140 of Sequence Listing (FIG. 30B) by serine, serine, valine, tyrosine, alanine, lysine, glycine, phenylalanine, threonine, glutamine, proline, phenylalanine, threonine, glutamine, isoleucine, and threonine, respectively, was designated as "h#11B7-T19L"-type light chain variable region.

7.1.3.20 h#11B7-T20L-Type Light Chain:

A humanized #11B7 light chain variable region designed by substituting, amino acid Nos. 7 (alanine), 12 (proline), 15 (leucine), 36 (phenylalanine), 43 (serine), 45 (arginine), 47 (methionine), 66 (arginine), 71 (tyrosine), 72 (serine), 79 (glutamic acid), 80 (serine), 83 (methionine), 85 (aspartic acid), 100 (glycine), 106 (leucine), and 109 (proline) of #11B7 light chain variable region represented by SEQ ID NO: 140 of Sequence Listing (FIG. 30B) by serine, serine, valine, tyrosine, alanine, lysine, leucine, glycine, phenylalanine, threonine, glutamine, proline, phenylalanine, threonine, glutamine, isoleucine, and threonine, respectively, was designated as "h#11B7-T20L"-type light chain variable region.

7.1.4 Humanization of #11B7 heavy chain (FIGS. 4 and 5)

7.1.4.1 h#11B7-T1H-Type Heavy Chain:

A humanized #11B7 heavy chain variable region designed by substituting amino acid Nos. 1 (glutamic acid), 2 (valine), 17 (serine), 23 (serine), 25 (threonine), 39 (lysine), 40 (phenylalanine), 43 (aspartic acid), 44 (lysine), 45 (methionine), 48 (methionine), 67 (isoleucine), 68 (serine), 70 (threonine), 71 (arginine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, isoleucine, threonine, alanine, serine, glutamine, proline, lysine, glycine, leucine, isoleucine, valine, threonine, serine, valine, serine, lysine, serine, alanine, alanine, valine, threonine, and leucine, respectively, was designated as "h#11B7-T1H"-type heavy chain variable region.

7.1.4.2 h#11B7-12H-Type Heavy Chain:

A humanized #11B7 heavy chain variable region designed by substituting amino acid Nos. 1 (glutamic acid), 2 (valine), 17 (serine), 23 (serine), 25 (threonine), 39 (lysine), 40 (phenylalanine), 43 (aspartic acid), 44 (lysine), 45 (methionine), 70 (threonine), 71 (arginine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, isoleucine, threonine, alanine, serine, glutamine, proline, lysine, glycine, leucine, serine, valine, serine, lysine, serine, alanine, alanine, valine, threonine, and leucine, respectively, was designated as "h#11B7-T2H"-type heavy chain variable region.

7.1.4.3 h#11B7-T3H-Type Heavy Chain:

A humanized #11B7 heavy chain variable region designed by substituting amino acid Nos. 1 (glutamic acid), 17 (serine), 23 (serine), 25 (threonine), 40 (phenylalanine), 44 (lysine), 45 (methionine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, threonine, alanine, serine, proline, glycine, leucine, serine, lysine, serine, alanine, alanine, valine, threonine, and leucine, respectively, was designated as "h#11B7-T3H"-type heavy chain variable region.

7.1.4.4 h#11B7-T4H-Type Heavy Chain:

A humanized #11B7 heavy chain variable region designed by substituting amino acid Nos. 1 (glutamic acid), 6 (glutamic acid), 7 (serine), 9 (proline), 12 (valine), 16 (glutamine), 17 (serine), 23 (serine), 25 (threonine), 39 (lysine), 40 (phenylalanine), 43 (aspartic acid), 44 (lysine), 45 (methionine), 48 (methionine), 67 (isoleucine), 68 (serine), 70 (threonine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, glutamine, tryptophan, alanine, leucine, glutamic acid, threonine, threonine, serine, glutamine, proline, lysine, glycine, leucine, isoleucine, valine, threonine, serine, serine, lysine, serine, alanine, alanine, valine, threonine, and threonine, respectively, was designated as "h#11B7-T4H"-type heavy chain variable region.

7.1.4.5 h#11B7-T5H-Type Heavy Chain:

A humanized #11B7 heavy chain variable region designed by substituting amino acid Nos. 1 (glutamic acid), 6 (glutamic acid), 7 (serine), 9 (proline), 12 (valine), 16 (glutamine), 17 (serine), 23 (serine), 25 (threonine), 39 (lysine), 40 (phenylalanine), 43 (aspartic acid), 44 (lysine), 45 (methionine), 70 (threonine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, glutamine, tryptophan, alanine, leucine, glutamic acid, threonine, threonine, serine, glutamine, proline, lysine, glycine, leucine, serine, serine, lysine, serine, alanine, alanine, valine, threonine, and threonine, respectively, was designated as "h#11B7-T5H"-type heavy chain variable region.

7.1.4.6 h#11B7-T6H-Type Heavy Chain:

A humanized #11B7 heavy chain variable region designed by substituting amino acid Nos. 1 (glutamic acid), 16 (glutamine), 17 (serine), 23 (serine), 25 (threonine), 39 (lysine), 40 (phenylalanine), 43 (aspartic acid), 44 (lysine), 45 (methionine), 70 (threonine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, glutamic acid, threonine, threonine, serine, glutamine, proline, lysine, glycine, leucine, serine, serine, lysine, serine, alanine, alanine, valine, threonine, and leucine, respectively, was designated as "h#11B7-T6H"-type heavy chain variable region.

7.1.4.7 h#11B7-T7H-Type Heavy Chain:

A humanized #11B7 heavy chain variable region designed by substituting amino acid Nos. 1 (glutamic acid), 16 (glutamine), 17 (serine), 23 (serine), 25 (threonine), 39 (lysine), 40 (phenylalanine), 43 (aspartic acid), 44 (lysine), 45 (methionine), 48 (methionine), 67 (isoleucine), 70 (threonine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, glutamic acid, threonine, threonine, serine, glutamine, proline, lysine, glycine, leucine, isoleucine, valine, serine, serine, lysine, serine, alanine, alanine, valine, threonine, and leucine, respectively, was designated as "h#11B7-T7H"-type heavy chain variable region.

7.1.4.8 h#11B7-T8H-Type Heavy Chain:

A humanized #11B7 heavy chain variable region designed by substituting amino acid Nos. 1 (glutamic acid), 16 (glutamine), 17 (serine), 23 (serine), 25 (threonine), 39 (lysine), 40 (phenylalanine), 43 (aspartic acid), 44 (lysine), 45 (methionine), 68 (serine), 70 (threonine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, glutamic acid, threonine, threonine, serine, glutamine, proline, lysine, glycine, leucine, threonine, serine, serine, lysine, serine, alanine, alanine, valine, threonine, and leucine, respectively, was designated as "h#11B7-T8H"-type heavy chain variable region.

7.1.4.9 h#11B7-T9H-Type Heavy Chain:

A humanized #11B7 heavy chain variable region designed by substituting amino acid Nos. 1 (glutamic acid), 16 (glutamine), 17 (serine), 23 (serine), 25 (threonine), 39 (lysine), 40 (phenylalanine), 43 (aspartic acid), 44 (lysine), 45 (methionine), 67 (isoleucine), 68 (serine), 70 (threonine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, glutamic acid, threonine, threonine, serine, glutamine, proline, lysine, glycine, leucine, isoleucine, valine, threonine, serine, serine, lysine, serine, alanine, alanine, valine, threonine, and leucine, respectively, was designated as "h#11B7-T9H"-type heavy chain variable region.

7.1.4.10 h#11B7-T10H-Type Heavy Chain:

A humanized #11B7 heavy chain variable region designed by substituting amino acid Nos. 1 (glutamic acid), 6 (glutamic acid), 7 (serine), 9 (proline), 12 (valine), 16 (glutamine), 17 (serine), 23 (serine), 25 (threonine), 39 (lysine), 40 (phenylalanine), 43 (aspartic acid), 44 (lysine), 45 (methionine), 48 (methionine), 67 (isoleucine), 70 (threonine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, glutamine, tryptophan, alanine, leucine, glutamic acid, threonine, threonine, serine, glutamine, proline, lysine, glycine, leucine, isoleucine, valine, serine, serine, lysine, serine, alanine, alanine, valine, threonine, and threonine, respectively, was designated as "h#11B7-T10H"-type heavy chain variable region.

7.1.4.11 h#11B7-T11H-Type Heavy Chain:

A humanized #11B7 heavy chain variable region designed by substituting amino acid Nos. 1 (glutamic acid), 6 (glutamic acid), 7 (serine), 9 (proline), 12 (valine), 16 (glutamine), 17 (serine), 23 (serine), 25 (threonine), 39 (lysine), 40 (phenylalanine), 43 (aspartic acid), 44 (lysine), 45 (methionine), 68 (serine), 70 (threonine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, glutamine, tryptophan, alanine, leucine, glutamic acid, threonine, threonine, serine, glutamine, proline, lysine, glycine, leucine, threonine, serine, serine, lysine, serine, alanine, alanine, valine, threonine, and threonine, respectively, was designated as "h#11B7-T11H"-type heavy chain variable region.

7.1.4.12 h#11B7-T12H-Type Heavy Chain:

A humanized #11B7 heavy chain variable region designed by substituting amino acid Nos. 1 (glutamic acid), 6 (glutamic acid), 7 (serine), 9 (proline), 12 (valine), 16 (glutamine), 17 (serine), 23 (serine), 25 (threonine), 39 (lysine), 40 (phenylalanine), 43 (aspartic acid), 44 (lysine), 45 (methionine), 48 (methionine), 67 (isoleucine), 68 (serine), 70 (threonine), 79 (phenylalanine), 81 (glutamine), 83 (asparagine), 87 (serine), 88 (glutamic acid), 92 (threonine), 107 (valine), and 108 (methionine) of #11B7 heavy chain variable region represented by SEQ ID NO: 141 of Sequence Listing (FIG. 30C) by glutamine, glutamine, tryptophan, alanine, leucine, glutamic acid, threonine, threonine, serine, glutamine, proline, lysine, glycine, leucine, isoleucine, valine, threonine, serine, serine, lysine, serine, alanine, alanine, valine, threonine, and threonine, respectively, was designated as "h#11B7-T12H"-type heavy chain variable region.

7.2 Design of Humanized Version of #11D5

7.2.1 Molecular Modeling of #11D5 variable Domains

The molecular modeling of #11D5 variable domains was practiced according to the method generally known in the art as homology modeling (Methods in Enzymology, 203, 121-153, (1991)). The primary sequences (three-dimensional structures derived from X-ray crystal structures are available) of human immunoglobulin variable domains registered in Protein Data Bank (Nuc. Acid Res. 35, D301-D303 (2007)) were compared with the #11D5 variable domains thus determined. As a result, 1D5I was selected as having the highest sequence homology to the #11D5 light chain variable domain. Moreover, 1ORS was selected as having the highest sequence homology to the #11D5 heavy chain variable domain. The three-dimensional structures of framework domains were prepared based on a "framework model" obtained by combining the coordinates of 1D5I and 1ORS corresponding to the #11D5 light and heavy chains. For #11D5 CDRs, CDRL$_1$, CDRL$_2$, CDRL$_3$, CDRH$_1$, and CDRH$_2$ were assigned to clusters 11A, 7A, 9A, 10A, and 9A, respectively, according to the classification of Thornton et al. (J. Mol. Biol., 263, 800-815, (1996)). CDRH$_3$ was classified in k (3)—according to the H3-rules (FEBS letters 399, 1-8 (1996)). Subsequently, the typical conformation of each CDR was incorporated in the framework model.

Finally, to obtain possible molecular models of the #11D5 variable domains in terms of energy, energy calculation was conducted for excluding disadvantageous interatomic contact. These procedures were performed using a commercially available three-dimensional protein structure prediction program Prime and coordinate search program MacroModel (Schrödinger, LLC).

7.2.2 Design of Amino Acid Sequence of Humanized #11D5

Humanized #11D5 antibodies were constructed according to the method generally known in the art as CDR grafting (Proc. Natl. Acad. Sci. USA 86, 10029-10033 (1989)). Acceptor antibodies were selected in two ways based on amino acid homology within the framework domains.

The sequences of the #11D5 framework domains were compared with those of all human frameworks registered in the Kabat Database (Nuc. Acid Res. 29, 205-206 (2001)) involving antibody amino acid sequences. As a result, a T33-4'CL antibody was selected as an acceptor due to 70% sequence homology between their framework domains. The amino acid residues of the framework domains in T33-4'CL were aligned with the corresponding amino acid residues in #11D5 to identify positions where different amino acids there between were used. The positions of these residues were analysed using the three-dimensional model of #11D5 thus constructed. Then, donor residues to be grafted on the acceptor were selected according to the criteria provided by Queen et al. (Proc. Natl. Acad. Sci. USA 86, 10029-10033 (1989)).

The sequences of the #11D5 framework domains were compared with those of all human frameworks registered in IgBLAST (Nuc. Acid Res. 36, D25-D30 (2007)). As a result, 1603260B was selected as an L chain acceptor due to 74% sequence homology between their framework domains. AAF80028 was selected as an H chain acceptor due to 66% sequence homology between their framework domains. The amino acid residues of the framework domains in the 1603260B L chain and in the AAF80028 H chain were aligned with the corresponding amino acid residues in #11D5 to identify positions where different amino acids therebetween were used. The positions of these residues were analysed using the three-dimensional model of #11D5 thus constructed. Then, donor residues to be grafted on the acceptor were selected according to the criteria provided by Queen et al. (Proc. Natl. Acad. Sci. USA 86, 10029-10033 (1989)).

In all methods, humanized #11D5 sequences were constructed as described in Examples below by transferring some selected donor residues to the acceptor antibodies.

7.2.3 Humanization of #11D5 Light Chain (FIGS. 6, 7, 8, 9, 10 and 11)

7.2.3.1 h#11D5-T1L-Type Light Chain:

A humanized #11D5 light chain variable region designed by substituting amino acid Nos. 2 (isoleucine), 11 (methionine), 13 (threonine), 15 (leucine), 36 (phenylalanine), 40 (valine), 43 (serine), 45 (arginine), 46 (arginine), 47 (methionine), 66 (arginine), 69 (serine), 71 (tyrosine), 72 (serine), 79 (glutamic acid), 80 (serine), 83 (methionine), 85 (isoleucine), 100 (serine), 106 (leucine), and 109 (proline) of #11D5 light chain variable region represented by SEQ ID NO: 142 of Sequence Listing (FIG. 30D) by valine, leucine, alanine, valine, tyrosine, proline, alanine, lysine, leucine, leucine, glycine, threonine, phenylalanine, threonine, glutamine, proline, phenylalanine, threonine, glutamine, isoleucine, and threonine, respectively, was designated as "h#11D5-T1L"-type light chain variable region.

7.2.3.2 h#11D5-T2L-Type Light Chain:

A humanized #11D5 light chain variable region designed by substituting amino acid Nos. 11 (methionine), 13 (threonine), 15 (leucine), 40 (valine), 43 (serine), 46 (arginine), 66 (arginine), 69 (serine), 72 (serine), 79 (glutamic acid), 80 (serine), 83 (methionine), 85 (isoleucine), 100 (serine), 106 (leucine), and 109 (proline) of #11D5 light chain variable region represented by SEQ ID NO: 142 of Sequence Listing (FIG. 30D) by leucine, alanine, valine, proline, alanine, leucine, glycine, threonine, threonine, glutamine, proline, phenylalanine, threonine, glutamine, isoleucine, and threonine, respectively, was designated as "h#11D5-T2L"-type light chain variable region.

7.2.3.3 h#11D5-T3L-Type Light Chain:

A humanized #11D5 light chain variable region designed by substituting amino acid Nos. 11 (methionine), 13 (threonine), 15 (leucine), 72 (serine), 79 (glutamic acid), 80 (serine), 83 (methionine), 106 (leucine), and 109 (proline) of #11D5 light chain variable region represented by SEQ ID NO: 142 of Sequence Listing (FIG. 30D) by leucine, alanine, valine, threonine, glutamine, proline, phenylalanine, isoleucine, and threonine, respectively, was designated as "h#11D5-T3L"-type light chain variable region.

7.2.3.4 h#11D5-T4L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 45 (arginine), 47 (methionine), 66 (arginine), 69 (serine), 70 (aspartic acid), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, lysine, leucine, glycine, threonine, glutamic acid, phenylalanine, threonine, glutamine, proline, phenylalanine, threonine, glycine, valine, isoleucine, and threonine, respectively, was designated as "h#11D5-T4L"-type light chain variable region.

7.2.3.5 h#11D5-T5L-Type Light Chain:

A humanized #11D5 light chain variable region designed by substituting amino acid Nos. 11 (methionine), 13 (threonine), 15 (leucine), 40 (valine), 43 (serine), 66 (arginine), 69 (serine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, glycine, threonine, threonine, glutamine, proline, phenylalanine, threonine, glycine, valine, isoleucine, and threonine, respectively, was designated as "h#11D5-T5L"-type light chain variable region.

7.2.3.6 h#11D5-T6L-Type Light Chain:

A humanized #11D5 light chain variable region designed by substituting amino acid Nos. 11 (methionine), 13 (threonine), 15 (leucine), 40 (valine), 43 (serine), 66 (arginine), 69 (serine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, glycine, threonine, threonine, glutamine, proline, phenylalanine, threonine, glutamine, valine, isoleucine, and threonine, respectively, was designated as "h#11D5-T6L"-type light chain variable region.

7.2.3.7 h#11D5-T7L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 45 (arginine), 47 (methionine), 66 (arginine), 69 (serine), 70 (aspartic acid), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, lysine, leucine, glycine, threonine, glutamic acid, phenylalanine, threonine, glutamine, proline, phenylalanine, threonine, glutamine, valine, isoleucine, and threonine, respectively, was designated as "h#11D5-T7L"-type light chain variable region.

7.2.3.8 h#11D5-T8L-Type Light Chain:

A humanized #11D5 light chain variable region designed by substituting amino acid Nos. 11 (methionine), 13 (threonine), 15 (leucine), 40 (valine), 43 (serine), 45 (arginine), 47 (methionine), 66 (arginine), 69 (serine), 70 (aspartic acid), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, lysine, leucine, glycine, threonine, glutamic acid, phenylalanine, threonine, glutamine, proline, phenylalanine, threonine, glutamine, valine, isoleucine, and threonine, respectively, was designated as "h#11D5-T8L"-type light chain variable region.

7.2.3.9 h#11D5-T9L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 47 (methionine), 66 (arginine), 69 (serine), 70 (aspartic acid), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, leucine, glycine, threonine, glutamic acid, phenylalanine, threonine, glutamine, proline, phenylalanine, threonine, glutamine, valine, isoleucine, and threonine, respectively, was designated as "h#11D5-T9L"-type light chain variable region.

7.2.3.10 h#11D5-T10L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 45 (arginine), 66 (arginine), 69 (serine), 70 (aspartic acid), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, lysine, glycine, threonine, glutamic acid, phenylalanine, threonine, glutamine, proline, phenylalanine, threonine, glutamine, valine, isoleucine, and threonine, respectively, was designated as "h#11D5-T10L"-type light chain variable region.

7.2.3.11 h#11D5-T11L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 45 (arginine), 47 (methionine), 66 (arginine), 69 (serine), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, lysine, leucine, glycine, threonine, phenylalanine, threonine, glutamine, proline, phenylalanine, threonine, glutamine, valine, isoleucine, and threonine, respectively, was designated as "h#11D5-T11L"-type light chain variable region.

7.2.3.12 h#11D5-T12L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 45 (arginine), 47 (methionine), 66 (arginine), 69 (serine), 70 (aspartic acid), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, lysine, leucine, glycine, threonine, glutamic acid, threonine, glutamine, proline, phenylalanine, threonine, glutamine, valine, isoleucine, and threonine, respectively, was designated as "h#11D5-T12L"-type light chain variable region.

7.2.3.13 h#11D5-T13L-Type Light Chain:

A humanized #11D5 light chain variable region designed by substituting amino acid Nos. 11 (methionine), 13 (threonine), 15 (leucine), 40 (valine), 43 (serine), 47 (methionine), 66 (arginine), 69 (serine), 70 (aspartic acid), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, leucine, glycine, threonine, glutamic acid, phenylalanine, threonine, glutamine, proline, phenylalanine, threonine, glutamine, valine, isoleucine, and threonine, respectively, was designated as "h#11D5-T13L"-type light chain variable region.

7.2.3.14 h#11D5-T14L-Type Light Chain:

A humanized #11D5 light chain variable region designed by substituting amino acid Nos. 11 (methionine), 13 (threonine), 15 (leucine), 40 (valine), 43 (serine), 45 (arginine), 66 (arginine), 69 (serine), 70 (aspartic acid), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, lysine, glycine, threonine, glutamic acid, phenylalanine, threonine, glutamine, proline, phenylalanine, threonine, glutamine, valine, isoleucine, and threonine, respectively, was designated as "h#11D5-T14L"-type light chain variable region.

7.2.3.15 h#11D5-T15L-Type Light Chain:

A humanized #11D5 light chain variable region designed by substituting amino acid Nos. 11 (methionine), 13 (threonine), 15 (leucine), 40 (valine), 43 (serine), 45 (arginine), 47 (methionine), 66 (arginine), 69 (serine), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, lysine, leucine, glycine, threonine, phenylalanine, threonine, glutamine, proline, phenylalanine, threonine, glutamine, valine, isoleucine, and threonine, respectively, was designated as "h#11D5-T15L"-type light chain variable region.

7.2.3.16 h#11D5-T16L-Type Light Chain:

A humanized #11D5 light chain variable region designed by substituting amino acid Nos. 11 (methionine), 13 (threonine), 15 (leucine), 40 (valine), 43 (serine), 45 (arginine), 47 (methionine), 66 (arginine), 69 (serine), 70 (aspartic acid), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, lysine, leucine, glycine, threonine, glutamic acid, threonine, glutamine, proline, phenylalanine, threonine, glutamine, valine, isoleucine, and threonine, respectively, was designated as "h#11D5-T16L"-type light chain variable region.

7.2.3.17 h#11D5-T17L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 66 (arginine), 69 (serine), 70 (aspartic acid), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, glycine, threonine, glutamic acid, phenylalanine, threonine, glutamine, proline, phenylalanine, threonine, glutamine, valine, isoleucine, and threonine, respectively, was designated as "h#11D5-T17L"-type light chain variable region.

7.2.3.18 h#11D5-T18L-Type Light Chain:

A humanized #11D5 light chain variable region designed by substituting amino acid Nos. 11 (methionine), 13 (threonine), 15 (leucine), 36 (phenylalanine), 40 (valine), 43

(serine), 47 (methionine), 66 (arginine), 69 (serine), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, leucine, glycine, threonine, phenylalanine, threonine, glutamine, proline, phenylalanine, threonine, glutamine, valine, isoleucine, and threonine, respectively, was designated as "h#11D5-T18L"-type light chain variable region.

7.2.3.19 h#11D5-T19L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 47 (methionine), 66 (arginine), 69 (serine), 70 (aspartic acid), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, leucine, glycine, threonine, glutamic acid, threonine, glutamine, proline, phenylalanine, threonine, glutamine, valine, isoleucine, and threonine, respectively, was designated as "h#11D5-T19L"-type light chain variable region.

7.2.3.20 h#11D5-T20L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 45 (arginine), 66 (arginine), 69 (serine), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, lysine, glycine, threonine, phenylalanine, threonine, glutamine, proline, phenylalanine, threonine, glutamine, valine, isoleucine, and threonine, respectively, was designated as "h#11D5-T20L"-type light chain variable region.

7.2.3.21 h#11D5-T21L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 45 (arginine), 66 (arginine), 69 (serine), 70 (aspartic acid), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, lysine, glycine, threonine, glutamic acid, threonine, glutamine, proline, phenylalanine, threonine, glutamine, valine, isoleucine, and threonine, respectively, was designated as "h#11D5-T21L"-type light chain variable region.

7.2.3.22 h#11D5-T22L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 45 (arginine), 47 (methionine), 66 (arginine), 69 (serine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, lysine, leucine, glycine, threonine, threonine, glutamine, proline, phenylalanine, threonine, glutamine, valine, isoleucine, and threonine, respectively, was designated as "h#11D5-T22L"-type light chain variable region.

7.2.3.23 h#11D5-T23L-Type Light Chain:

A humanized #11D5 light chain variable region designed by substituting amino acid Nos. 11 (methionine), 13 (threonine), 15 (leucine), 40 (valine), 43 (serine), 66 (arginine), 69 (serine), 70 (aspartic acid), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, glycine, threonine, glutamic acid, phenylalanine, threonine, glutamine, proline, phenylalanine, threonine, glutamine, valine, isoleucine, and threonine, respectively, was designated as "h#11D5-T23L"-type light chain variable region.

7.2.3.24 h#11D5-T24L-Type Light Chain:

A humanized #11D5 light chain variable region designed by substituting amino acid Nos. 11 (methionine), 13 (threonine), 15 (leucine), 40 (valine), 43 (serine), 47 (methionine), 66 (arginine), 69 (serine), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, leucine, glycine, threonine, phenylalanine, threonine, glutamine, proline, phenylalanine, threonine, glutamine, valine, isoleucine, and threonine, respectively, was designated as "h#11D5-T24L"-type light chain variable region.

7.2.3.25 h#11D5-T25L-Type Light Chain:

A humanized #11D5 light chain variable region designed by substituting amino acid Nos. 11 (methionine), 13 (threonine), 15 (leucine), 40 (valine), 43 (serine), 47 (methionine), 66 (arginine), 69 (serine), 70 (aspartic acid), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, leucine, glycine, threonine, glutamic acid, threonine, glutamine, proline, phenylalanine, threonine, glutamine, valine, isoleucine, and threonine, respectively, was designated as "h#11D5-T25L"-type light chain variable region.

7.2.3.26 h#11D5-T26L-Type Light Chain:

A humanized #11D5 light chain variable region designed by substituting amino acid Nos. 11 (methionine), 13 (threonine), 15 (leucine), 40 (valine), 43 (serine), 45 (arginine), 66 (arginine), 69 (serine), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, lysine, glycine, threonine, phenylalanine, threonine, glutamine, proline, phenylalanine, threonine, glutamine, valine, isoleucine, and threonine, respectively, was designated as "h#11D5-T26L"-type light chain variable region.

7.2.3.27 h#11D5-T27L-Type Light Chain:

A humanized #11D5 light chain variable region designed by substituting amino acid Nos. 11 (methionine), 13 (threonine), 15 (leucine), 40 (valine), 43 (serine), 45 (arginine), 66 (arginine), 69 (serine), 70 (aspartic acid), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, lysine, glycine, threonine, glutamic acid, threonine, glutamine, proline, phenylalanine, threonine, glutamine, valine, isoleucine, and threonine, respectively, was designated as "h#11D5-T27L"-type light chain variable region.

7.2.3.28 h#11D5-T28L-Type Light Chain:

A humanized #11D5 light chain variable region designed by substituting amino acid Nos. 11 (methionine), 13 (threonine), 15 (leucine), 40 (valine), 43 (serine), 45 (arginine), 47 (methionine), 66 (arginine), 69 (serine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, lysine, leucine, glycine, threonine, threonine, glutamine, proline, phenylalanine, threonine, glutamine, valine, isoleucine, and threonine, respectively, was designated as "h#11D5-T28L"-type light chain variable region.

7.2.3.29 h#11D5-T29L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 66 (arginine), 69 (serine), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, glycine, threonine, phenylalanine, threonine, glutamine, proline, phenylalanine, threonine, glutamine, valine, isoleucine, and threonine, respectively, was designated as "h#11D5-T29L"-type light chain variable region.

7.2.3.30 h#11D5-T30L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 66 (arginine), 69 (serine), 70 (aspartic acid), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, glycine, threonine, glutamic acid, threonine, glutamine, proline, phenylalanine, threonine, glutamine, valine, isoleucine, and threonine, respectively, was designated as "h#11D5-T30L"-type light chain variable region.

7.2.3.31 h#11D5-T31L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 47 (methionine), 66 (arginine), 69 (serine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, leucine, glycine, threonine, threonine, glutamine, proline, phenylalanine, threonine, glutamine, valine, isoleucine, and threonine, respectively, was designated as "h#11D5-T31L"-type light chain variable region.

7.2.3.32 h#11D5-T32L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 45 (arginine), 66 (arginine), 69 (serine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, lysine, glycine, threonine, threonine, glutamine, proline, phenylalanine, threonine, glutamine, valine, isoleucine, and threonine, respectively, was designated as "h#11D5-T32L"-type light chain variable region.

7.2.3.33 h#11D5-T33L-Type Light Chain:

A humanized #11D5 light chain variable region designed by substituting amino acid Nos. 11 (methionine), 13 (threonine), 15 (leucine), 40 (valine), 43 (serine), 66 (arginine), 69 (serine), 71 (tyrosine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, glycine, threonine, phenylalanine, threonine, glutamine, proline, phenylalanine, threonine, glutamine, valine, isoleucine, and threonine, respectively, was designated as "h#11D5-T33L"-type light chain variable region.

7.2.3.34 h#11D5-T34L-Type Light Chain:

A humanized #11D5 light chain variable region designed by substituting amino acid Nos. 11 (methionine), 13 (threonine), 15 (leucine), 40 (valine), 43 (serine), 66 (arginine), 69 (serine), 70 (aspartic acid), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, glycine, threonine, glutamic acid, threonine, glutamine, proline, phenylalanine, threonine, glutamine, valine, isoleucine, and threonine, respectively, was designated as "h#11D5-T34L"-type light chain variable region.

7.2.3.35 h#11D5-T35L-Type Light Chain:

A humanized #11D5 light chain variable region designed by substituting amino acid Nos. 11 (methionine), 13 (threonine), 15 (leucine), 40 (valine), 43 (serine), 47 (methionine), 66 (arginine), 69 (serine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, proline, alanine, leucine, glycine, threonine, threonine, glutamine, proline, phenylalanine, threonine, glutamine, valine, isoleucine, and threonine, respectively, was designated as "h#11D5-T35L"-type light chain variable region.

7.2.3.36 h#11D5-T36L-Type Light Chain:

A humanized #11D5 light chain variable region designed by substituting amino acid Nos. 11 (methionine), 13 (threonine), 15 (leucine), 40 (valine), 43 (serine), 45 (arginine), 66 (arginine), 69 (serine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine; alanine, valine, proline, alanine, lysine, glycine, threonine, threonine, glutamine, proline, phenylalanine, threonine, glutamine, valine, isoleucine, and threonine, respectively, was designated as "h#11D5-T36L"-type light chain variable region.

7.2.3.37 h#11D5-T37L-Type Light Chain:

A humanized #11D5 light chain variable region designed by substituting amino acid Nos. 11 (methionine), 13 (threonine), 15 (leucine), 36 (phenylalanine), 40 (valine), 43 (serine), 66 (arginine), 69 (serine), 72 (serine), 79 (glutamic acid), 80 (serine), 83 (methionine), 85 (isoleucine), 100 (serine), 104 (leucine), 106 (leucine), and 109 (proline) of #11D5 light chain variable region represented by SEQ ID NO: 142 of Sequence Listing (FIG. 30D) by leucine, alanine, valine, tyrosine, proline, alanine, glycine, threonine, threonine, glutamine, proline, phenylalanine, threonine, glutamine, valine, isoleucine, and threonine, respectively, was designated as "h#11D5-T37L"-type light chain variable region.

7.2.4 Humanization of #11D5 heavy chain (FIGS. 12 and 13)

7.2.4.1 h#11D5-T1H-Type Heavy Chain:

A humanized #11D5 heavy chain variable region designed by substituting amino acid Nos. 1 (glutamic acid), 17 (serine), 23 (serine), 25 (threonine), 39 (lysine), 40 (phenylalanine), 43 (asparagine), 44 (lysine), 45 (methionine), 67 (isoleucine), 68 (serine), 71 (arginine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamine, threonine, threonine, serine, glutamine, proline, methionine, glycine, leucine, valine, threonine, valine, glutamic acid, serine, lysine, serine, proline, alanine, valine, threonine, and leucine, respectively, was designated as "h#11D5-T1H"-type heavy chain variable region.

7.2.4.2 h#11D5-T2H-Type Heavy Chain:

A humanized #11D5 heavy chain variable region designed by substituting amino acid Nos. 17 (serine), 23 (serine), 25 (threonine), 39 (lysine), 40 (phenylalanine), 43 (asparagine), 44 (lysine), 45 (methionine), 71 (arginine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by threonine, threonine, serine, glutamine, proline, methionine, glycine, leucine, valine, glutamic acid, serine, lysine, serine, proline, alanine, valine, threonine, and leucine, respectively, was designated as "h#11D5-T2H"-type heavy chain variable region.

7.2.4.3 h#11D5-T3H-Type Heavy Chain:

A humanized #11D5 heavy chain variable region designed by substituting amino acid Nos. 17 (serine), 23 (serine), 25 (threonine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by threonine, threonine, serine, lysine, serine, lysine, serine, proline, alanine, valine, threonine, and leucine, respectively, was designated as "h#11D5-T3H"-type heavy chain variable region.

7.2.4.4 h#11D5-T4H-Type Heavy Chain:

A humanized #11D5 heavy chain variable region designed by substituting amino acid Nos. 1 (glutamic acid), 6 (glutamic acid), 7 (serine), 9 (proline), 12 (valine), 16 (glutamine), 17 (serine), 23 (serine), 25 (threonine), 39 (lysine), 40 (phenylalanine), 43 (asparagine), 44 (lysine), 45 (methionine), 67 (isoleucine), 68 (serine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamine, glutamine, tryptophan, alanine, leucine, glutamic acid, threonine, threonine, serine, glutamine, proline, lysine, glycine, leucine, valine, threonine, lysine, serine, lysine, serine, alanine, alanine, valine, threonine, and leucine, respectively, was designated as "h#11D5-T4H"-type heavy chain variable region.

7.2.4.5 h#11D5-T5H-Type Heavy Chain:

A humanized #11D5 heavy chain variable region designed by substituting amino acid Nos. 6 (glutamic acid), 7 (serine), 9 (proline), 12 (valine), 16 (glutamine), 17 (serine), 23 (serine), 25 (threonine), 39 (lysine), 40 (phenylalanine), 43 (asparagine), 44 (lysine), 45 (methionine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamine, tryptophan, alanine, leucine, glutamic acid, threonine, threonine, serine, glutamine, proline, lysine, glycine, leucine, lysine, serine, lysine, serine, alanine, alanine, valine, threonine, and leucine, respectively, was designated as "h#11D5-T5H"-type heavy chain variable region.

7.2.4.6 h#11D5-T6H-Type Heavy Chain:

A humanized #11D5 heavy chain variable region designed by substituting amino acid Nos. 16 (glutamine), 17 (serine), 23 (serine), 25 (threonine), 39 (lysine), 40 (phenylalanine), 43 (asparagine), 44 (lysine), 45 (methionine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamic acid, threonine, threonine, serine, glutamine, proline, lysine, glycine, leucine, lysine, serine, lysine, serine, alanine, alanine, valine, threonine, and leucine, respectively, was designated as "h#11D5-T6H"-type heavy chain variable region.

7.2.4.7 h#11D5-T7H-Type Heavy Chain:

A humanized #11D5 heavy chain variable region designed by substituting amino acid Nos. 1 (glutamic acid), 16 (glutamine), 17 (serine), 23 (serine), 25 (threonine), 39 (lysine), 40 (phenylalanine), 43 (asparagine), 44 (lysine), 45 (methionine), 67 (isoleucine), 68 (serine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamine, glutamic acid, threonine, threonine, serine, glutamine, proline, lysine, glycine, leucine, valine, threonine, lysine, serine, lysine, serine, alanine, alanine, valine, threonine, and leucine, respectively, was designated as "h#11D5-T7H"-type heavy chain variable region.

7.2.4.8 h#11D5-T8H-Type Heavy Chain:

A humanized #11D5 heavy chain variable region designed by substituting amino acid Nos. 16 (glutamine), 17 (serine), 23 (serine), 25 (threonine), 39 (lysine), 40 (phenylalanine), 43 (asparagine), 44 (lysine), 45 (methionine), 67 (isoleucine), 68 (serine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamic acid, threonine, threonine, serine, glutamine, proline, lysine, glycine, leucine, valine, threonine, lysine, serine, lysine, serine, alanine, alanine, valine, threonine, and leucine, respectively, was designated as "h#11D5-T8H"-type heavy chain variable region.

7.2.4.9 h#11D5-T9H-Type Heavy Chain:

A humanized #11D5 heavy chain variable region designed by substituting amino acid Nos. 1 (glutamic acid), 16 (glutamine), 17 (serine), 23 (serine), 25 (threonine), 39 (lysine), 40 (phenylalanine), 43 (asparagine), 44 (lysine), 45 (methionine), 68 (serine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamine,- glutamic acid, threonine, threonine, serine, glutamine, proline, lysine, glycine, leucine, threonine, lysine, serine, lysine, serine, alanine, alanine, valine, threonine, and leucine, respectively, was designated as "h#11D5-T9H"-type heavy chain variable region.

7.2.4.10 h#11D5-T10H-Type Heavy Chain:

A humanized #11D5 heavy chain variable region designed by substituting amino acid Nos. 1 (glutamic acid), 16 (glutamine), 17 (serine), 23 (serine), 25 (threonine), 39 (lysine), 40 (phenylalanine), 43 (asparagine), 44 (lysine), 45 (methionine), 67 (isoleucine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamine, glutamic acid, threonine, threonine, serine, glutamine, proline, lysine, glycine, leucine, valine, lysine, serine, lysine, serine, alanine, alanine, valine, threonine, and leucine, respectively, was designated as "h#11D5-T10H"-type heavy chain variable region.

7.2.4.11 h#11D5-T11H-Type Heavy Chain:

A humanized #11D5 heavy chain variable region designed by substituting amino acid Nos. 16 (glutamine), 17 (serine), 23 (serine), 25 (threonine), 39 (lysine), 40 (phenylalanine), 43 (asparagine), 44 (lysine), 45 (methionine), 68 (serine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamic acid, threonine, threonine, serine, glutamine, proline, lysine, glycine, leucine, threonine, lysine, serine, lysine, serine, alanine, alanine, valine, threonine, and leucine, respectively, was designated as "h#11D5-T11H"-type heavy chain variable region.

7.2.4.12 h#11D5-T12H-Type Heavy Chain:

A humanized #11D5 heavy chain variable region designed by substituting amino acid Nos. 16 (glutamine), 17 (serine), 23 (serine), 25 (threonine), 39 (lysine), 40 (phenylalanine), 43 (asparagine), 44 (lysine), 45 (methionine), 67 (isoleucine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamic acid, threonine, threonine, serine, glutamine, proline, lysine, glycine, leucine, valine, lysine, serine, lysine, serine, alanine, alanine, valine, threonine, and leucine, respectively, was designated as "h#11D5-T12H"-type heavy chain variable region.

7.2.4.13 h#11D5-T13H-Type Heavy Chain:

A humanized #11D5 heavy chain variable region designed by substituting amino acid Nos. 1 (glutamic acid), 16 (glutamine), 17 (serine), 23 (serine), 25 (threonine), 39 (lysine), 40 (phenylalanine), 43 (asparagine), 44 (lysine), 45 (methionine), 75 (arginine), 79 (phenylalanine), 81 (glutamine), 83 (asparagine), 87 (threonine), 88 (glutamic acid), 92 (threonine), 107 (valine), and 108 (methionine) of #11D5 heavy chain variable region represented by SEQ ID NO: 143 of Sequence Listing (FIG. 30E) by glutamine, glutamic acid, threonine, threonine, serine, glutamine, proline, lysine, glycine, leucine, lysine, serine, lysine, serine, alanine, alanine, valine, threonine, and leucine, respectively, was designated as "h#11D5-T13H"-type heavy chain variable region.

Example 8

Construction of General-purpose Vectors for Humanized antibody expression 8.1 Construction of a Vector, pEF6KCL, for Humanized Antibody Light Chain Expression.

PCR was performed using a plasmid pEF6/V5-His B (In-vitrogen Corp.) as a template and the following primers to obtain a DNA fragment from immediately following BGHpA (2174) to SmaI (2958) (DNA fragment containing the f1 origin of replication, and the SV40 promotor and origin; hereinafter, referred to as a "fragment A"):

```
                        (primer EFF1: SEQ ID NO: 1)
   5'-ccacgcgccctgtagcggcgcattaagc-3',
   and (primer EFsmaR: SEQ ID NO: 2)
   5'-aaacccgggagcttttttgcaaaagcctagg-3'.
```

The obtained fragment A was ligated by overlap PCR to a DNA fragment comprising a DNA sequence encoding a human κ-chain secretion signal, a human κ-chain constant region, and a human poly(A) addition signal (SEQ ID NO:3; hereinafter, referred to as a "fragment B"). The obtained DNA fragment in which the fragment A is ligated to fragment B (hereinafter, referred to as a "fragment A+B") was digested with restriction enzymes KpnI and SmaI and ligated to a plasmid pEF6/V5-His B (Invitrogen Corp.) digested in advance with restriction enzymes KpnI and SmaI to construct a human L chain expression plasmid "pEF6KCL" (FIG. 19) having the signal sequence, the cloning site, the human κ-chain constant region-encoding sequence, and the human poly(A) addition signal sequence downstream of the EF1 promoter.

8.2 Construction of a Vector, pEF1/FCCU-1, for Humanized Antibody Heavy Chain Expression 8.2.1 Construction of pEF1/KCL A plasmid pEF6KCL obtained by the method described above was digested with restriction enzymes KpnI and SmaI. The resulting DNA fragment was ligated to pEF1/myc-His B (Invitrogen Corp.) digested in advance with KpnI and SmaI to construct a plasmid pEF1/KCL.

8.2.2 Construction of pEF1/FCCU-1

A DNA fragment comprising a DNA sequence encoding the amino acid sequence of the signal sequence and constant region of human IgG1 (SEQ ID NO: 4) was digested with restriction enzymes NheI and PmeI and ligated to the plasmid pEF1/KCL digested in advance with NheI and PmeI to construct a human heavy chain expression plasmid pEF1/FCCU-1 having the signal sequence, the cloning site, the human heavy chain constant region-encoding sequence, and the human poly(A) addition signal sequence downstream of the EF1 promoter.

Example 9

Production of Humanized Antibody Gene of Rat Anti-human AXL Monoclonal Antibody #11B7 a) Construction of h#11B7-T1L, h#11B7-T2L, h#11B7-T3L, h#11B7-T4L, h#11B7-T5L, h#11B7-T6L, h#11B7-T7L, h#11B7-T8L, h#11B7-T9L, h#11B7-T10L, h#11B7-T11L, h#11B7-T12L, and h#11B7-T13L, Light Chain Expression Vectors Each DNA containing a gene encoding a h#11B7-T1L, h#11B7-T2L, h#11B7-T3L, h#11B7-T4L, h#11B7-T5L, h#11B7-T6L, h#11B7-T7L, h#11B7-T8L, h#11B7-T9L, h#11B7-T10L, h#11B7-T11L, h#11B7-T12L, or h#11B7-T13L light chain variable region (FIGS. 1 and 2) represented by amino acid Nos. 21 to 129 of SEQ ID NO:18, 19, 20, 21, 22, 23, 24, 25, 26, 27, 28, 29, or 30, respectively, of the Sequence Listing, fused with a secretion signal was synthesized (MBL Medical & Biological Laboratories Co., Ltd, Artificial Gene Synthesis Service) and digested with restriction enzymes NheI and BsiWI. The resulting DNA fragments were separately inserted into sites of general-purpose vectors for humanized antibody light chain expression (pEF6KCL) digested in advance with restriction enzymes NheI and BsiWI to thereby construct h#11B7-T1L, h#11B7-T2L, h#11B7-T3L, h#11B7-T4L, h#11B7-T5L, h#11B7-T6L, h#11B7-T7L, h#11B7-T8L, h#11B7-T9L, h#11B7-T10L, h#11B7-T11L, h#11B7-T12L, and h#11B7-T13L light chain expression vectors. The obtained expression vectors were designated as "pEF6KCL/h#11B7-T1L", "pEF6KCL/h#11B7-T2L", "pEF6KCL/h#11B7-T3L", "pEF6KCL/h#11B7-T4L", "pEF6KCL/h#11B7-T5L", "pEF6KCL/h#11B7-T6L", "pEF6KCL/h#11B7-T7L", "pEF6KCL/h#11B7-T8L", "pEF6KCL/h#11B7-T9L", "pEF6KCL/h#11B7-T10L", "pEF6KCL/h#11B7-T11L", "pEF6KCL/h#11B7-T12L", or "pEF6KCL/h#11B7-T13L", and the insert of each expression vector is represented by the nucleotide sequence of SEQ ID NO: 5, 6, 7, 8, 9, 10, 11, 12, 13, 14, 15, 16, or 17 of the Sequence Listing, respectively.

b) Construction of h#11B7-T1H, h#11B7-T2H, h#11B7-T3H, h#11B7-T4H, h#11B7-T5H, h#11B7-T6H, h#11B7-T7H, h#11B7-T8H, and h#11B7-T9H Heavy Chain Expression Vectors Each DNA containing a gene encoding a h#11B7-T1H, h#11B7-T2H, h#11B7-T3H, h#11B7-T4H, h#11B7-T5H, h#11B7-T6H, h#11B7-T7H, h#11B7-T8H, or h#11B7-T9H heavy chain variable region (FIGS. 4 and 5) represented by amino acid Nos. 20 to 132 of SEQ ID NO:40, 41, 42, 43, 44, 45, 46, 47, or 48, respectively, of the Sequence Listing was synthesized (MBL Medical & Biological Laboratories Co., Ltd, Artificial Gene Synthesis Service) and digested with a restriction enzyme BlpI. The resulting DNA fragments were separately inserted into sites of general-purpose vectors for humanized antibody heavy chain expression (pEF1/FCCU-1) digested in advance with a restriction enzyme BlpI to thereby construct h#11B7-T1H, h#11B7-T2H, h#11B7-T3H, h#11B7-T4H, h#11B7-T5H, h#11B7-T6H, h#11B7-T7H, h#11B7-T8H, and h#11B7-T9H heavy chain expression vectors. The obtained expression vectors were designated as "pEF1/FCCU/h#11B7-T1H", "pEF1/FCCU/h#11B7-T2H", "pEF1/FCCU/h#11B7-T3H", "pEF1/FCCU/h#11B7-T4H", "pEF1/FCCU/h#11B7-T5H", "pEF1/FCCU/h#11B7-T6H", "pEF1/FCCU/h#11B7-T7H", "pEF1/FCCU/h#11B7-T8H", or "pEF1/FCCU/h#11B7-T9H", and the insert of each expression vector is represented by the nucleotide sequence of SEQ ID NO:31, 32, 33, 34, 35, 36, 37, 38, or 39 of the Sequence Listing, respectively.

Example 10

Preparation of Humanized Antibody of Rat Anti-human AXL Monoclonal Antibody #11B7 a) Production of Humanized Antibody $1.5 \times 10^8$ FreeStyle 293-F cells at the log growth phase were seeded onto 100 mL of fresh FreeStyle 293 Expression Medium (Invitrogen Corp.) and shake-cultured (125 rpm) in an incubator at 37° C. in 8% $CO_2$. 1 mg of Polyethyleneimine (Polyscience #24765) was dissolved in 4 mL of an Opti-Pro SFM medium (Invitrogen Corp.) and left at room temperature for 5 minutes. A heavy chain expression plasmid (0.05 mg) and a light chain expression plasmid (0.15 mg) prepared using a PureLink HiPure Plasmid kit (Invitrogen Corp.) were suspended in 4 mL of an Opti-Pro SFM medium (Invitrogen Corp.). 4 mL of the expression plasmid/Opti-Pro SFM mixed solution was added to 4 mL of the Polyethyleneimine/Opti-Pro SFM mixed solution thus left at room temperature for 5 minutes and further left at room temperature for 5 minutes. Next, 8 mL of the Polyethyleneimine/expression plasmid/Opti-Pro SFM mixed solution was added to the FreeStyle 293-F cell suspension, and shake-culture was continued. After 7-day culture at 37° C. in 8% $CO_2$, the culture supernatant was collected.

b) Purification of Humanized Antibody

The culture supernatant obtained in the preceding paragraph a) was purified by Protein A affinity column chromatography. 100 mL of the culture supernatant was placed in a 500-mL flask with a cap, to which 1 mL of a MabSelect SuRe (GE Healthcare Bio-science Ltd.) suspension (50% slurry) equilibrated with PBS was in turn added. The mixture was stirred overnight at 100 rpm in an incubator at 10° C. The FreeStyle 293-F cell culture supernatant/MabSelect SuRe suspension was applied to 5 mL of Zeba Spin Column, empty (PIERCE). The whole resin was placed in the column and then washed with 10 mL of 1M NaCl. Next, 1 mL of a 1 M arginine solution (pH 4.0) was applied thereto to collect antibody-containing fractions. The fractions were added to Centrifugal Filter Device (Amicon Ultra-4, molecular weight cut off: 50 K, Millipore Corp.), followed by solution replacement by a citrate buffer and concentration was adjusted to 200 µL to prepare purified samples.

A humanized antibody #11B7 obtained by the combination between pEF6KCL/h#11B7-T1L and pEF1/FCCU/h#11B7-T1H was designated as "h#11B7-T1"; a humanized antibody #11B7 obtained by the combination between pEF6KCL/h#11B7-T2L and pEF1/FCCU/h#11B7-T2H was designated as "h#11B7-T2"; a humanized antibody #11B7 obtained by the combination between pEF6KCL/h#11B7-T3L and pEF1/FCCU/h#11B7-T3H was designated as "h#11B7-T3"; a humanized antibody #11B7 obtained by the combination between pEF6KCL/h#11B7-T4L and pEF1/FCCU/h#11B7-T4H was designated as "h#11B7-T4"; a humanized antibody #11B7 obtained by the combination between pEF6KCL/h#11B7-T5L and pEF1/FCCU/h#11B7-T5H was designated as "h#11B7-T5"; a humanized antibody #11B7 obtained by the combination between pEF6KCL/h#11B7-T6L and pEF1/FCCU/h#11B7-T6H was designated as "h#11B7-T6"; a humanized antibody #11B7 obtained by the combination between pEF6KCL/h#11B7-T7L and pEF1/FCCU/h#11B7-T7H was designated as "h#11B7-T7"; a humanized antibody #11B7 obtained by the combination between pEF6KCL/h#11B7-T8L and pEF1/FCCU/h#11B7-T7H was designated as "h#11B7-T8"; a humanized antibody #11B7 obtained by the combination between pEF6KCL/h#11B7-T9L and pEF1/FCCU/h#11B7-T7H was designated as "h#11B7-T9"; a humanized antibody #11B7 obtained by the combination between pEF6KCL/h#11B7-T10L and pEF1/FCCU/h#11B7-T7H was designated as "h#11B7-T10"; a humanized antibody #11B7 obtained by the combination between pEF6KCL/h#11B7-T11L and pEF1/FCCU/h#11B7-T7H was designated as "h#11B7-T11"; a humanized antibody #11B7 obtained by the combination between pEF6KCL/h#11B7-T12L and pEF1/FCCU/h#11B7-T7H was designated as "h#11B7-T12"; a humanized antibody #11B7 obtained by the combination between pEF6KCL/h#11B7-T13L and pEF1/FCCU/h#11B7-T7H was designated as "h#11B7-T13"; a humanized antibody #11B7 obtained by the combination between pEF6KCL/h#11B7-T7L and pEF1/FCCU/h#11B7-T8H was designated as "h#11B7-T14"; a humanized antibody #11B7 obtained by the combination between pEF6KCL/h#11B7-T8L and pEF1/FCCU/h#11B7-T8H was designated as "h#11B7-T15"; a humanized antibody #11B7 obtained by the combination between pEF6KCL/h#11B7-T9L and pEF1/FCCU/h#11B7-T8H was designated as "h#11B7-T16"; a humanized antibody #11B7 obtained by the combination between pEF6KCL/h#11B7-T10L and pEF1/FCCU/h#11B7-T8H was designated as "h#11B7-T17"; a humanized antibody #11B7 obtained by the combination between pEF6KCL/h#11B7-T11L and pEF1/FCCU/h#11B7-T8H was designated as "h#11B7-T18"; a humanized antibody #11B7 obtained by the combination between pEF6KCL/h#11B7-T12L and pEF1/FCCU/h#11B7-T8H was designated as "h#11B7-T19"; a humanized antibody #11B7 obtained by the combination between pEF6KCL/h#11B7-T13L and pEF1/FCCU/h#11B7-T8H was designated as "h#11B7-T20"; a humanized antibody #11B7 obtained by the combination between pEF6KCL/h#11B7-T7L and pEF1/FCCU/h#11B7-T9H was designated as "h#11B7-T21"; a humanized antibody #11B7 obtained by the combination between pEF6KCL/h#11B7-T8L and pEF1/FCCU/h#11B7-T9H was designated as "h#11B7-T22"; a humanized antibody #11B7 obtained by the combination between pEF6KCL/h#11B7-T9L and pEF1/FCCU/h#11B7-T9H was designated as "h#11B7-T23"; a humanized antibody #11B7 obtained by the combination between pEF6KCL/h#11B7-T10L and pEF1/FCCU/h#11B7-T9H was designated as "h#11B7-T24"; a humanized antibody #11B7 obtained by the combination between pEF6KCL/h#11B7-T11L and pEF1/FCCU/h#11B7-T9H was designated as "h#11B7-T25"; a humanized antibody #11B7 obtained by the combination between pEF6KCL/h#11B7-T12L and pEF1/FCCU/h#11B7-T9H was designated as "h#11B7-T26"; and a humanized antibody #11B7 obtained by the combination between pEF6KCL/h#11B7-T13L and pEF1/FCCU/h#11B7-T9H was designated as "h#11B7-T27".

TABLE 1

| h#11B7 | H plasmid | L plasmid |
| --- | --- | --- |
| h#11B7-T☐ | pEF1/FCCU/h#11B7-T1H | pEF6KCL/h#11B7-T1L |
| h#11B7-T2 | pEF1/FCCU/h#11B7-T2H | pEF6KCL/h#11B7-T2L |
| h#11B7-T3 | pEF1/FCCU/h#11B7-T3H | pEF6KCL/h#11B7-T3L |
| h#11B7-T4 | pEF1/FCCU/h#11B7-T4H | pEF6KCL/h#11B7-T4L |
| h#11B7-T5 | pEF1/FCCU/h#11B7-T5H | pEF6KCL/h#11B7-T5L |
| h#11B7-T6 | pEF1/FCCU/h#11B7-T6H | pEF6KCL/h#11B7-T6L |
| h#11B7-T7 | pEF1/FCCU/h#11B7-T7H | pEF6KCL/h#11B7-T7L |
| h#11B7-T8 | pEF1/FCCU/h#11B7-T7H | pEF6KCL/h#11B7-T8L |
| h#11B7-T9 | pEF1/FCCU/h#11B7-T7H | pEF6KCL/h#11B7-T9L |
| h#11B7-T10 | pEF1/FCCU/h#11B7-T7H | pEF6KCL/h#11B7-T10L |
| h#11B7-T11 | pEF1/FCCU/h#11B7-T7H | pEF6KCL/h#11B7-T11L |
| h#11B7-T12 | pEF1/FCCU/h#11B7-T7H | pEF6KCL/h#11B7-T12L |
| h#11B7-T13 | pEF1/FCCU/h#11B7-T7H | pEF6KCL/h#11B7-T13L |
| h#11B7-T14 | pEF1/FCCU/h#11B7-T8H | pEF6KCL/h#11B7-T7L |
| h#11B7-T15 | pEF1/FCCU/h#11B7-T8H | pEF6KCL/h#11B7-T8L |
| h#11B7-T16 | pEF1/FCCU/h#11B7-T8H | pEF6KCL/h#11B7-T9L |
| h#11B7-T17 | pEF1/FCCU/h#11B7-T8H | pEF6KCL/h#11B7-T10L |
| h#11B7-T18 | pEF1/FCCU/h#11B7-T8H | pEF6KCL/h#11B7-T11L |
| h#11B7-T19 | pEF1/FCCU/h#11B7-T8H | pEF6KCL/h#11B7-T12L |
| h#11B7-T20 | pEF1/FCCU/h#11B7-T8H | pEF6KCL/h#11B7-T13L |
| h#11B7-T21 | pEF1/FCCU/h#11B7-T9H | pEF6KCL/h#11B7-T7L |
| h#11B7-T22 | pEF1/FCCU/h#11B7-T9H | pEF6KCL/h#11B7-T8L |
| h#11B7-T23 | pEF1/FCCU/h#11B7-T9H | pEF6KCL/h#11B7-T9L |
| h#11B7-T24 | pEF1/FCCU/h#11B7-T9H | pEF6KCL/h#11B7-T10L |
| h#11B7-T25 | pEF1/FCCU/h#11B7-T9H | pEF6KCL/h#11B7-T11L |
| h#11B7-T26 | pEF1/FCCU/h#11B7-T9H | pEF6KCL/h#11B7-T12L |
| h#11B7-T27 | pEF1/FCCU/h#11B7-T9H | pEF6KCL/h#11B7-T13L |

Example 11

Production of Humanized Antibody Gene of Rat Anti-human AXL Monoclonal Antibody #11D5 a) Construction of h#11D5-T1L, h#11D5-T2L, h#11D5-T3L, h#11D5-T4L, h#11D5-T5L, and h#11D5-T6L Light Chain Expression Vectors Each DNA containing a gene encoding a h#11D5-T1L, h#11D5-T2L, h#11D5-T3L, h#11D5-T4L, h#11D5-T5L, and h#11D5-T6L light chain variable region (FIG. 6) represented by amino acid Nos. 21 to 129 of SEQ ID NO:55, 56, 57, 58, 59, or 60, respectively, of the Sequence Listing, fused with a secretion signal was synthesized (MBL Medical & Biological Laboratories Co., Ltd, Artificial Gene Synthesis Service) and digested with restriction enzymes NheI and BsiWI. The resulting DNA fragments were separately inserted into sites of general-purpose vectors for humanized antibody light chain expression (pEF6KCL) digested in advance with restriction enzymes NheI and BsiWI to thereby construct h#11D5-T1L, h#11D5-T2L, h#11D5-T3L, h#11D5-T4L, h#11D5-T5L, and h#11D5-T6L light chain expression vectors. The obtained expression vectors were designated as "pEF6KCL/h#11D5-T1L", "pEF6KCL/h#11D5-T2L", "pEF6KCL/h#11D5-T3L", "pEF6KCL/h#11D5-T4L", "pEF6KCL/h#11D5-T5L", or "pEF6KCL/h#11B7-T6L", and the insert of each expression vector is represented by the nucleotide sequence of SEQ ID NO:49, 50, 51, 52, 53, or 54 of the Sequence Listing, respectively.

b) Construction of h#11D5-T1H, h#11D5-T2H, h#11D5-T3H, h#11D5-T4H, h#11D5-T5H, and h#11D5-T6H Heavy Chain Expression Vectors Each DNA containing a gene encoding a h#11D5-T1H, h#11D5-T2H, h#11D5-T3H, h#11D5-T4H, h#11D5-T5H, or h#11D5-T6H heavy chain variable region (FIG. 12) represented by amino acid Nos. 20 to 132 of SEQ ID NO:67, 68, 69, 70, 71, or 72, respectively, of the Sequence Listing was synthesized (MBL Medical & Biological Laboratories Co., Ltd, Artificial Gene Synthesis Service) and digested with a restriction enzyme BlpI. The resulting DNA fragments were separately inserted into sites of general-purpose vectors for humanized antibody heavy chain expression (pEF1/FCCU-1) digested in advance with a restriction enzyme BlpI to thereby construct h#11D5-T1H, h#11D5-T2H, h#11D5-T3H, h#11D5-T4H, h#11D5-T5H, and h#11D5-T6H heavy chain expression vectors. The obtained expression vectors were designated as "pEF1/FCCU/h#11D5-T1H", "pEF1/FCCU/h#11D5-T2H", "pEF1/FCCU/h#11D5-T3H", "pEF1/FCCU/h#11D5-T4H", "pEF1/FCCU/h#11D5-T5H", or "pEF1/FCCU/h#11D5-T6H", and the insert of each expression vector is represented by the nucleotide sequence of SEQ ID NO:61, 62, 63, 64, 65, or 66 of the Sequence Listing, respectively.

Example 12

Preparation of Humanized Antibody of Rat Anti-human AXL Monoclonal Antibody #11D5 a) Production of Humanized Antibody $1.5 \times 10^8$ FreeStyle 293-F cells at the log growth phase were seeded onto 100 mL of fresh FreeStyle 293 Expression Medium (Invitrogen Corp.) and shake-cultured (125 rpm) in an incubator at 37° C. in 8% $CO_2$. 1 mg of Polyethyleneimine (Polyscience #24765) was dissolved in 4 mL of an Opti-Pro SFM medium (Invitrogen Corp.) and left at room temperature for 5 minutes. A heavy chain expression plasmid (0.05 mg) and a light chain expression plasmid (0.15 mg) prepared using a PureLink HiPure Plasmid kit (Invitrogen Corp.) were suspended in 4 mL of an Opti-Pro SFM medium (Invitrogen Corp.). 4 mL of the expression plasmid/Opti-Pro SFM mixed solution was added to 4 mL of the Polyethyleneimine/Opti-Pro SFM mixed solution thus left at room temperature for 5 minutes and further left at room temperature for 5 minutes. Next, 8 mL of the Polyethyleneimine/expression plasmid/Opti-Pro SFM mixed solution was added to the FreeStyle 293-F cell suspension, and shake-culture was continued. After 7-day culture at 37° C. in 8% $CO_2$, the culture supernatant was collected.

b) Purification of Humanized Antibody

The culture supernatant obtained in the preceding paragraph a) was purified by Protein A affinity column chromatography. 100 mL of the culture supernatant was placed in a 500-mL flask with a cap, to which 1 mL of a MabSelect SuRe (GE Healthcare Bio-science Ltd.) suspension (50% slurry) equilibrated with PBS was in turn added. The mixture was stirred overnight at 100 rpm in an incubator at 10° C. The FreeStyle 293-F cell culture supernatant/MabSelect SuRe suspension was applied to 5 mL of Zeba Spin Column, empty (PIERCE). The whole resin was placed in the column and then washed with 10 mL of 1M NaCl. Next, 1 mL of a 1 M arginine solution (pH 4.0) was applied thereto to collect antibody-containing fractions. The fractions were added to Centrifugal Filter Device (Amicon Ultra-4, molecular weight cut off: 50 K, Millipore Corp.), followed by solution replacement by a citrate buffer and concentration. The final capacity was adjusted to 200 μl to prepare purified samples.

A humanized antibody #11D5 obtained by the combination between pEF6KCL/h#11D5-T1L and pEF1/FCCU/h#11D5-T1H was designated as "h#11D5-T1", a humanized antibody #11D5 obtained by the combination between pEF6KCL/h#11D5-T2L and pEF1/FCCU/h#11D5-T2H was designated as "h#11D5-T2"; a humanized antibody #11D5 obtained by the combination between pEF6KCL/h#11D5-T3L and pEF1/FCCU/h#11D5-T3H was designated as "h#11D5-T3"; a humanized antibody #11D5 obtained by the combination between pEF6KCL/h#11D5-T4L and pEF1/FCCU/h#11D5-T4H was designated as "h#11D5-T4"; a humanized antibody #11D5 obtained by the combination between pEF6KCL/h#11D5-T5L and pEF1/FCCU/h#11D5-T5H was designated as "h#11D5-T5"; and a humanized antibody #11D5 obtained by the combination between pEF6KCL/h#11D5-T6L and pEF1/FCCU/h#11D5-T6H was designated as "h#11D5-T6".

Example 13

Evaluation of Affinity of Humanized Antibody of Rat Anti-human AXL Monoclonal Antibody #11B7 for Human AXL-Fc Fusion Protein The humanized antibodies h#11B7-T1 to h#11B7-T27 derived from rat anti-human AXL monoclonal antibody #11B7 were evaluated for their affinity for human AXL-Fc by method shown below. Human AXL-Fc (manufactured by R&D Systems, #154-AL) was diluted with PBS to 1 μg/ml. Then, the solution was dispensed in an amount of 100 μl/well to Immuno Plate (manufactured by Nalge Nunc International K.K., #437111) and left standing overnight at 4° C. to adsorb the protein onto the plate. The next day, the wells were washed 5 times with a PBS-T solution (PBS and 0.05% (v/v) Tween 20). Then, a solution containing skim milk (manufactured by Morinaga Milk Industry Co., Ltd.) diluted with PBS to 5% was dispensed in an amount of 100 μl/well and left standing at room temperature for 2 hours. The solutions in the wells were removed and the wells were washed 5 times with a PBS-T solution. Then, the purified humanized antibodies T1 to T27 of rat anti-human AXL monoclonal antibody #11B7 prepared in Example 10 were separately diluted at a final concentration of 1 μg/ml to 0.00256 ng/ml (5-fold dilution series) with a PBS solution containing 0.5% skim milk. Then, the solution was dispensed in an amount of 100 μl/well and left standing at room temperature for 2 hours. In this procedure, each antibody concentration was determined according to Example 15. The wells were washed 5 times with a PBS-T solution. Then, Alkaline Phosphatase-conjugated AffiniPure Goat Anti-Human IgG (manufactured by Jackson ImmunoResearch Laboratories, Inc., #109-055-097) diluted 2500 times with a TBS-T solution (TBS and 0.05% (v/v) Tween 20) was added in an amount of 100 μl/well and left standing at room temperature for 1 hour. The solutions in the wells were removed and the wells were washed 5 times with a TBS-T solution. Then, a fluorescent substrate solution (manufactured by Roche Diagnostics K.K., #11681982001) was added in an amount of 100 μl/well to perform fluorescence reaction. The fluorescence intensity on the human AXL-Fc-adsorbed plate was measured 15 minutes after the addition of the fluorescent substrate solution using SpectraMax M5 (manufactured by Molecular Devices Corp.). As a result, of the examined 27 samples of humanized antibodies of rat anti-human AXL monoclonal antibody #11B7, #11B7-T1 and h#11B7-T4 were confirmed to have lower binding activity than that of human chimeric antibody. However, the other 25 samples were confirmed to have binding activity almost equal to that of human chimeric antibody for human AXL-Fc protein in an antibody concentration-dependent manner (FIGS. 19, 20, 21 and 22).

Example 14

Evaluation of Affinity of Humanized Antibody of Rat Anti-human AXL Monoclonal Antibody #11D5 for Human AXL-Fc Fusion Protein The humanized antibodies h#11D5-T1 to h#11D5-T6 of rat anti-human AXL monoclonal antibody #11D5 were evaluated for their affinity for human AXL-Fc by method shown below. Human AXL-Fc (manufactured by R&D Systems, #154-AL) was diluted with PBS to 1 μg/ml. Then, the solution was dispensed in an amount of 100 μl/well to Immuno Plate (manufactured by Nalge Nunc International K.K., #437111) and left standing overnight at 4° C. to adsorb the protein onto the plate. The next day, the wells were washed 5 times with a PBS-T solution (PBS and 0.05% (v/v) Tween 20). Then, a solution containing skim milk (manufactured by Morinaga Milk Industry Co., Ltd.) diluted with PBS to 5% was dispensed in an amount of 100 μl/well and left standing at room temperature for 2 hours. The solutions in the wells were removed and the wells were washed 5 times with a PBS-T solution. Then, the purified humanized antibodies T1 to T6 of rat anti-human AXL monoclonal antibody #11D5 prepared in Example 12 were separately diluted at a final concentration of 1 μg/ml to 0.00256 ng/ml (5-fold dilution series) with a PBS solution containing 0.5% skim milk. Then, the solution was dispensed in an amount of 100 μl/well and left standing at room temperature for 2 hours. In this procedure, each antibody concentration was determined according to Example 15. The wells were washed 5 times with a PBS-T solution. Then, Alkaline Phosphatase-conjugated AffiniPure Goat Anti-Human IgG (manufactured by Jackson ImmunoResearch Laboratories, Inc., #109-055-097) diluted 2500 times with a TBS-T solution (TBS and 0.05% (v/v) Tween 20) was added in an amount of 100 μl/well and left standing at room temperature for 1 hour. The solutions in the wells were removed and the wells were washed 5 times with a TBS-T solution. Then, a fluorescent substrate solution (manufactured by Roche Diagnostics K.K., #11681982001) was added in an amount of 100 μl/well to perform fluorescence reaction. The fluorescence intensity on human AXL-Fc-adsorbed plate was measured 15 minutes after the addition of the fluorescent substrate solution using SpectraMax M5 (manufactured by Molecular Devices Corp.). As a result, of examined 6 samples of humanized antibodies of rat anti-human AXL monoclonal antibody #11D5, h#11D5-T4, h#11D5-T5, and h#11D5-T6 were confirmed to have binding activity almost equal to that of human chimeric antibody for human AXL-Fc protein in an antibody concentration-dependent manner (FIG. 23).

Example 15

The Absorption Coefficient Calculation and Direct Protein Absorbance Assay of Humanized Antibody of Rat Anti-human AXL Monoclonal Antibodies #11B7 and #11D5

The protein concentration of humanized antibodies h#11B7-T1 to h#11B7-T27 derived from the rat anti-human AXL monoclonal antibody #11B7 and h#11D5-T1 to h#11D5-T6 derived from the rat anti-human AXL monoclonal antibody #11D5 was determined by the protocol shown below. Each humanized antibody of rat anti-human AXL monoclonal antibody #11B7 or #11D5 prepared in Example 10 or 12, respectively, was diluted by its mass using an MX5 Automated-S microbalance (METTLER TOLEDO). The absorbance at 280 nm (A280) was measured for each antibody with a DU-7400 UV-vis Spectrophotometer (Beckman Coulter, Inc.) using quartz cells at room temperature. The protein concentration of each antibody was determined by the absorption coefficient. The absorption coefficient of each antibody was determined using the software Sednterp, which can be downloaded from the website of the National Institute of Health (http://iphilo.mailway.com/download.htm). The results are described in FIG. 24 (upper panel for h#11B7-T1 to h#11B7-T14; lower panel for h#11B7-T15 to h#11B7-T27) and 25 (for h#11D5-T1 to h#11D5-T6).

Example 16

Determination of Binding Site (Epitope) for the Rat Anti-human AXL Monoclonal Antibody #11B7 a) Expression and Purification of Human AXL Tandem IG Domain

DNA encoding a protein comprising human AXL IG domains (amino acid Nos. 26 to 220 in NCBI protein database ACCESSION No. P_30530: SEQ ID NO: 139) linked to an N-terminal His-tag and a Thrombin recognition sequence was incorporated in a vector pDEST14 (Invitrogen Corp., catalog No.: 11801-016). E. coli Rosetta-gami B(DE3) (Novagen, catalog No.: 71136-4) was transformed with this plasmid and cultured in a TB medium (Invitrogen Corp., catalog No.: 22711-022). The bacterial cells thus cultured were ultrasonically disrupted and centrifuged, and the super- natant was purified using a HisTrap HP column (GE Healthcare, catalog No.: 17-5247-01). The elution was pooled and desalted by PD-10 column (GE Healthcare, catalog No.: 17-0851-01) then His-tag was cleaved by Thrombin (Sigma-Aldrich, catalog No.: T-7009). Cleaved protein was then subjected to MONO Q 5/50 GL (GE Healthcare, catalog No.: 17-5166-01) and Superdex 75 10/300 column (GE Healthcare, catalog No.: 17-5174-01) until a single band with a molecular weight of 21 kDa was obtained.

b) Expression and Purification of Human AXL Single IG Domain

DNA encoding a protein comprising human AXL IG domains (amino acid Nos. 26 to 131 and 129 to 220 in NCBI protein database ACCESSION No. P_30530) linked to an N-terminal His-tag and a Factor Xa recognition sequence was incorporated in a vector pDEST14 (Invitrogen Corp., catalog No.: 11801-016). E. coli Rosetta-gami B(DE3) (Novagen, catalog No.: 71136-4) was transformed with this plasmid and cultured in a TB medium (Invitrogen Corp., catalog No.: 22711-022). The bacterial cells thus cultured were ultrasonically disrupted and centrifuged, and the supernatant was purified using a HisTrap HP column (GE Healthcare, catalog No.: 17-5247-01). Then, the human AXL IG domains were purified by electrophoresis using a Superdex 75 10/300 column (GE Healthcare, catalog No.: 17-5174-01) until a single band with a molecular weight of 11 kDa was obtained.

c) Determination of the Binding Site (epitope) on the Human AXL-IG Domain for Rat Anti-Human AXL Monoclonal Antibody #11B7

The binding site (epitope) on the human AXL-IG domain for the rat anti-human AXL monoclonal antibody #11B7 was evaluated by the following method: Peptides containing either of the two IG domains in human AXL (NHis-hAXL26-131 and NHis-hAXL129-220), and a peptide containing both of the two IG domains in human AXL (hAXL26-220) were separately diluted with PBS to 1 μg/ml. Then, each solution was dispensed in the amount of 100 gwell to an Immuno Plate (manufactured by Nalge Nunc International K.K., #437111) and left standing overnight at 4° C. to adsorb the peptide onto the plate. On the next day, the wells were washed 5 times with a PBS-T solution (PBS and 0.05% (v/v) Tween 20). Then, a solution containing skim milk (manufactured by Morinaga Milk Industry Co., Ltd.) diluted with PBS to 5% was dispensed in an amount of 100 μl/well and left standing at room temperature for 2 hours. The solutions in the wells were removed, and the wells were washed 5 times with a PBS-T solution. The rat anti-human AXL monoclonal antibody #11B7 was diluted to 0.04 μg/ml with a PBS solution containing 0.5% skim milk. Then, the solution was dispensed in amount of 100 μl/well and left standing at room temperature for 2 hours. The wells were washed 5 times with a PBS-T solution. Then, Alkaline Phosphatase-conjugated AffiniPure Goat Anti-Human IgG (manufactured by Jackson ImmunoResearch Laboratories, Inc., #109-055-097) diluted 2500 times with a TBS-T solution (TBS and 0.05% (v/v) Tween 20) was added in an amount of 100 μl/well and left standing at room temperature for 1 hour. The solutions in the wells were removed, and the wells were washed 5 times with a TBS-T solution. Then, a fluorescent substrate solution (manufactured by Roche Diagnostics K.K., #11681982001) was added in the amount of 100 μl/well to perform fluorescence reaction. The fluorescence intensity on the human AXL-IG domain-adsorbed plate was measured 15 minutes after the addition of the fluorescent substrate solution using a SpectraMax M5 (manufactured by Molecular Devices Corp.). As a result of the ELISA, only hAXL26-220 and NHis-hAXL129-220 were confirmed to have binding activity. Therefore, it was demonstrated that the epitope for the rat anti-human AXL monoclonal antibody #11B7 is, of the two IG domains in human AXL, the domain closer to the carboxy terminus (the domain comprising amino acid residues of amino acid Nos. 129-220 in NCBI protein database ACCESSION No. P_30530: SEQ ID NO: 139; FIG. 30A) (FIG. 26).

Example 17

Humanized Anti-AXL Antibodies of the Invention Inhibit Ligand-induced AXL Phosphorylation in vitro The protein encoded by the growth arrest specific gene 6, Gas6, represents a natural ligand of the receptor tyrosine kinase AXL. Binding of Gas6 to AXL results in receptor activation which is reflected by increased receptor tyrosine kinase phosphorylation levels. The experiments described in example 17 were set out to address the potential of the humanized anti-AXL antibodies h#11B7-T2, h#11B7-T3, h#11B7-T4, h#11B7-T5, and h#11B7-T6 of the invention to interfere with Gas6-mediated activation of the receptor tyrosine kinase AXL.

Example 17.1

Humanized Anti-AXL Antibodies of the Invention Inhibit Ligand-Induced AXL Phosphorylation in vitro as Determined by ELISA ELISA experiments were performed in order to investigate whether the humanized anti-AXL antibodies of the invention are able to block ligand Gas6-induced phosphorylation of AXL. In brief, on day 1, $3 \times 10^4$ cells per well were seeded in normal growth medium in flat-bottom 96 well plates. The next day, growth medium was replaced by serum-free medium to starve cells over night for 24 h. Also over night, black Maxi-Sorp 96 well plates (Nunc) were coated with mouse anti-phospho-tyrosine antibody 4G10 at 2 µg/ml PBS and 4° C. On day 3, the 4G10 antibody solution was removed and Maxi-Sorp wells were blocked with PBS, 0.5% BSA for at least 4 h at room temperature. In parallel, cells were pre-incubated with 10 µg/ml of Gammagard control antibody (Sigma), the chimeric anti-AXL mAb #11B7 as well as the humanized anti-AXL antibodies h#11B7-T2, h#11B7-T3, h#11B7-T4, h#11B7-T5, and h#11B7-T6 for 3 h at 37° C., and then treated with or without 400 ng/ml Gas6 (R&D Systems) for 15 min at 37° C. Medium was then flicked out and cells were lysed in lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) for 30 min on ice. Meanwhile, blocking buffer was removed and Maxi-Sorp plates were washed 6× with wash buffer (PBS, 0.05% Tween 20), before lysates were transferred and incubated over night at 4° C. After plates were washed 6× with wash buffer on day 4, wells were incubated with biotinylated rat anti-AXL antibody 12B7 at 0.5 µg/ml PBS for 2 h at room temperature. Plates were washed 6× with wash buffer and AP-conjugated streptavidin (Chemicon #SA110) diluted 1:4.000 in PBS was added to each well and incubated for 30 min at room temperature. Afterwards, wells were washed 6× with wash buffer and AttoPhos substrate solution (Roche #11681982) was added. Using a Victor plate reader (Perkin Elmer), the fluorescence of each well was collected at an excitation wavelength of 430 nm and an emission wavelength of 580 nm.

FIG. 27 shows representative results of this experiment for Hs578T breast cancer cells. Compared with Gammagard control antibody, the chimeric anti-AXL antibody #11B7 as well as the humanized anti-AXL antibodies h#11B7-T2, h#11B7-T3, h#11B7-T4, h#11B7-T5, and h#11B7-T6 of the invention were able to block or significantly reduce Gas6-mediated AXL activation in Hs578T breast cancer cells as indicated by decreased AXL tyrosine phosphorylation levels. Similar effects with the same panel of antibodies were observed in AXL over-expressing NIH3T3-AXL cl. 7 fibroblasts, the lung cancer cell line NCI-H292, the melanoma cell line C-8161, as well as the prostate cancer cell lines PC-3 and DU-145.

Example 17.2

Humanized Anti-AXL Antibodies of the Invention Inhibit Ligand-Induced AXL Phosphorylation in vitro as Determined by Western-Blot Analysis Moreover, Western Blot analyses were conducted in order to confirm the humanized antibodies' ability to interfere with ligand Gas6-induced activation of AXL. For this purpose, $1.5 \times 10^6$ Hs578T breast cancer cells were seeded on 10 cm culture dishes on day 1. The day after, growth medium was replaced by serum-free medium in order to starve cells over night for 24 h. On day 3, cells were pre-incubated with 10 µg/ml of Gammagard control antibody (Sigma), the chimeric anti-AXL mAb #11B7 as well as the humanized anti-AXL antibodies h#11B7-T2, h#11B7-T3, h#11B7-T4, h#11B7-T5, and h#11B7-T6 for 3 h at 37° C., and then treated with or without 400 ng/ml Gas6 (R&D Systems) for 15 min at 37° C. Afterwards, medium was removed, cells were lysed in 1 ml of lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) on ice for 30 min, and cell debris were removed by centrifugation for 10 minutes at 10,000×g and 4° C. For immunoprecipitation, the protein concentrations of supernatants were determined, and 500 µg of whole cell lysates were incubated with 30 µl of a protein A-sepharose suspension and 1 µg of the rat anti-AXL monoclonal antibody 12B7 on a rotation wheel for 3 h at 4° C. The precipitates were washed three times with 0.7 ml of chilled HNTG buffer (20 mM HEPES pH 7.5, 150 mM NaCl, 0.1% Triton-X-100, 10% glycerol, and 10 mM $Na_4P_2O_7$), suspended and boiled in 40 µl of 3×SDS Laemmli sample buffer, and subjected to SDS PAGE. For Western Blot analysis, proteins were transferred to nitrocellulose membrane. Afterwards, the membrane was blocked with NET-Gelatine and incubated with mouse monoclonal anti-phospho-tyrosine primary antibody 4G10 (Upstate) over night. After 3 washes with NET-Gelatine the next day, the membrane was incubated with HRP-conjugated anti-mouse secondary antibody for 1 h at room temperature and then washed 3 times with NET-Gelatine again. Applying the chemiluminescence detection kit according to the manufacturer's instructions (GE Healthcare), filters were finally exposed to films (Kodak). Afterwards, the same filters were re-probed with anti-AXL antibody.

FIG. 27 shows representative results of this experiment. Compared with Gammagard control antibody, the chimeric anti-AXL antibody #11B7 as well as the humanized anti- AXL antibodies h#11B7-T2, h#11B7-T3, h#11B7-T4, h#11B7-T5, and h#11B7-T6 of the invention were able to block or significantly reduce Gas6-induced AXL activation in Hs578T breast cancer cells as indicated by decreased AXL tyrosine phosphorylation levels.

Example 18

Humanized Anti-AXL Antibodies of the Invention Inhibit Ligand-induced Phosphorylation of AXL Downstream Signaling Molecules in vitro Gas6-induced activation of the receptor tyrosine kinase Axl is not only reflected by increased tyrosine phosphorylation levels of Axl itself, but is also associated with the induction of downstream signaling cascades, including the ERK1/2 and the PKB/AKT pathways. We therefore continued with experiments to address the potential of the humanized anti-Axl antibodies h#11B7-T2, h#11B7-T3, h#11B7-T4, h#11B7-T5, and h#11B7-T6 of the invention to interfere with Gas6-mediated activation of ERK1 and ERK2 as well as AKT. Moreover, we found the phosphorylation status of the signaling molecules GSK-3β, TSC2, mTOR, and S6K1 to be modulated upon stimulation with Gas6 as well, and thus investigated the inhibitory effect of the humanized anti-Axl antibodies h#11B7-T2, h#11B7-T3, h#11B7-T4, h#11B7-T5, and h#11B7-T6 of the invention on those molecules as well.

Example 18.1

Humanized 11B7 Anti-Axl Antibodies of the Invention Inhibit Ligand-Induced Phosphorylation of ERK1/2 in vitro Western Blot analyses were conducted in order to investigate whether the humanized antibodies of the invention have the potential to interfere with Gas6-induced activation of ERK1/2. Gas6-mediated activation of ERK1/2 is reflected by increased phosphorylation levels at its positions Thr202 and Tyr204. For this purpose, $5 \times 10^6$ Hs578T breast cancer cells or $3 \times 10^6$ NCI-H292 lung cancer cells were seeded on 10 cm culture dishes on day 1. The day after, growth medium was replaced by serum-free medium in order to starve cells over night for 24 h. On day 3, cells were pre-incubated with 10 μg/ml of Gammagard control antibody (Baxter), the chimeric anti-Axl mAb chm11B7 as well as the humanized anti-Axl antibodies h#11B7-T2, h#11B7-T3, h#11B7-T4, h#11B7-T5, and h#11B7-T6 for 3 h at 37° C., and then treated with or without 400 ng/ml Gas6 (R&D Systems) for 15 min at 37° C. Afterwards, medium was removed, cells were lysed in 800 μl of lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) on ice for 30 min, and cell debris were removed by centrifugation for 10 minutes at 10,000×g and 4° C. The protein concentrations of supernatants were determined, 50 μg of whole cell lysates were suspended and boiled in 3×SDS Laemmli sample buffer, and subjected to SDS PAGE. Upon transfer of the proteins to nitrocellulose membrane, the membrane was blocked with NET-Gelatine and incubated with rabbit polyclonal anti-phospho-p44/42 MAP kinase (Thr202/Tyr204) primary antibody (Cell Signaling Technologies, #9101) over night. After 3 washes with NET-Gelatine the next day, the membrane was incubated with HRP-conjugated anti-rabbit secondary antibody (Dianova, #111-036-045) for 1 h at room temperature and then washed 3 times with NET-Gelatine again. Applying the chemiluminescence detection kit according to the manufacturer's instructions (GE Healthcare), filters were finally exposed to films (Kodak). Afterwards, the same filters were re-probed with anti-p44/42 MAP kinase antibody (Santa Cruz K-23, #sc-153).

FIG. 28A shows representative results of this experiment. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention interfered with the weak, Gas6-induced increase of ERK1/2 activation in Hs578T breast cancer cells. Due to the high basal activity of ERK1/2 in this cell line, however, these effects which are indicated by decreased ERK1/2 Thr202/Tyr204 phosphorylation levels in Gas6-stimulated versus corresponding non-stimulated cells appear relatively moderate only (top). In contrast, the inhibitory effects of the chimeric anti-Axl antibody chm11B7 as well as the humanized anti-Axl antibodies h#11B7-T2, h#11B7-T3, h#11B7-T4, h#11B7-T5, or h#11B7-T6 on ERK1/2 Thr202/Tyr204 phosphorylation are much clearer reflected in NCI-H292 lung cancer cells (bottom).

Example 18.2

Humanized 11B7 Anti-Axl Antibodies of the Invention Inhibit Ligand-Induced Phosphorylation of AKT in vitro Western Blot analyses were conducted in order to investigate whether the humanized antibodies of the invention have the potential to interfere with Gas6-induced activation of AKT. Gas6-mediated AKT activation is thereby reflected by increased phosphorylation levels at its position Ser473. For this purpose, $5 \times 10^6$ Hs578T breast cancer cells or $3 \times 10^6$ NCI-H292 lung cancer cells were seeded on 10 cm culture dishes on day 1. The day after, growth medium was replaced by serum-free medium in order to starve cells over night for 24 h. On day 3, cells were pre-incubated with 10 μg/ml of Gammagard control antibody (Baxter), the chimeric anti-Axl mAb chm11B7 as well as the humanized anti-Axl antibodies h#11B7-T2, h#11B7-T3, h#11B7-T4, h#11B7-T5, and h#11B7-T6 for 3 h at 37° C., and then treated with or without 400 ng/ml Gas6 (R&D Systems) for 15 min at 37° C. Afterwards, medium was removed, cells were lysed in 800 μl of lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) on ice for 30 min, and cell debris were removed by centrifugation for 10 minutes at 10,000×g and 4° C. The protein concentrations of supernatants were determined, 50 μg of whole cell lysates were suspended and boiled in 3×SDS Laemmli sample buffer, and subjected to SDS PAGE. Upon transfer of the proteins to nitrocellulose membrane, the membrane was blocked with NET-Gelatine and incubated with rabbit polyclonal anti-AKT1/2/3 primary antibody (Cell Signaling Technologies, #9272) over night. After 3 washes with NET-Gelatine the next day, the membrane was incubated with HRP-conjugated anti-rabbit secondary antibody (Dianova, #111-036-045) for 1 h at room temperature and then washed 3 times with NET-Gelatine again. Applying the chemiluminescence detection kit according to the manufacturer's instructions (GE Healthcare), filters were finally exposed to films (Kodak). Afterwards, the same filters were re-probed with anti-phospho-AKT (Ser473) antibody (Cell Signaling Technologies, #9271).

FIG. 28B shows representative results of this experiment. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention were able to significantly reduce Gas6-induced AKT activation in Hs578T breast cancer cells (top) and NCI-H292 lung cancer cells (bottom) as indicated by decreased AKT Ser473 phosphorylation levels in Gas6-stimulated versus corresponding non-stimulated cells.

Example 18.3

Humanized 11B7 Anti-Axl Antibodies of the Invention Inhibit Ligand-Induced Phosphorylation of GSK-3β in vitro Western Blot analyses were conducted in order to investigate whether the humanized antibodies of the invention have the potential to interfere with Gas6-induced activation of GSK-3β which is reflected by increased phosphorylation levels at its position Ser9. For this purpose, $5 \times 10^6$ Hs578T breast cancer cells or $3 \times 10^6$ NCI-H292 lung cancer cells were seeded on 10 cm culture dishes on day 1. The day after, growth medium was replaced by serum-free medium in order to starve cells over night for 24 h. On day 3, cells were pre-incubated with 10 µg/ml of Gammagard control antibody (Baxter), the chimeric anti-Axl mAb chm11B7 as well as the humanized anti-Axl antibodies h#11B7-T2, h#11B7-T3, h#11B7-T4, h#11B7-T5, and h#11B7-T6 for 3 h at 37° C., and then treated with or without 400 ng/ml Gas6 (R&D Systems) for 15 min at 37° C. Afterwards, medium was removed, cells were lysed in 800 µl of lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) on ice for 30 min, and cell debris were removed by centrifugation for 10 minutes at 10,000×g and 4° C. The protein concentrations of supernatants were determined, 50 µg of whole cell lysates were suspended and boiled in 3×SDS Laemmli sample buffer, and subjected to SDS PAGE. Upon transfer of the proteins to nitrocellulose membrane, the membrane was blocked with NET-Gelatine and incubated with rabbit polyclonal anti-phospho-GSK-3β (Ser9) primary antibody (Cell Signaling Technologies, #9336) over night. After 3 washes with NET-Gelatine the next day, the membrane was incubated with HRP-conjugated anti-rabbit secondary antibody (Dianova, #111-036-045) for 1 h at room temperature and then washed 3 times with NET-Gelatine again. Applying the chemiluminescence detection kit according to the manufacturer's instructions (GE Healthcare), filters were finally exposed to films (Kodak). Afterwards, the same filters were re-probed with anti-GSK-3β antibody (Becton Dickinson, #610201) and HRP-conjugated anti-mouse secondary antibody (Dianova, #315-036-045).

FIG. 28C shows representative results of this experiment. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention were able to significantly reduce Gas6-induced GSK-3β activation in Hs578T breast cancer cells (top) and NCI-H292 lung cancer cells (bottom) as indicated by decreased GSK-3β Ser9 phosphorylation levels in Gas6-stimulated versus corresponding non-stimulated cells.

Example 18.4

Humanized 11B7 Anti-Axl Antibodies of the Invention Inhibit Ligand-Induced Phosphorylation of TSC2 in vitro Western Blot analyses were performed in order to investigate whether the humanized antibodies of the invention have the potential to interfere with Gas6-induced and PI3K/AKT-mediated phosphorylation of TSC2 at its amino acid residue Thr1462. The phosphorylation of TSC2 on Thr1462 is generally associated with an inhibition of the tumor suppressor function of the TSC complex and, as a consequence, the activation of the downstream mTOR pathway. In brief, $5 \times 10^6$ Hs578T breast cancer cells or $3 \times 10^6$ NCI-H292 lung cancer cells were seeded on 10 cm culture dishes on day 1. The day after, growth medium was replaced by serum-free medium in order to starve cells over night for 24 h. On day 3, cells were pre-incubated with 10 µg/ml of Gammagard control antibody (Baxter), the chimeric anti-Axl mAb chm11B7 as well as the humanized anti-Axl antibodies h#11B7-T2, h#11B7-T3, h#11B7-T4, h#11B7-T5, and h#11B7-T6 for 3 h at 37° C., and then treated with or without 400 ng/ml Gas6 (R&D Systems) for 15 min at 37° C. Afterwards, medium was removed, cells were lysed in 800 µl of lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) on ice for 30 min, and cell debris were removed by centrifugation for 10 minutes at 10,000×g and 4° C. The protein concentrations of supernatants were determined, 50 µg of whole cell lysates were suspended and boiled in 3×SDS Laemmli sample buffer, and subjected to SDS PAGE. Upon transfer of the proteins to nitrocellulose membrane, the membrane was blocked with NET-Gelatine and incubated with rabbit polyclonal anti-TSC2 primary antibody (Cell Signaling Technologies, #3612) over night. After 3 washes with NET-Gelatine the next day, the membrane was incubated with HRP-conjugated anti-rabbit secondary antibody (Dianova, #111-036-045) for 1 h at room temperature and then washed 3 times with NET-Gelatine again. Applying the chemiluminescence detection kit according to the manufacturer's instructions (GE Healthcare), filters were finally exposed to films (Kodak). Afterwards, the same filters were re-probed with anti-phospho-TSC2 (Thr1462) antibody (Cell Signaling Technologies, #3617).

FIG. 28D shows representative results of this experiment. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention were able to significantly reduce Gas6-induced phosphorylation of TCS2 on Thr1462 in Hs578T breast cancer cells (top) and NCI-H292 lung cancer cells (bottom) as indicated by decreased phosphorylation levels of this amino acid residue in Gas6-stimulated versus corresponding non-stimulated cells.

Example 18.5

Humanized 11B7 Anti-Axl Antibodies of the Invention Inhibit Ligand-Induced Phosphorylation of mTOR in vitro Given the effects on TSC2 phosphorylation, Western Blot analyses were conducted in order to investigate whether the humanized antibodies of the invention do also have the potential to interfere with Gas6-induced activation of mTOR. Gas6-mediated mTOR activation is reflected by increased phosphorylation levels at its position Ser2448. For this purpose, $5\times10^6$ Hs578T breast cancer cells or $3\times10^6$ NCI-H292 lung cancer cells were seeded on 10 cm culture dishes on day 1. The day after, growth medium was replaced by serum-free medium in order to starve cells over night for 24 h. On day 3, cells were pre-incubated with 10 µg/ml of Gammagard control antibody (Baxter), the chimeric anti-Axl mAb chm11B7 as well as the humanized anti-Axl antibodies h#11B7-T2, h#11B7-T3, h#11B7-T4, h#11B7-T5, and h#11B7-T6 for 3 h at 37° C., and then treated with or without 400 ng/ml Gas6 (R&D Systems) for 15 min at 37° C. Afterwards, medium was removed, cells were lysed in 800 µl of lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) on ice for 30 min, and cell debris were removed by centrifugation for 10 minutes at 10,000×g and 4° C. The protein concentrations of supernatants were determined, 50 µg of whole cell lysates were suspended and boiled in 3×SDS Laemmli sample buffer, and subjected to SDS PAGE. Upon transfer of the proteins to nitrocellulose membrane, the membrane was blocked with NET-Gelatine and incubated with rabbit polyclonal anti-phospho-mTOR (Ser2448) primary antibody (Cell Signaling Technologies, #2971) over night. After 3 washes with NET-Gelatine the next day, the membrane was incubated with HRP-conjugated anti-rabbit secondary antibody (Dianova, #111-036-045) for 1 h at room temperature and then washed 3 times with NET-Gelatine again. Applying the chemiluminescence detection kit according to the manufacturer's instructions (GE Healthcare), filters were finally exposed to films (Kodak). Afterwards, the same filters were re-probed with anti-mTOR kinase antibody (Cell Signaling Technologies, #2972).

FIG. 28E shows representative results of this experiment. The inhibitory effects of the anti-Axl antibodies were relatively weak in Hs578T breast cancer cells (top). However, compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention were able to interfere with the Gas6-induced mTOR activation in NCI-H292 lung cancer cells as indicated by decreased mTOR Ser2448 phosphorylation levels in Gas6-stimulated versus corresponding non-stimulated cells (bottom).

Example 18.6

Humanized 11B7 Anti-Axl Antibodies of the Invention Inhibit Ligand-Induced Phosphorylation of S6K1 in vitro Finally, Western Blot analyses were performed in order to investigate whether the humanized antibodies of the invention have the potential to interfere with Gas6-induced activation of S6K1. Gas6-mediated S6K1 activation is reflected by increased phosphorylation levels at its positions Thr421 and Ser424. For this purpose, $5\times10^6$ Hs578T breast cancer cells or $3\times10^6$ NCI-H292 lung cancer cells were seeded on 10 cm culture dishes on day 1. The day after, growth medium was replaced by serum-free medium in order to starve cells over night for 24 h. On day 3, cells were pre-incubated with 10 µg/ml of Gammagard control antibody (Baxter), the chimeric anti-Axl mAb chm11B7 as well as the humanized anti-Axl antibodies h#11B7-T2, h#11B7-T3, h#11B7-T4, h#11B7-T5, and h#11B7-T6 for 3 h at 37° C., and then treated with or without 400 ng/ml Gas6 (R&D Systems) for 15 min at 37° C. Afterwards, medium was removed, cells were lysed in 800 µl of lysis buffer (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) on ice for 30 min, and cell debris were removed by centrifugation for 10 minutes at 10,000×g and 4° C. The protein concentrations of supernatants were determined, 50 µg of whole cell lysates were suspended and boiled in 3×SDS Laemmli sample buffer, and subjected to SDS PAGE. Upon transfer of the proteins to nitrocellulose membrane, the membrane was blocked with NET-Gelatine and incubated with rabbit polyclonal anti-phospho-p70 S6 Kinase 1 (Thr421/Ser424) primary antibody (Cell Signaling Technologies, #9204) over night. After 3 washes with NET-Gelatine the next day, the membrane was incubated with HRP-conjugated anti-rabbit secondary antibody (Dianova, #111-036-045) for 1 h at room temperature and then washed 3 times with NET-Gelatine again. Applying the chemiluminescence detection kit according to the manufacturer's instructions (GE Healthcare), filters were finally exposed to films (Kodak). Afterwards, the same filters were re-probed with anti—actin antibody (Cell Signaling Technologies, #4967).

FIG. 28F shows representative results of this experiment. Compared with Gammagard control antibody, the chimeric anti-Axl antibody chm11B7 as well as the humanized anti-Axl antibodies h#11B7-T2, h#11B7-T3, h#11B7-T4, h#11B7-T5, and h#11B7-T6 of the invention showed some inhibitory effects on Gas6-induced S6K1 activation in Hs578T breast cancer cells as indicated by decreased S6K1 Thr421/Ser424 phosphorylation levels in Gas6-stimulated versus corresponding non-stimulated cells (top). However, a much stronger decrease of Gas6-induced S6K1 Thr421/Ser424 phosphorylation and thus activation upon pre-treatment with the chimeric anti-Axl antibody chm11B7 as well as the humanized anti-Axl antibodies h#11B7-T2, h#11B7-T3, h#11B7-T4, h#11B7-T5, or h#11B7-T6 of the invention could be observed in NCI-H292 lung cancer cells (bottom).

Example 19

Humanized 11D5 Anti-Axl Antibodies of the Invention Inhibit Ligand-induced Axl Phosphorylation in vitro as Determined by ELISA In addition to the characterization of humanized h#11B7-T2, h#11B7-T3, h#11B7-T4, h#11B7-T5 and h#11B7-T6 anti-Axl mAb series, ELISA experiments were performed in order to investigate the potential of the humanized anti-Axl antibodies h#11D5-T2, h#11D5-T3, h#11D5-T4, h#11D5-T5, and h#11D5-T6 of the invention to interfere with Gas6-induced phosphorylation and thus activation of the receptor tyrosine kinase Axl.

In brief, on day one $3\times10^4$ Hs578T breast cancer cells per well were seeded in normal growth medium in flat-bottom 96 well plates. The next day, growth medium was replaced by serum-free medium to starve cells over night for 24 h. Also over night, black Maxi-Sorp 96 well plates (Nunc) were coated with mouse anti-phospho-tyrosine antibody 4G10 at 2 µg/ml PBS at 4° C. On day 3, the 4G10 antibody solution was removed and Maxi-Sorp wells were blocked with blocking buffer (PBS, 0.5% BSA) for at lest 4 h at room temperature. In parallel, cells were pre-incubated with 10 µg/ml of Gammagard control antibody (Baxter), the chimeric anti-Axl mAb chm11D5 as well as the humanized anti-Axl antibodies h#11D5-T2, h#11D5-T3, h#11D5-T4, h#11D5-T5, and h#11D5-T6 for 3 h at 37° C., and then treated with or without 400 ng/ml Gas6 (R&D Systems) for 15 min at 37° C. Medium was then flicked out and cells were lysed in 110 µl of lysis buffer per well (50 mM HEPES, pH 7.5, 150 mM NaCl, 1 mM EDTA, 10% glycerine, and 1% Triton X-100) supplemented with phosphatase and protease inhibitors (10 mM Na$_4$P$_2$O$_7$, 1 mM phenylmethylsulfonyl fluoride, 1 mM orthovanadate, 1 mM NaF, and 0.5% aprotinin) for 30 min on ice. Meanwhile, blocking buffer was removed and Maxi-Sorp plates were washed 6× with wash buffer (PBS, 0.05% Tween 20), before 100 µl lysate of each well were transferred and incubated over night at 4° C. After plates were washed 6× with wash buffer on day 4, wells were incubated with biotinylated rat anti-Axl antibody 12B7 at 0.125 µg/ml dilution buffer (20 mM Tris, 50 mM NaCl, pH7.3, 0.05% Tween 20, 0.1% BSA) for 2 h at room temperature. Plates were washed 6× with wash buffer and AP-conjugated streptavidin (Chemicon #SA110) diluted 1:20000 in dilution buffer was added to each well and incubated for 30 min at room temperature. Afterwards, wells were washed 6× with wash buffer and AttoPhos substrate solution (Roche #11681982) was added. Using a SpectraMax-GeminiEM plate reader (Molecular Devices), the fluorescence of each well was collected at an excitation wavelength of 430 nm and an emission wavelength of 580 nm.

FIG. 29 shows representative results of this experiment. Compared with Gammagard control antibody, the chimeric anti-Axl antibody chm11D5 as well as the humanized anti-Axl antibodies h#11D5-T2, h#11D5-T3, h#11D5-T4, h#11D5-T5, and h#11D5-T6 of the invention were able to block or significantly reduce Gas6-mediated Axl activation as indicated by decreased Axl tyrosine phosphorylation levels in Gas6-stimulated versus corresponding non-stimulated cells.

Example 20

Rat and Chimeric Anti-Axl Antibodies of the Invention Inhibit Ligand-induced Axl Phosphorylation in vitro to Similar Extent Chimeric derivatives of the rat anti-Axl antibodies 11B7 and 11D5 were generated as part of this invention (see above), In order to investigate whether the rat anti-Axl antibodies of the invention and the corresponding chimeric anti-Axl antibodies of the invention were able to inhibit ligand Gas6 mediated Axl activation in vitro to similar extent, ELISA experiments on CaSki cervical cancer cells were performed. Gas6-mediated Axl activation was thereby detected by increased receptor tyrosine phosphorylation, In brief, on day 1, 3×104 cells per well were seeded in normal growth medium in flat-bottom 96 well plates. The next day, growth medium was replaced by serum-free medium to starve cells over night for 24 h. Also over night, black Maxi-Sorp 96 well plates (Nunc) were coated with mouse anti-phosphotyrosine antibody 4G10 at 2 IJg/ml PBS and 4° C., On day 3, the 4G10 antibody solution was removed and Maxi-Sorp wells were blocked with PBS, 0.5% BSA for at lest 4 h at room temperature. In parallel, cells were preincubated with 50 ng/ml, 100 ng/ml, 300 ng/ml, 750 ng/ml, 1 IJg/ml, and 10 IJg/ml of rat anti-Axl antibody 11B7 or chimeric anti-Axl antibody ch11B7 for 1 h at 37° C. and subsequently treated with or without 400 ng/ml Gas6 (R&D Systems) for 10 min at 37° C. Medium was then flicked out and cells were lysed in lysis buffer (50 mM HEPES, pH 7.5, 150 mM NaCl, 1 mM EDTA, 10% glycerine, and 1% Triton X-100) supplemented with phosphatase and protease inhibitors (10 mM Na4P207, 1 mM phenylmethylsulfonyl fluoride, 1 mM orlhovanadate, 1 mM NaF, and 0.5% aprotinin) for 30 min on ice. Meanwhile, blocking buffer was removed and Maxl-Sorp plates were washed 6× with wash buffer (PBS, 0.05% Tween 20), before lysates were transferred and incubated over night at 4° C. After plates were washed 6× with wash buffer on day 4, wells were incubated with biotinylated rat anti-Axl antibody 12B7 at 0.5 IJg/ml PBS for 2 h at room temperature. Plates were washed 6× with wash buffer and AP-conjugated streptavidin (Chemicon #SA110) diluted 1:4,000 in PBS was added to each well and incubated for 30 min at room temperature. Afterwards, wells were washed 6× with wash buffer and AttoPhos substrate solution (Roche #11681982) was added. Using a Victor plate reader (Perkin Elmer), the fluorescence of each well was collected at an excitation wavelength of 430 nm and an emission wavelength of 580 nm. FIG. 31 shows representative results of this experiment for the cervical cancer cell line CaSki. As demonstrated by concentration-dependent decrease of the relative Axl phosphorylation, the rat anti-Axl antibody 11B7 (A) and the chimeric anti-Axl antibody ch11B7 (B) of the invention were able to block ligand-induced activation of the receptor tyrosine kinase Axl to similar extent. Comparable effects applying the same experimental settings were observed with the melanoma cell line C-8161.

Example 21

Production of Humanized Antibody Gene of Rat Anti-human AXL Monoclonal Antibody #11B7 a) Construction of h#11B7-T15L and h#11B7-T18L, Light Chain Expression Vectors

Each DNA containing a gene encoding a #11B7-T15L or h#11B7-T18L light chain variable region (FIG. 32A) represented by amino acid Nos. 21 to 129 of SEQ ID NO: 146 or 147, respectively, of the Sequence isting, fused with a secretion signal was synthesized (MBL Medical & Biological Laboratories Co., Ltd, Artificial Gene Synthesis Service) and digested with restriction enzymes NheI and BsiWI. The resulting DNA fragments were separately inserted into sites of general-purpose vectors for humanized antibody light chain expression (pEF6KCL) digested in advance with restriction enzymes NheI and BsiWI to thereby construct h#11B7-T15L and h#11B7-T18L light chain expression vectors. The obtained expression vectors were designated as "pEF6KCL/h#11B7-T15L" or "pEF6KCL/h#11B7-T18L", and the insert of each expression vector is represented by the nucleotide sequence of SEQ ID NO: 144 or 145 of the Sequence Listing, respectively.

b) Construction of h#11B7-T11H and h#11B7-T12H Heavy Chain Expression Vectors

Each DNA containing a gene encoding a h#11B7-T11H or h#11B7-T12H heavy chain variable region (FIG. 32B) represented by amino acid Nos. 20 to 132 of SEQ ID NO: 150 or 151, respectively, of the Sequence Listing was synthesized (MBL Medical & Biological Laboratories Co., Ltd, Artificial Gene Synthesis Service) and digested with a restriction enzyme BlpI. The resulting DNA fragments were separately inserted into sites of general-purpose vectors for humanized antibody heavy chain expression (pEF1/FCCU-1) digested in advance with a restriction enzyme BlpI to thereby construct h#11B7-T11H and h#11B7-T12H heavy chain expression vectors. The obtained expression vectors were designated as "pEF1/FCCU/h#11B7-T11H" or "pEF1/FCCU/h#11B7-T12H", and the insert of each expression vector is represented by the nucleotide sequence of SEQ ID NO: 148 or 149 of the Sequence Listing, respectively.

Example 22

Preparation of Humanized Antibody of Rat Anti-human AXL Monoclonal Antibody #11B7 a) Production of Humanized Antibody
See a) of Example 10.
b) Purification of Humanized Antibody The culture supernatant obtained in the preceding paragraph a) was purified by Protein A affinity column chromatography. 100 mL of the culture supernatant was placed in a 500-mL flask with a cap, to which 1 mL of a MabSelect SuRe (GE Healthcare Bio-science Ltd.) suspension (50% slurry) equilibrated with PBS was in turn added. The mixture was stirred overnight at 100 rpm in an incubator at 10° C. The FreeStyle 293-F cell culture supernatant/MabSelect SuRe suspension was applied to 5 mL of Zeba Spin Column, empty (PIERCE). The whole resin was placed in the column and then washed with 10 mL of 1M NaCl. Next, 1 mL of a 1 M arginine solution (pH 4.0) was applied thereto to collect antibody-containing fractions. The fractions were added to Centrifugal Filter Device (Amicon Ultra-4, molecular weight cut off: 50 K, Millipore Corp.), followed by solution replacement by a citrate buffer and concentration was adjusted to 200 µL to prepare purified samples.

A humanized antibody #11B7 obtained by the combination between pEF6KCL/h#11B7-T15L and pEF1/FCCU/h#11B7-T11H was designated as "h#11B7-T28"; a humanized antibody #11B7 obtained by the combination between pEF6KCL/h#11B7-T18L and pEF1/FCCU/h#11B7-T11H was designated as "h#11B7-T29"; a humanized antibody #11B7 obtained by the combination between pEF6KCL/h#11B7-T15L and pEF1/FCCU/h#11B7-T12H was designated as "h#11B7-T30"; a humanized antibody #11B7 obtained by the combination between pEF6KCL/h#11B7-T18L and pEF1/FCCU/h#11B7-T12H was designated as "h#11B7-T31".

TABLE 2

| h#11B7 | H plasmid | L plasmid |
|---|---|---|
| h#11B7-T28 | pEF1/FCCU/h#11B7-T11H | pEF6KCL/h#11B7-T15L |
| h#11B7-T29 | pEF1/FCCU/h#11B7-T11H | pEF6KCL/h#11B7-T18L |
| h#11B7-T30 | pEF1/FCCU/h#11B7-T12H | pEF6KCL/h#11B7-T15L |
| h#11B7-T31 | pEF1/FCCU/h#11B7-T12H | pEF6KCL/h#11B7-T18L |

Example 23

Evaluation of Affinity of Humanized Antibody of Rat Anti-human AXL Monoclonal Antibody #11B7 for Human AXL-Fc Fusion Protein The humanized antibodies h#11B7-T28 to h#11B7-T31 derived from rat anti-human AXL monoclonal antibody #11B7 were evaluated for their affinity for human AXL-Fc by method shown below. Human AXL-Fc (manufactured by R&D Systems, #154-AL) was diluted with PBS to 1 µg/ml. Then, the solution was dispensed in an amount of 100 µl/well to immuno Plate (manufactured by Nalge Nunc International K.K., #437111) and left standing overnight at 4° C. to adsorb the protein onto the plate. The next day, the wells were washed 5 times with a PBS-T solution (PBS and 0.05% (v/v) Tween 20). Then, a solution containing skim milk (manufactured by Morinaga Milk Industry Co., Ltd.) diluted with PBS to 5% was dispensed in an amount of 100 µl/well and left standing at room temperature for 2 hours. The solutions in the wells were removed and the wells were washed 5 times with a PBS-T solution. Then, the purified humanized antibodies T28 to 131 of rat anti-human AXL monoclonal antibody #11B7 prepared in Example 10 were separately diluted at a final concentration of 1 µg/ml to 0.00256 ng/ml (5-fold dilution series) with a PBS solution containing 0.5% skim milk. Then, the solution was dispensed in an amount of 100 µl/well and left standing at room temperature for 2 hours. In this procedure, each antibody concentration was determined according to Example 15. The wells were washed 5 times with a PBS-T solution. Then, Alkaline Phosphatase-conjugated AffiniPure Goat Anti-Human IgG (manufactured by Jackson ImmunoResearch Laboratories, Inc., #109-055-097) diluted 2500 times with a TBS-T solution (TBS and 0.05% (v/v) Tween 20) was added in an amount of 100 µl/well and left standing at room temperature for 1 hour. The solutions in the wells were removed and the wells were washed 5 times with a TBS-T solution. Then, a fluorescent substrate solution (manufactured by Roche Diagnostics K.K., #11681982001) was added in an amount of 100 µl/well to perform fluorescence reaction. The fluorescence intensity on the human AXL-Fc-adsorbed plate was measured 15 minutes after the addition of the fluorescent substrate solution using SpectraMax M5 (manufactured by Molecular Devices Corp.). As a result, the humanized antibodies of rat anti-human AXL monoclonal antibody h#11B7-T28 to #11B7-T31 were confirmed to have binding activity almost equal to that of human chimeric antibody for human AXL-Fc protein in an antibody concentration-dependent manner (FIGS. 19 and 33).

Example 24

HPLC Assay of Humanized Antibody of Rat Anti-human AXL Monoclonal Antibodies #11B7

The protein concentration of humanized antibodies h#11B7-T28 to h#11B7-T31 derived from the rat anti-human AXL monoclonal antibody #11B7 was determined by the protocol shown below. Each humanized antibody samples was injected onto size exclusion column (Tosoh SW3000XL) and protein concentration was determined by the resulting HPLC (Agilent 1200 SL) peak area and abdorption coefficient of each antibody using sample of tigatuzumab, an IgG1-type humanized anti-human DR5 monoclonal antibody, as a standard. Concentration of tigatuzumab antibody standard sample was determined by the direct absorption protocol described in Example 15. The results are summarized in FIG. 34.

Example 25

Measurement of Thermal Stability of Humanized Antibody Using Differential Scanning Calorimetry (DSC)

One example of an index for comparing antibody properties can include antibody stability. Examples of an index for the antibody stability can include thermal stability.

Antibodies having a low thermal denaturation midpoint (Tm) are highly likely to be denatured. The denatured antibodies are prone to aggregate and are also thought to have increased antigenicity. By contrast, antibodies having high Tm are less prone to be denatured (unfolded) or inactivated and can be prepared into solution formulations that can be stored stably for a long time.

Differential scanning calorimetry (DSC) is an apparatus that can rapidly and accurately measure Tm, which serves as a good index for the relative structural stability of proteins. Tm values can be measured using DSC, and these measured values can be compared to thereby determine difference in thermal stability thereamong.

h#11B7-T1, h#11B7-T2, h#11B7-T3, h#11B7-T4, h#11B7-T5, h#11B7-T6, h#11B7-T7, h#11B7-T8, h#11B7-T9, h#11B7-T10, h#11B7-T11, h#11B7-T12, h#11B7-T13, h#11B7-T14, h#11B7-T15, h#11B7-T16, h#11B7-T17, h#11B7-T18, #11B7-T19, h#11B7-T20, h#11B7-T21, h#11B7-T22, h#11B7-T23, h#11B7-T24, h#11B7-T25, h#11B7-T26, h#11B7-T27, h#11B7-T28, h#11B7-T29, h#11B7-T30, h#11B7-T31, and chimera 11B7 were measured for their thermal stability. These samples were separately adjusted to a concentration of 0.5 mg/mL (CBS solution), and 400 µL aliquots thereof were used as sample solutions in DSC measurement. The DSC measurement conditions were set as follows: initial temperature: 20° C., final temperature: 100° C., and rate of temperature rise: 60° C./1 hr., and filtering time: 10 sec. CBS was used as a reference solution. VP-Capillary DSC Platform manufactured by MicroCal Inc., US was used as a DSC measurement apparatus. Baseline correction was conducted by subtracting a baseline (scan curve obtained by charging the reference solution to sample cells) from scan curves obtained from the sample solutions.

Figure 35:
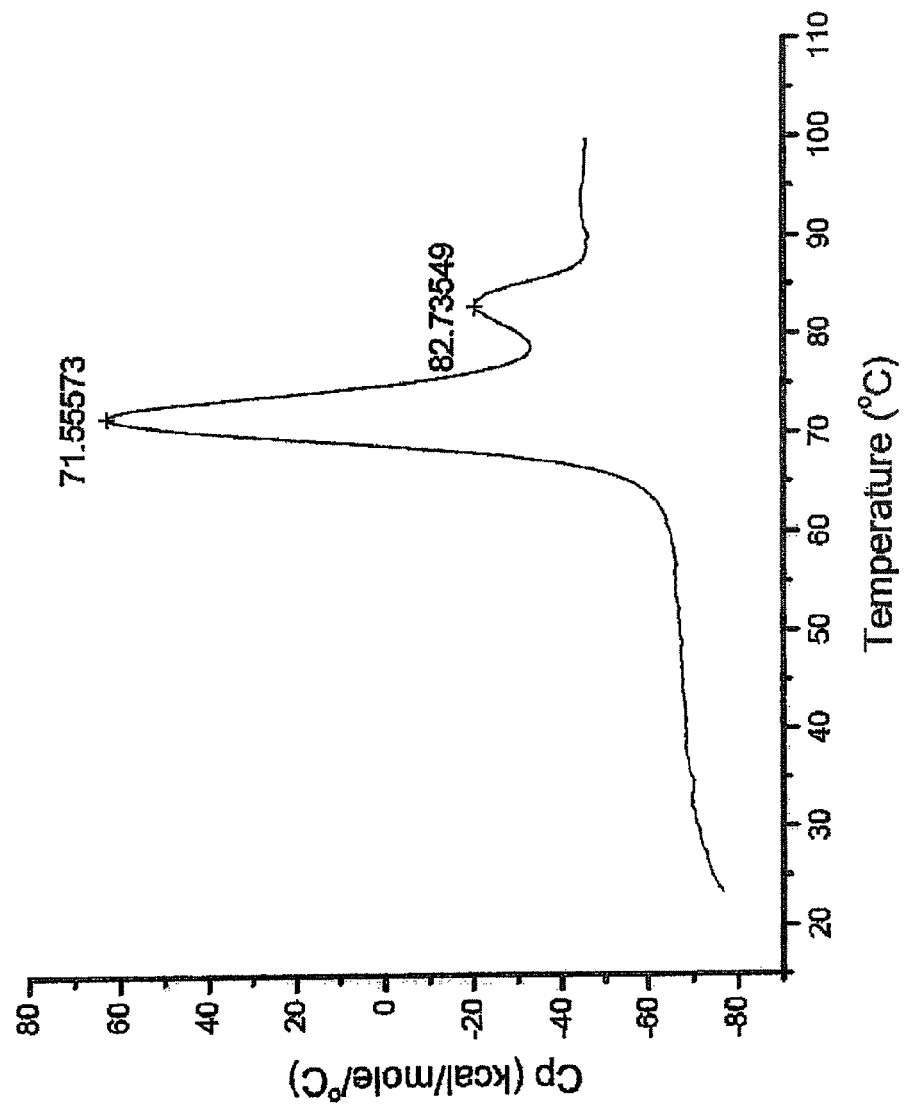
Figure 35:
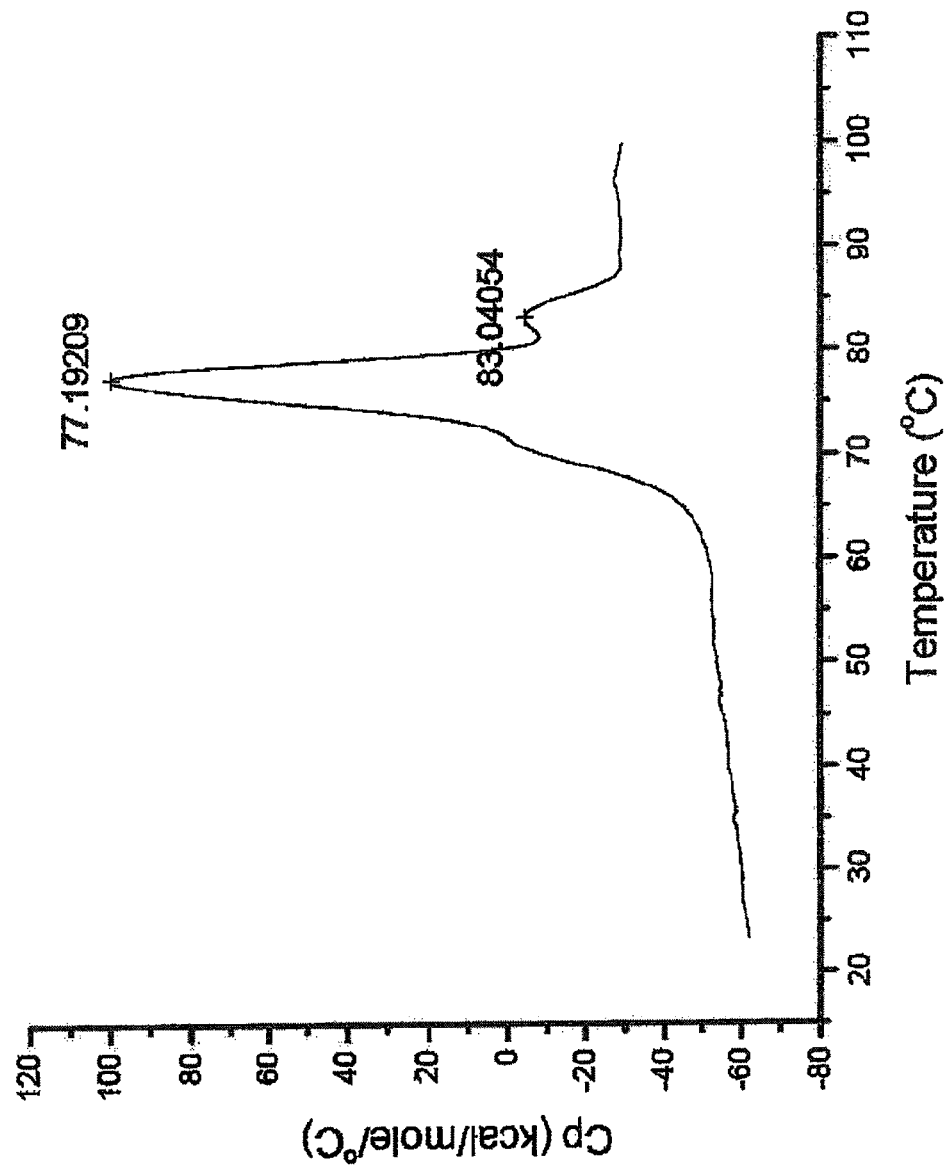
Figure 35:
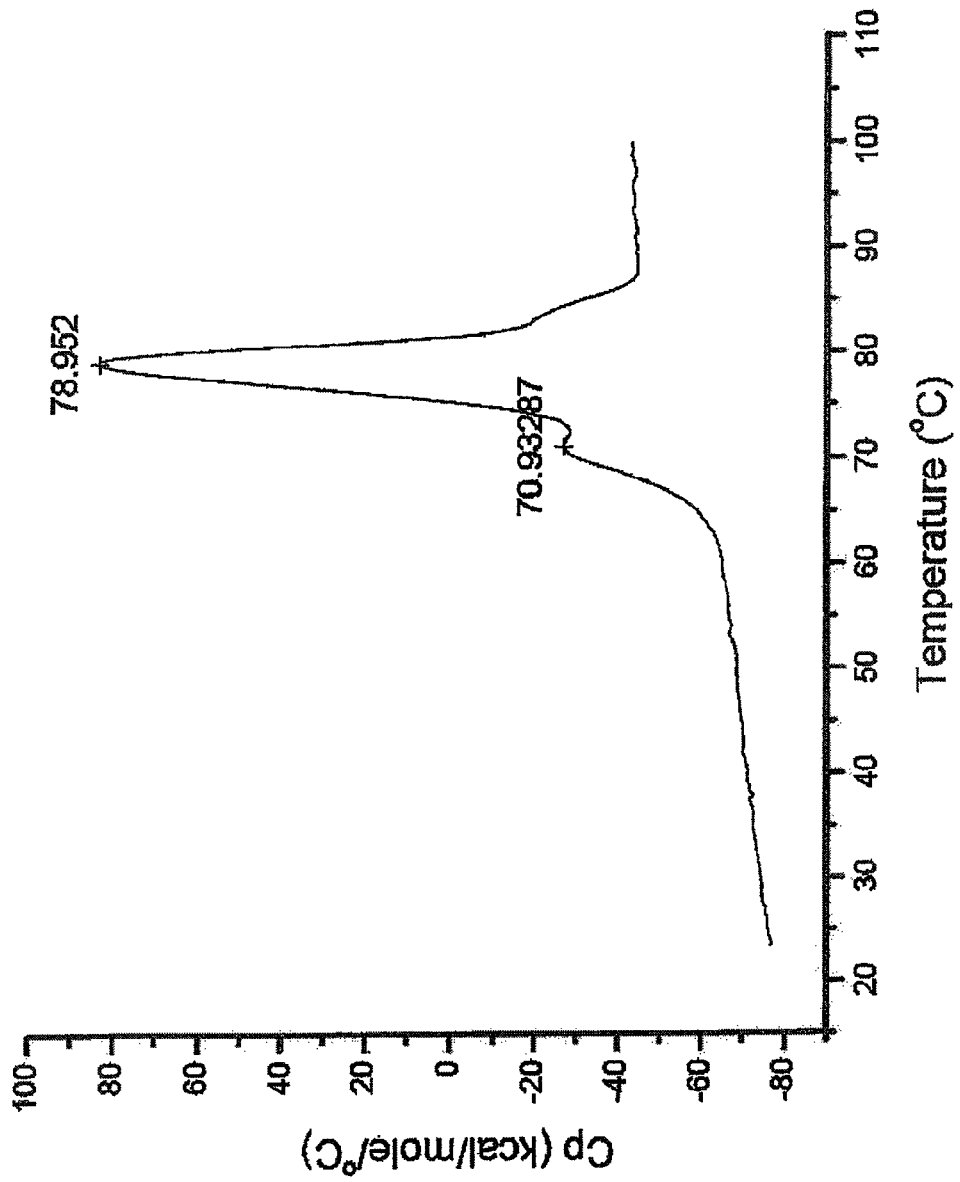
Figure 35H:
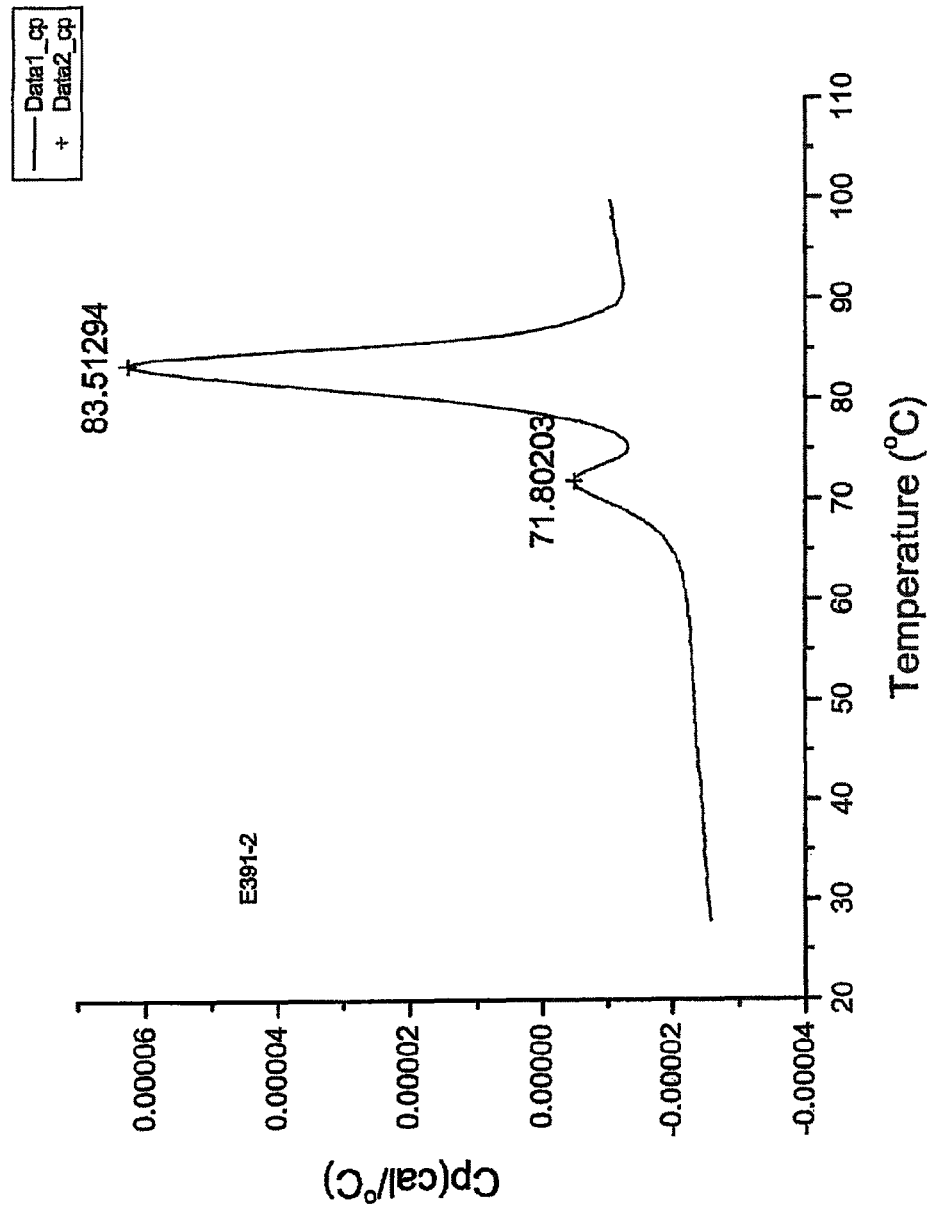
Figure 35:
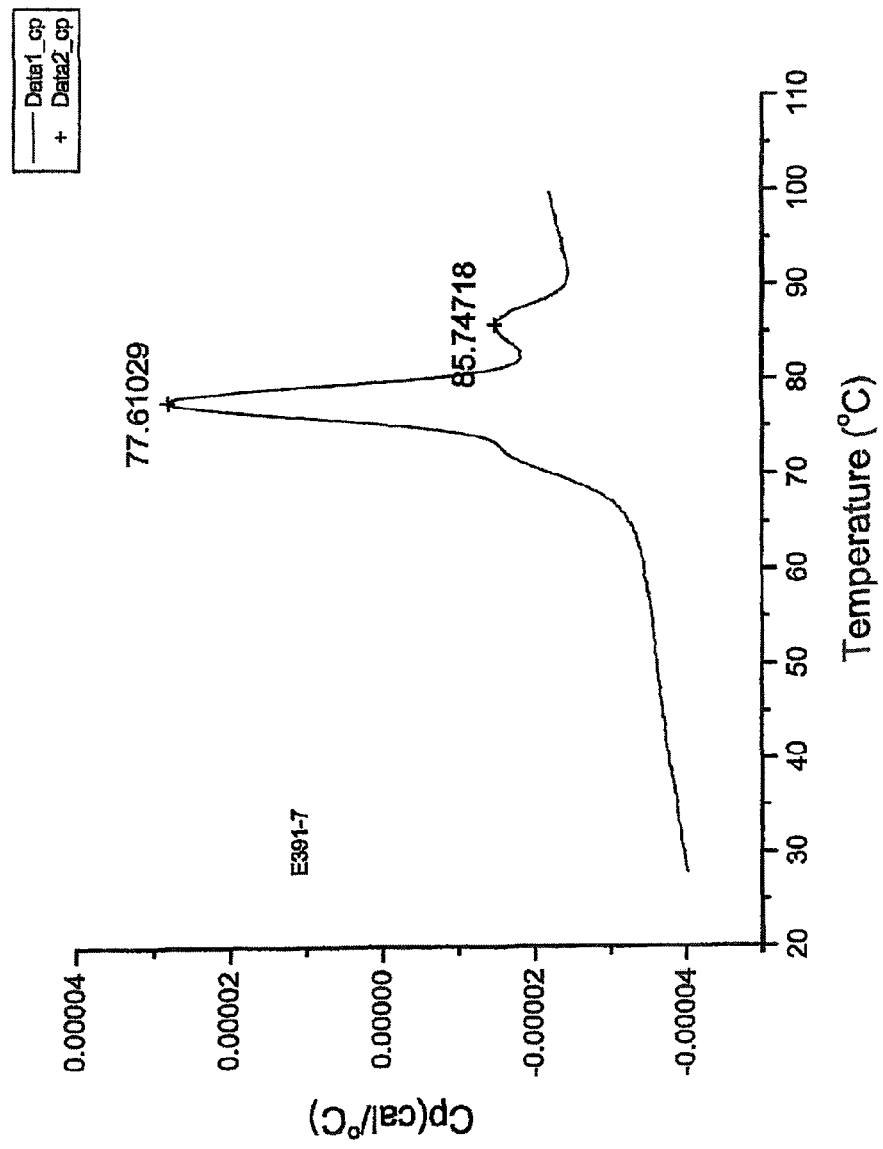
Figure 35:
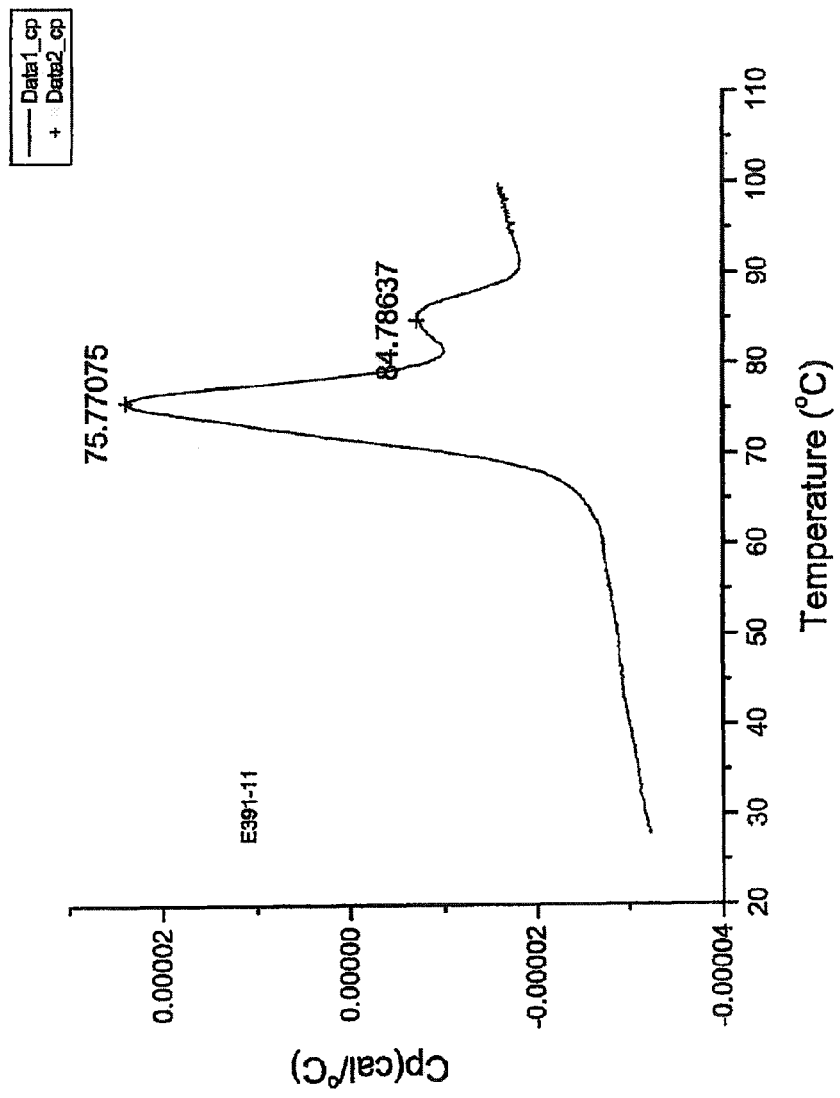
Figure 35:
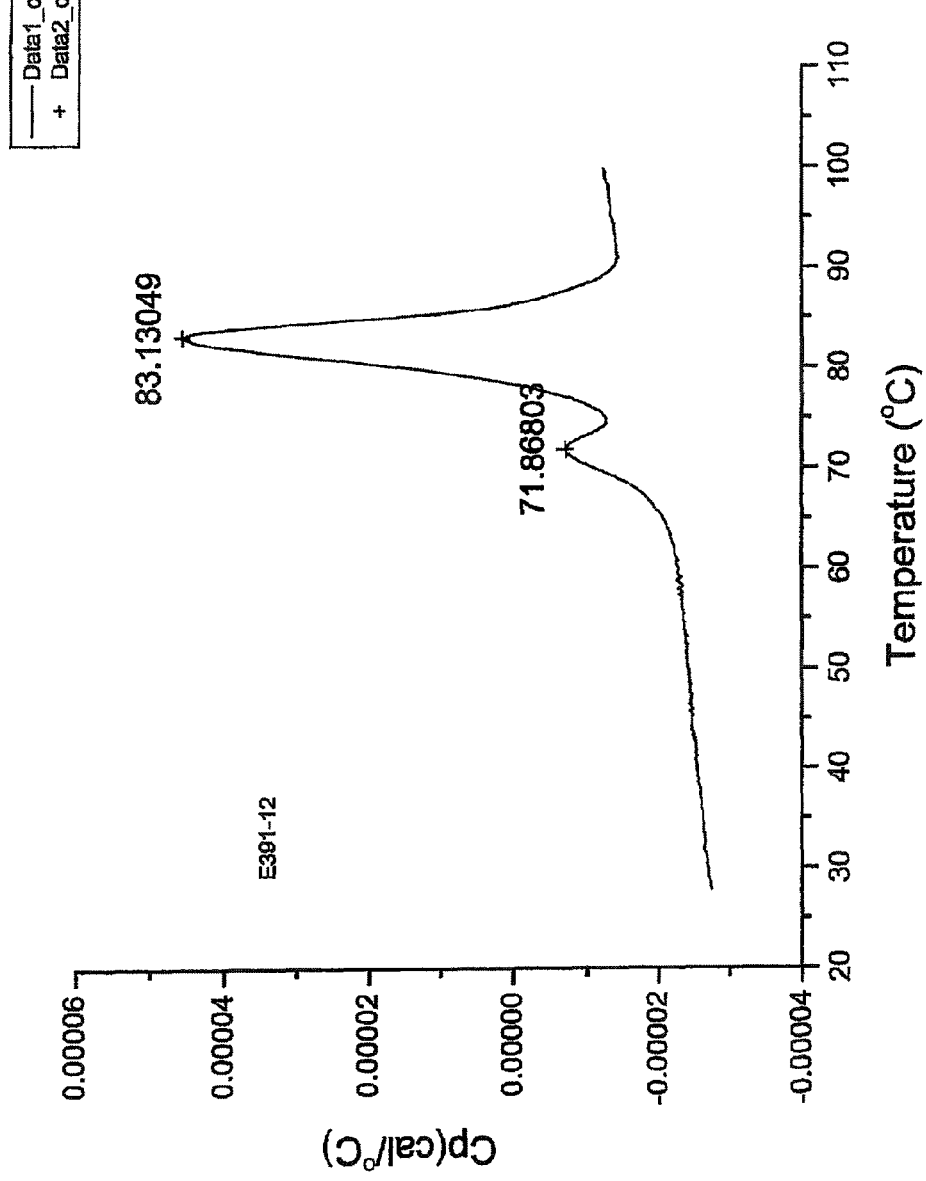
Figure 35:
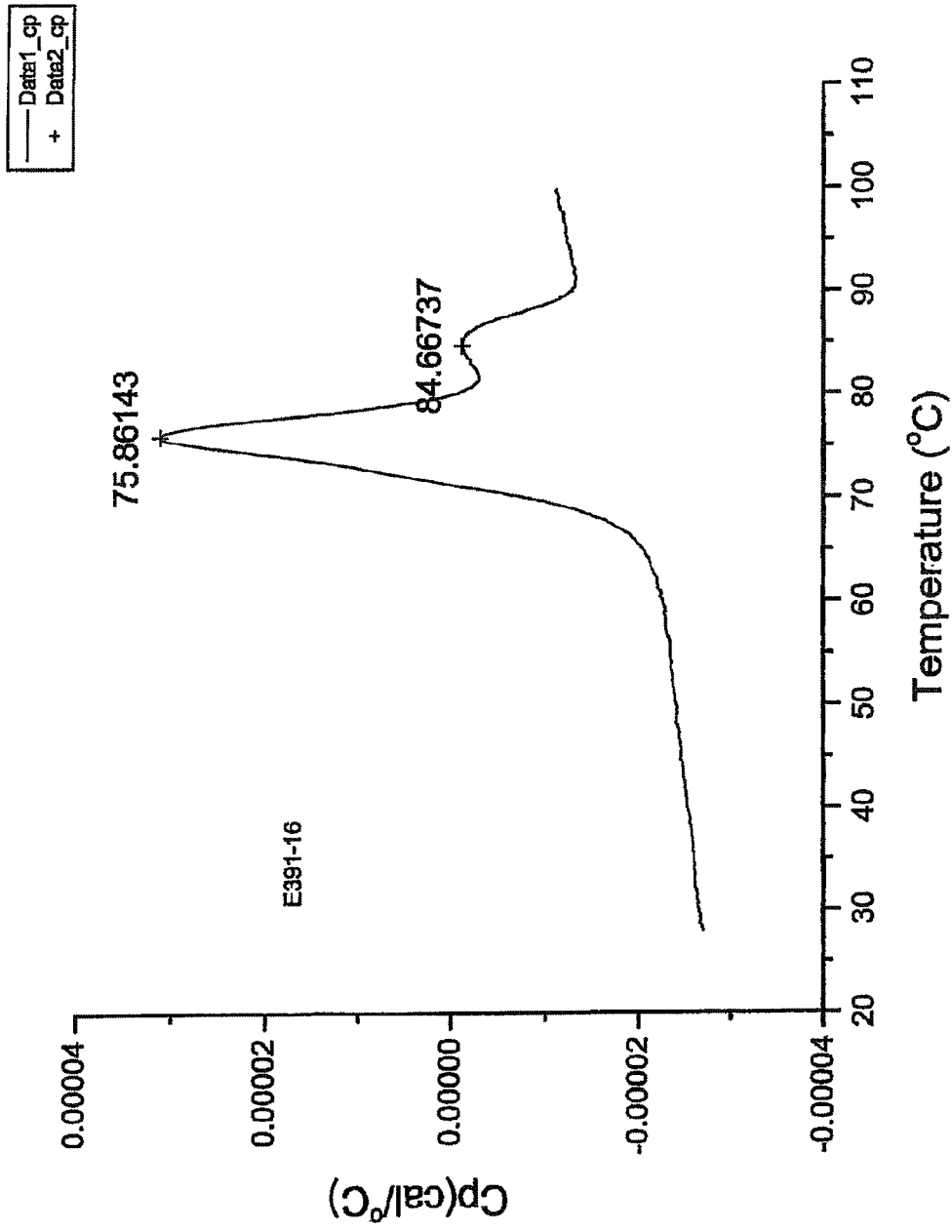
Figure 35:
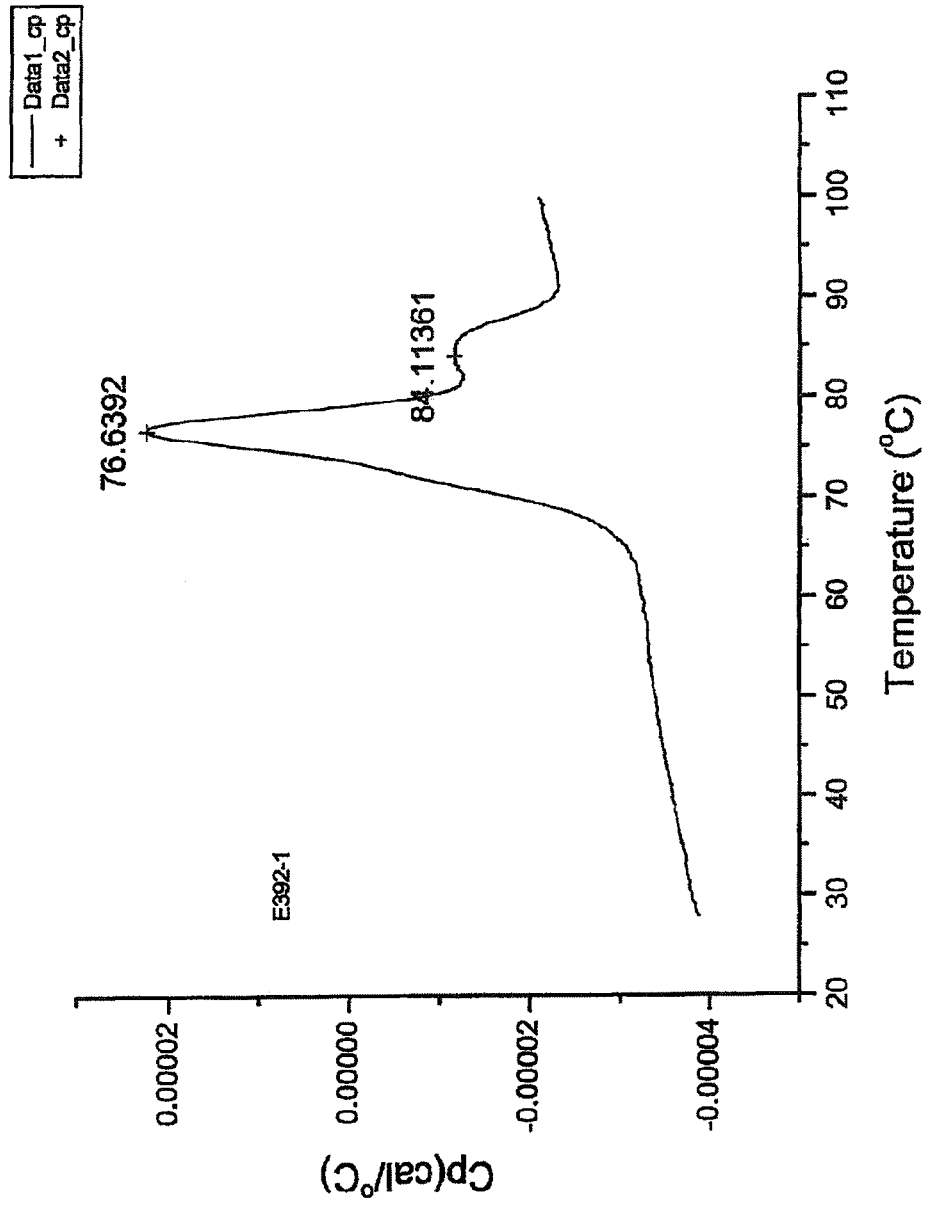
Figure 35:
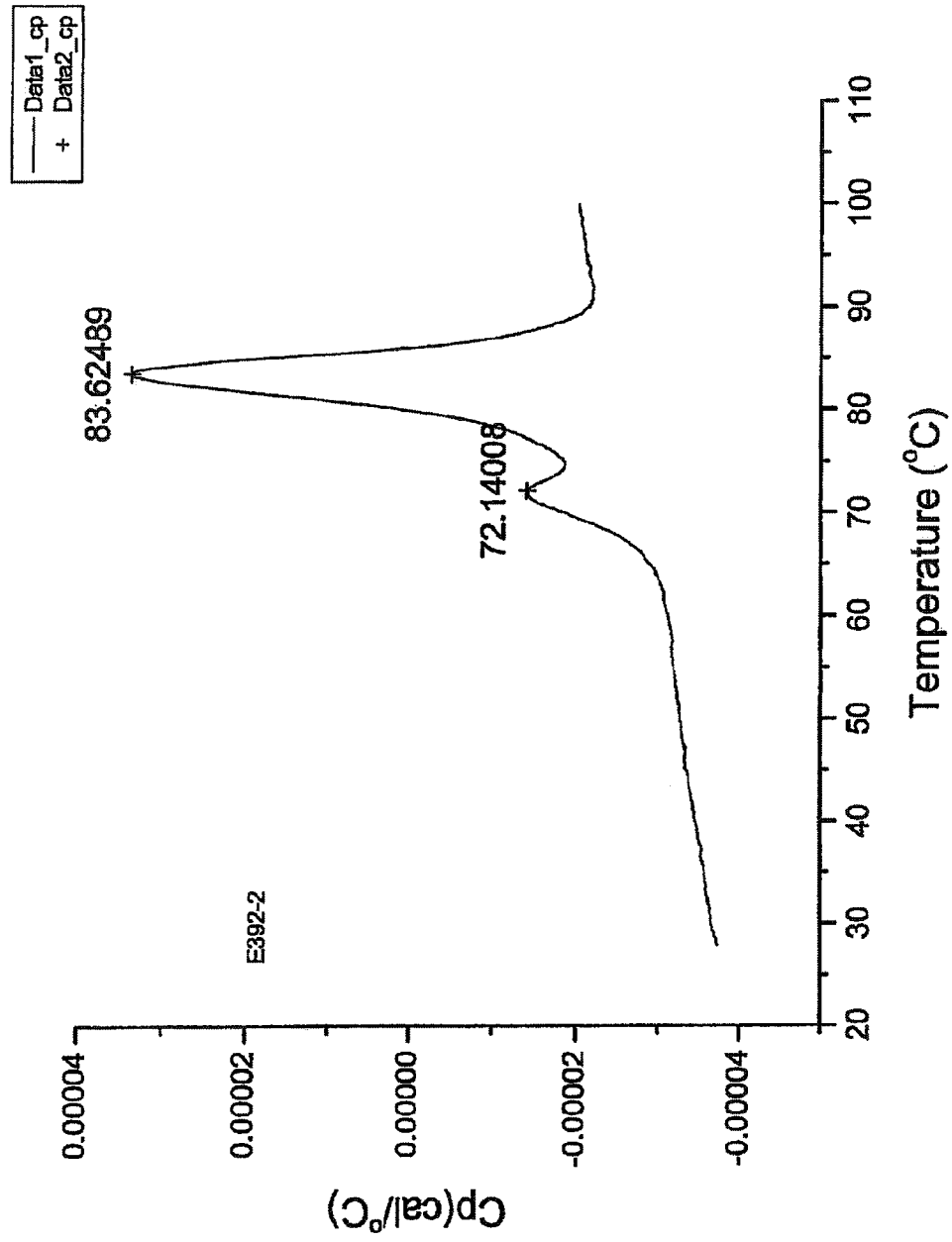
Figure 35:
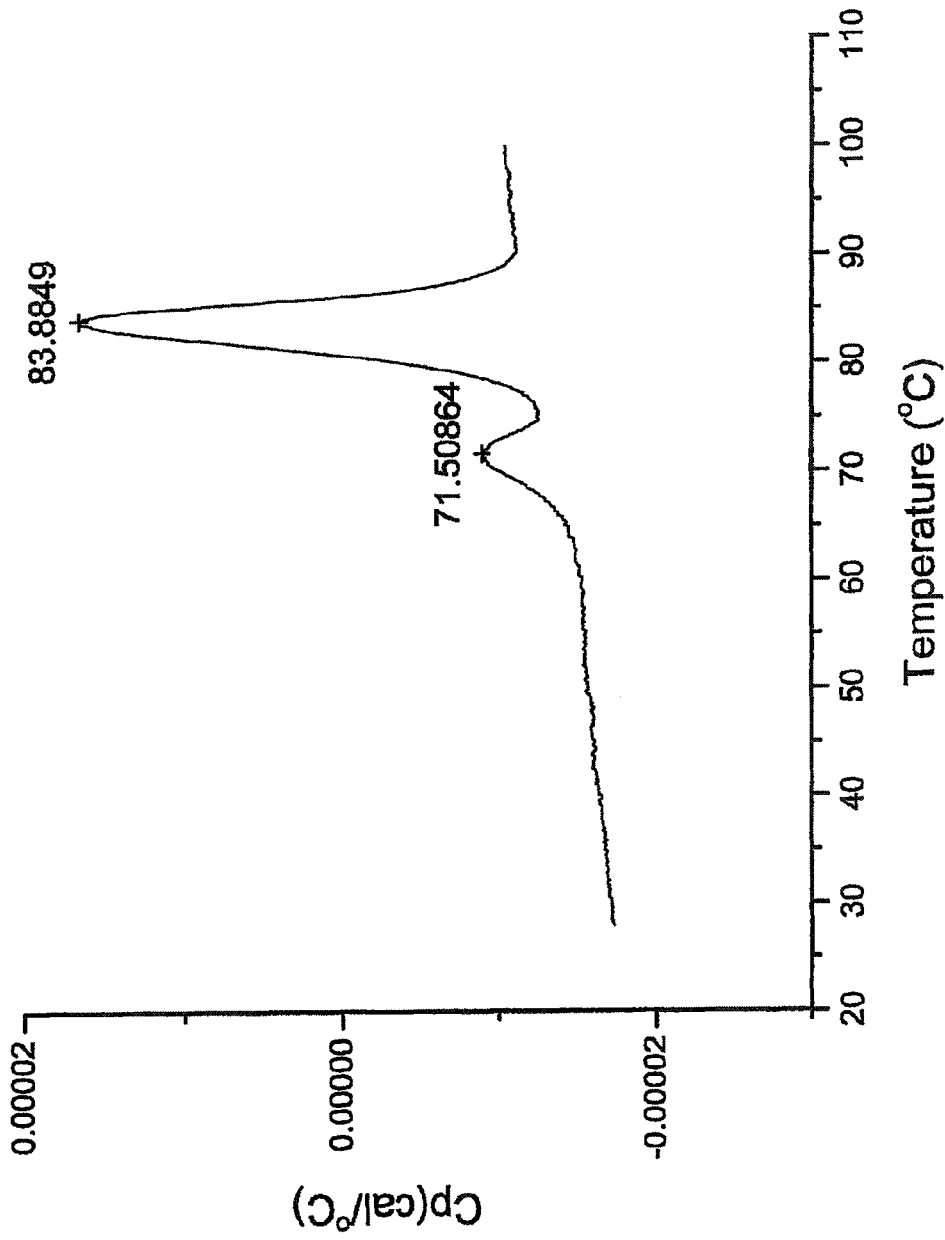
Figure 35:
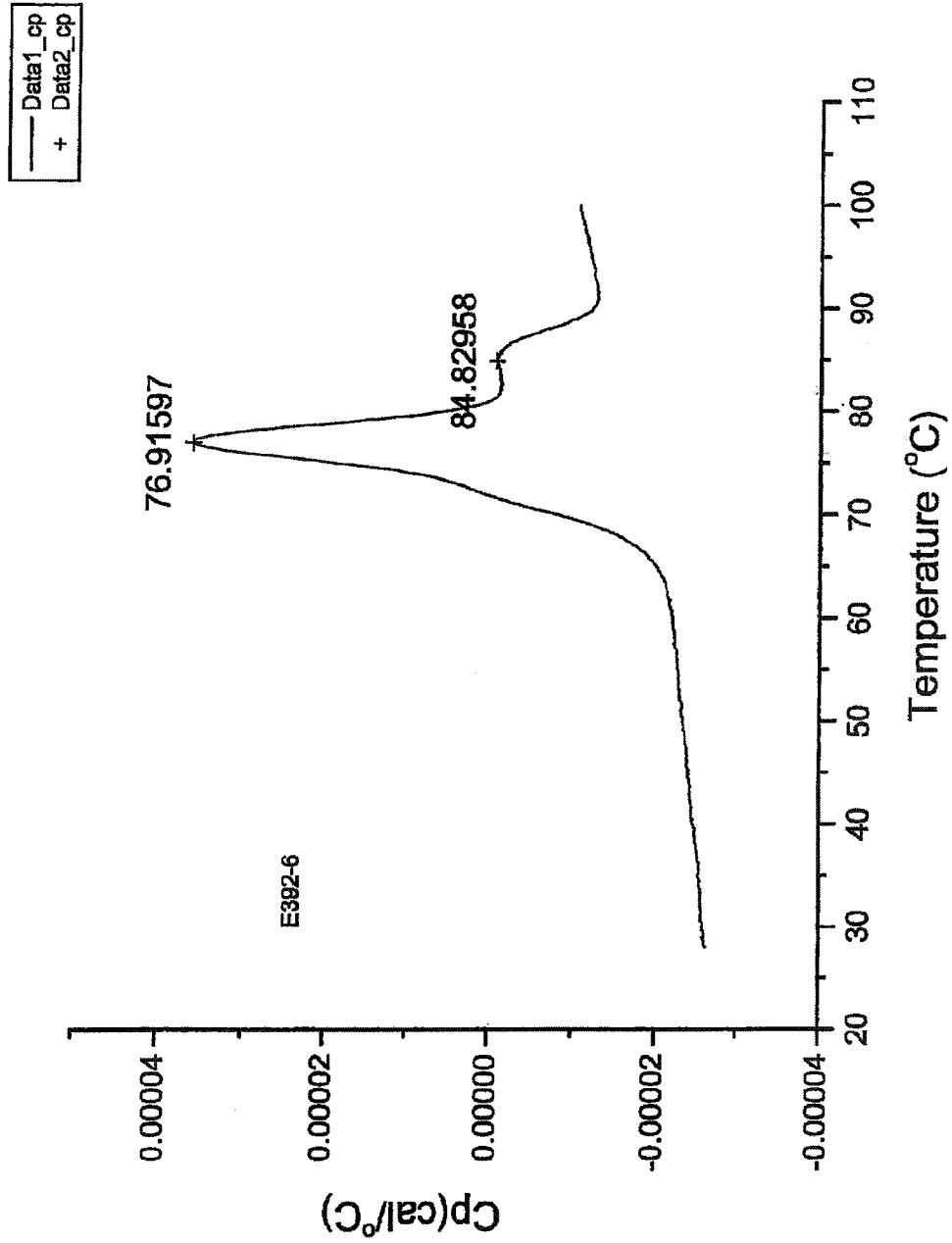

FIG. 35(1) shows the thermogram of h#11B7-T1; FIG. 35(2) shows the thermogram of h#11B7-T2; FIG. 35(3) shows the thermogram of h#11B7-T3; FIG. 35(4) shows the thermogram of h#11B7-T4; FIG. 35(5) shows the thermogram of h#11B7-T5; FIG. 35(6) shows the thermogram of h#11B7-T6; FIG. 35(7) shows the thermogram of h#11B7-T7; FIG. 35(8) shows the thermogram of h#11B7-T8; FIG. 35(9) shows the thermogram of h#11B7-T9; FIG. 35(10) shows the thermogram of h#11B7-T10; FIG. 35(11) shows the thermogram of h#11B7-T11; FIG. 35(12) shows the thermogram of h#11B7-T12; FIG. 35(13) shows the thermogram of h#11B7-T13;

FIG. 35(14) shows the thermogram of h#11B7-T14; FIG. 35(15) shows the thermogram of h#11B7-T15; FIG. 35(16) shows the thermogram of h#11B7-T16; FIG. 35(17) shows the thermogram of h#11B7-T17; FIG. 35(18) shows the thermogram of h#11B7-T18; FIG. 35(19) shows the thermogram of h#11B7-T19; FIG. 35(20) shows the thermogram of h#11B7-T20; FIG. 35(21) shows the thermogram of h#11B7-T21; FIG. 35(22) shows the thermogram of h#11B7-T22; FIG. 35(23) shows the thermogram of h#11B7-T23; FIG. 35(24) shows the thermogram of h#11B7-T24; FIG. 35(25) shows the thermogram of h#11B7-T25; FIG. 35(26) shows the thermogram of h#11B7-T26; FIG. 35(27) shows the thermogram of h#11B7-T27; FIG. 35(28) shows the thermogram of h#11B7-T28; FIG. 35(29) shows the thermogram of h#11B7-T29; FIG. 35(30) shows the thermogram of h#11B7-T30; FIG. 35(31) shows the thermogram of h#11B7-T31; and FIG. 35(32) shows the thermogram of chimera h#11B7.

In this context, the value of the peak top in the whole thermogram is defined as the thermal denaturation midpoint Tm of the Fab region. As a result of the measurement, h#11B7-T1 had Tm of 71.6° C.; h#11B7-T2 had Tm of 77.2° C.; h#11B7-T3 had Tm of 73.0° C.; h#11B7-T4 had Tm of 70.2° C.; h#11B7-T5 had Tm of 73.1° C.; h#11B7-T6 had Tm of 79.0° C.; h#11B7-T7 had Tm of 76.5° C.; h#11B7-T8 had Tm of 83.5° C.; h#11B7-T9 had Tm of 82.5° C.; h#11B7-T10 had Tm of 77.4° C.; h#11B7-T11 had Tm of 83.5° C.; h#11B7-T12 had Tm of 76.6° C.; h#11B7-T13 had Tm of 77.6° C.; h#11B7-T14 had Tm of 75.8° C.; h#11B7-T15 had Tm of 83.1° C.; h#11B7-T16 had Tm of 82.2° C.; h#11B7-T17 had Tm of 76.6° C.; h#11B7-T18 had Tm of 83.0° C.; h#11B7-T19 had Tm of 75.9° C.; h#11B7-T20 had Tm of 76.9° C.; h#11B7-T21 had Tm of 76.6° C.; h#11B7-T22 had Tm of 83.6° C.; h#11B7-T23 had Tm of 83.0° C.; h#11B7-T24 had Tm of 77.6° C.; h#11B7-T25 had Tm of 83.9° C.; h#11B7-T26 had Tm of 76.9° C.; h#11B7-T27 had Tm of 77.9° C.; h#11B7-T28 had Tm of 77.4° C.; h#11B7-T29 had Tm of 77.4° C.; h#11B7-T30 had Tm of 77.8° C.; h#11B7-T31 had Tm of 77.9° C.; and chimera h#11B7 had Tm of 73.1° C.

Example 26

Humanized 11B7 Anti-Axl Antibodies of the Invention Inhibit Ligand-induced Axl Phosphorylation in vitro as Determined by ELISA The protein encoded by the growth arrest specific gene 6, Gas6, represents a natural ligand of the receptor tyrosine kinase Axl. Binding of Gas6 to Axl results in receptor activation which is reflected by increased receptor tyrosine kinase phosphorylation levels. ELISA experiments were performed in order to investigate the potential of the humanized anti-Axl antibodies 11B7-T5 and 11B7-T6 as well as the 11B7-T6 derivatives 11B7-T11, 11B7-T23, and 11B7-T25 of the invention to interfere with Gas6-induced phosphorylation and thus activation of the receptor tyrosine kinase Axl.

In brief, on day 1, $3 \times 10^4$ cells per well were seeded in normal growth medium in flat-bottom 96 well plates. The next day, growth medium was replaced by serum-free medium to starve cells over night for 24 h. Also over night, black Maxi-Sorp 96 well plates (Nunc) were coated with mouse anti-phospho-tyrosine antibody 4G10 at 2 µg/ml PBS at 4° C. On day 3, the 4G10 antibody solution was removed and Maxi-Sorp wells were blocked with blocking buffer (PBS, 0.5% BSA) for at least 4 h at room temperature. In parallel, cells remained untreated or were pre-incubated with 10 µg/ml of Gammagard control antibody (Baxter) as well as the humanized anti-Axl antibodies 11B7-T5, 11B7-T6, 11B7-T11, 11B7-T23, and 11B7-T25 for 1 h at 37° C., and were then treated with or without 400 ng/ml Gas6 (R&D Systems) for 15 min at 37° C. Afterwards, medium was flicked out and cells were lysed in 110 µl of lysis buffer per well (50 mM HEPES, pH 7.5, 150 mM NaCl, 1 mM EDTA, 10% glycerine, and 1% Triton X-100) supplemented with phosphatase and protease inhibitors (10 mM $Na_4P_2O_7$, 1 mM phenylmethylsulfonyl fluoride, 1 mM orthovanadate, 1 mM NaF, and 0.5% aprotinin) for 30 min on ice. Meanwhile, blocking buffer was removed and Maxi-Sorp plates were washed 6× with wash buffer (PBS, 0.05% Tween 20), before 100 µl lysate of each well were transferred and incubated over night at 4° C. After plates were washed 6× with wash buffer on day 4, wells were incubated with biotinylated rat anti-Axl antibody 12B7 at 0.125 µg/ml dilution buffer (20 mM Tris, 50 mM NaCl, pH7.3, 0.05% Tween 20, 0.1% BSA) for 2 h at room temperature. Plates were washed 6× with wash buffer and AP-conjugated streptavidin (Chemicon #SA110) diluted 1:20000 in dilution buffer was added to each well and incubated for 30 min at room temperature. Afterwards, wells were washed 6× with wash buffer and AttoPhos substrate solution (Roche #11681982) was added. Using a SpectraMax-GeminiEM plate reader (Molecular Devices), the fluorescence of each well was collected at an excitation wavelength of 430 nm and an emission wavelength of 580 nm.

FIG. 37 shows representative results of this experiment for Hs578T breast cancer cells (top) and NCI-H292 lung cancer cells (bottom). Compared with Gammagard control antibody, the humanized anti-Axl antibodies 11B7-T5, 11B7-T6, 11B7-T11, 11B7-T23, and 11B7-T25 of the invention significantly reduced Gas6-mediated Axl activation in both cell lines as indicated by decreased Axl tyrosine phosphorylation levels in Gas6-stimulated versus corresponding non-stimulated cells.

Example 27

Humanized 11B7 Anti-Axl Antibodies of the Invention Inhibit Ligand-induced Akt Phosphorylation in vitro as Determined by ELISA Furthermore, ELISA experiments were performed in order to investigate whether the humanized anti-Axl antibodies 11B7-T5 and 11B7-T6 as well as the 11B7-T6 derivatives 11B7-T11, 11B7-T23, and 11B7-T25 of the invention are able to block ligand Gas6-mediated activation of Akt-Kinase. Gas6-mediated Akt-Kinase activation was detected by increased protein (Ser473) phosphorylation.

In brief, on day 1, $2\times10^4$ cells per well were seeded in flat-bottom 96 well plates. The next day, normal growth medium was replaced by serum-free medium to starve cells for 36 h. Thereafter, cells remained untreated or were pre-incubated with 10 µg/ml of Gammagard control antibody (Baxter) as well as the humanized anti-Axl antibodies 11B7-T5, 11B7-T6, 11B7-T11, 11B7-T23, and 11B7-T25 for 1 h at 37° C., and were then treated with or without 400 ng/ml Gas6 (R&D Systems) for 15 min at 37° C. Medium was flicked out and cells were fixed with 4% formaldehyde in PBS (pH 7.5) for 30 min at room temperature. Formaldehyde solution was removed and cells were washed twice with wash buffer (PBS, 0.1% Tween 20). Cells were quenched with 1% $H_2O_2$, 0.1% $NaN_3$ in wash buffer and incubated for 20 min at room temperature. Afterwards, the quenching solution was removed, and cells were washed twice with wash buffer and blocked with PBS, 0.5% BSA for 4 h at room temperature. Anti-phospho-Akt (Ser473) primary antibody (polyclonal rabbit; Cell Signaling #9271) diluted 1:500 in PBS, 0.5% BSA, 5 mM EDTA was added over night at 4° C. On day 4, the antibody solution was removed and the plate was washed 3× with wash buffer. HRP-conjugated anti-rabbit secondary antibody (Dianova #111-036-045) diluted 1:2500 in PBS, 0.5% BSA was then added to each well and incubated for 1.5 h at room temperature. The plate was washed 3× with wash buffer and twice with PBS for 5 min each. Tetramethylbenzidine (TMB, Calbiochem) was added and monitored at 620 nm. The reaction was stopped by addition of 100 µl of 250 nM HCl and the absorbance was read at 450 nm with a reference wavelength of 620 nm using a Vmax plate reader (Thermo Lab Systems).

FIG. 38 shows representative results of this experiment for Hs578T breast cancer cells (top) and NCI-H292 lung cancer cells (bottom). Compared with Gammagard control antibody, the humanized anti-Axl antibodies 11B7-T5, 11B7-T6, 11B7-T11, 11B7-T23, and 11B7-T25 of the invention were able to block or reduce Gas6-mediated Akt-kinase activation in both cell lines as indicated by decreased Akt (Ser473) phosphorylation levels in Gas6-stimulated versus corresponding non-stimulated cells.

Example 28

Humanized 11B7 Anti-Axl Antibodies of the Invention Induce Axl Receptor Internalization Axl has been identified as a factor that can influence migration and survival of tumor cells through Axl-mediated signal transduction pathways including the Akt pathway addressed above. Thus, if Axl is effectively cleared from the cell surface/ membrane by receptor internalization, cell signaling and therefore maintenance of cells as well as tumor growth and metastasis can be ultimately diminished or suppressed.

In order to investigate whether the humanized anti-Axl antibodies 11B7-T5 and 11B7-T6 as well as the 11B7-T6 derivatives 11B7-T11, 11B7-T23, and 11B7-T25 of the invention are capable of inducing accelerated endocytosis of Axl, the relative amount of Axl molecules on the cell surface after 2, 4, 6 and 20 h incubation of the cells with the humanized anti-Axl antibodies of the invention were compared.

In brief, on day 1, $2\times10^5$ cells were seeded in normal growth medium in 6-well dishes and left to grow overnight. The next day, medium was removed and cells were washed with serum-free medium. Then, cells remained untreated or were incubated with 10 µg/ml of Gammagard control antibody (Baxter), as well as the humanized anti-Axl antibodies 11B7-T5, 11B7-T6, 11B7-T11, 11B7-T23, and 11B7-T25 in serum-free medium supplemented with 10 mM HEPES for 40 min at 4° C. Subsequently, cells were transferred to 37° C. for the indicated periods of time to allow internalization to occur. Afterwards, cells were detached with 10 mM EDTA, and re-suspended in 100 µl of wash buffer (PBS, 3% FCS). For subsequent fixation, 100 µl of 2% paraformaldehyde in PBS were added dropwise while vigorously shaking cells. After 20 min of incubation at room temperature, cells were washed and re-suspended in 100 µl of wash buffer for storage in the fridge until all samples were collected. In order to finally stain cells for Axl expression levels, samples were transferred to round-bottom 96-well plates and incubated with 3 µg/ml rat anti-Axl mAb 2A1 in wash buffer for 1 h at 4° C. Cells were washed twice with wash buffer, incubated with donkey-anti-rat IgG-PE secondary antibody (Dianova) diluted 1:100 for 60 min at 4° C., washed twice with wash buffer again and analyzed by FACS (Beckman Coulter EPICS, EXPO32).

Representative data in FIG. 38 demonstrate that treatment of Hs578T breast cancer cells with the humanized anti-Axl antibodies 11B7-T5, 11B7-T6, 11B7-T11, 11B7-T23, and 11B7-T25 leads to internalization of the Axl receptor, whereas Gammagard control antibody did not have any effect. Relative Axl expression levels in %, defined as mean fluorescence intensity of anti-Axl mAb treated samples relative to untreated samples of the respective treatment period is shown.

Example 29

Humanized 11B7 Anti-Axl Antibodies of the Invention Inhibit Spheroid-based Cellular Angiogenesis in vitro Axl is a key regulator of multiple angiogenic behaviors including endothelial cell migration, proliferation, and tube formation in vitro (Holland et al., Cancer Res: 65, 9294-9303, 2005). Therefore, the humanized anti-Axl antibodies 11B7-T5 and 11B7-T6 as well as the 11B7-T6 derivatives 11B7-T11, 11B7-T23, and 11B7-T25 of the invention were tested for inhibitory effects on Gas6-induced vessel sprouting of HUVEC-spheroids. The experiments were pursued in modification of the originally published protocol (Korff and Augustin: J Cell Sci 112: 3249-58, 1999).

In brief, spheroids were prepared as described (Korff and Augustin: J Cell Biol 143: 1341-52, 1998) by pipetting 500 human umbilical vein endothelial cells (HUVEC) in combination with VEGF-A [25 ng/ml] in a hanging drop on plastic dishes to allow over night spheroid aggregation. 50 HUVEC spheroids were then seeded in 0.9 ml of a collagen solution (2 mg/ml) and pipetted into individual wells of a 24 well plate to allow polymerization. After 30 min, decreasing concentrations of Gammagard control antibody (Baxter) or the humanized anti-Axl antibodies 11B7-T5, 11B7-T6, 11B7-T11, 11B7-T23, and 11B7-T25 ($1\times10^{-6}$ M, $3\times10^{-7}$ M, $1\times10^{-7}$ M, $3\times10^{-8}$ M, $1\times10^{-8}$ M, $3\times10^{-9}$ M, $1\times10^{-10}$ M) together with human GAS6 (R&D Systems) were added by pipetting 100 µl of a 10-fold concentrated working dilution on top of the polymerized gel (final human GAS6 concentration 1 µg/ml). Plates were incubated at 37° C. for 24 hours and fixed by adding 4% Roti-Histofix (Roth, Karlsruhe, Germany). Sprouting intensity of HUVEC spheroids was quantified by an image analysis system that determines the cumulative sprout length per spheroid using an inverted microscope and the digital imaging software Analysis 3.2 (Soft imaging system, Munster, Germany). The mean of the cumulative sprout length of 10 randomly selected spheroids was analyzed as an individual data point.

FIG. 39 shows representative results of this experiment.

The invention claimed is:

1. A monoclonal humanized antibody that binds to the extracellular domain of AXL and at least partially inhibits AXL activity, wherein said antibody comprises a heavy chain amino acid sequence selected from the group consisting of SEQ ID NO:67 to SEQ ID NO:72, or at least the variable domain thereof, or a variable domain of a heavy chain amino acid sequence selected from the group consisting of SEQ ID NO:114 to SEQ ID NO:120 and a light chain amino acid sequence selected from the group consisting of SEQ ID NO:55 to SEQ ID NO:60, or a variable domain of a light chain amino acid sequence selected from the group consisting of SEQ ID NO:83 to SEQ ID NO:113.

2. The monoclonal humanized antibody of claim 1, which reduces and/or blocks AXL-mediated signal transduction, AXL phosphorylation, cell proliferation, angiogenesis, cell migration, tumor metastasis and/or AXL mediated anti-apoptosis.

3. The monoclonal humanized antibody of claims 1, which reduces and/or blocks ligand induced phosphorylation of AXL downstream signaling molecules such as ERK1/2, AKT, GSK-3β, TSC2, mTOR and/or S6K1.

4. The monoclonal humanized antibody according to claim 1, which contains at least one mutation in the frame work region of at least one variable domain of the chimeric anti-AXL antibody 11D5 (SEQ ID NO: 137, 138).

5. The monoclonal humanized antibody of claim 1, selected from the group of humanized h#11D5 antibodies selected from the group consisting of h#11D5-T1, h#11D5-

T2, h#11D5-T3, h#11D5-T4, h#11D5-T5 and h#11D5-T6, wherein h#11D5-T1 comprises SEQ ID NO:55 and SEQ ID NO: 67, h#11D5-T2 comprises SEQ ID NO:56 and SEQ ID NO: 68, h#11D5-T3 comprises SEQ ID NO:57 and SEQ ID NO: 69, h#11D5-T4 comprises SEQ ID NO:58 and SEQ ID NO: 70, h#11D5-T5 comprises SEQ ID NO:59 and SEQ ID NO: 71 and h#11D5-T6 comprises SEQ ID NO:60 and SEQ ID NO: 72.

6. The monoclonal humanized antibody according to claim 1, which is coupled to a labeling group.

7. The monoclonal humanized antibody according to claim 1, which is coupled to an effector-group.

8. A pharmaceutical composition comprising a humanized antibody according to claim 1.

9. The pharmaceutical composition of claim 8 comprising pharmaceutically acceptable carriers, diluents and/or adjuvants.

10. The pharmaceutical composition according to claim 9, wherein said pharmaceutically acceptable carriers, diluents and/or adjuvants are suitable for the diagnosis, prevention or treatment of a hyperproliferative disease associated with AXL expression, overexpression and/or hyperactivity.

11. A kit comprising an anti-AXL-antibody according to claim 1 and an antineoplastic agent.

* * * * *

```
                        SEQUENCE LISTING

<160> NUMBER OF SEQ ID NOS: 169

<210> SEQ ID NO 1
<211> LENGTH: 28
<212> TYPE: DNA
<213> ORGANISM: Artificial
<220> FEATURE:
<223> OTHER INFORMATION: Primer EFF1

<400> SEQUENCE: 1
ccacgcgccc tgtagcggcg cattaagc                                            28

<210> SEQ ID NO 2
<211> LENGTH: 30
<212> TYPE: DNA
<213> ORGANISM: Artificial
<220> FEATURE:
<223> OTHER INFORMATION: Primer EFsmaR

<400> SEQUENCE: 2
aaacccggga gcttttttgca aaagcctagg                                          30

<210> SEQ ID NO 3
<211> LENGTH: 1704
<212> TYPE: DNA
<213> ORGANISM: Homo sapiens

<400> SEQUENCE: 3
ggtaccaccc aagctggcta ggtaagcttg ctagcgccac catggtgctg cagacccagg         60
tgttcatctc cctgctgctg tggatctccg gcgcatatgg cgatatcgtg atgattaaac        120
gtacggtggc cgcccccctcc gtgttcatct tccccccctc cgacgagcag ctgaagtccg        180
gcaccgcctc cgtggtgtgc ctgctgaata acttctaccc cagagaggcc aaggtgcagt        240
ggaaggtgga caacgccctg cagtccggga actcccagga gagcgtgacc gagcaggaca        300
gcaaggacag cacctacagc ctgagcagca ccctgaccct gagcaaagcc gactacgaga        360
agcacaaggt gtacgcctgc gaggtgaccc accagggcct gagctccccc gtcaccaaga        420
gcttcaacag gggggagtgt taggggcccg tttaaacggg tggcatccct gtgaccctc         480 cccagtgcct ctcctggccc tggaagttgc cactccagtg cccaccagcc ttgtcctaat        540
aaaattaagt tgcatcattt tgtctgacta ggtgtccttc tataatatta tggggtggag        600
gggggtggta tggagcaagg ggcaagttgg gaagacaacc tgtagggcct gcggggtcta        660
ttgggaacca agctggagtg cagtggcaca atcttggctc actgcaatct ccgcctcctg        720
ggttcaagcg attctcctgc ctcagcctcc cgagttgttg ggattccagg catgcatgac        780
caggctcacc taatttttgt ttttttggta gagacggggt ttcaccatat tggccaggct        840
```

```
ggtctccaac tcctaatctc aggtgatcta cccaccttgg cctcccaaat tgctgggatt      900
acaggcgtga accactgctc cacgcgccct gtagcggcgc attaagcgcg gcgggtgtgg      960
tggttacgcg cagcgtgacc gctacacttg ccagcgccct agcgcccgct cctttcgctt     1020
tcttcccttc ctttctcgcc acgttcgccg gctttccccg tcaagctcta aatcgggggc     1080 tcccttagg gttccgattt agtgctttac ggcacctcga ccccaaaaaa cttgattagg     1140
gtgatggttc acgtagtggg ccatcgccct gatagacggt ttttcgccct ttgacgttgg     1200
agtccacgtt ctttaatagt ggactcttgt tccaaactgg aacaacactc aaccctatct     1260
cggtctattc ttttgattta taagggattt tgccgatttc ggcctattgg ttaaaaaatg     1320
agctgattta acaaaaattt aacgcgaatt aattctgtgg aatgtgtgtc agttagggtg     1380
tggaaagtcc ccaggctccc cagcaggcag aagtatgcaa agcatgcatc tcaattagtc     1440
agcaaccagg tgtggaaagt ccccaggctc cccagcaggc agaagtatgc aaagcatgca     1500
tctcaattag tcagcaacca tagtcccgcc cctaactccg cccatcccgc cctaactcc     1560 gcccagttcc gcccattctc cgccccatgg ctgactaatt ttttttattt atgcagaggc     1620
cgaggccgcc tctgcctctg agctattcca gaagtagtga ggaggctttt ttggaggcct     1680
aggcttttgc aaaaagctcc cggg                                          1704

<210> SEQ ID NO 4
<211> LENGTH: 1120
<212> TYPE: DNA
<213> ORGANISM: Homo sapiens

<400> SEQUENCE: 4
tgctagcgcc accatgaaac acctgtggtt cttcctcctg ctggtggcag ctcccagatg       60
ggtgctgagc caggtgcaat gtgcaggcg gttagctcag cctccaccaa gggcccaagc      120
gtcttccccc tggcaccctc ctccaagagc acctctggcg gcacagccgc cctgggctgc      180
ctggtcaagg actacttccc cgaacccgtg accgtgagct ggaactcagg cgccctgacc      240
agcggcgtgc acaccttccc cgctgtcctg cagtcctcag gactctactc cctcagcagc      300
gtggtgaccg tgccctccag cagcttgggc acccagacct acatctgcaa cgtgaatcac      360
aagcccagca acaccaaggt ggacaagaga gttgagccca aatcttgtga caaaactcac      420
acatgcccac cctgcccagc acctgaactc ctggggggac cctcagtctt cctcttcccc      480
ccaaaaccca aggacaccct catgatctcc cggacccctg aggtcacatg cgtggtggtg      540
gacgtgagcc acgaagaccc tgaggtcaag ttcaactggt acgtggacgg cgtggaggtg      600
cataatgcca agacaaagcc ccgggaggag cagtacaaca gcacgtaccg ggtggtcagc      660
gtcctcaccg tcctgcacca ggactggctg aatggcaagg agtacaagtg caaggtctcc      720
aacaaagccc tcccagcccc catcgagaaa accatctcca aagccaaagg ccagccccgg      780
gaaccacagg tgtacaccct gcccccatcc cgggaggaga tgaccaagaa ccaggtcagc      840
ctgacctgcc tggtcaaagg cttctatccc agcgacatcg ccgtggagtg ggagagcaat      900
ggccagcccg agaacaacta caagaccacc cctcccgtgc tggactccga cggctccttc      960
ttcctctaca gcaagctcac cgtggacaag agcaggtggc agcagggcaa cgtcttctca     1020
tgctccgtga tgcatgaggc tctgcacaac cactacaccc agaagagcct ctccctgtct     1080
cccggcaaat gagatatcgg gcccgtttaa acgggtggca                          1120

<210> SEQ ID NO 5
```

```
<211> LENGTH: 702
<212> TYPE: DNA
<213> ORGANISM: Artificial
<220> FEATURE:
<223> OTHER INFORMATION: h#11B7-T1L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 5
atggtgctgc agacccaggt gttcatctcc ctgctgctgt ggatctccgg cgcatatggc      60
gacatccaga tgacccagag ccctagctct ctgagcgcct ctgtgggcga ccgggtgacc     120
atcacctgtc gggccagcca ggacatcggc aactacctga tggtaccca gcagaagcct     180 ggaaaggccc ctaagctgct gatcagcggc gccaccaacc tggccgccgg cgtgcctagc     240
cggttctctg aaccggatc tggcaccgac ttcaccttca ccatcagctc tctgcagcct     300
gaggacttcg ccacctacta ctgtctgcag agcaaggagt ctccttggac cttcggcgga     360
ggcaccaagg tggagatcaa gcgtacggtg gccgcccct ccgtgttcat cttcccccc      420 tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag caccctgacc     600
ctgagcaaag ccgactacga aagcacaag gtgtacgcct gcgaggtgac ccaccagggc     660
ctgagctccc ccgtcaccaa gagcttcaac aggggggagt gt                        702

<210> SEQ ID NO 6
<211> LENGTH: 702
<212> TYPE: DNA
<213> ORGANISM: Artificial
<220> FEATURE:
<223> OTHER INFORMATION: h#11B7-T2L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 6
atggtgctgc agacccaggt gttcatctcc ctgctgctgt ggatctccgg cgcatatggc      60
gacatccaga tgacccagag ccctagctct ctgagcgcct ctgtgggcga ccgggtgacc     120
atcacctgtc gggccagcca ggacatcggc aactacctga tggttccca gcagaagcct     180 ggaaaggccc ctaagctgat gatcagcggc gccaccaacc tggccgccgg cgtgcctagc     240
cggttctctg aaccggatc tggcaccgac tacaccttca ccatcagctc tctgcagcct     300
gaggacttcg ccacctacta ctgtctgcag agcaaggagt ctccttggac cttcggcgga     360
ggcaccaagg tggagatcaa gcgtacggtg gccgcccct ccgtgttcat cttcccccc      420 tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
```

| | |
|---|---|
| gagagcgtga ccgagcagga cagcaaggac agcacctaca gcctgagcag caccctgacc | 600 |
| ctgagcaaag ccgactacga aagcacaag gtgtacgcct gcgaggtgac ccaccagggc | 660 |
| ctgagctccc ccgtcaccaa gagcttcaac agggggagt gt | 702 |

<210> SEQ ID NO 7
<211> LENGTH: 702
<212> TYPE: DNA
<213> ORGANISM: Artificial
<220> FEATURE:
<223> OTHER INFORMATION: h#11B7-T3L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 7

| | |
|---|---|
| atggtgctgc agacccaggt gttcatctcc ctgctgctgt ggatctccgg cgcatatggc | 60 |
| gacatccaga tgacccagag ccctagctct ctgagcgcct ctgtgggcga ccgggtgacc | 120 |
| atcacctgtc gggccagcca ggacatcggc aactacctga tggttcca gcagaagcct | 180 |
| ggaaaggccc ctaagctgat gatcagcggc gccaccaacc tggccgccgg cgtgcctagc | 240 |
| cggttctctg gaagccggtc tggcagcgac tacaccctga ccatcagctc tctgcagcct | 300 |
| gaggacttcg ccacctacta ctgtctgcag agcaaggagt ctccttggac cttcggcgga | 360 |
| ggcaccaagg tggagatcaa gcgtacggtg gccgcccct ccgtgttcat cttcccccc | 420 |
| tccgacgagc agctgaagtc cggcaccgcc tccgtggtgt gcctgctgaa taacttctac | 480 |
| cccagagagg ccaaggtgca gtggaaggtg gacaacgccc tgcagtccgg gaactcccag | 540 |
| gagagcgtga ccgagcagga cagcaaggac agcacctaca gcctgagcag caccctgacc | 600 |
| ctgagcaaag ccgactacga aagcacaag gtgtacgcct gcgaggtgac ccaccagggc | 660 |
| ctgagctccc ccgtcaccaa gagcttcaac agggggagt gt | 702 |

<210> SEQ ID NO 8
<211> LENGTH: 702
<212> TYPE: DNA
<213> ORGANISM: Artificial
<220> FEATURE:
<223> OTHER INFORMATION: h#11B7-T4L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 8

| | |
|---|---|
| atggtgctgc agacccaggt gttcatctcc ctgctgctgt ggatctccgg cgcatatggc | 60 |
| gacatccaga tgacccagag ccctagctct ctgagcgcct ctgtgggcga ccgggtgacc | 120 |
| atcacctgtc gggccagcca ggacatcggc aactacctga tggtacca gcagaagcct | 180 |
| ggaaaggccc ctaagctgct gatcagcggc gccaccaacc tggccgccgg cgtgcctagc | 240 |

```
cggttctctg aagcggatc tggcagcgac ttcaccctga ccatcagctc tctgcagcct    300
gaggacttcg ccacctacta ctgtctgcag agcaaggagt ctccttggac cttcggccag    360
ggcaccaagc tggagatcaa gcgtacggtg gccgccccct ccgtgttcat cttcccccc    420 tccgacgagc agctgaagtc cggcaccgcc tccgtggtgt gcctgctgaa taacttctac    480
cccagagagg ccaaggtgca gtggaaggtg acaacgccc tgcagtccgg gaactcccag    540
gagagcgtga ccgagcagga cagcaaggac agcacctaca gcctgagcag caccctgacc    600
ctgagcaaag ccgactacga gaagcacaag gtgtacgcct gcgaggtgac ccaccagggc    660
ctgagctccc ccgtcaccaa gagcttcaac aggggggagt gt                      702
```

<210> SEQ ID NO 9
<211> LENGTH: 702
<212> TYPE: DNA
<213> ORGANISM: Artificial
<220> FEATURE:
<223> OTHER INFORMATION: h#11B7-T5L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 9

```
atggtgctgc agacccaggt gttcatctcc ctgctgctgt ggatctccgg cgcatatggc     60
gacatccaga tgacccagag ccctagctct ctgagcgcct ctgtgggcga ccgggtgacc    120
atcacctgtc gggccagcca ggacatcggc aactacctga atggttcca gcagaagcct    180 ggaaaggccc ctaagctgat gatcagcggc gccaccaacc tggccgccgg cgtgcctagc    240
cggttctctg aagcggatc tggcagcgac tacaccctga ccatcagctc tctgcagcct    300
gaggacttcg ccacctacta ctgtctgcag agcaaggagt ctccttggac cttcggccag    360
ggcaccaagc tggagatcaa gcgtacggtg gccgccccct ccgtgttcat cttcccccc    420 tccgacgagc agctgaagtc cggcaccgcc tccgtggtgt gcctgctgaa taacttctac    480
cccagagagg ccaaggtgca gtggaaggtg acaacgccc tgcagtccgg gaactcccag    540
gagagcgtga ccgagcagga cagcaaggac agcacctaca gcctgagcag caccctgacc    600
ctgagcaaag ccgactacga gaagcacaag gtgtacgcct gcgaggtgac ccaccagggc    660
ctgagctccc ccgtcaccaa gagcttcaac aggggggagt gt                      702
```

<210> SEQ ID NO 10
<211> LENGTH: 702
<212> TYPE: DNA
<213> ORGANISM: Artificial
<220> FEATURE:
<223> OTHER INFORMATION: h#11B7-T6L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 10

```
atggtgctgc agacccaggt gttcatctcc ctgctgctgt ggatctccgg cgcatatggc    60
gacatccaga tgacccagag ccctagctct ctgagcgcct ctgtgggcga ccgggtgacc   120
atcacctgtc gggccagcca ggacatcggc aactacctga tggttcca gcagaagcct    180 ggaaaggccc ctaagctgat gatcagcggc gccaccaacc tggccgccgg cgtgcctagc   240
cggttctctg gaagcggatc tggcagcgac tacaccctga ccatcagctc tctgcagcct   300
gaggacttcg ccacctacta ctgtctgcag agcaaggagt ctccttggac cttcggccag   360
ggcaccaagg tggagatcaa gcgtacggtg gccgccccct ccgtgttcat cttccccccc   420
tccgacgagc agctgaagtc cggcaccgcc tccgtggtgt gcctgctgaa taacttctac   480
cccagagagg ccaaggtgca gtggaaggtg gacaacgccc tgcagtccgg gaactcccag   540
gagagcgtga ccgagcagga cagcaaggac agcacctaca gcctgagcag caccctgacc   600
ctgagcaaag ccgactacga gaagcacaag gtgtacgcct gcgaggtgac ccaccagggc   660
ctgagctccc ccgtcaccaa gagcttcaac agggggagt gt                     702
```

<210> SEQ ID NO 11
<211> LENGTH: 702
<212> TYPE: DNA
<213> ORGANISM: Artificial
<220> FEATURE:
<223> OTHER INFORMATION: h#11B7-T7L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 11

```
atggtgctgc agacccaggt gttcatctcc ctgctgctgt ggatctccgg cgcatatggc    60
gacatccaga tgacccagag ccctagctct ctgagcgcct ctgtgggcga ccgggtgacc   120
atcacctgtc gggccagcca ggacatcggc aactacctga tggtacca gcagaagcct    180 ggaaaggccc ctaagctgat gatcagcggc gccaccaacc tggccgccgg cgtgcctagc   240
cggttctctg gaagcggatc tggcagcgac tacaccctga ccatcagctc tctgcagcct   300
gaggacttcg ccacctacta ctgtctgcag agcaaggagt ctccttggac cttcggccag   360
ggcaccaagg tggagatcaa gcgtacggtg gccgccccct ccgtgttcat cttccccccc   420
tccgacgagc agctgaagtc cggcaccgcc tccgtggtgt gcctgctgaa taacttctac   480
cccagagagg ccaaggtgca gtggaaggtg gacaacgccc tgcagtccgg gaactcccag   540
gagagcgtga ccgagcagga cagcaaggac agcacctaca gcctgagcag caccctgacc   600
ctgagcaaag ccgactacga gaagcacaag gtgtacgcct gcgaggtgac ccaccagggc   660
ctgagctccc ccgtcaccaa gagcttcaac agggggagt gt                     702
```

<210> SEQ ID NO 12
<211> LENGTH: 702
<212> TYPE: DNA
<213> ORGANISM: Artificial
<220> FEATURE:
<223> OTHER INFORMATION: h#11B7-T8L light chain (DNA)
<220> FEATURE:
<221> NAME/KEY: misc_feature
<222> LOCATION: (1)..(60)

<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 12

```
atggtgctgc agacccaggt gttcatctcc ctgctgctgt ggatctccgg cgcatatggc      60
gacatccaga tgacccagag ccctagctct ctgagcgcct ctgtgggcga ccgggtgacc     120
atcacctgtc gggccagcca ggacatcggc aactacctga tggttcca gcagaagcct      180
ggaaaggccc ctaagctgct gatcagcggc gccaccaacc tggccgccgg cgtgcctagc     240
cggttctctg gaagcggatc tggcagcgac tacaccctga ccatcagctc tctgcagcct     300
gaggacttcg ccacctacta ctgtctgcag agcaaggagt ctccttggac cttcggccag     360
ggcaccaagg tggagatcaa gcgtacggtg gccgccccct ccgtgttcat cttccccccc     420
tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac aggggggagt gt                       702
```

<210> SEQ ID NO 13
<211> LENGTH: 702
<212> TYPE: DNA
<213> ORGANISM: Artificial
<220> FEATURE:
<223> OTHER INFORMATION: h#11B7-T9L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 13

```
atggtgctgc agacccaggt gttcatctcc ctgctgctgt ggatctccgg cgcatatggc      60
gacatccaga tgacccagag ccctagctct ctgagcgcct ctgtgggcga ccgggtgacc     120
atcacctgtc gggccagcca ggacatcggc aactacctga tggttcca gcagaagcct      180
ggaaaggccc ctaagctgat gatcagcggc gccaccaacc tggccgccgg cgtgcctagc     240
cggttctctg gaagcggatc tggcagcgac ttcaccctga ccatcagctc tctgcagcct     300
gaggacttcg ccacctacta ctgtctgcag agcaaggagt ctccttggac cttcggccag     360
ggcaccaagg tggagatcaa gcgtacggtg gccgccccct ccgtgttcat cttccccccc     420
tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac aggggggagt gt                       702
```

<210> SEQ ID NO 14
<211> LENGTH: 702
<212> TYPE: DNA
<213> ORGANISM: Artificial
<220> FEATURE:
<223> OTHER INFORMATION: h#11B7-T10L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 14

```
atggtgctgc agacccaggt gttcatctcc ctgctgctgt ggatctccgg cgcatatggc      60
gacatccaga tgacccagag ccctagctct ctgagcgcct ctgtgggcga ccgggtgacc     120
atcacctgtc gggccagcca ggacatcggc aactacctga tggtaccag cagaagcct      180 ggaaaggccc ctaagctgct gatcagcggc gccaccaacc tggccgccgg cgtgcctagc     240
cggttctctg aagcggatc tggcagcgac tacaccctga ccatcagctc tctgcagcct     300
gaggacttcg ccacctacta ctgtctgcag agcaaggagt ctccttggac cttcggccag     360
ggcaccaagg tggagatcaa gcgtacggtg gccgccccct ccgtgttcat cttccccccc     420
tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag cacccctgacc    600 ctgagcaaag ccgactacga gaagcacaag gtgtacgcct gcgaggtgac ccaccagggc     660
ctgagctccc ccgtcaccaa gagcttcaac aggggggagt gt                        702
```

<210> SEQ ID NO 15
<211> LENGTH: 702
<212> TYPE: DNA
<213> ORGANISM: Artificial
<220> FEATURE:
<223> OTHER INFORMATION: h#11B7-T11L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 15

```
atggtgctgc agacccaggt gttcatctcc ctgctgctgt ggatctccgg cgcatatggc      60
gacatccaga tgacccagag ccctagctct ctgagcgcct ctgtgggcga ccgggtgacc     120
atcacctgtc gggccagcca ggacatcggc aactacctga tggttccag cagaagcct      180 ggaaaggccc ctaagctgct gatcagcggc gccaccaacc tggccgccgg cgtgcctagc     240
cggttctctg aagcggatc tggcagcgac ttcaccctga ccatcagctc tctgcagcct     300
gaggacttcg ccacctacta ctgtctgcag agcaaggagt ctccttggac cttcggccag     360
ggcaccaagg tggagatcaa gcgtacggtg gccgccccct ccgtgttcat cttccccccc     420
tccgacgagc agctgaagtc cggcaccgcc tccgtggtgt gcctgctgaa taacttctac     480
```

```
cccagagagg ccaaggtgca gtggaaggtg acaacgccc tgcagtccgg gaactcccag    540
gagagcgtga ccgagcagga cagcaaggac agcacctaca gcctgagcag caccctgacc    600
ctgagcaaag ccgactacga gaagcacaag gtgtacgcct gcgaggtgac ccaccagggc    660
ctgagctccc ccgtcaccaa gagcttcaac agggggagt gt                       702

<210> SEQ ID NO 16
<211> LENGTH: 702
<212> TYPE: DNA
<213> ORGANISM: Artificial
<220> FEATURE:
<223> OTHER INFORMATION: h#11B7-T12L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 16
atggtgctgc agacccaggt gttcatctcc ctgctgctgt ggatctccgg cgcatatggc    60
gacatccaga tgacccagag ccctagctct ctgagcgcct ctgtgggcga ccgggtgacc    120
atcacctgtc gggccagcca ggacatcggc aactacctga tggtacca gcagaagcct    180 ggaaaggccc ctaagctgat gatcagcggc gccaccaacc tggccgccgg cgtgcctagc    240
cggttctctg gaagcggatc tggcagcgac ttcaccctga ccatcagctc tctgcagcct    300
gaggacttcg ccacctacta ctgtctgcag agcaaggagt ctccttggac cttcggccag    360
ggcaccaagg tggagatcaa gcgtacggtg gccgccccct ccgtgttcat cttcccccc    420 tccgacgagc agctgaagtc cggcaccgcc tccgtggtgt gcctgctgaa taacttctac    480
cccagagagg ccaaggtgca gtggaaggtg acaacgccc tgcagtccgg gaactcccag    540
gagagcgtga ccgagcagga cagcaaggac agcacctaca gcctgagcag caccctgacc    600
ctgagcaaag ccgactacga gaagcacaag gtgtacgcct gcgaggtgac ccaccagggc    660
ctgagctccc ccgtcaccaa gagcttcaac agggggagt gt                       702

<210> SEQ ID NO 17
<211> LENGTH: 702
<212> TYPE: DNA
<213> ORGANISM: Artificial
<220> FEATURE:
<223> OTHER INFORMATION: h#11B7-T13L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 17
atggtgctgc agacccaggt gttcatctcc ctgctgctgt ggatctccgg cgcatatggc    60
gacatccaga tgacccagag ccctagctct ctgagcgcct ctgtgggcga ccgggtgacc    120
atcacctgtc gggccagcca ggacatcggc aactacctga tggtacca gcagaagcct    180 ggaaaggccc ctaagctgct gatcagcggc gccaccaacc tggccgccgg cgtgcctagc    240
```

-continued

```
cggttctctg gaagcggatc tggcagcgac ttcaccctga ccatcagctc tctgcagcct    300
gaggacttcg ccacctacta ctgtctgcag agcaaggagt ctccttggac cttcggccag    360
ggcaccaagg tggagatcaa gcgtacggtg gccgccccct ccgtgttcat cttcccccc     420 tccgacgagc agctgaagtc cggcaccgcc tccgtggtgt gcctgctgaa taacttctac    480
cccagagagg ccaaggtgca gtggaaggtg acaacgccc tgcagtccgg gaactcccag     540
gagagcgtga ccgagcagga cagcaaggac agcacctaca gcctgagcag caccctgacc    600
ctgagcaaag ccgactacga gaagcacaag gtgtacgcct gcgaggtgac ccaccagggc    660
ctgagctccc ccgtcaccaa gagcttcaac agggggagt gt                       702
```

<210> SEQ ID NO 18
<211> LENGTH: 234
<212> TYPE: PRT
<213> ORGANISM: Artificial
<220> FEATURE:
<223> OTHER INFORMATION: h#11B7-T1L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 18

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Arg Trp Tyr Gln Gln Lys Pro Gly Lys Ala Pro
    50                  55                  60

Lys Leu Leu Ile Ser Gly Ala Thr Asn Leu Ala Ala Gly Val Pro Ser
65                  70                  75                  80

Arg Phe Ser Gly Thr Gly Ser Gly Thr Asp Phe Thr Phe Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220
```

```
Val Thr Lys Ser Phe Asn Arg Gly Glu Cys
225                 230

<210> SEQ ID NO 19
<211> LENGTH: 234
<212> TYPE: PRT
<213> ORGANISM: Artificial
<220> FEATURE:
<223> OTHER INFORMATION: h#11B7-T2L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 19

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Ile Gly Asn Tyr Leu Arg Trp Phe Gln Gln Lys Pro Gly Lys Ala Pro
        50                  55                  60

Lys Leu Met Ile Ser Gly Ala Thr Asn Leu Ala Ala Gly Val Pro Ser
65                  70                  75                  80

Arg Phe Ser Gly Thr Gly Ser Gly Thr Asp Tyr Thr Phe Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 20
<211> LENGTH: 234
<212> TYPE: PRT
<213> ORGANISM: Artificial
<220> FEATURE:
<223> OTHER INFORMATION: h#11B7-T3L light chain (AA)
<220> FEATURE:
<221> NAME/KEY: SIGNAL
```

```
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 20

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Arg Trp Phe Gln Gln Lys Pro Gly Lys Ala Pro
    50                  55                  60

Lys Leu Met Ile Ser Gly Ala Thr Asn Leu Ala Ala Gly Val Pro Ser
65                  70                  75                  80

Arg Phe Ser Gly Ser Arg Ser Gly Ser Asp Tyr Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gly Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 21
<211> LENGTH: 234
<212> TYPE: PRT
<213> ORGANISM: Artificial
<220> FEATURE:
<223> OTHER INFORMATION: h#11B7-T4L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 21

Met Val Leu Gln Thr Gln Val Phe Ile Ser Leu Leu Trp Ile Ser
```

```
1               5                   10                  15
Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Ile Gly Asn Tyr Leu Arg Trp Tyr Gln Gln Lys Pro Gly Lys Ala Pro
 50                     55                  60

Lys Leu Leu Ile Ser Gly Ala Thr Asn Leu Ala Ala Gly Val Pro Ser
 65                 70                  75                  80

Arg Phe Ser Gly Ser Gly Ser Gly Ser Asp Phe Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 22
<211> LENGTH: 234
<212> TYPE: PRT
<213> ORGANISM: Artificial
<220> FEATURE:
<223> OTHER INFORMATION: h#11B7-T5L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 22

Met Val Leu Gln Thr Gln Val Phe Ile Ser Leu Leu Leu Trp Ile Ser
 1               5                  10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Ile Gly Asn Tyr Leu Arg Trp Phe Gln Gln Lys Pro Gly Lys Ala Pro
 50                     55                  60

Lys Leu Met Ile Ser Gly Ala Thr Asn Leu Ala Ala Gly Val Pro Ser
 65                 70                  75                  80
```

```
Arg Phe Ser Gly Ser Gly Ser Gly Ser Asp Tyr Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 23
<211> LENGTH: 234
<212> TYPE: PRT
<213> ORGANISM: Artificial
<220> FEATURE:
<223> OTHER INFORMATION: h#11B7-T6L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 23

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Arg Trp Phe Gln Gln Lys Pro Gly Lys Ala Pro
    50                  55                  60

Lys Leu Met Ile Ser Gly Ala Thr Asn Leu Ala Ala Gly Val Pro Ser
65                  70                  75                  80

Arg Phe Ser Gly Ser Gly Ser Gly Ser Asp Tyr Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140
```

```
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 24
<211> LENGTH: 234
<212> TYPE: PRT
<213> ORGANISM: Artificial
<220> FEATURE:
<223> OTHER INFORMATION: h#11B7-T7L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 24

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Arg Trp Tyr Gln Gln Lys Pro Gly Lys Ala Pro
    50                  55                  60

Lys Leu Met Ile Ser Gly Ala Thr Asn Leu Ala Ala Gly Val Pro Ser
65                  70                  75                  80

Arg Phe Ser Gly Ser Gly Ser Gly Ser Asp Tyr Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
```

Val Thr Lys Ser Phe Asn Arg Gly Glu Cys
225                 230

<210> SEQ ID NO 25
<211> LENGTH: 234
<212> TYPE: PRT
<213> ORGANISM: Artificial
<220> FEATURE:
<223> OTHER INFORMATION: h#11B7-T8L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 25

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Arg Trp Phe Gln Gln Lys Pro Gly Lys Ala Pro
    50                  55                  60

Lys Leu Leu Ile Ser Gly Ala Thr Asn Leu Ala Ala Gly Val Pro Ser
65                  70                  75                  80

Arg Phe Ser Gly Ser Gly Ser Gly Ser Asp Tyr Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 26
<211> LENGTH: 234
<212> TYPE: PRT
<213> ORGANISM: Artificial
<220> FEATURE:
<223> OTHER INFORMATION: h#11B7-T9L light chain (AA)
<220> FEATURE:

<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 26

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Arg Trp Phe Gln Gln Lys Pro Gly Lys Ala Pro
    50                  55                  60

Lys Leu Met Ile Ser Gly Ala Thr Asn Leu Ala Ala Gly Val Pro Ser
65                  70                  75                  80

Arg Phe Ser Gly Ser Gly Ser Gly Ser Asp Phe Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 27
<211> LENGTH: 234
<212> TYPE: PRT
<213> ORGANISM: Artificial
<220> FEATURE:
<223> OTHER INFORMATION: h#11B7-T10L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 27

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Ile Gly Asn Tyr Leu Arg Trp Tyr Gln Gln Lys Pro Gly Lys Ala Pro
        50                  55                  60

Lys Leu Leu Ile Ser Gly Ala Thr Asn Leu Ala Ala Gly Val Pro Ser
65                  70                  75                  80

Arg Phe Ser Gly Ser Gly Ser Gly Ser Asp Tyr Thr Leu Thr Ile Ser
                85                  90                  95

Ser Leu Gln Pro Glu Asp Phe Ala Thr Tyr Tyr Cys Leu Gln Ser Lys
                100                 105                 110

Glu Ser Pro Trp Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 28
<211> LENGTH: 234
<212> TYPE: PRT
<213> ORGANISM: Artificial
<220> FEATURE:
<223> OTHER INFORMATION: h#11B7-T11L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 28

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Ile Gly Asn Tyr Leu Arg Trp Phe Gln Gln Lys Pro Gly Lys Ala Pro
        50                  55                  60

Lys Leu Leu Ile Ser Gly Ala Thr Asn Leu Ala Ala Gly Val Pro Ser

```
            65                  70                  75                  80
Arg Phe Ser Gly Ser Gly Ser Gly Ser Asp Phe Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 29
<211> LENGTH: 234
<212> TYPE: PRT
<213> ORGANISM: Artificial
<220> FEATURE:
<223> OTHER INFORMATION: h#11B7-T12L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 29

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Arg Trp Tyr Gln Gln Lys Pro Gly Lys Ala Pro
    50                  55                  60

Lys Leu Met Ile Ser Gly Ala Thr Asn Leu Ala Ala Gly Val Pro Ser
65                  70                  75                  80

Arg Phe Ser Gly Ser Gly Ser Gly Ser Asp Phe Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140
```

```
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 30
<211> LENGTH: 234
<212> TYPE: PRT
<213> ORGANISM: Artificial
<220> FEATURE:
<223> OTHER INFORMATION: h#11B7-T13L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 30

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Arg Trp Tyr Gln Gln Lys Pro Gly Lys Ala Pro
    50                  55                  60

Lys Leu Leu Ile Ser Gly Ala Thr Asn Leu Ala Ala Gly Val Pro Ser
65                  70                  75                  80

Arg Phe Ser Gly Ser Gly Ser Gly Ser Asp Phe Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205
```

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 31
<211> LENGTH: 1386
<212> TYPE: DNA
<213> ORGANISM: Artificial
<220> FEATURE:
<223> OTHER INFORMATION: h#11B7-T1H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 31
atgaaacacc tgtggttctt cctcctgctg gtggcagctc ccagatgggt gctgagccag      60
atccagctgc aggagagcgg ccctggcctg gtgaagcca gccagaccct gagcctgacc     120
tgtgccgtgt ctggatacag catcaccagc aactactggg gctggatccg gcagcctcct     180
ggcaagggac tggagtggat cggctacatc acctacagcg gctctaccag ctacaaccct     240
agcctgaagt ctagagtgac catcagcgtg gacacctcta agaaccagtt cagcctgaag     300
ctgtcttctg tgaccgccgc cgacaccgcc gtgtactact gtgccatcac caccttctac     360
tactggggac agggaaccct ggtgaccgtg agctcagcct ccaccaaggg cccaagcgtc     420
ttccccctgg cacctcctc aagagcacc tctggcggca cagccgccct gggctgcctg     480
gtcaaggact acttccccga acccgtgacc gtgagctgga actcaggcgc cctgaccagc     540
ggcgtgcaca ccttccccgc tgtcctgcag tcctcaggac tctactccct cagcagcgtg     600
gtgaccgtgc cctccagcag cttgggcacc cagacctaca tctgcaacgt gaatcacaag     660
cccagcaaca ccaaggtgga caagagagtt gagcccaaat cttgtgacaa aactcacaca     720
tgcccaccct gcccagcacc tgaactcctg ggggaccct cagtcttcct cttccccca     780 aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagcccg ggaggagcag tacaacagca cgtaccgggt ggtcagcgtc     960
ctcaccgtcc tgcaccagga ctggctgaat ggcaaggagt acaagtgcaa ggtctccaac    1020
aaagccctcc cagcccccat cgagaaaacc atctccaaag ccaaaggcca gccccgggaa    1080
ccacaggtgt acaccctgcc cccatcccgg gaggagatga ccaagaacca ggtcagcctg    1140
acctgcctgg tcaaaggctt ctatcccagc gacatcgccg tggagtggga gagcaatggc    1200
cagcccgaga caactacaa gaccacccct cccgtgctgg actccgacgg ctccttcttc    1260
ctctacagca agctcaccgt ggacaagagc aggtggcagc agggcaacgt cttctcatgc    1320
tccgtgatgc atgaggctct gcacaaccac tacacccaga gagcctctc cctgtctccc    1380 ggcaaa                                                              1386

<210> SEQ ID NO 32
<211> LENGTH: 1386
<212> TYPE: DNA
<213> ORGANISM: Artificial
<220> FEATURE:
<223> OTHER INFORMATION: h#11B7-T2H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 32

| | | | | | |
|---|---|---|---|---|---|
| atgaaacacc | tgtggttctt | cctcctgctg | gtggcagctc | ccagatgggt | gctgagccag | 60 |
| atccagctgc | aggagagcgg | ccctggcctg | gtgaagccta | gccagaccct | gagcctgacc | 120 |
| tgtgccgtgt | ctggatacag | catcaccagc | aactactggg | gctggatccg | gcagcctcct | 180 |
| ggcaagggac | tggagtggat | gggctacatc | acctacagcg | gctctaccag | ctacaaccct | 240 |
| agcctgaagt | ctagaatcag | catcagcgtg | gacacctcta | agaaccagtt | cagcctgaag | 300 |
| ctgtcttctg | tgaccgccgc | cgacaccgcc | gtgtactact | gtgccatcac | caccttctac | 360 |
| tactggggac | agggaaccct | ggtgaccgtg | agctcagcct | ccaccaaggg | cccaagcgtc | 420 |
| ttccccctgg | caccctcctc | caagagcacc | tctggcggca | cagccgccct | gggctgcctg | 480 |
| gtcaaggact | acttccccga | acccgtgacc | gtgagctgga | actcaggcgc | cctgaccagc | 540 |
| ggcgtgcaca | ccttccccgc | tgtcctgcag | tcctcaggac | tctactccct | cagcagcgtg | 600 |
| gtgaccgtgc | cctccagcag | cttgggcacc | cagacctaca | tctgcaacgt | gaatcacaag | 660 |
| cccagcaaca | ccaaggtgga | caagagagtt | gagcccaaat | cttgtgacaa | aactcacaca | 720 |
| tgcccaccct | gcccagcacc | tgaactcctg | gggggaccct | cagtcttcct | cttcccccca | 780 |
| aaacccaagg | acaccctcat | gatctcccgg | acccctgagg | tcacatgcgt | ggtggtggac | 840 |
| gtgagccacg | aagaccctga | ggtcaagttc | aactggtacg | tggacggcgt | ggaggtgcat | 900 |
| aatgccaaga | caaagccccg | ggaggagcag | tacaacagca | cgtaccgggt | ggtcagcgtc | 960 |
| ctcaccgtcc | tgcaccagga | ctggctgaat | ggcaaggagt | acaagtgcaa | ggtctccaac | 1020 |
| aaagccctcc | cagcccccat | cgagaaaacc | atctccaaag | ccaaaggcca | gccccgggaa | 1080 |
| ccacaggtgt | acaccctgcc | cccatcccgg | gaggagatga | ccaagaacca | ggtcagcctg | 1140 |
| acctgcctgg | tcaaaggctt | ctatcccagc | gacatcgccg | tggagtggga | gagcaatggc | 1200 |
| cagcccgaga | acaactacaa | gaccaccccc | ccgtgctgg | actccgacgg | ctccttcttc | 1260 |
| ctctacagca | agctcaccgt | ggacaagagc | aggtggcagc | agggcaacgt | cttctcatgc | 1320 |
| tccgtgatgc | atgaggctct | gcacaaccac | tacacccaga | agagcctctc | cctgtctccc | 1380 |
| ggcaaa | | | | | | 1386 |

<210> SEQ ID NO 33
<211> LENGTH: 1386
<212> TYPE: DNA
<213> ORGANISM: Artificial
<220> FEATURE:
<223> OTHER INFORMATION: h#11B7-T3H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region

<222> LOCATION: (397)..(1386)

<400> SEQUENCE: 33

| | |
|---|---|
| atgaaacacc tgtggttctt cctcctgctg gtggcagctc ccagatgggt gctgagccag | 60 |
| gtgcagctgc aggagagcgg ccctggcctg gtgaagccta gccagaccct gagcctgacc | 120 |
| tgtgccgtgt ctggatacag catcaccagc aactactggg gctggatccg gaagcctcct | 180 |
| ggcgacggac tggagtggat gggctacatc acctacagcg gctctaccag ctacaaccct | 240 |
| agcctgaagt ctagaatcag catcacccgg gacacctcta agaaccagtt cagcctgaag | 300 |
| ctgtcttctg tgaccgccgc cgacaccgcc gtgtactact gtgccatcac caccttctac | 360 |
| tactggggac agggaaccct ggtgaccgtg agctcagcct ccaccaaggg cccaagcgtc | 420 |
| ttccccctgg caccctcctc aagagcacct ctggcggca cagccgccct gggctgcctg | 480 |
| gtcaaggact acttccccga acccgtgacc gtgagctgga ctcaggcgc cctgaccagc | 540 |
| ggcgtgcaca ccttcccgc tgtcctgcag tcctcaggac tctactccct cagcagcgtg | 600 |
| gtgaccgtgc cctccagcag cttgggcacc cagacctaca tctgcaacgt gaatcacaag | 660 |
| cccagcaaca ccaaggtgga caagagagtt gagcccaaat cttgtgacaa aactcacaca | 720 |
| tgcccaccct gcccagcacc tgaactcctg ggggaccct cagtcttcct cttccccca | 780 |
| aaacccaagg acaccctcat gatctcccgg accctgagg tcacatgcgt ggtggtggac | 840 |
| gtgagccacg aagaccctga ggtcaagttc aactggtacg tggacggcgt ggaggtgcat | 900 |
| aatgccaaga caaagcccg ggaggagcag tacaacagca cgtaccgggt ggtcagcgtc | 960 |
| ctcaccgtcc tgcaccagga ctggctgaat ggcaaggagt acaagtgcaa ggtctccaac | 1020 |
| aaagccctcc cagcccccat cgagaaaacc atctccaaag ccaaaggcca gccccgggaa | 1080 |
| ccacaggtgt acaccctgcc cccatcccgg gaggagatga ccaagaacca ggtcagcctg | 1140 |
| acctgcctgg tcaaaggctt ctatcccagc gacatcgccg tggagtggga gagcaatggc | 1200 |
| cagcccgaga caactacaa gaccaccct cccgtgctgg actccgacgg ctccttcttc | 1260 |
| ctctacagca agctcaccgt ggacaagagc aggtggcagc agggcaacgt cttctcatgc | 1320 |
| tccgtgatgc atgaggctct gcacaaccac tacacccaga agagcctctc cctgtctccc | 1380 |
| ggcaaa | 1386 |

<210> SEQ ID NO 34
<211> LENGTH: 1386
<212> TYPE: DNA
<213> ORGANISM: Artificial
<220> FEATURE:
<223> OTHER INFORMATION: h#11B7-T4H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 34

| | |
|---|---|
| atgaaacacc tgtggttctt cctcctgctg gtggcagctc ccagatgggt gctgagccag | 60 |
| gtgcagctgc agcagtgggg cgccggcctg ctgaagccta gcgagaccct gagcctgacc | 120 |
| tgtaccgtgt ctggatacag catcaccagc aactactggg gctggatccg gcagcctcct | 180 |
| ggcaagggac tggagtggat cggctacatc acctacagcg gctctaccag ctacaaccct | 240 |

```
agcctgaagt ctagagtgac catcagccgg acacctcta agaaccagtt cagcctgaag    300
ctgtcttctg tgaccgccgc cgacaccgcc gtgtactact gtgccatcac caccttctac    360
tactggggac agggaaccac cgtgaccgtg agctcagcct ccaccaaggg cccaagcgtc    420
ttccccctgg caccctcctc caagagcacc tctggcggca cagccgccct gggctgcctg    480
gtcaaggact acttccccga acccgtgacc gtgagctgga actcaggcgc cctgaccagc    540
ggcgtgcaca ccttccccgc tgtcctgcag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccct gcccagcacc tgaactcctg ggggaccct cagtcttcct cttccccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagcccg ggaggagcag tacaacagca cgtaccgggt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaaggcca gccccgggaa   1080
ccacaggtgt acaccctgcc cccatcccgg gaggagatga ccaagaacca ggtcagcctg   1140
acctgcctgg tcaaaggctt ctatcccagc gacatcgccg tggagtggga gagcaatggc   1200
cagcccgaga caactacaa gaccacccct cccgtgctgg actccgacgg ctccttcttc    1260
ctctacagca agctcaccgt ggacaagagc aggtggcagc agggcaacgt cttctcatgc   1320
tccgtgatgc atgaggctct gcacaaccac tacacccaga gagcctctc cctgtctccc    1380
ggcaaa                                                              1386

<210> SEQ ID NO 35
<211> LENGTH: 1386
<212> TYPE: DNA
<213> ORGANISM: Artificial
<220> FEATURE:
<223> OTHER INFORMATION: h#11B7-T5H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 35
atgaaacacc tgtggttctt cctcctgctg gtggcagctc ccagatgggt gctgagccag     60
gtgcagctgc agcagtgggg cgccggcctg ctgaagccta gcgagaccct gagcctgacc    120
tgtaccgtgt ctggatacag catcaccagc aactactggg gctggatccg cagcctcct    180
ggcaagggac tggagtggat gggctacatc acctacagcg gctctaccag ctacaaccct    240
agcctgaagt ctagaatcag catcagccgg acacctcta agaaccagtt cagcctgaag    300
ctgtcttctg tgaccgccgc cgacaccgcc gtgtactact gtgccatcac caccttctac    360
tactggggac agggaaccac cgtgaccgtg agctcagcct ccaccaaggg cccaagcgtc    420
ttccccctgg caccctcctc caagagcacc tctggcggca cagccgccct gggctgcctg    480
gtcaaggact acttccccga acccgtgacc gtgagctgga actcaggcgc cctgaccagc    540
```

```
ggcgtgcaca ccttccccgc tgtcctgcag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccct gcccagcacc tgaactcctg ggggaccct cagtcttcct cttcccccca     780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccccg ggaggagcag tacaacagca cgtaccgggt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaaggcca gccccgggaa   1080
ccacaggtgt acaccctgcc cccatcccgg gaggagatga ccaagaacca ggtcagcctg   1140
acctgcctgg tcaaaggctt ctatcccagc gacatcgccg tggagtggga gagcaatggc   1200
cagcccgaga caactacaa gaccacccct cccgtgctgg actccgacgg ctccttcttc    1260
ctctacagca agctcaccgt ggacaagagc aggtggcagc agggcaacgt cttctcatgc   1320
tccgtgatgc atgaggctct gcacaaccac tacacccaga gagcctctcc cctgtctccc   1380
ggcaaa                                                              1386
```

<210> SEQ ID NO 36
<211> LENGTH: 1386
<212> TYPE: DNA
<213> ORGANISM: Artificial
<220> FEATURE:
<223> OTHER INFORMATION: h#11B7-T6H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 36

```
atgaaacacc tgtggttctt cctcctgctg gtggcagctc ccagatgggt gctgagccag     60
gtgcagctgc aggagagcgg ccctggcctg gtgaagccta cgagaccct gagcctgacc     120 tgtaccgtgt ctggatacag catcaccagc aactactggg gctggatccg cagcctcct    180 ggcaagggac tggagtggat gggctacatc cctacagcg ctctaccag ctacaaccct     240 agcctgaagt ctagaatcag catcagccgg gacacctcta gaaccagtt cagcctgaag    300 ctgtcttctg tgaccgccgc cgacaccgcc gtgtactact gtgccatcac cccttctac     360 tactggggac agggaaccct ggtgaccgtg agctcagcct ccaccaaggg cccaagcgtc    420
ttccccctgg cacctcctc caagagcacc tctggcggca gccgccct gggctgcctg      480 gtcaaggact acttcccga acccgtgacc gtgagctgga actcaggcgc cctgaccagc    540
ggcgtgcaca ccttccccgc tgtcctgcag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccct gcccagcacc tgaactcctg ggggaccct cagtcttcct cttcccccca     780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
```

```
aatgccaaga caaagccccg ggaggagcag tacaacagca cgtaccgggt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaaggcca gccccgggaa   1080
ccacaggtgt acaccctgcc cccatcccgg gaggagatga ccaagaacca ggtcagcctg   1140
acctgcctgg tcaaaggctt ctatcccagc gacatcgccg tggagtggga gagcaatggc   1200
cagcccgaga caactacaa gaccaccct cccgtgctgg actccgacgg ctccttcttc   1260
ctctacagca agctcaccgt ggacaagagc aggtggcagc agggcaacgt cttctcatgc   1320
tccgtgatgc atgaggctct gcacaaccac tacacccaga gagcctctc cctgtctccc   1380 ggcaaa                                                             1386

<210> SEQ ID NO 37
<211> LENGTH: 1386
<212> TYPE: DNA
<213> ORGANISM: Artificial
<220> FEATURE:
<223> OTHER INFORMATION: h#11B7-T7H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 37
atgaaacacc tgtggttctt cctcctgctg gtggcagctc ccagatgggt gctgagccag     60
gtgcagctgc aggagagcgg ccctggcctg gtgaagccta cgagaccct gagcctgacc    120 tgtaccgtgt ctggatacag catcaccagc aactactggg gctggatccg gcagcctcct    180
ggcaagggac tggagtggat cggctacatc acctacagcg gctctaccag ctacaaccct    240
agcctgaagt ctagagtgag catcagccgg gacacctcta gaaccagtt cagcctgaag    300 ctgtcttctg tgaccgccgc cgacaccgcc gtgtactact gtgccatcac caccttctac    360
tactggggac agggaaccct ggtgaccgtg agctcagcct ccaccaaggg cccaagcgtc    420
ttccccctgg caccctcctc caagagcacc tctggcggca cagccgccct gggctgcctg    480
gtcaaggact acttccccga acccgtgacc gtgagctgga actcaggcgc cctgaccagc    540
ggcgtgcaca ccttccccgc tgtcctgcag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccct gcccagcacc tgaactcctg ggggaccct cagtcttcct cttccccca    780 aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccccg ggaggagcag tacaacagca cgtaccgggt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaaggcca gccccgggaa   1080
ccacaggtgt acaccctgcc cccatcccgg gaggagatga ccaagaacca ggtcagcctg   1140
acctgcctgg tcaaaggctt ctatcccagc gacatcgccg tggagtggga gagcaatggc   1200
```
cagcccgaga caactacaa gaccacccct cccgtgctgg actccgacgg ctccttcttc    1260
ctctacagca agctcaccgt ggacaagagc aggtggcagc agggcaacgt cttctcatgc    1320
tccgtgatgc atgaggctct gcacaaccac tacacccaga gagcctctc cctgtctccc     1380 ggcaaa                                                                1386

<210> SEQ ID NO 38
<211> LENGTH: 1386
<212> TYPE: DNA
<213> ORGANISM: Artificial
<220> FEATURE:
<223> OTHER INFORMATION: h#11B7-T8H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 38
atgaaacacc tgtggttctt cctcctgctg gtggcagctc ccagatgggt gctgagccag     60
gtgcagctgc aggagagcgg ccctggcctg gtgaagccta gcgagaccct gagcctgacc    120
tgtaccgtgt ctggatacag catcaccagc aactactggg gctggatccg cagcctcct    180 ggcaagggac tggagtggat gggctacatc acctacagcg gctctaccag ctacaaccct    240
agcctgaagt ctagaatcac catcagccgg gacacctcta agaaccagtt cagcctgaag    300
ctgtcttctg tgaccgccgc cgacaccgcc gtgtactact gtgccatcac caccttctac    360 tactgggac agggaaccct ggtgaccgtg agctcagcct ccaccaaggg cccaagcgtc    420
ttccccctgg caccctcctc aagagcacc tctggcggca gccgccct gggctgcctg     480 gtcaaggact acttccccga acccgtgacc gtgagctgga actcaggcgc cctgaccagc    540
ggcgtgcaca ccttccccgc tgtcctgcag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccct gcccagcacc tgaactcctg ggggaccct cagtcttcct cttccccccc    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccccg ggaggagcag tacaacagca cgtaccgggt ggtcagcgtc    960
ctcaccgtcc tgcaccagga ctggctgaat ggcaaggagt acaagtgcaa ggtctccaac    1020
aaagccctcc cagcccccat cgagaaaacc atctccaaag ccaaaggcca gccccgggaa    1080
ccacaggtgt acaccctgcc cccatcccgg gaggagatga ccaagaacca ggtcagcctg    1140
acctgcctgg tcaaaggctt ctatcccagc gacatcgccg tggagtggga gagcaatggc    1200
cagcccgaga caactacaa gaccacccct cccgtgctgg actccgacgg ctccttcttc    1260
ctctacagca agctcaccgt ggacaagagc aggtggcagc agggcaacgt cttctcatgc    1320
tccgtgatgc atgaggctct gcacaaccac tacacccaga gagcctctc cctgtctccc     1380 ggcaaa                                                                1386

<210> SEQ ID NO 39
<211> LENGTH: 1386

```
<212> TYPE: DNA
<213> ORGANISM: Artificial
<220> FEATURE:
<223> OTHER INFORMATION: h#11B7-T9H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 39
atgaaacacc tgtggttctt cctcctgctg gtggcagctc ccagatgggt gctgagccag      60
gtgcagctgc aggagagcgg ccctggcctg gtgaagccta gcgagaccct gagcctgacc     120
tgtaccgtgt ctggatacag catcaccagc aactactggg gctggatccg gcagcctcct     180
ggcaagggac tggagtggat cggctacatc acctacagcg gctctaccag ctacaaccct     240
agcctgaagt ctagagtgac catcagccgg gacacctcta gaaccagtt cagcctgaag     300
ctgtcttctg tgaccgccgc cgacaccgcc gtgtactact gtgccatcac caccttctac     360
tactggggac agggaaccct ggtgaccgtg agctcagcct ccaccaaggg cccaagcgtc     420
ttccccctgg cacctcctc aagagcacc tctggcggca gccgccct gggctgcctg     480
gtcaaggact acttccccga accgtgacc gtgagctgga actcaggcgc cctgaccagc     540
ggcgtgcaca ccttcccgc tgtcctgcag tcctcaggac tctactccct cagcagcgtg     600
gtgaccgtgc cctccagcag cttgggcacc cagacctaca tctgcaacgt gaatcacaag     660
cccagcaaca ccaaggtgga caagagagtt gagcccaaat cttgtgacaa aactcacaca     720
tgcccaccct gcccagcacc tgaactcctg ggggaccct cagtcttcct cttccccca     780
aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagcccg gaggagcag tacaacagca cgtaccgggt ggtcagcgtc     960
ctcaccgtcc tgcaccagga ctggctgaat ggcaaggagt acaagtgcaa ggtctccaac    1020
aaagccctcc cagcccccat cgagaaaacc atctccaaag ccaaaggcca gccccgggaa    1080
ccacaggtgt acaccctgcc cccatcccgg gaggagatga ccaagaacca ggtcagcctg    1140
acctgcctgg tcaaaggctt ctatcccagc gacatcgccg tggagtggga gagcaatggc    1200
cagcccgaga caactacaa gaccaccccct cccgtgctgg actccgacgg ctccttcttc    1260
ctctacagca agctcaccgt ggacaagagc aggtggcagc agggcaacgt cttctcatgc    1320
tccgtgatgc atgaggctct gcacaaccac tacacccaga gagcctctc cctgtctccc    1380
ggcaaa                                                               1386

<210> SEQ ID NO 40
<211> LENGTH: 462
<212> TYPE: PRT
<213> ORGANISM: Artificial
<220> FEATURE:
<223> OTHER INFORMATION: h#11B7-T1H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
```

```
<220> FEATURE:
<221> NAME/KEY: SITE
<222> LOCATION: (133)..(462)
<223> OTHER INFORMATION: constant region

<400> SEQUENCE: 40
```

| | | | | | | | | | | | | | | |
|---|---|---|---|---|---|---|---|---|---|---|---|---|---|---|
| Met | Lys | His | Leu | Trp | Phe | Phe | Leu | Leu | Leu | Val | Ala | Ala | Pro | Arg | Trp |
| 1 | | | | 5 | | | | | 10 | | | | | 15 |

| Val | Leu | Ser | Gln | Ile | Gln | Leu | Gln | Glu | Ser | Gly | Pro | Gly | Leu | Val | Lys |
|---|---|---|---|---|---|---|---|---|---|---|---|---|---|---|---|
| | | | 20 | | | | | 25 | | | | | 30 | | |

| Pro | Ser | Gln | Thr | Leu | Ser | Leu | Thr | Cys | Ala | Val | Ser | Gly | Tyr | Ser | Ile |
|---|---|---|---|---|---|---|---|---|---|---|---|---|---|---|---|
| | | | | 35 | | | | | 40 | | | | | 45 | |

| Thr | Ser | Asn | Tyr | Trp | Gly | Trp | Ile | Arg | Gln | Pro | Pro | Gly | Lys | Gly | Leu |
|---|---|---|---|---|---|---|---|---|---|---|---|---|---|---|---|
| | 50 | | | | | 55 | | | | | 60 | | | | |

| Glu | Trp | Ile | Gly | Tyr | Ile | Thr | Tyr | Ser | Gly | Ser | Thr | Ser | Tyr | Asn | Pro |
|---|---|---|---|---|---|---|---|---|---|---|---|---|---|---|---|
| 65 | | | | | 70 | | | | | 75 | | | | | 80 |

| Ser | Leu | Lys | Ser | Arg | Val | Thr | Ile | Ser | Val | Asp | Thr | Ser | Lys | Asn | Gln |
|---|---|---|---|---|---|---|---|---|---|---|---|---|---|---|---|
| | | | | 85 | | | | | 90 | | | | | 95 | |

| Phe | Ser | Leu | Lys | Leu | Ser | Ser | Val | Thr | Ala | Ala | Asp | Thr | Ala | Val | Tyr |
|---|---|---|---|---|---|---|---|---|---|---|---|---|---|---|---|
| | | | 100 | | | | | 105 | | | | | 110 | | |

| Tyr | Cys | Ala | Ile | Thr | Thr | Phe | Tyr | Tyr | Trp | Gly | Gln | Gly | Thr | Leu | Val |
|---|---|---|---|---|---|---|---|---|---|---|---|---|---|---|---|
| | | | 115 | | | | | 120 | | | | | 125 | | |

| Thr | Val | Ser | Ser | Ala | Ser | Thr | Lys | Gly | Pro | Ser | Val | Phe | Pro | Leu | Ala |
|---|---|---|---|---|---|---|---|---|---|---|---|---|---|---|---|
| 130 | | | | | 135 | | | | | 140 | | | | | |

| Pro | Ser | Ser | Lys | Ser | Thr | Ser | Gly | Gly | Thr | Ala | Ala | Leu | Gly | Cys | Leu |
|---|---|---|---|---|---|---|---|---|---|---|---|---|---|---|---|
| 145 | | | | | 150 | | | | | 155 | | | | | 160 |

| Val | Lys | Asp | Tyr | Phe | Pro | Glu | Pro | Val | Thr | Val | Ser | Trp | Asn | Ser | Gly |
|---|---|---|---|---|---|---|---|---|---|---|---|---|---|---|---|
| | | | | 165 | | | | | 170 | | | | | 175 | |

| Ala | Leu | Thr | Ser | Gly | Val | His | Thr | Phe | Pro | Ala | Val | Leu | Gln | Ser | Ser |
|---|---|---|---|---|---|---|---|---|---|---|---|---|---|---|---|
| | | | 180 | | | | | 185 | | | | | 190 | | |

| Gly | Leu | Tyr | Ser | Leu | Ser | Ser | Val | Val | Thr | Val | Pro | Ser | Ser | Ser | Leu |
|---|---|---|---|---|---|---|---|---|---|---|---|---|---|---|---|
| | | | 195 | | | | | 200 | | | | | 205 | | |

| Gly | Thr | Gln | Thr | Tyr | Ile | Cys | Asn | Val | Asn | His | Lys | Pro | Ser | Asn | Thr |
|---|---|---|---|---|---|---|---|---|---|---|---|---|---|---|---|
| | 210 | | | | | 215 | | | | | 220 | | | | |

| Lys | Val | Asp | Lys | Arg | Val | Glu | Pro | Lys | Ser | Cys | Asp | Lys | Thr | His | Thr |
|---|---|---|---|---|---|---|---|---|---|---|---|---|---|---|---|
| 225 | | | | | 230 | | | | | 235 | | | | | 240 |

| Cys | Pro | Pro | Cys | Pro | Ala | Pro | Glu | Leu | Leu | Gly | Gly | Pro | Ser | Val | Phe |
|---|---|---|---|---|---|---|---|---|---|---|---|---|---|---|---|
| | | | | 245 | | | | | 250 | | | | | 255 | |

| Leu | Phe | Pro | Pro | Lys | Pro | Lys | Asp | Thr | Leu | Met | Ile | Ser | Arg | Thr | Pro |
|---|---|---|---|---|---|---|---|---|---|---|---|---|---|---|---|
| | | | 260 | | | | | 265 | | | | | 270 | | |

| Glu | Val | Thr | Cys | Val | Val | Val | Asp | Val | Ser | His | Glu | Asp | Pro | Glu | Val |
|---|---|---|---|---|---|---|---|---|---|---|---|---|---|---|---|
| | | | 275 | | | | | 280 | | | | | 285 | | |

| Lys | Phe | Asn | Trp | Tyr | Val | Asp | Gly | Val | Glu | Val | His | Asn | Ala | Lys | Thr |
|---|---|---|---|---|---|---|---|---|---|---|---|---|---|---|---|
| | 290 | | | | | 295 | | | | | 300 | | | | |

| Lys | Pro | Arg | Glu | Glu | Gln | Tyr | Asn | Ser | Thr | Tyr | Arg | Val | Val | Ser | Val |
|---|---|---|---|---|---|---|---|---|---|---|---|---|---|---|---|
| 305 | | | | | 310 | | | | | 315 | | | | | 320 |

| Leu | Thr | Val | Leu | His | Gln | Asp | Trp | Leu | Asn | Gly | Lys | Glu | Tyr | Lys | Cys |
|---|---|---|---|---|---|---|---|---|---|---|---|---|---|---|---|
| | | | | 325 | | | | | 330 | | | | | 335 | |

| Lys | Val | Ser | Asn | Lys | Ala | Leu | Pro | Ala | Pro | Ile | Glu | Lys | Thr | Ile | Ser |
|---|---|---|---|---|---|---|---|---|---|---|---|---|---|---|---|
| | | | 340 | | | | | 345 | | | | | 350 | | |

| Lys | Ala | Lys | Gly | Gln | Pro | Arg | Glu | Pro | Gln | Val | Tyr | Thr | Leu | Pro | Pro |
|---|---|---|---|---|---|---|---|---|---|---|---|---|---|---|---|
| | | | 355 | | | | | 360 | | | | | 365 | | |

| Ser | Arg | Glu | Glu | Met | Thr | Lys | Asn | Gln | Val | Ser | Leu | Thr | Cys | Leu | Val |
|---|---|---|---|---|---|---|---|---|---|---|---|---|---|---|---|
| | 370 | | | | | 375 | | | | | 380 | | | | |

```
Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
        450                 455                 460

<210> SEQ ID NO 41
<211> LENGTH: 462
<212> TYPE: PRT
<213> ORGANISM: Artificial
<220> FEATURE:
<223> OTHER INFORMATION: h#11B7-T2H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 41

Met Lys His Leu Trp Phe Phe Leu Leu Leu Val Ala Ala Pro Arg Trp
1               5                   10                  15

Val Leu Ser Gln Ile Gln Leu Gln Glu Ser Gly Pro Gly Leu Val Lys
            20                  25                  30

Pro Ser Gln Thr Leu Ser Leu Thr Cys Ala Val Ser Gly Tyr Ser Ile
        35                  40                  45

Thr Ser Asn Tyr Trp Gly Trp Ile Arg Gln Pro Pro Gly Lys Gly Leu
    50                  55                  60

Glu Trp Met Gly Tyr Ile Thr Tyr Ser Gly Ser Thr Ser Tyr Asn Pro
65                  70                  75                  80

Ser Leu Lys Ser Arg Ile Ser Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Ile Thr Thr Phe Tyr Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
```

-continued

```
                225                 230                 235                 240
Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
    275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
    435                 440                 445

Asn His Tyr Thr Gln Lys Ser Leu Ser Leu Ser Pro Gly Lys
450                 455                 460

<210> SEQ ID NO 42
<211> LENGTH: 462
<212> TYPE: PRT
<213> ORGANISM: Artificial
<220> FEATURE:
<223> OTHER INFORMATION: h#11B7-T3H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 42

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Ala Val Ser Gly Tyr Ser Ile
        35                  40                  45

Thr Ser Asn Tyr Trp Gly Trp Ile Arg Lys Pro Pro Gly Asp Gly Leu
    50                  55                  60

Glu Trp Met Gly Tyr Ile Thr Tyr Ser Gly Ser Thr Ser Tyr Asn Pro
65                  70                  75                  80
```

Ser Leu Lys Ser Arg Ile Ser Ile Thr Arg Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Ile Thr Thr Phe Tyr Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 43
<211> LENGTH: 462
<212> TYPE: PRT
<213> ORGANISM: Artificial
<220> FEATURE:

```
<223> OTHER INFORMATION: h#11B7-T4H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 43
```

Met Lys His Leu Trp Phe Phe Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Thr Val Ser Gly Tyr Ser Ile
                35                  40                  45

Thr Ser Asn Tyr Trp Gly Trp Ile Arg Gln Pro Pro Gly Lys Gly Leu
    50                  55                  60

Glu Trp Ile Gly Tyr Ile Thr Tyr Ser Gly Ser Thr Ser Tyr Asn Pro
65                  70                  75                  80

Ser Leu Lys Ser Arg Val Thr Ile Ser Arg Asp Thr Ser Lys Asn Gln
                85                  90                  95

Phe Ser Leu Lys Leu Ser Ser Val Thr Ala Ala Asp Thr Ala Val Tyr
                100                 105                 110

Tyr Cys Ala Ile Thr Thr Phe Tyr Tyr Trp Gly Gln Gly Thr Thr Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser

```
                340              345              350
Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 44
<211> LENGTH: 462
<212> TYPE: PRT
<213> ORGANISM: Artificial
<220> FEATURE:
<223> OTHER INFORMATION: h#11B7-T5H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 44

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Thr Val Ser Gly Tyr Ser Ile
        35                  40                  45

Thr Ser Asn Tyr Trp Gly Trp Ile Arg Gln Pro Pro Gly Lys Gly Leu
    50                  55                  60

Glu Trp Met Gly Tyr Ile Thr Tyr Ser Gly Ser Thr Ser Tyr Asn Pro
65                  70                  75                  80

Ser Leu Lys Ser Arg Ile Ser Ile Ser Arg Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Ile Thr Thr Phe Tyr Tyr Trp Gly Gln Gly Thr Thr Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190
```

```
Gly Leu Tyr Ser Leu Ser Ser Val Val Thr Val Pro Ser Ser Ser Leu
            195                 200                 205
Gly Thr Gln Thr Tyr Ile Cys Asn Val Asn His Lys Pro Ser Asn Thr
        210                 215                 220
Lys Val Asp Lys Arg Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
290                 295                 300
Lys Pro Arg Glu Glu Gln Tyr Asn Ser Thr Tyr Arg Val Val Ser Val
                310                 315                 320
305
Leu Thr Val Leu His Gln Asp Trp Leu Asn Gly Lys Glu Tyr Lys Cys
            325                 330                 335
Lys Val Ser Asn Lys Ala Leu Pro Ala Pro Ile Glu Lys Thr Ile Ser
        340                 345                 350
Lys Ala Lys Gly Gln Pro Arg Glu Pro Gln Val Tyr Thr Leu Pro Pro
355                 360                 365
Ser Arg Glu Glu Met Thr Lys Asn Gln Val Ser Leu Thr Cys Leu Val
                370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
450                 455                 460

<210> SEQ ID NO 45
<211> LENGTH: 462
<212> TYPE: PRT
<213> ORGANISM: Artificial
<220> FEATURE:
<223> OTHER INFORMATION: h#11B7-T6H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 45

Met Lys His Leu Trp Phe Phe Leu Leu Leu Val Ala Ala Pro Arg Trp
1               5                   10                  15
Val Leu Ser Gln Val Gln Leu Gln Glu Ser Gly Pro Gly Leu Val Lys
            20                  25                  30
```

```
Pro Ser Glu Thr Leu Ser Leu Thr Cys Thr Val Ser Gly Tyr Ser Ile
         35                  40                  45
Thr Ser Asn Tyr Trp Gly Trp Ile Arg Gln Pro Pro Gly Lys Gly Leu
 50                  55                  60
Glu Trp Met Gly Tyr Ile Thr Tyr Ser Gly Ser Thr Ser Tyr Asn Pro
 65                  70                  75                  80
Ser Leu Lys Ser Arg Ile Ser Ile Ser Arg Asp Thr Ser Lys Asn Gln
                 85                  90                  95
Phe Ser Leu Lys Leu Ser Ser Val Thr Ala Ala Asp Thr Ala Val Tyr
            100                 105                 110
Tyr Cys Ala Ile Thr Thr Phe Tyr Tyr Trp Gly Gln Gly Thr Leu Val
        115                 120                 125
Thr Val Ser Ser Ala Ser Thr Lys Gly Pro Ser Val Phe Pro Leu Ala
130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
210                 215                 220
Lys Val Asp Lys Arg Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Glu Glu Met Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
```

-continued

```
<210> SEQ ID NO 46
<211> LENGTH: 462
<212> TYPE: PRT
<213> ORGANISM: Artificial
<220> FEATURE:
<223> OTHER INFORMATION: h#11B7-T7H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 46
```

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Tyr Ser Ile
        35                  40                  45

Thr Ser Asn Tyr Trp Gly Trp Ile Arg Gln Pro Pro Gly Lys Gly Leu
    50                  55                  60

Glu Trp Ile Gly Tyr Ile Thr Tyr Ser Gly Ser Thr Ser Tyr Asn Pro
65                  70                  75                  80

Ser Leu Lys Ser Arg Val Ser Ile Ser Arg Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Ile Thr Thr Phe Tyr Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

```
Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 47
<211> LENGTH: 462
<212> TYPE: PRT
<213> ORGANISM: Artificial
<220> FEATURE:
<223> OTHER INFORMATION: h#11B7-T8H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 47

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Tyr Ser Ile
            35                  40                  45

Thr Ser Asn Tyr Trp Gly Trp Ile Arg Gln Pro Pro Gly Lys Gly Leu
        50                  55                  60

Glu Trp Met Gly Tyr Ile Thr Tyr Ser Gly Thr Ser Tyr Asn Pro
65                  70                  75                  80

Ser Leu Lys Ser Arg Ile Thr Ile Ser Arg Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Ile Thr Thr Phe Tyr Tyr Trp Gly Gln Gly Thr Leu Val
            115                 120                 125

Thr Val Ser Ser Ala Ser Thr Lys Gly Pro Ser Val Phe Pro Leu Ala
    130                 135                 140
```

```
Pro Ser Ser Lys Ser Thr Ser Gly Gly Thr Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 48
<211> LENGTH: 462
<212> TYPE: PRT
<213> ORGANISM: Artificial
<220> FEATURE:
<223> OTHER INFORMATION: h#11B7-T9H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region
```

-continued

```
<400> SEQUENCE: 48

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Tyr Ser Ile
        35                  40                  45

Thr Ser Asn Tyr Trp Gly Trp Ile Arg Gln Pro Pro Gly Lys Gly Leu
    50                  55                  60

Glu Trp Ile Gly Tyr Ile Thr Tyr Ser Gly Ser Thr Ser Tyr Asn Pro
65                  70                  75                  80

Ser Leu Lys Ser Arg Val Thr Ile Ser Arg Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Ile Thr Thr Phe Tyr Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415
```

```
Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 49
<211> LENGTH: 702
<212> TYPE: DNA
<213> ORGANISM: Artificial
<220> FEATURE:
<223> OTHER INFORMATION: h#11D5-T1L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 49
atggtgctgc agacccaggt gttcatctcc ctgctgctgt ggatctccgg cgcatatggc      60
gacgtgcaaa tgacccagag cccttccagc ctgtccgcca gcgtgggcga cagagtgacc     120
atcacctgtc gggcctccca agacatcggc aactacctga ctggtacca gcaaaagcct     180 ggcaaggccc ctaagcttct gatctacggc gccatcaagc tggccgtggg agtgccttcc     240
cggtttagcg gctccggcag cggcaccgac tttacccta ccatctccag cctgcagcct     300
gaggactttg ccacctacta ctgtctgcaa tacatccagt ttcctcttac ctttggccaa     360
ggaaccaagc tggagatcaa gcgtacggtg gccgcccct ccgtgttcat cttcccccc     420 tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac agggggagt gt                         702

<210> SEQ ID NO 50
<211> LENGTH: 702
<212> TYPE: DNA
<213> ORGANISM: Artificial
<220> FEATURE:
<223> OTHER INFORMATION: h#11D5-T2L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 50
atggtgctgc agacccaggt gttcatctcc ctgctgctgt ggatctccgg cgcatatggc      60
gacatccaaa tgacccagag cccttccagc ctgtccgcca gcgtgggcga cagagtgacc     120
atcacctgtc gggcctccca agacatcggc aactacctga ctggtttca gcaaaagcct     180
```

```
ggcaaggccc ctagacttat gatctacggc gccatcaagc tggccgtggg agtgccttcc    240
cggtttagcg gctccggcag cggcaccgac tacaccctga ccatctccag ccttcagcct    300
gaggactttg ccacctacta ctgtctgcaa tacatccagt ttcctctgac ctttggccaa    360
ggaaccaagc ttgagatcaa gcgtacggtg gccgccccct ccgtgttcat cttcccccc    420 tccgacgagc agctgaagtc cggcaccgcc tccgtggtgt gcctgctgaa taacttctac    480
cccagagagg ccaaggtgca gtggaaggtg gacaacgccc tgcagtccgg gaactcccag    540
gagagcgtga ccgagcagga cagcaaggac agcacctaca gcctgagcag cacccctgacc    600 ctgagcaaag ccgactacga aagcacaag gtgtacgcct gcgaggtgac ccaccagggc    660
ctgagctccc ccgtcaccaa gagcttcaac aggggggagt gt                      702
```

```
<210> SEQ ID NO 51
<211> LENGTH: 702
<212> TYPE: DNA
<213> ORGANISM: Artificial
<220> FEATURE:
<223> OTHER INFORMATION: h#11D5-T3L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 51
```

```
atggtgctgc agacccaggt gttcatctcc ctgctgctgt ggatctccgg cgcatatggc     60
gacatccaaa tgacccagag cccctccagc ctgtccgcca gcgtgggcga cagagtgacc    120
atcacctgtc gggcctccca agacatcggc aactacctga ctggttttca acagaaggtg    180
ggcaagtccc ctagacggat gatctacggc gccatcaagc ttgccgtggg agtgcctagc    240
agattttccg gcagccggtc cggcagcgac tacaccctga ccatctccag cctgcaacct    300
gaggactttg ccatctacta ctgtcttcag tacatccaat ttcctctgac ctttggctcc    360
ggaaccaagc tggagatcaa gcgtacggtg gccgccccct ccgtgttcat cttcccccc    420 tccgacgagc agctgaagtc cggcaccgcc tccgtggtgt gcctgctgaa taacttctac    480
cccagagagg ccaaggtgca gtggaaggtg gacaacgccc tgcagtccgg gaactcccag    540
gagagcgtga ccgagcagga cagcaaggac agcacctaca gcctgagcag cacccctgacc    600 ctgagcaaag ccgactacga aagcacaag gtgtacgcct gcgaggtgac ccaccagggc    660
ctgagctccc ccgtcaccaa gagcttcaac aggggggagt gt                      702
```

```
<210> SEQ ID NO 52
<211> LENGTH: 702
<212> TYPE: DNA
<213> ORGANISM: Artificial
<220> FEATURE:
<223> OTHER INFORMATION: h#11D5-T4L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
```

<222> LOCATION: (388)..(702)

<400> SEQUENCE: 52

| | | | | | |
|---|---|---|---|---|---|
| atggtgctgc | agacccaggt | gttcatctcc | ctgctgctgt | ggatctccgg | cgcatatggc | 60 |
| gacatccaaa | tgacccagag | cccttccagc | ctgtccgcca | gcgtgggcga | cagagtgacc | 120 |
| atcacctgtc | gggcctccca | agacatcggc | aactacctga | gctggtacca | gcaaaagcct | 180 |
| ggcaaggccc | ctaagagact | tatctacggc | gccatcaagc | tggccgtggg | agtgccttcc | 240 |
| cggtttagcg | gctccggcag | cggcaccgag | tttaccctga | ccatctccag | ccttcagcct | 300 |
| gaggactttg | ccacctacta | ctgtctgcaa | tacatccagt | ttcctctgac | ctttggcgga | 360 |
| ggcaccaagg | tggagatcaa | gcgtacggtg | gccgccccct | ccgtgttcat | cttcccccc | 420 |
| tccgacgagc | agctgaagtc | cggcaccgcc | tccgtggtgt | gcctgctgaa | taacttctac | 480 |
| cccagagagg | ccaaggtgca | gtggaaggtg | gacaacgccc | tgcagtccgg | gaactcccag | 540 |
| gagagcgtga | ccgagcagga | cagcaaggac | agcacctaca | gcctgagcag | caccctgacc | 600 |
| ctgagcaaag | ccgactacga | gaagcacaag | gtgtacgcct | gcgaggtgac | ccaccagggc | 660 |
| ctgagctccc | ccgtcaccaa | gagcttcaac | agggggagt | gt | | 702 |

<210> SEQ ID NO 53
<211> LENGTH: 702
<212> TYPE: DNA
<213> ORGANISM: Artificial
<220> FEATURE:
<223> OTHER INFORMATION: h#11D5-T5L light chain (DNA)
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 53

| | | | | | |
|---|---|---|---|---|---|
| atggtgctgc | agacccaggt | gttcatctcc | ctgctgctgt | ggatctccgg | cgcatatggc | 60 |
| gacatccaaa | tgacccagag | cccttccagc | ctgtccgcca | gcgtgggcga | cagagtgacc | 120 |
| atcacctgtc | gggcctccca | agacatcggc | aactacctga | gctggtttca | gcaaaagcct | 180 |
| ggcaaggccc | ctagacggat | gatctacggc | gccatcaagc | ttgccgtggg | agtgccttcc | 240 |
| agatttagcg | gctccggcag | cggcaccgac | tacaccctga | ccatctccag | cctgcagcct | 300 |
| gaggactttg | ccacctacta | ctgtcttcaa | tacatccagt | ttcctctgac | ctttggcgga | 360 |
| ggcaccaagg | tggagatcaa | gcgtacggtg | gccgccccct | ccgtgttcat | cttcccccc | 420 |
| tccgacgagc | agctgaagtc | cggcaccgcc | tccgtggtgt | gcctgctgaa | taacttctac | 480 |
| cccagagagg | ccaaggtgca | gtggaaggtg | gacaacgccc | tgcagtccgg | gaactcccag | 540 |
| gagagcgtga | ccgagcagga | cagcaaggac | agcacctaca | gcctgagcag | caccctgacc | 600 |
| ctgagcaaag | ccgactacga | gaagcacaag | gtgtacgcct | gcgaggtgac | ccaccagggc | 660 |
| ctgagctccc | ccgtcaccaa | gagcttcaac | agggggagt | gt | | 702 |

<210> SEQ ID NO 54
<211> LENGTH: 702
<212> TYPE: DNA
<213> ORGANISM: Artificial
<220> FEATURE:
<223> OTHER INFORMATION: h#11D5-T6L light chain (DNA)

```
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 54
atggtgctgc agacccaggt gttcatctcc ctgctgctgt ggatctccgg cgcatatggc      60
gacatccaaa tgacccagag cccttccagc ctgtccgcca gcgtgggcga cagagtgacc     120
atcacctgtc gggcctccca gacatcggc aactacctga ctggtttca gcaaaagcct      180
ggcaaggccc ctagacggat gatctacggc gccatcaagc ttgccgtggg agtgccttcc     240
agatttagcg gctccggcag cggcaccgac tacaccctga ccatctccag cctgcagcct     300
gaggactttg ccacctacta ctgtcttcaa tacatccagt ttcctctgac ctttggccaa     360
ggaaccaagg tggagatcaa gctacggtg gccgccccct ccgtgttcat cttcccccc      420
tccgacgagc agctgaagtc cggcaccgcc tccgtggtgt gcctgctgaa taacttctac     480
cccagagagg ccaaggtgca gtggaaggtg acaacgccc tgcagtccgg gaactcccag     540
gagagcgtga ccgagcagga cagcaaggac agcaccctaca gcctgagcag cacccctgacc     600
ctgagcaaag ccgactacga aagcacaaag gtgtacgcct gcgaggtgac ccaccagggc     660
ctgagctccc ccgtcaccaa gagcttcaac agggggagt gt                        702

<210> SEQ ID NO 55
<211> LENGTH: 234
<212> TYPE: PRT
<213> ORGANISM: Artificial
<220> FEATURE:
<223> OTHER INFORMATION: h#11D5-T1L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 55

Met Val Leu Gln Thr Gln Val Phe Ile Ser Leu Leu Leu Trp Ile Ser
1               5                   10                  15

Gly Ala Tyr Gly Asp Val Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Ser Trp Tyr Gln Gln Lys Pro Gly Lys Ala Pro
    50                  55                  60

Lys Leu Leu Ile Tyr Gly Ala Ile Lys Leu Ala Val Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Tyr Ile
            100                 105                 110
```

```
Gln Phe Pro Leu Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 56
<211> LENGTH: 234
<212> TYPE: PRT
<213> ORGANISM: Artificial
<220> FEATURE:
<223> OTHER INFORMATION: h#11D5-T2L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 56

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Ser Trp Phe Gln Gln Lys Pro Gly Lys Ala Pro
    50                  55                  60

Arg Leu Met Ile Tyr Gly Ala Ile Lys Leu Ala Val Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Leu Gln Tyr Ile
            100                 105                 110

Gln Phe Pro Leu Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
```

```
                    180                 185                 190
Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 57
<211> LENGTH: 234
<212> TYPE: PRT
<213> ORGANISM: Artificial
<220> FEATURE:
<223> OTHER INFORMATION: h#11D5-T3L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 57

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Ser Trp Phe Gln Gln Lys Val Gly Lys Ser Pro
    50                  55                  60

Arg Arg Met Ile Tyr Gly Ala Ile Lys Leu Ala Val Gly Val Pro Ser
65                  70                  75                  80

Arg Phe Ser Gly Ser Arg Ser Gly Ser Asp Tyr Thr Leu Thr Ile Ser
                85                  90                  95

Ser Leu Gln Pro Glu Asp Phe Ala Ile Tyr Tyr Cys Leu Gln Tyr Ile
            100                 105                 110

Gln Phe Pro Leu Thr Phe Gly Ser Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 58
```

-continued

```
<211> LENGTH: 234
<212> TYPE: PRT
<213> ORGANISM: Artificial
<220> FEATURE:
<223> OTHER INFORMATION: h#11D5-T4L light chain(AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 58
```

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Gly Asn Tyr Leu Ser Trp Tyr Gln Gln Lys Pro Gly Lys Ala Pro
    50                  55                  60

Lys Arg Leu Ile Tyr Gly Ala Ile Lys Leu Ala Val Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys Leu Gln Tyr Ile
            100                 105                 110

Gln Phe Pro Leu Thr Phe Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

```
<210> SEQ ID NO 59
<211> LENGTH: 234
<212> TYPE: PRT
<213> ORGANISM: Artificial
<220> FEATURE:
<223> OTHER INFORMATION: h#11D5-T5L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
```

-continued

```
<221> NAME/KEY: SITE
<222> LOCATION: (130)..(234)
<223> OTHER INFORMATION: constant region

<400> SEQUENCE: 59

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Ile Gly Asn Tyr Leu Ser Trp Phe Gln Gln Lys Pro Gly Lys Ala Pro
50                  55                  60

Arg Arg Met Ile Tyr Gly Ala Ile Lys Leu Ala Val Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Leu Gln Tyr Ile
            100                 105                 110

Gln Phe Pro Leu Thr Phe Gly Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 60
<211> LENGTH: 234
<212> TYPE: PRT
<213> ORGANISM: Artificial
<220> FEATURE:
<223> OTHER INFORMATION: h#11D5-T6L light chain (AA)
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 60

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
```

```
                35                  40                  45
Ile Gly Asn Tyr Leu Ser Trp Phe Gln Gln Lys Pro Gly Lys Ala Pro
 50                  55                  60

Arg Arg Met Ile Tyr Gly Ala Ile Lys Leu Ala Val Gly Val Pro Ser
 65                  70                  75                  80

Arg Phe Ser Gly Ser Gly Ser Gly Thr Asp Tyr Thr Leu Thr Ile Ser
                 85                  90                  95

Ser Leu Gln Pro Glu Asp Phe Ala Thr Tyr Tyr Cys Leu Gln Tyr Ile
                100                 105                 110

Gln Phe Pro Leu Thr Phe Gly Gln Gly Thr Lys Val Glu Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 61
<211> LENGTH: 1386
<212> TYPE: DNA
<213> ORGANISM: Artificial
<220> FEATURE:
<223> OTHER INFORMATION: h#11D5-T1H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (297)..(1386)

<400> SEQUENCE: 61
atgaaacacc tgtggttctt cctcctgctg gtggcagctc ccagatgggt gctgagccaa      60
gtgcaactgc aagagagcgg ccctggcctg gtgaagcctt ccaaacccct tagcctgacc     120
tgtaccgtga gcggctactc catcaccagc aactactggg gctggatcag acaacctcct     180
ggcatgggcc tggagtggat cggacacatc accaatagcg gcaacaccac ctacaatccc     240
tcccttaaga gccgggtgac catctccgtg gacaccagcg agaaccaatt ttccctgaag     300
ctgtcttccg tgaccctgc cgacaccgcc gtgtactact gtgccaaggg cgcctttgac     360
tactggggcc aaggaaccct tgtgaccgtg agctcagcct ccaccaaggg cccaagcgtc     420
ttccccctgg caccctcctc aagagcacc tctggcggca gccgccct gggctgcctg     480 gtcaaggact acttcccga acccgtgacc gtgagctgga actcaggcgc cctgaccagc     540
ggcgtgcaca cctccccgc tgtcctgcag tcctcaggac tctactccct cagcagcgtg     600
gtgaccgtgc cctccagcag cttgggcacc cagacctaca tctgcaacgt gaatcacaag     660
```

```
cccagcaaca ccaaggtgga caagagagtt gagcccaaat cttgtgacaa aactcacaca      720
tgcccaccct gcccagcacc tgaactcctg gggggaccct cagtcttcct cttccccccca     780 aaacccaagg acaccctcat gatctcccgg acccctgagg tcacatgcgt ggtggtggac      840
gtgagccacg aagaccctga ggtcaagttc aactggtacg tggacggcgt ggaggtgcat     900
aatgccaaga caaagccccg ggaggagcag tacaacagca cgtaccgggt ggtcagcgtc     960
ctcaccgtcc tgcaccagga ctggctgaat ggcaaggagt acaagtgcaa ggtctccaac    1020
aaagccctcc cagcccccat cgagaaaacc atctccaaag ccaaaggcca gccccgggaa    1080
ccacaggtgt acaccctgcc cccatcccgg gaggagatga ccaagaacca ggtcagcctg    1140
acctgcctgg tcaaaggctt ctatcccagc gacatcgccg tggagtggga gagcaatggc    1200
cagcccgaga caactacaa gaccaccct cccgtgctgg actccgacgg ctccttcttc       1260
ctctacagca agctcaccgt ggacaagagc aggtggcagc agggcaacgt cttctcatgc    1320
tccgtgatgc atgaggctct gcacaaccac tacacccaga gagcctctc cctgtctccc     1380 ggcaaa                                                                1386
```

<210> SEQ ID NO 62
<211> LENGTH: 1386
<212> TYPE: DNA
<213> ORGANISM: Artificial
<220> FEATURE:
<223> OTHER INFORMATION: h#11D5-T2H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (297)..(1386)

<400> SEQUENCE: 62

```
atgaaacacc tgtggttctt cctcctgctg gtggcagctc ccagatgggt gctgagcgag      60
gtgcaactgc aagagagcgg ccctggcctg gtgaagcctt cccaaaccct tagcctgacc     120
tgtaccgtgt ccggctacag catcaccctcc aactactggg gctggatcag acaacctcct    180
ggcatgggcc tggagtggat cggacacatc accaatagcg gcaacaccac ctacaatccc    240
tcccttaaga gccggatctc catcagcgtg gacacctccg agaaccaatt tagcctgaag    300
ctgtccagcg tgacccctgc cgacaccgcc gtgtactact gtgccaaggg cgccttttgac    360 tactggggcc aaggaaccct tgtgaccgtg agctcagcct ccaccaaggg cccaagcgtc    420 ttcccctgg caccctcctc caagagcacc tctggcggca gccgccct gggctgcctg        480 gtcaaggact acttccccga acccgtgacc gtgagctgga actcaggcgc cctgaccagc    540
ggcgtgcaca ccttccccgc tgtcctgcag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccct gcccagcacc tgaactcctg gggggaccct cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccccg ggaggagcag tacaacagca cgtaccgggt ggtcagcgtc    960
```

| | |
|---|---|
| ctcaccgtcc tgcaccagga ctggctgaat ggcaaggagt acaagtgcaa ggtctccaac | 1020 |
| aaagccctcc cagcccccat cgagaaaacc atctccaaag ccaaaggcca gccccgggaa | 1080 |
| ccacaggtgt acaccctgcc cccatcccgg gaggagatga ccaagaacca ggtcagcctg | 1140 |
| acctgcctgg tcaaaggctt ctatcccagc gacatcgccg tggagtggga gagcaatggc | 1200 |
| cagcccgaga caactacaa gaccaccct cccgtgctgg actccgacgg ctccttcttc | 1260 |
| ctctacagca agctcaccgt ggacaagagc aggtggcagc agggcaacgt cttctcatgc | 1320 |
| tccgtgatgc atgaggctct gcacaaccac tacacccaga gagcctctc cctgtctccc | 1380 |
| ggcaaa | 1386 |

<210> SEQ ID NO 63
<211> LENGTH: 1386
<212> TYPE: DNA
<213> ORGANISM: Artificial
<220> FEATURE:
<223> OTHER INFORMATION: h#11D5-T3H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (297)..(1386)

<400> SEQUENCE: 63

| | |
|---|---|
| atgaaacacc tgtggttctt cctcctgctg gtggcagctc ccagatgggt gctgagcgag | 60 |
| gtgcaactgc aagagagcgg ccctggcctg gtgaagcctt cccaaaccct tagcctgacc | 120 |
| tgtaccgtgt ccggctacag catcacctcc aactactggg gctggatcag aaagtttcct | 180 |
| ggcaacaaga tggagtggat cggacacatc accaatagcg caacaccac ctacaatccc | 240 |
| tccctgaaga gccggatctc catcagccgg gacacctcca gaaccaatt tagccttaag | 300 |
| ctgtccagcg tgacccctgc cgacaccgcc gtgtactact gtgccaaggg cgcctttgac | 360 |
| tactggggcc aaggaaccct ggtgaccgtg agctcagcct ccaccaaggg cccaagcgtc | 420 |
| ttccccctgg caccctcctc caagagcacc tctgcggca gccgccct gggctgcctg | 480 |
| gtcaaggact acttccccga acccgtgacc gtgagctgga actcaggcgc cctgaccagc | 540 |
| ggcgtgcaca ccttccccgc tgtcctgcag tcctcaggac tctactccct cagcagcgtg | 600 |
| gtgaccgtgc cctccagcag cttgggcacc cagacctaca tctgcaacgt gaatcacaag | 660 |
| cccagcaaca ccaaggtgga caagagagtt gagcccaaat cttgtgacaa aactcacaca | 720 |
| tgcccaccct gcccagcacc tgaactcctg ggggaccct cagtcttcct cttcccccca | 780 |
| aaacccaagg acaccctcat gatctcccgg acccctgagg tcacatgcgt ggtggtggac | 840 |
| gtgagccacg aagaccctga ggtcaagttc aactggtacg tggacggcgt ggaggtgcat | 900 |
| aatgccaaga caaagcccg ggaggagcag tacaacagca cgtaccgggt ggtcagcgtc | 960 |
| ctcaccgtcc tgcaccagga ctggctgaat ggcaaggagt acaagtgcaa ggtctccaac | 1020 |
| aaagccctcc cagcccccat cgagaaaacc atctccaaag ccaaaggcca gccccgggaa | 1080 |
| ccacaggtgt acaccctgcc cccatcccgg gaggagatga ccaagaacca ggtcagcctg | 1140 |
| acctgcctgg tcaaaggctt ctatcccagc gacatcgccg tggagtggga gagcaatggc | 1200 |
| cagcccgaga caactacaa gaccaccct cccgtgctgg actccgacgg ctccttcttc | 1260 |
| ctctacagca agctcaccgt ggacaagagc aggtggcagc agggcaacgt cttctcatgc | 1320 | tccgtgatgc atgaggctct gcacaaccac tacacccaga agagcctctc cctgtctccc    1380 ggcaaa    1386

<210> SEQ ID NO 64
<211> LENGTH: 1386
<212> TYPE: DNA
<213> ORGANISM: Artificial
<220> FEATURE:
<223> OTHER INFORMATION: h#11D5-T4H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (297)..(1386)

<400> SEQUENCE: 64
atgaaacacc tgtggttctt cctcctgctg gtggcagctc ccagatgggt gctgagccaa    60
gtgcaactgc aacaatgggg cgccggcctg cttaagccta gcgagaccct gtccctgacc    120
tgtaccgtga gcggctactc catcaccagc aactactggg gctggatcag acaacctcct    180
ggcaagggcc ttgagtggat cggacacatc accaattccg gcaacaccac ctacaatccc    240
agcctgaagt cccgggtgac catcagcaga gacacctcca agaaccaatt tagcctgaag    300
ctttccagcg tgaccgccgc cgacaccgcc gtgtactact gtgccaaggg cgcctttgac    360
tactggggcc aaggaaccct ggtgaccgtg agctcagcct ccaccaaggg cccaagcgtc    420
ttccccctgg cacctcctc aagagcacc tctggcggca cagccgccct gggctgcctg    480
gtcaaggact acttccccga acccgtgacc gtgagctgga actcaggcgc cctgaccagc    540
ggcgtgcaca ccttccccgc tgtcctgcag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccct gcccagcacc tgaactcctg ggggaccct cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccccg ggaggagcag tacaacagca cgtaccgggt ggtcagcgtc    960
ctcaccgtcc tgcaccagga ctggctgaat ggcaaggagt acaagtgcaa ggtctccaac    1020
aaagccctcc cagcccccat cgagaaaacc atctccaaag ccaaaggcca gccccgggaa    1080
ccacaggtgt acaccctgcc cccatcccgg gaggagatga ccaagaacca ggtcagcctg    1140
acctgcctgg tcaaaggctt ctatcccagc gacatcgccg tggagtggga gagcaatggc    1200
cagcccgaga caactacaa gaccacccct cccgtgctgg actccgacgg ctccttcttc    1260
ctctacagca agctcaccgt ggacaagagc aggtggcagc agggcaacgt cttctcatgc    1320
tccgtgatgc atgaggctct gcacaaccac tacacccaga agagcctctc cctgtctccc    1380
ggcaaa    1386

<210> SEQ ID NO 65
<211> LENGTH: 1386
<212> TYPE: DNA
<213> ORGANISM: Artificial
<220> FEATURE:

```
<223> OTHER INFORMATION: h#11D5-T5H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (297)..(1386)

<400> SEQUENCE: 65
atgaaacacc tgtggttctt cctcctgctg gtggcagctc ccagatgggt gctgagcgag      60
gtgcaactgc aacaatgggg cgccggcctg cttaagccta gcgagaccct gtccctgacc     120
tgtaccgtga gcggctactc catcaccagc aactactggg gctggatcag acaacctcct     180
ggcaagggcc ttgagtggat cggacacatc accaattccg gcaacaccac ctacaatccc     240
agcctgaagt cccggatcag catctccaga gacaccagca gaaccaatt ttccctgaag      300 ctttccagcg tgaccgccgc cgacaccgcc gtgtactact gtgccaaggg cgcctttgac     360
tactggggcc aaggaaccct ggtgaccgtg agctcagcct ccaccaaggg cccaagcgtc     420
ttccccctgg caccctcctc aagagcacc tctggcggca cagccgccct gggctgcctg      480
gtcaaggact acttccccga acccgtgacc gtgagctgga actcaggcgc cctgaccagc     540
ggcgtgcaca ccttccccgc tgtcctgcag tcctcaggac tctactccct cagcagcgtg     600
gtgaccgtgc cctccagcag cttgggcacc cagacctaca tctgcaacgt gaatcacaag     660
cccagcaaca ccaaggtgga caagagagtt gagcccaaat cttgtgacaa aactcacaca     720
tgcccaccct gcccagcacc tgaactcctg ggggaccct cagtcttcct cttccccca      780 aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagcccg ggaggagcag tacaacagca cgtaccgggt ggtcagcgtc      960
ctcaccgtcc tgcaccagga ctggctgaat ggcaaggagt acaagtgcaa ggtctccaac    1020
aaagccctcc cagcccccat cgagaaaacc atctccaaag ccaaaggcca gccccgggaa    1080
ccacaggtgt acaccctgcc cccatcccgg gaggagatga ccaagaacca ggtcagcctg    1140
acctgcctgg tcaaaggctt ctatcccagc gacatcgccg tggagtggga gagcaatggc    1200
cagcccgaga caactacaa gaccacccct cccgtgctgg actccgacgg ctccttcttc     1260
ctctacagca agctcaccgt ggacaagagc aggtggcagc agggcaacgt cttctcatgc    1320
tccgtgatgc atgaggctct gcacaaccac tacacccaga gagcctctc cctgtctccc     1380 ggcaaa                                                              1386

<210> SEQ ID NO 66
<211> LENGTH: 1386
<212> TYPE: DNA
<213> ORGANISM: Artificial
<220> FEATURE:
<223> OTHER INFORMATION: h#11D5-T6H heavy chain (DNA)
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (297)..(1386)
```

<400> SEQUENCE: 66

```
atgaaacacc tgtggttctt cctcctgctg gtggcagctc ccagatgggt gctgagcgag      60
gtgcaactgc aagagagcgg ccctggcctg gtgaagcctt ccgagaccct tagcctgacc     120
tgtaccgtgt ccggctacag catcacctcc aactactggg gctggatcag acaacctcct     180
ggcaagggcc tggagtggat cggacacatc accaatagcg gcaacaccac ctacaatccc     240
tcccttaaga gccggatctc catcagcaga gacacctcca agaaccaatt tagcctgaag     300
ctgtccagcg tgaccgccgc cgacaccgcc gtgtactact gtgccaaggg cgcctttgac     360
tactgggggc aaggaaccct tgtgaccgtg agctcagcct ccaccaaggg cccaagcgtc     420
ttccccctgg caccctcctc caagagcacc tctggcggca gccgccctgg gctgcctg       480
gtcaaggact acttccccga acccgtgacc gtgagctgga actcaggcgc cctgaccagc     540
ggcgtgcaca ccttccccgc tgtcctgcag tcctcaggac tctactccct cagcagcgtg     600
gtgaccgtgc cctccagcag cttgggcacc cagacctaca tctgcaacgt gaatcacaag     660
cccagcaaca ccaaggtgga caagagagtt gagcccaaat cttgtgacaa aactcacaca     720
tgcccaccct gcccagcacc tgaactcctg ggggggaccct cagtcttcct cttccccccc     780
aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagccccg ggaggagcag tacaacagca cgtaccgggt ggtcagcgtc     960
ctcaccgtcc tgcaccagga ctggctgaat ggcaaggagt acaagtgcaa ggtctccaac    1020
aaagccctcc cagcccccat cgagaaaacc atctccaaag ccaaaggcca gccccgggaa    1080
ccacaggtgt acaccctgcc cccatcccgg gaggagatga ccaagaacca ggtcagcctg    1140
acctgcctgg tcaaaggctt ctatcccagc gacatcgccg tggagtggga gagcaatggc    1200
cagcccgaga caactacaa gaccaccccct cccgtgctgg actccgacgg ctccttcttc    1260
ctctacagca agctcaccgt ggacaagagc aggtggcagc agggcaacgt cttctcatgc    1320
tccgtgatgc atgaggctct gcacaaccac tacacccaga gagcctctc cctgtctccc    1380
ggcaaa                                                                1386
```

<210> SEQ ID NO 67
<211> LENGTH: 462
<212> TYPE: PRT
<213> ORGANISM: Artificial
<220> FEATURE:
<223> OTHER INFORMATION: h#11D5-T1H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 67

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Tyr Ser Ile
```

-continued

```
            35                  40                  45
Thr Ser Asn Tyr Trp Gly Trp Ile Arg Gln Pro Pro Gly Met Gly Leu
 50                  55                  60

Glu Trp Ile Gly His Ile Thr Asn Ser Gly Asn Thr Thr Tyr Asn Pro
 65                  70                  75                  80

Ser Leu Lys Ser Arg Val Thr Ile Ser Val Asp Thr Ser Glu Asn Gln
                 85                  90                  95

Phe Ser Leu Lys Leu Ser Ser Val Thr Pro Ala Asp Thr Ala Val Tyr
                100                 105                 110

Tyr Cys Ala Lys Gly Ala Phe Asp Tyr Trp Gly Gln Gly Thr Leu Val
                115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
                195                 200                 205

Gly Thr Gln Thr Tyr Ile Cys Asn Val Asn His Lys Pro Ser Asn Thr
210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
450                 455                 460
```

```
<210> SEQ ID NO 68
<211> LENGTH: 462
<212> TYPE: PRT
<213> ORGANISM: Artificial
<220> FEATURE:
<223> OTHER INFORMATION: h#11D5-T2H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 68
```

| | | | | | | | | | | | | | | |
|---|---|---|---|---|---|---|---|---|---|---|---|---|---|---|
| Met | Lys | His | Leu | Trp | Phe | Leu | Leu | Leu | Val | Ala | Ala | Pro | Arg | Trp |
| 1 | | | | 5 | | | | | 10 | | | | | 15 |
| Val | Leu | Ser | Glu | Val | Gln | Leu | Gln | Glu | Ser | Gly | Pro | Gly | Leu | Val | Lys |
| | | | 20 | | | | | 25 | | | | | 30 | | |
| Pro | Ser | Gln | Thr | Leu | Ser | Leu | Thr | Cys | Thr | Val | Ser | Gly | Tyr | Ser | Ile |
| | | 35 | | | | | 40 | | | | | 45 | | | |
| Thr | Ser | Asn | Tyr | Trp | Gly | Trp | Ile | Arg | Gln | Pro | Pro | Gly | Met | Gly | Leu |
| 50 | | | | | 55 | | | | | 60 | | | | | |
| Glu | Trp | Ile | Gly | His | Ile | Thr | Asn | Ser | Gly | Asn | Thr | Thr | Tyr | Asn | Pro |
| 65 | | | | | 70 | | | | | 75 | | | | | 80 |
| Ser | Leu | Lys | Ser | Arg | Ile | Ser | Ile | Ser | Val | Asp | Thr | Ser | Glu | Asn | Gln |
| | | | | 85 | | | | | 90 | | | | | 95 | |
| Phe | Ser | Leu | Lys | Leu | Ser | Ser | Val | Thr | Pro | Ala | Asp | Thr | Ala | Val | Tyr |
| | | | 100 | | | | | 105 | | | | | 110 | | |
| Tyr | Cys | Ala | Lys | Gly | Ala | Phe | Asp | Tyr | Trp | Gly | Gln | Gly | Thr | Leu | Val |
| | | 115 | | | | | 120 | | | | | 125 | | | |
| Thr | Val | Ser | Ser | Ala | Ser | Thr | Lys | Gly | Pro | Ser | Val | Phe | Pro | Leu | Ala |
| 130 | | | | | 135 | | | | | 140 | | | | | |
| Pro | Ser | Ser | Lys | Ser | Thr | Ser | Gly | Gly | Thr | Ala | Ala | Leu | Gly | Cys | Leu |
| 145 | | | | | 150 | | | | | 155 | | | | | 160 |
| Val | Lys | Asp | Tyr | Phe | Pro | Glu | Pro | Val | Thr | Val | Ser | Trp | Asn | Ser | Gly |
| | | | | 165 | | | | | 170 | | | | | 175 | |
| Ala | Leu | Thr | Ser | Gly | Val | His | Thr | Phe | Pro | Ala | Val | Leu | Gln | Ser | Ser |
| | | | 180 | | | | | 185 | | | | | 190 | | |
| Gly | Leu | Tyr | Ser | Leu | Ser | Ser | Val | Val | Thr | Val | Pro | Ser | Ser | Ser | Leu |
| | | 195 | | | | | 200 | | | | | 205 | | | |
| Gly | Thr | Gln | Thr | Tyr | Ile | Cys | Asn | Val | Asn | His | Lys | Pro | Ser | Asn | Thr |
| 210 | | | | | 215 | | | | | 220 | | | | | |
| Lys | Val | Asp | Lys | Arg | Val | Glu | Pro | Lys | Ser | Cys | Asp | Lys | Thr | His | Thr |
| 225 | | | | | 230 | | | | | 235 | | | | | 240 |
| Cys | Pro | Pro | Cys | Pro | Ala | Pro | Glu | Leu | Leu | Gly | Gly | Pro | Ser | Val | Phe |
| | | | | 245 | | | | | 250 | | | | | 255 | |
| Leu | Phe | Pro | Pro | Lys | Pro | Lys | Asp | Thr | Leu | Met | Ile | Ser | Arg | Thr | Pro |
| | | | 260 | | | | | 265 | | | | | 270 | | |
| Glu | Val | Thr | Cys | Val | Val | Val | Asp | Val | Ser | His | Glu | Asp | Pro | Glu | Val |
| | | 275 | | | | | 280 | | | | | 285 | | | |
| Lys | Phe | Asn | Trp | Tyr | Val | Asp | Gly | Val | Glu | Val | His | Asn | Ala | Lys | Thr |
| | 290 | | | | | 295 | | | | | 300 | | | | |

```
Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 69
<211> LENGTH: 462
<212> TYPE: PRT
<213> ORGANISM: Artificial
<220> FEATURE:
<223> OTHER INFORMATION: h#11D5-T3H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 69

Met Lys His Leu Trp Phe Phe Leu Leu Leu Val Ala Ala Pro Arg Trp
1                   5                   10                  15

Val Leu Ser Glu Val Gln Leu Gln Glu Ser Gly Pro Gly Leu Val Lys
                20                  25                  30

Pro Ser Gln Thr Leu Ser Leu Thr Cys Thr Val Ser Gly Tyr Ser Ile
            35                  40                  45

Thr Ser Asn Tyr Trp Gly Trp Ile Arg Lys Phe Pro Gly Asn Lys Met
        50                  55                  60

Glu Trp Ile Gly His Ile Thr Asn Ser Gly Asn Thr Thr Tyr Asn Pro
65                  70                  75                  80

Ser Leu Lys Ser Arg Ile Ser Ile Ser Arg Asp Thr Ser Lys Asn Gln
                85                  90                  95

Phe Ser Leu Lys Leu Ser Ser Val Thr Pro Ala Asp Thr Ala Val Tyr
            100                 105                 110

Tyr Cys Ala Lys Gly Ala Phe Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
```

```
                145                 150                 155                 160
Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
        210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
        450                 455                 460

<210> SEQ ID NO 70
<211> LENGTH: 462
<212> TYPE: PRT
<213> ORGANISM: Artificial
<220> FEATURE:
<223> OTHER INFORMATION: h#11D5-T4H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 70
```

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Thr Val Ser Gly Tyr Ser Ile
            35                  40                  45

Thr Ser Asn Tyr Trp Gly Trp Ile Arg Gln Pro Pro Gly Lys Gly Leu
        50                  55                  60

Glu Trp Ile Gly His Ile Thr Asn Ser Gly Asn Thr Thr Tyr Asn Pro
65                  70                  75                  80

Ser Leu Lys Ser Arg Val Thr Ile Ser Arg Asp Thr Ser Lys Asn Gln
                85                  90                  95

Phe Ser Leu Lys Leu Ser Ser Val Thr Ala Ala Asp Thr Ala Val Tyr
                100                 105                 110

Tyr Cys Ala Lys Gly Ala Phe Asp Tyr Trp Gly Gln Gly Thr Leu Val
            115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415
```

```
Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 71
<211> LENGTH: 462
<212> TYPE: PRT
<213> ORGANISM: Artificial
<220> FEATURE:
<223> OTHER INFORMATION: h#11D5-T5H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 71

Met Lys His Leu Trp Phe Phe Leu Leu Leu Val Ala Ala Pro Arg Trp
1               5                   10                  15

Val Leu Ser Glu Val Gln Leu Gln Gln Trp Gly Ala Gly Leu Leu Lys
            20                  25                  30

Pro Ser Glu Thr Leu Ser Leu Thr Cys Thr Val Ser Gly Tyr Ser Ile
        35                  40                  45

Thr Ser Asn Tyr Trp Gly Trp Ile Arg Gln Pro Pro Gly Lys Gly Leu
    50                  55                  60

Glu Trp Ile Gly His Ile Thr Asn Ser Gly Asn Thr Thr Tyr Asn Pro
65                  70                  75                  80

Ser Leu Lys Ser Arg Ile Ser Ile Ser Arg Asp Thr Ser Lys Asn Gln
            85                  90                  95

Phe Ser Leu Lys Leu Ser Ser Val Thr Ala Ala Asp Thr Ala Val Tyr
        100                 105                 110

Tyr Cys Ala Lys Gly Ala Phe Asp Tyr Trp Gly Gln Gly Thr Leu Val
    115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
```

```
                260                 265                 270
Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 72
<211> LENGTH: 462
<212> TYPE: PRT
<213> ORGANISM: Artificial
<220> FEATURE:
<223> OTHER INFORMATION: h#11D5-T6H heavy chain (AA)
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 72

Met Lys His Leu Trp Phe Phe Leu Leu Leu Val Ala Ala Pro Arg Trp
1               5                   10                  15

Val Leu Ser Glu Val Gln Leu Gln Glu Ser Gly Pro Gly Leu Val Lys
            20                  25                  30

Pro Ser Glu Thr Leu Ser Leu Thr Cys Thr Val Ser Gly Tyr Ser Ile
        35                  40                  45

Thr Ser Asn Tyr Trp Gly Trp Ile Arg Gln Pro Pro Gly Lys Gly Leu
    50                  55                  60

Glu Trp Ile Gly His Ile Thr Asn Ser Gly Asn Thr Thr Tyr Asn Pro
65                  70                  75                  80

Ser Leu Lys Ser Arg Ile Ser Ile Ser Arg Asp Thr Ser Lys Asn Gln
                85                  90                  95

Phe Ser Leu Lys Leu Ser Ser Val Thr Ala Ala Asp Thr Ala Val Tyr
            100                 105                 110
```

Tyr Cys Ala Lys Gly Ala Phe Asp Tyr Trp Gly Gln Gly Thr Leu Val
            115                 120                 125

Thr Val Ser Ser Ala Ser Thr Lys Gly Pro Ser Val Phe Pro Leu Ala
        130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 73
<211> LENGTH: 109
<212> TYPE: PRT
<213> ORGANISM: Artificial
<220> FEATURE:
<223> OTHER INFORMATION: h#11B7-T14L light chain variable region (AA)

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Arg Trp Tyr Gln Gln Lys Pro Gly Lys Ala Pro Lys Leu Met Ile
        35                  40                  45

Ser Gly Ala Thr Asn Leu Ala Ala Gly Val Pro Ser Arg Phe Ser Gly
 50                  55                  60

Ser Gly Ser Gly Ser Asp Tyr Thr Leu Thr Ile Ser Ser Leu Gln Pro
65                  70                  75                  80

Glu Asp Phe Ala Thr Tyr Tyr Cys Leu Gln Ser Lys Glu Ser Pro Trp
                85                  90                  95

Thr Phe Gly Gln Gly Thr Lys Leu Glu Ile Lys Arg Thr
            100                 105

<210> SEQ ID NO 74
<211> LENGTH: 109
<212> TYPE: PRT
<213> ORGANISM: Artificial
<220> FEATURE:
<223> OTHER INFORMATION: h#11B7-T15L light chain variable region (AA)

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Arg Trp Phe Gln Gln Lys Pro Gly Lys Ala Pro Lys Leu Leu Ile
        35                  40                  45

Ser Gly Ala Thr Asn Leu Ala Ala Gly Val Pro Ser Arg Phe Ser Gly
 50                  55                  60

Ser Gly Ser Gly Ser Asp Tyr Thr Leu Thr Ile Ser Ser Leu Gln Pro
65                  70                  75                  80

Glu Asp Phe Ala Thr Tyr Tyr Cys Leu Gln Ser Lys Glu Ser Pro Trp
                85                  90                  95

Thr Phe Gly Gln Gly Thr Lys Leu Glu Ile Lys Arg Thr
            100                 105

<210> SEQ ID NO 75
<211> LENGTH: 109
<212> TYPE: PRT
<213> ORGANISM: Artificial
<220> FEATURE:
<223> OTHER INFORMATION: h#11B7-T16L light chain variable region (AA)

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Arg Trp Phe Gln Gln Lys Pro Gly Lys Ala Pro Lys Leu Met Ile
        35                  40                  45

Ser Gly Ala Thr Asn Leu Ala Ala Gly Val Pro Ser Arg Phe Ser Gly
 50                  55                  60

Ser Gly Ser Gly Ser Asp Phe Thr Leu Thr Ile Ser Ser Leu Gln Pro
65                  70                  75                  80

Glu Asp Phe Ala Thr Tyr Tyr Cys Leu Gln Ser Lys Glu Ser Pro Trp
                85                  90                  95

Thr Phe Gly Gln Gly Thr Lys Leu Glu Ile Lys Arg Thr

<210> SEQ ID NO 76
<211> LENGTH: 109
<212> TYPE: PRT
<213> ORGANISM: Artificial
<220> FEATURE:
<223> OTHER INFORMATION: h#11B7-T17L light chain variable region (AA)

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Arg Trp Tyr Gln Gln Lys Pro Gly Lys Ala Pro Lys Leu Leu Ile
        35                  40                  45

Ser Gly Ala Thr Asn Leu Ala Ala Gly Val Pro Ser Arg Phe Ser Gly
    50                  55                  60

Ser Gly Ser Gly Ser Asp Tyr Thr Leu Thr Ile Ser Ser Leu Gln Pro
65                  70                  75                  80

Glu Asp Phe Ala Thr Tyr Tyr Cys Leu Gln Ser Lys Glu Ser Pro Trp
                85                  90                  95

Thr Phe Gly Gln Gly Thr Lys Leu Glu Ile Lys Arg Thr
            100                 105

<210> SEQ ID NO 77
<211> LENGTH: 109
<212> TYPE: PRT
<213> ORGANISM: Artificial
<220> FEATURE:
<223> OTHER INFORMATION: h#11B7-T18L light chain variable region (AA)

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Arg Trp Phe Gln Gln Lys Pro Gly Lys Ala Pro Lys Leu Leu Ile
        35                  40                  45

Ser Gly Ala Thr Asn Leu Ala Ala Gly Val Pro Ser Arg Phe Ser Gly
    50                  55                  60

Ser Gly Ser Gly Ser Asp Phe Thr Leu Thr Ile Ser Ser Leu Gln Pro
65                  70                  75                  80

Glu Asp Phe Ala Thr Tyr Tyr Cys Leu Gln Ser Lys Glu Ser Pro Trp
                85                  90                  95

Thr Phe Gly Gln Gly Thr Lys Leu Glu Ile Lys Arg Thr
            100                 105

<210> SEQ ID NO 78
<211> LENGTH: 109
<212> TYPE: PRT
<213> ORGANISM: Artificial
<220> FEATURE:
<223> OTHER INFORMATION: h#11B7-T19L light chain variable region (AA)

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

```
Leu Arg Trp Tyr Gln Gln Lys Pro Gly Lys Ala Pro Lys Leu Met Ile
        35                  40                  45

Ser Gly Ala Thr Asn Leu Ala Ala Gly Val Pro Ser Arg Phe Ser Gly
 50                  55                  60

Ser Gly Ser Gly Ser Asp Phe Thr Leu Thr Ile Ser Ser Leu Gln Pro
65                  70                  75                  80

Glu Asp Phe Ala Thr Tyr Tyr Cys Leu Gln Ser Lys Glu Ser Pro Trp
                85                  90                  95

Thr Phe Gly Gln Gly Thr Lys Leu Glu Ile Lys Arg Thr
            100                 105

<210> SEQ ID NO 79
<211> LENGTH: 109
<212> TYPE: PRT
<213> ORGANISM: Artificial
<220> FEATURE:
<223> OTHER INFORMATION: h#11B7-T20L light chain variable region (AA)

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Arg Trp Tyr Gln Gln Lys Pro Gly Lys Ala Pro Lys Leu Leu Ile
        35                  40                  45

Ser Gly Ala Thr Asn Leu Ala Ala Gly Val Pro Ser Arg Phe Ser Gly
 50                  55                  60

Ser Gly Ser Gly Ser Asp Phe Thr Leu Thr Ile Ser Ser Leu Gln Pro
65                  70                  75                  80

Glu Asp Phe Ala Thr Tyr Tyr Cys Leu Gln Ser Lys Glu Ser Pro Trp
                85                  90                  95

Thr Phe Gly Gln Gly Thr Lys Leu Glu Ile Lys Arg Thr
            100                 105

<210> SEQ ID NO 80
<211> LENGTH: 113
<212> TYPE: PRT
<213> ORGANISM: Artificial
<220> FEATURE:
<223> OTHER INFORMATION: h#11B7-T10H heavy chain variable region (AA)

<400> SEQUENCE: 80

Gln Val Gln Leu Gln Gln Trp Gly Ala Gly Leu Leu Lys Pro Ser Glu
1               5                   10                  15

Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Ile
        35                  40                  45

Gly Tyr Ile Thr Tyr Ser Gly Ser Thr Ser Tyr Asn Pro Ser Leu Lys
 50                  55                  60

Ser Arg Val Ser Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ile Thr Thr Phe Tyr Tyr Trp Gly Gln Gly Thr Thr Val Thr Val Ser
            100                 105                 110

Ser
```

```
<210> SEQ ID NO 81
<211> LENGTH: 113
<212> TYPE: PRT
<213> ORGANISM: Artificial
<220> FEATURE:
<223> OTHER INFORMATION: h#11B7-T11H heavy chain variable region (AA)

<400> SEQUENCE: 81
```

Gln Val Gln Leu Gln Gln Trp Gly Ala Gly Leu Leu Lys Pro Ser Glu
1               5                   10                  15

Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Met
        35                  40                  45

Gly Tyr Ile Thr Tyr Ser Gly Ser Thr Ser Tyr Asn Pro Ser Leu Lys
    50                  55                  60

Ser Arg Ile Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ile Thr Thr Phe Tyr Tyr Trp Gly Gln Gly Thr Thr Val Thr Val Ser
            100                 105                 110

Ser

```
<210> SEQ ID NO 82
<211> LENGTH: 113
<212> TYPE: PRT
<213> ORGANISM: Artificial
<220> FEATURE:
<223> OTHER INFORMATION: h#11B7-T12H heavy chain variable region (AA)

<400> SEQUENCE: 82
```

Gln Val Gln Leu Gln Gln Trp Gly Ala Gly Leu Leu Lys Pro Ser Glu
1               5                   10                  15

Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Ile
        35                  40                  45

Gly Tyr Ile Thr Tyr Ser Gly Ser Thr Ser Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ile Thr Thr Phe Tyr Tyr Trp Gly Gln Gly Thr Thr Val Thr Val Ser
            100                 105                 110

Ser

```
<210> SEQ ID NO 83
<211> LENGTH: 109
<212> TYPE: PRT
<213> ORGANISM: Artificial
<220> FEATURE:
<223> OTHER INFORMATION: h#11D5-T7L light chain variable region (AA)

<400> SEQUENCE: 83
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Lys Arg Leu Ile
        35                  40                  45

Tyr Gly Ala Ile Lys Leu Ala Val Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 84
<211> LENGTH: 109
<212> TYPE: PRT
<213> ORGANISM: Artificial
<220> FEATURE:
<223> OTHER INFORMATION: h#11D5-T8L light chain variable region (AA)

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Lys Arg Leu Ile
        35                  40                  45

Tyr Gly Ala Ile Lys Leu Ala Val Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 85
<211> LENGTH: 109
<212> TYPE: PRT
<213> ORGANISM: Artificial
<220> FEATURE:
<223> OTHER INFORMATION: h#11D5-T9L light chain variable region (AA)

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Arg Arg Leu Ile
        35                  40                  45

Tyr Gly Ala Ile Lys Leu Ala Val Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr

<210> SEQ ID NO 86
<211> LENGTH: 109
<212> TYPE: PRT
<213> ORGANISM: Artificial
<220> FEATURE:
<223> OTHER INFORMATION: h#11D5-T10L light chain variable region (AA)

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Lys Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 87
<211> LENGTH: 109
<212> TYPE: PRT
<213> ORGANISM: Artificial
<220> FEATURE:
<223> OTHER INFORMATION: h#11D5-T11L light chain variable region (AA)

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Lys Arg Leu Ile
        35                  40                  45

Tyr Gly Ala Ile Lys Leu Ala Val Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 88
<211> LENGTH: 109
<212> TYPE: PRT
<213> ORGANISM: Artificial
<220> FEATURE:
<223> OTHER INFORMATION: h#11D5-T12L light chain variable region (AA)

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Lys Arg Leu Ile
        35                  40                  45

Tyr Gly Ala Ile Lys Leu Ala Val Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
                100                 105

<210> SEQ ID NO 89
<211> LENGTH: 109
<212> TYPE: PRT
<213> ORGANISM: Artificial
<220> FEATURE:
<223> OTHER INFORMATION: h#11D5-T13L light chain variable region (AA)

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Arg Arg Leu Ile
        35                  40                  45

Tyr Gly Ala Ile Lys Leu Ala Val Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
                100                 105

<210> SEQ ID NO 90
<211> LENGTH: 109
<212> TYPE: PRT
<213> ORGANISM: Artificial
<220> FEATURE:
<223> OTHER INFORMATION: h#11D5-T14L light chain variable region (AA)

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Lys Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
                100                 105

-continued

```
<210> SEQ ID NO 91
<211> LENGTH: 109
<212> TYPE: PRT
<213> ORGANISM: Artificial
<220> FEATURE:
<223> OTHER INFORMATION: h#11D5-T15L light chain variable region (AA)

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Lys Arg Leu Ile
        35                  40                  45

Tyr Gly Ala Ile Lys Leu Ala Val Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 92
<211> LENGTH: 109
<212> TYPE: PRT
<213> ORGANISM: Artificial
<220> FEATURE:
<223> OTHER INFORMATION: h#11D5-T16L light chain variable reigon (AA)

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Lys Arg Leu Ile
        35                  40                  45

Tyr Gly Ala Ile Lys Leu Ala Val Gly Val Pro Ser Arg Phe Ser Gly
50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 93
<211> LENGTH: 109
<212> TYPE: PRT
<213> ORGANISM: Artificial
<220> FEATURE:
<223> OTHER INFORMATION: h#11D5-T17L light chain variable region (AA)

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Arg Arg Met Ile
        35                  40                  45
```

Tyr Gly Ala Ile Lys Leu Ala Val Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
                100                 105

<210> SEQ ID NO 94
<211> LENGTH: 109
<212> TYPE: PRT
<213> ORGANISM: Artificial
<220> FEATURE:
<223> OTHER INFORMATION: h#11D5-T18L light chain variable region (AA)

<400> SEQUENCE: 94

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asn Tyr
                20                  25                  30

Leu Ser Trp Tyr Gln Gln Lys Pro Gly Lys Ala Pro Arg Arg Leu Ile
            35                  40                  45

Tyr Gly Ala Ile Lys Leu Ala Val Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
                100                 105

<210> SEQ ID NO 95
<211> LENGTH: 109
<212> TYPE: PRT
<213> ORGANISM: Artificial
<220> FEATURE:
<223> OTHER INFORMATION: h#11D5-T19L light chain variable region (AA)

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Gly Asn Tyr
                20                  25                  30

Leu Ser Trp Tyr Gln Gln Lys Pro Gly Lys Ala Pro Arg Arg Leu Ile
            35                  40                  45

Tyr Gly Ala Ile Lys Leu Ala Val Gly Val Pro Ser Arg Phe Ser Gly
            50                  55                  60

Ser Gly Ser Gly Thr Glu Tyr Thr Leu Thr Ile Ser Ser Leu Gln Pro
 65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
                100                 105

<210> SEQ ID NO 96
<211> LENGTH: 109
<212> TYPE: PRT

<213> ORGANISM: Artificial
<220> FEATURE:
<223> OTHER INFORMATION: h#11D5-T20L light chain variable region (AA)

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Lys Arg Met Ile
        35                  40                  45

Tyr Gly Ala Ile Lys Leu Ala Val Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 97
<211> LENGTH: 109
<212> TYPE: PRT
<213> ORGANISM: Artificial
<220> FEATURE:
<223> OTHER INFORMATION: h#11D5-T21L light chain variable region (AA)

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Lys Arg Met Ile
        35                  40                  45

Tyr Gly Ala Ile Lys Leu Ala Val Gly Val Pro Ser Arg Phe Ser Gly
50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 98
<211> LENGTH: 109
<212> TYPE: PRT
<213> ORGANISM: Artificial
<220> FEATURE:
<223> OTHER INFORMATION: h#11D5-T22L light chain variable region (AA)

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Lys Arg Leu Ile
        35                  40                  45

Tyr Gly Ala Ile Lys Leu Ala Val Gly Val Pro Ser Arg Phe Ser Gly
50                  55                  60

-continued

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 99
<211> LENGTH: 109
<212> TYPE: PRT
<213> ORGANISM: Artificial
<220> FEATURE:
<223> OTHER INFORMATION: h#11D5-T23L light chain variable region (AA)

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
                20                  25                  30

Leu Ser Trp Phe Gln Gln Lys Pro Gly Lys Ala Pro Arg Arg Met Ile
            35                  40                  45

Tyr Gly Ala Ile Lys Leu Ala Val Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 100
<211> LENGTH: 109
<212> TYPE: PRT
<213> ORGANISM: Artificial
<220> FEATURE:
<223> OTHER INFORMATION: h#11D5-T24L light chain variable region (AA)

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
                20                  25                  30

Leu Ser Trp Phe Gln Gln Lys Pro Gly Lys Ala Pro Arg Arg Leu Ile
            35                  40                  45

Tyr Gly Ala Ile Lys Leu Ala Val Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 101
<211> LENGTH: 109
<212> TYPE: PRT
<213> ORGANISM: Artificial
<220> FEATURE:
<223> OTHER INFORMATION: h#11D5-T25L light chain variable region (AA)

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Arg Arg Leu Ile
        35                  40                  45

Tyr Gly Ala Ile Lys Leu Ala Val Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 102
<211> LENGTH: 109
<212> TYPE: PRT
<213> ORGANISM: Artificial
<220> FEATURE:
<223> OTHER INFORMATION: h#11D5-T26L light chain variable region (AA)

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Lys Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 103
<211> LENGTH: 109
<212> TYPE: PRT
<213> ORGANISM: Artificial
<220> FEATURE:
<223> OTHER INFORMATION: h#11D5-T27L light chain variable region (AA)

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Lys Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 104
<211> LENGTH: 109
<212> TYPE: PRT
<213> ORGANISM: Artificial
<220> FEATURE:
<223> OTHER INFORMATION: h#11D5-T28L light chain variable region(AA)

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Lys Arg Leu Ile
            35                  40                  45

Tyr Gly Ala Ile Lys Leu Ala Val Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 105
<211> LENGTH: 109
<212> TYPE: PRT
<213> ORGANISM: Artificial
<220> FEATURE:
<223> OTHER INFORMATION: h#11D5-T29L light chain variable region(AA)

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Arg Arg Met Ile
            35                  40                  45

Tyr Gly Ala Ile Lys Leu Ala Val Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 106
<211> LENGTH: 109
<212> TYPE: PRT
<213> ORGANISM: Artificial
<220> FEATURE:
<223> OTHER INFORMATION: h#11D5-T30L light chain variable region (AA)

<400> SEQUENCE: 106

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Arg Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105
```

<210> SEQ ID NO 107
<211> LENGTH: 109
<212> TYPE: PRT
<213> ORGANISM: Artificial
<220> FEATURE:
<223> OTHER INFORMATION: h#11D5-T31L light chain variable region(AA)

<400> SEQUENCE: 107

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Arg Leu Ile
        35                  40                  45

Tyr Gly Ala Ile Lys Leu Ala Val Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105
```

<210> SEQ ID NO 108
<211> LENGTH: 109
<212> TYPE: PRT
<213> ORGANISM: Artificial
<220> FEATURE:
<223> OTHER INFORMATION: h#11D5-T32L light chain variablre region(AA)

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Lys Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95
```

Thr Phe Gly Gln Gly Thr Lys Val Glu Ile Lys Arg Thr
            100                 105

<210> SEQ ID NO 109
<211> LENGTH: 109
<212> TYPE: PRT
<213> ORGANISM: Artificial
<220> FEATURE:
<223> OTHER INFORMATION: h#11D5-T33L light chain variable region (AA)

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Arg Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 110
<211> LENGTH: 109
<212> TYPE: PRT
<213> ORGANISM: Artificial
<220> FEATURE:
<223> OTHER INFORMATION: h#11D5-T34L light chain variable region (AA)

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Arg Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 111
<211> LENGTH: 109
<212> TYPE: PRT
<213> ORGANISM: Artificial
<220> FEATURE:
<223> OTHER INFORMATION: h#11D5-T35L light chain variable region (AA)

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Arg Arg Leu Ile
        35                  40                  45

Tyr Gly Ala Ile Lys Leu Ala Val Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 112
<211> LENGTH: 109
<212> TYPE: PRT
<213> ORGANISM: Artificial
<220> FEATURE:
<223> OTHER INFORMATION: h#11D5-T36L light chain variable region (AA)

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Pro Gly Lys Ala Pro Lys Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 113
<211> LENGTH: 109
<212> TYPE: PRT
<213> ORGANISM: Artificial
<220> FEATURE:
<223> OTHER INFORMATION: h#11D5-T37L light chain variable region (AA)

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ser Trp Tyr Gln Gln Lys Pro Gly Lys Ala Pro Arg Arg Met Ile
        35                  40                  45

Tyr Gly Ala Ile Lys Leu Ala Val Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ile Gln Phe Pro Leu
                85                  90                  95

Thr Phe Gly Gln Gly Thr Lys Val Glu Ile Lys Arg Thr
            100                 105

<210> SEQ ID NO 114
<211> LENGTH: 113
<212> TYPE: PRT
<213> ORGANISM: Artificial
<220> FEATURE:
<223> OTHER INFORMATION: h#11D5-T7H heavy chain variable region (AA)

<400> SEQUENCE: 114

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Ile
        35                  40                  45

Gly His Ile Thr Asn Ser Gly Asn Thr Thr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Gly Ala Phe Asp Tyr Trp Gly Gln Gly Thr Leu Val Thr Val Ser
            100                 105                 110

Ser

<210> SEQ ID NO 115
<211> LENGTH: 113
<212> TYPE: PRT
<213> ORGANISM: Artificial
<220> FEATURE:
<223> OTHER INFORMATION: h#11D5-T8H heavy chain variable region (AA)

<400> SEQUENCE: 115

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Ile
        35                  40                  45

Gly His Ile Thr Asn Ser Gly Asn Thr Thr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Gly Ala Phe Asp Tyr Trp Gly Gln Gly Thr Leu Val Thr Val Ser
            100                 105                 110

Ser

<210> SEQ ID NO 116
<211> LENGTH: 113
<212> TYPE: PRT
<213> ORGANISM: Artificial
<220> FEATURE:
<223> OTHER INFORMATION: h#11D5-T9H heavy chain variable region (AA)

<400> SEQUENCE: 116

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Ile
        35                  40                  45

Gly His Ile Thr Asn Ser Gly Asn Thr Thr Tyr Asn Pro Ser Leu Lys
    50                  55                  60

Ser Arg Ile Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Gly Ala Phe Asp Tyr Trp Gly Gln Gly Thr Leu Val Thr Val Ser
            100                 105                 110

Ser

<210> SEQ ID NO 117
<211> LENGTH: 113
<212> TYPE: PRT
<213> ORGANISM: Artificial
<220> FEATURE:
<223> OTHER INFORMATION: h#11D5-T10H heavy chain variable region (AA)

<400> SEQUENCE: 117

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Ile
        35                  40                  45

Gly His Ile Thr Asn Ser Gly Asn Thr Thr Tyr Asn Pro Ser Leu Lys
    50                  55                  60

Ser Arg Val Ser Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Gly Ala Phe Asp Tyr Trp Gly Gln Gly Thr Leu Val Thr Val Ser
            100                 105                 110

Ser

<210> SEQ ID NO 118
<211> LENGTH: 113
<212> TYPE: PRT
<213> ORGANISM: Artificial
<220> FEATURE:
<223> OTHER INFORMATION: h#11D5-T11H heavy chain variable region(AA)

<400> SEQUENCE: 118

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Ile
        35                  40                  45

Gly His Ile Thr Asn Ser Gly Asn Thr Thr Tyr Asn Pro Ser Leu Lys
    50                  55                  60

Ser Arg Ile Thr Ile Ser Arg Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Lys Gly Ala Phe Asp Tyr Trp Gly Gln Gly Thr Leu Val Thr Val Ser
            100                 105                 110

Ser

<210> SEQ ID NO 119
<211> LENGTH: 113
<212> TYPE: PRT
<213> ORGANISM: Artificial
<220> FEATURE:
<223> OTHER INFORMATION: h#11D5-T12H heavy chain variable region (AA)

<400> SEQUENCE: 119

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Ile
            35                  40                  45

Gly His Ile Thr Asn Ser Gly Asn Thr Thr Tyr Asn Pro Ser Leu Lys
    50                  55                  60

Ser Arg Val Ser Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Gly Ala Phe Asp Tyr Trp Gly Gln Gly Thr Leu Val Thr Val Ser
            100                 105                 110

Ser

<210> SEQ ID NO 120
<211> LENGTH: 113
<212> TYPE: PRT
<213> ORGANISM: Artificial
<220> FEATURE:
<223> OTHER INFORMATION: h#11D5-T13H heavy chain variable region (AA)

<400> SEQUENCE: 120

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Trp Gly Trp Ile Arg Gln Pro Pro Gly Lys Gly Leu Glu Trp Ile
            35                  40                  45

Gly His Ile Thr Asn Ser Gly Asn Thr Thr Tyr Asn Pro Ser Leu Lys
    50                  55                  60

Ser Arg Ile Ser Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Gly Ala Phe Asp Tyr Trp Gly Gln Gly Thr Leu Val Thr Val Ser
            100                 105                 110

Ser

<210> SEQ ID NO 121
<211> LENGTH: 11
<212> TYPE: PRT
<213> ORGANISM: Artificial
```

```
<220> FEATURE:
<223> OTHER INFORMATION: 11B7 Light chain CDRL4

<400> SEQUENCE: 121

Arg Ala Ser Gln Asp Ile Gly Asn Tyr Leu Arg
1               5                   10

<210> SEQ ID NO 122
<211> LENGTH: 7
<212> TYPE: PRT
<213> ORGANISM: Artificial
<220> FEATURE:
<223> OTHER INFORMATION: 11B7 Light chain CDRL5

<400> SEQUENCE: 122

Gly Ala Thr Asn Leu Ala Ala
1               5

<210> SEQ ID NO 123
<211> LENGTH: 9
<212> TYPE: PRT
<213> ORGANISM: Artificial
<220> FEATURE:
<223> OTHER INFORMATION: 11B7 Light chain CDRL6

<400> SEQUENCE: 123

Leu Gln Ser Lys Glu Ser Pro Trp Thr
1               5

<210> SEQ ID NO 124
<211> LENGTH: 5
<212> TYPE: PRT
<213> ORGANISM: Artificial
<220> FEATURE:
<223> OTHER INFORMATION: 11B7 Heavy chain CDRH1

<400> SEQUENCE: 124

Ser Asn Tyr Trp Gly
1               5

<210> SEQ ID NO 125
<211> LENGTH: 16
<212> TYPE: PRT
<213> ORGANISM: Artificial
<220> FEATURE:
<223> OTHER INFORMATION: 11B7 Heavy chain CDRH2

<400> SEQUENCE: 125

Tyr Ile Thr Tyr Ser Gly Ser Thr Ser Tyr Asn Pro Ser Leu Lys Ser
1               5                   10                  15

<210> SEQ ID NO 126
<211> LENGTH: 5
<212> TYPE: PRT
<213> ORGANISM: Artificial
<220> FEATURE:
<223> OTHER INFORMATION: 11B7 Heavy chain CDRH3

<400> SEQUENCE: 126

Thr Thr Phe Tyr Tyr
1               5

<210> SEQ ID NO 127
<211> LENGTH: 11
<212> TYPE: PRT
<213> ORGANISM: Artificial
<220> FEATURE:
```

```
<223> OTHER INFORMATION: 11D5 Light chain CDRL4

<400> SEQUENCE: 127

Arg Ala Ser Gln Asp Ile Gly Asn Tyr Leu Ser
1               5                   10

<210> SEQ ID NO 128
<211> LENGTH: 7
<212> TYPE: PRT
<213> ORGANISM: Artificial
<220> FEATURE:
<223> OTHER INFORMATION: 11D5 Light chain CDRL5

<400> SEQUENCE: 128

Gly Ala Ile Lys Leu Ala Val
1               5

<210> SEQ ID NO 129
<211> LENGTH: 9
<212> TYPE: PRT
<213> ORGANISM: Artificial
<220> FEATURE:
<223> OTHER INFORMATION: 11D5 Light chain CDRL6

<400> SEQUENCE: 129

Leu Gln Tyr Ile Gln Phe Pro Leu Thr
1               5

<210> SEQ ID NO 130
<211> LENGTH: 5
<212> TYPE: PRT
<213> ORGANISM: Artificial
<220> FEATURE:
<223> OTHER INFORMATION: 11D5 Light chain CDRH1

<400> SEQUENCE: 130

Ser Asn Tyr Trp Gly
1               5

<210> SEQ ID NO 131
<211> LENGTH: 16
<212> TYPE: PRT
<213> ORGANISM: Artificial
<220> FEATURE:
<223> OTHER INFORMATION: 11D5 Light chain CDRH2

<400> SEQUENCE: 131

His Ile Thr Asn Ser Gly Asn Thr Thr Tyr Asn Pro Ser Leu Lys Ser
1               5                   10                  15

<210> SEQ ID NO 132
<211> LENGTH: 5
<212> TYPE: PRT
<213> ORGANISM: Artificial
<220> FEATURE:
<223> OTHER INFORMATION: 11D5 Light chain CDRH3

<400> SEQUENCE: 132

Gly Ala Phe Asp Tyr
1               5

<210> SEQ ID NO 133
<211> LENGTH: 51
<212> TYPE: DNA
<213> ORGANISM: Artificial
<220> FEATURE:
<223> OTHER INFORMATION: Leader Sequence (nucleotide sequence)
```

<400> SEQUENCE: 133
atgggtgaca atgacatcca ctttgccttt ctctccacag gtgtgcattc c    51

<210> SEQ ID NO 134
<211> LENGTH: 17
<212> TYPE: PRT
<213> ORGANISM: Artificial
<220> FEATURE:
<223> OTHER INFORMATION: Leader Sequence (amino acid sequence)

<400> SEQUENCE: 134

Met Gly Asp Asn Asp Ile His Phe Ala Phe Leu Ser Thr Gly Val His
1               5                   10                  15

Ser

<210> SEQ ID NO 135
<211> LENGTH: 214
<212> TYPE: PRT
<213> ORGANISM: Artificial
<220> FEATURE:
<223> OTHER INFORMATION: #11B7-chimeric light chain

<400> SEQUENCE: 135

Asp Ile Gln Met Thr Gln Ala Pro Ser Ser Leu Pro Ala Ser Leu Gly
1               5                   10                  15

Asp Arg Val Thr Ile Thr Cys Arg Ala Ser Gln Asp Ile Gly Asn Tyr
                20                  25                  30

Leu Arg Trp Phe Gln Gln Lys Pro Gly Lys Ser Pro Arg Leu Met Ile
            35                  40                  45

Ser Gly Ala Thr Asn Leu Ala Ala Gly Val Pro Ser Arg Phe Ser Gly
        50                  55                  60

Ser Arg Ser Gly Ser Asp Tyr Ser Leu Thr Ile Ser Ser Leu Glu Ser
65                  70                  75                  80

Glu Asp Met Ala Asp Tyr Tyr Cys Leu Gln Ser Lys Glu Ser Pro Trp
                85                  90                  95

Thr Phe Gly Gly Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 136
<211> LENGTH: 443
<212> TYPE: PRT
<213> ORGANISM: Artificial
<220> FEATURE:
<223> OTHER INFORMATION: #11B7-chimeric heavy chain

<400> SEQUENCE: 136

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asp Lys Met Glu Trp Met
        35                  40                  45

Gly Tyr Ile Thr Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Ser Glu Asp Thr Ala Thr Tyr Tyr Cys Ala
                85                  90                  95

Ile Thr Thr Phe Tyr Tyr Trp Gly Gln Gly Val Met Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly

-continued

```
                405                 410                 415
Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 137
<211> LENGTH: 214
<212> TYPE: PRT
<213> ORGANISM: Artificial
<220> FEATURE:
<223> OTHER INFORMATION: #11D5-chimeric light chain

<400> SEQUENCE: 137

Asp Ile Gln Met Thr Gln Ser Pro Ser Ser Met Ser Thr Ser Leu Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Val Gly Lys Ser Pro Arg Arg Met Ile
        35                  40                  45

Tyr Gly Ala Ile Lys Leu Ala Val Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Met Ala Ile Tyr Tyr Cys Leu Gln Tyr Ile Gln Phe Pro Leu
                85                  90                  95

Thr Phe Gly Ser Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 138
<211> LENGTH: 443
<212> TYPE: PRT
<213> ORGANISM: Artificial
<220> FEATURE:
<223> OTHER INFORMATION: #11D5-chimeric heavy chain

<400> SEQUENCE: 138

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asn Lys Met Glu Trp Ile
        35                  40                  45
```

Gly His Ile Thr Asn Ser Gly Asn Thr Thr Tyr Asn Pro Ser Leu Lys
 50                  55                  60

Ser Arg Ile Ser Ile Ser Arg Asp Thr Ser Arg Asn Gln Phe Phe Leu
 65                  70                  75                  80

Gln Leu Asn Ser Val Thr Thr Glu Asp Thr Ala Thr Tyr Tyr Cys Ala
                 85                  90                  95

Lys Gly Ala Phe Asp Tyr Trp Gly Gln Gly Val Met Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 139
<211> LENGTH: 887
<212> TYPE: PRT

<213> ORGANISM: Homo sapiens

<400> SEQUENCE: 139

```
Met Gly Arg Val Pro Leu Ala Trp Cys Leu Ala Leu Cys Gly Trp Ala
1               5                   10                  15
Cys Met Ala Pro Arg Gly Thr Gln Ala Glu Glu Ser Pro Phe Val Gly
            20                  25                  30
Asn Pro Gly Asn Ile Thr Gly Ala Arg Gly Leu Thr Gly Thr Leu Arg
        35                  40                  45
Cys Gln Leu Gln Val Gln Gly Glu Pro Pro Glu Val His Trp Leu Arg
    50                  55                  60
Asp Gly Gln Ile Leu Glu Leu Ala Asp Ser Thr Gln Thr Gln Val Pro
65                  70                  75                  80
Leu Gly Glu Asp Glu Gln Asp Asp Trp Ile Val Val Ser Gln Leu Arg
                85                  90                  95
Ile Thr Ser Leu Gln Leu Ser Asp Thr Gly Gln Tyr Gln Cys Leu Val
            100                 105                 110
Phe Leu Gly His Gln Thr Phe Val Ser Gln Pro Gly Tyr Val Gly Leu
        115                 120                 125
Glu Gly Leu Pro Tyr Phe Leu Glu Glu Pro Glu Asp Arg Thr Val Ala
    130                 135                 140
Ala Asn Thr Pro Phe Asn Leu Ser Cys Gln Ala Gln Gly Pro Pro Glu
145                 150                 155                 160
Pro Val Asp Leu Leu Trp Leu Gln Asp Ala Val Pro Leu Ala Thr Ala
                165                 170                 175
Pro Gly His Gly Pro Gln Arg Ser Leu His Val Pro Gly Leu Asn Lys
            180                 185                 190
Thr Ser Ser Phe Ser Cys Glu Ala His Asn Ala Lys Gly Val Thr Thr
        195                 200                 205
Ser Arg Thr Ala Thr Ile Thr Val Leu Pro Gln Gln Pro Arg Asn Leu
    210                 215                 220
His Leu Val Ser Arg Gln Pro Thr Glu Leu Glu Val Ala Trp Thr Pro
225                 230                 235                 240
Gly Leu Ser Gly Ile Tyr Pro Leu Thr His Cys Thr Leu Gln Ala Val
                245                 250                 255
Leu Ser Asp Asp Gly Met Gly Ile Gln Ala Gly Glu Pro Asp Pro Pro
            260                 265                 270
Glu Glu Pro Leu Thr Ser Gln Ala Ser Val Pro Pro His Gln Leu Arg
        275                 280                 285
Leu Gly Ser Leu His Pro His Thr Pro Tyr His Ile Arg Val Ala Cys
    290                 295                 300
Thr Ser Ser Gln Gly Pro Ser Ser Trp Thr His Trp Leu Pro Val Glu
305                 310                 315                 320
Thr Pro Glu Gly Val Pro Leu Gly Pro Pro Glu Asn Ile Ser Ala Thr
                325                 330                 335
Arg Asn Gly Ser Gln Ala Phe Val His Trp Gln Glu Pro Arg Ala Pro
            340                 345                 350
Leu Gln Gly Thr Leu Leu Gly Tyr Arg Leu Ala Tyr Gln Gly Gln Asp
        355                 360                 365
Thr Pro Glu Val Leu Met Asp Ile Gly Leu Arg Gln Glu Val Thr Leu
    370                 375                 380
Glu Leu Gln Gly Asp Gly Ser Val Ser Asn Leu Thr Val Cys Val Ala
385                 390                 395                 400
```

```
Ala Tyr Thr Ala Ala Gly Asp Gly Pro Trp Ser Leu Pro Val Pro Leu
                405                 410                 415
Glu Ala Trp Arg Pro Gly Glu Ala Gln Pro Val His Gln Leu Val Lys
            420                 425                 430
Glu Pro Ser Thr Pro Ala Phe Ser Trp Pro Trp Trp Tyr Val Leu Leu
            435                 440                 445
Gly Ala Val Val Ala Ala Cys Val Leu Ile Leu Ala Leu Phe Leu
450                 455                 460
Val His Arg Arg Lys Lys Glu Thr Arg Tyr Gly Glu Val Phe Glu Pro
465                 470                 475                 480
Thr Val Glu Arg Gly Glu Leu Val Val Arg Tyr Arg Val Arg Lys Ser
            485                 490                 495
Tyr Ser Arg Arg Thr Thr Glu Ala Thr Leu Asn Ser Leu Gly Ile Ser
            500                 505                 510
Glu Glu Leu Lys Glu Lys Leu Arg Asp Val Met Val Asp Arg His Lys
            515                 520                 525
Val Ala Leu Gly Lys Thr Leu Gly Glu Gly Glu Phe Gly Ala Val Met
530                 535                 540
Glu Gly Gln Leu Asn Gln Asp Asp Ser Ile Leu Lys Val Ala Val Lys
545                 550                 555                 560
Thr Met Lys Ile Ala Ile Cys Thr Arg Ser Glu Leu Glu Asp Phe Leu
            565                 570                 575
Ser Glu Ala Val Cys Met Lys Glu Phe Asp His Pro Asn Val Met Arg
            580                 585                 590
Leu Ile Gly Val Cys Phe Gln Gly Ser Glu Arg Glu Ser Phe Pro Ala
            595                 600                 605
Pro Val Val Ile Leu Pro Phe Met Lys His Gly Asp Leu His Ser Phe
            610                 615                 620
Leu Leu Tyr Ser Arg Leu Gly Asp Gln Pro Val Tyr Leu Pro Thr Gln
625                 630                 635                 640
Met Leu Val Lys Phe Met Ala Asp Ile Ala Ser Gly Met Glu Tyr Leu
            645                 650                 655
Ser Thr Lys Arg Phe Ile His Arg Asp Leu Ala Ala Arg Asn Cys Met
            660                 665                 670
Leu Asn Glu Asn Met Ser Val Cys Val Ala Asp Phe Gly Leu Ser Lys
            675                 680                 685
Lys Ile Tyr Asn Gly Asp Tyr Tyr Arg Gln Gly Arg Ile Ala Lys Met
            690                 695                 700
Pro Val Lys Trp Ile Ala Ile Glu Ser Leu Ala Asp Arg Val Tyr Thr
705                 710                 715                 720
Ser Lys Ser Asp Val Trp Ser Phe Gly Val Thr Met Trp Glu Ile Ala
            725                 730                 735
Thr Arg Gly Gln Thr Pro Tyr Pro Gly Val Glu Asn Ser Glu Ile Tyr
            740                 745                 750
Asp Tyr Leu Arg Gln Gly Asn Arg Leu Lys Gln Pro Ala Asp Cys Leu
            755                 760                 765
Asp Gly Leu Tyr Ala Leu Met Ser Arg Cys Trp Glu Leu Asn Pro Gln
            770                 775                 780
Asp Arg Pro Ser Phe Thr Glu Leu Arg Glu Asp Leu Glu Asn Thr Leu
785                 790                 795                 800
Lys Ala Leu Pro Pro Ala Gln Glu Pro Asp Glu Ile Leu Tyr Val Asn
            805                 810                 815
Met Asp Glu Gly Gly Gly Tyr Pro Glu Pro Pro Gly Ala Ala Gly Gly
```

```
                    820                 825                 830

Ala Asp Pro Pro Thr Gln Pro Asp Pro Lys Asp Ser Cys Ser Cys Leu
                835                 840                 845

Thr Ala Ala Glu Val His Pro Ala Gly Arg Tyr Val Leu Cys Pro Ser
            850                 855                 860

Thr Thr Pro Ser Pro Ala Gln Pro Ala Asp Arg Gly Ser Pro Ala Ala
865                 870                 875                 880

Pro Gly Gln Glu Asp Gly Ala
                885

<210> SEQ ID NO 140
<211> LENGTH: 108
<212> TYPE: PRT
<213> ORGANISM: Artificial
<220> FEATURE:
<223> OTHER INFORMATION: 11B7 light chain variable region

<400> SEQUENCE: 140

Asp Ile Gln Met Thr Gln Ala Pro Ser Ser Leu Pro Ala Ser Leu Gly
1               5                   10                  15

Asp Arg Val Thr Ile Thr Cys Arg Ala Ser Gln Asp Ile Gly Asn Tyr
            20                  25                  30

Leu Arg Trp Phe Gln Gln Lys Pro Gly Lys Ser Pro Arg Leu Met Ile
        35                  40                  45

Ser Gly Ala Thr Asn Leu Ala Ala Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Met Ala Asp Tyr Tyr Cys Leu Gln Ser Lys Glu Ser Pro Trp
                85                  90                  95

Thr Phe Gly Gly Gly Thr Lys Leu Glu Leu Lys Arg
            100                 105

<210> SEQ ID NO 141
<211> LENGTH: 113
<212> TYPE: PRT
<213> ORGANISM: Artificial
<220> FEATURE:
<223> OTHER INFORMATION: 11B7 heavy chain variable region

<400> SEQUENCE: 141

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asp Lys Met Glu Trp Met
        35                  40                  45

Gly Tyr Ile Thr Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Ser Glu Asp Thr Ala Thr Tyr Tyr Cys Ala
                85                  90                  95

Ile Thr Thr Phe Tyr Tyr Trp Gly Gln Gly Val Met Val Thr Val Ser
            100                 105                 110

Ser
```

```
<210> SEQ ID NO 142
<211> LENGTH: 108
<212> TYPE: PRT
<213> ORGANISM: Artificial
<220> FEATURE:
<223> OTHER INFORMATION: 11D5 light chain variable region

<400> SEQUENCE: 142

Asp Ile Gln Met Thr Gln Ser Pro Ser Ser Met Ser Thr Ser Leu Gly
1               5                   10                  15

Asp Arg Val Thr Ile Thr Cys Arg Ala Ser Gln Asp Ile Gly Asn Tyr
            20                  25                  30

Leu Ser Trp Phe Gln Gln Lys Val Gly Lys Ser Pro Arg Arg Met Ile
        35                  40                  45

Tyr Gly Ala Ile Lys Leu Ala Val Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Met Ala Ile Tyr Tyr Cys Leu Gln Tyr Ile Gln Phe Pro Leu
                85                  90                  95

Thr Phe Gly Ser Gly Thr Lys Leu Glu Leu Lys Arg
            100                 105

<210> SEQ ID NO 143
<211> LENGTH: 113
<212> TYPE: PRT
<213> ORGANISM: Artificial
<220> FEATURE:
<223> OTHER INFORMATION: 11D5 heavy chain variable region

<400> SEQUENCE: 143

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asn Lys Met Glu Trp Ile
        35                  40                  45

Gly His Ile Thr Asn Ser Gly Asn Thr Thr Tyr Asn Pro Ser Leu Lys
    50                  55                  60

Ser Arg Ile Ser Ile Ser Arg Asp Thr Ser Arg Asn Gln Phe Phe Leu
65                  70                  75                  80

Gln Leu Asn Ser Val Thr Thr Glu Asp Thr Ala Thr Tyr Tyr Cys Ala
                85                  90                  95

Lys Gly Ala Phe Asp Tyr Trp Gly Gln Gly Val Met Val Thr Val Ser
            100                 105                 110

Ser

<210> SEQ ID NO 144
<211> LENGTH: 702
<212> TYPE: DNA
<213> ORGANISM: Artificial
<220> FEATURE:
<223> OTHER INFORMATION: h#11B7-T15L light chain
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
```

<222> LOCATION: (388)..(702)

<400> SEQUENCE: 144

```
atggtgctgc agacccaggt gttcatctcc ctgctgctgt ggatctccgg cgcatatggc    60
gatatccaga tgacccagtc accctccagt ctcagtgcga cgtcggcga tcgggtgaca   120
atcacatgta gggcatctca ggatatcggg aattaccta ggtggttcca gcaaaagccc   180
ggaaaagctc ccaaactgtt gatttctggg gccaccaatc ttgccgcagg ggtgccctca   240
aggttctccg gtccggcag cggatccgat tataccttga caatttctag tttgcagcct   300
gaggatttcg caacttacta ctgtcttcag agcaaggaat ctccatggac cttcggacag   360
gggactaaac tcgaaatcaa gcgtacggtg gccgcccct ccgtgttcat cttcccccc    420
tccgacgagc agctgaagtc cggcaccgcc tccgtggtgt gcctgctgaa taacttctac   480
cccagagagg ccaaggtgca gtggaaggtg gacaacgccc tgcagtccgg gaactcccag   540
gagagcgtga ccgagcagga cagcaaggac agcacctaca gcctgagcag caccctgacc   600
ctgagcaaag ccgactacga gaagcacaag gtgtacgcct gcgaggtgac caccagggc   660
ctgagctccc ccgtcaccaa gagcttcaac aggggggagt gt                     702
```

<210> SEQ ID NO 145
<211> LENGTH: 702
<212> TYPE: DNA
<213> ORGANISM: Artificial
<220> FEATURE:
<223> OTHER INFORMATION: h#11B7-T18L light chain
<220> FEATURE:
<221> NAME/KEY: misc_feature
<222> LOCATION: (1)..(60)
<223> OTHER INFORMATION: signal sequence
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 145

```
atggtgctgc agacccaggt gttcatctcc ctgctgctgt ggatctccgg cgcatatggc    60
gatattcaga tgacacagag cccatcctcc cttagcgcat ccgttgggga tagagttacc   120
attacctgca gagccagcca ggacatcggc aactacctgc gctggttcca gcagaagcct   180
ggcaaagcgc ccaaactgct tatcagcgga gccacaaacc tggccgccgg tgtgccctct   240
cggttcagcg gtctggcag cgggagcgat ttcactctta caatatcttc ccttcagccc   300
gaagatttcg cgacatatta ctgcttgcaa tccaaggaaa gtccctggac attcggccaa   360
ggaactaaac tggaaattaa gcgtacggtg gccgcccct ccgtgttcat cttcccccc    420
tccgacgagc agctgaagtc cggcaccgcc tccgtggtgt gcctgctgaa taacttctac   480
cccagagagg ccaaggtgca gtggaaggtg gacaacgccc tgcagtccgg gaactcccag   540
gagagcgtga ccgagcagga cagcaaggac agcacctaca gcctgagcag caccctgacc   600
ctgagcaaag ccgactacga gaagcacaag gtgtacgcct gcgaggtgac caccagggc   660
ctgagctccc ccgtcaccaa gagcttcaac aggggggagt gt                     702
```

<210> SEQ ID NO 146
<211> LENGTH: 234
<212> TYPE: PRT
<213> ORGANISM: Artificial
<220> FEATURE:
<223> OTHER INFORMATION: h#11B7-T15L light chain

```
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 146

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Ile Gly Asn Tyr Leu Arg Trp Phe Gln Gln Lys Pro Gly Lys Ala Pro
        50                  55                  60

Lys Leu Leu Ile Ser Gly Ala Thr Asn Leu Ala Ala Gly Val Pro Ser
65                  70                  75                  80

Arg Phe Ser Gly Ser Gly Ser Gly Ser Asp Tyr Thr Leu Thr Ile Ser
                85                  90                  95

Ser Leu Gln Pro Glu Asp Phe Ala Thr Tyr Tyr Cys Leu Gln Ser Lys
            100                 105                 110

Glu Ser Pro Trp Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 147
<211> LENGTH: 234
<212> TYPE: PRT
<213> ORGANISM: Artificial
<220> FEATURE:
<223> OTHER INFORMATION: h#11B7-T18L light chain
<220> FEATURE:
<221> NAME/KEY: SIGNAL
<222> LOCATION: (1)..(20)
<220> FEATURE:
<221> NAME/KEY: SITE
<222> LOCATION: (21)..(129)
<223> OTHER INFORMATION: variable region
<220> FEATURE:
<221> NAME/KEY: SITE
<222> LOCATION: (130)..(234)
<223> OTHER INFORMATION: constant region

<400> SEQUENCE: 147
```

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Ile Gly Asn Tyr Leu Arg Trp Phe Gln Gln Lys Pro Gly Lys Ala Pro
        50                  55                  60

Lys Leu Leu Ile Ser Gly Ala Thr Asn Leu Ala Ala Gly Val Pro Ser
65                  70                  75                  80

Arg Phe Ser Gly Ser Gly Ser Gly Ser Asp Phe Thr Leu Thr Ile Ser
                85                  90                  95

Ser Leu Gln Pro Glu Asp Phe Ala Thr Tyr Tyr Cys Leu Gln Ser Lys
                100                 105                 110

Glu Ser Pro Trp Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 148
<211> LENGTH: 1386
<212> TYPE: DNA
<213> ORGANISM: Artificial
<220> FEATURE:
<223> OTHER INFORMATION: h#11B7-T11H heavy chain
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 148
atgaaacacc tgtggttctt cctcctgctg gtggcagctc ccagatgggt gctgagccag      60
gttcaactgc agcagtgggg tgctggtctg ttgaagccaa gtgaaacctt gtctctgacc     120
tgcacagtca gcggatatag tattacatct aactactggg gctggatcag acagccccct     180 ggcaagggc tggagtggat ggggtatatt acgtattctg ggtcaacatc ttataatccc      240
tccctgaagt cccgcattac catcagccgc gacacttcca agaaccagtt ttcacttaag     300
ctgtctagcg taacagccgc ggacactgca gtgtattatt gcgctattac cactttctat     360 tattggggc agggcacgac ggtaacggtg agctcagcct ccaccaaggg cccaagcgtc     420
```

-continued

```
ttcccctgg cacctcctc caagagcacc tctggcggca cagccgccct gggctgcctg    480
gtcaaggact acttccccga acccgtgacc gtgagctgga ctcaggcgc cctgaccagc    540
ggcgtgcaca ccttccccgc tgtcctgcag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccct gcccagcacc tgaactcctg ggggaccct cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagcccg ggaggagcag tacaacagca cgtaccgggt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaaggcca gccccgggaa   1080
ccacaggtgt acaccctgcc cccatcccgg gaggagatga ccaagaacca ggtcagcctg   1140
acctgcctgg tcaaaggctt ctatcccagc gacatcgccg tggagtggga gagcaatggc   1200
cagcccgaga caactacaa gaccacccct cccgtgctgg actccgacgg ctccttcttc   1260
ctctacagca agctcaccgt ggacaagagc aggtggcagc agggcaacgt cttctcatgc   1320
tccgtgatgc atgaggctct gcacaaccac tacacccaga gagcctctc cctgtctccc   1380
ggcaaa                                                              1386
```

<210> SEQ ID NO 149
<211> LENGTH: 1386
<212> TYPE: DNA
<213> ORGANISM: Artificial
<220> FEATURE:
<223> OTHER INFORMATION: h#11B7-T12H heavy chain
<220> FEATURE:
<221> NAME/KEY: misc_feature
<222> LOCATION: (1)..(57)
<223> OTHER INFORMATION: signal sequence
<220> FEATURE:
<221> NAME/KEY: V_region
<222> LOCATION: (58)..(396)
<220> FEATURE:
<221> NAME/KEY: C_region
<222> LOCATION: (397)..(1386)

<400> SEQUENCE: 149

```
atgaaacacc tgtggttctt cctcctgctg gtggcagctc ccagatgggt gctgagccag     60
gttcagctgc aacagtgggg agctggttg ctgaagccaa gtgaaccct gtcccttaca    120
tgtaccgtct ctggttacag tattacctcc aactactggg ggtggatcag acagcctcca    180
ggtaaagggc tggagtggat aggatatatt acctattccg gctccacgtc ttataatcca    240
tccctgaaat ctagggtgac catctctagg gacacttcaa aaatcaatt tagcctcaaa    300
ctttcttctg tcacagccgc cgataccgct gtctactact gtgcgatcac acatttttac    360
tattggggcc aggggacaac agtgaccgtt agctcagcct ccaccaaggg cccaagcgtc    420
ttcccctgg cacctcctc caagagcacc tctggcggca cagccgccct gggctgcctg    480
gtcaaggact acttccccga acccgtgacc gtgagctgga ctcaggcgc cctgaccagc    540
ggcgtgcaca ccttccccgc tgtcctgcag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
```

```
tgcccaccct gcccagcacc tgaactcctg gggggaccct cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagcccag ggaggagcag tacaacagca cgtaccgggt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaaggcca gccccgggaa   1080
ccacaggtgt acaccctgcc cccatcccgg gaggagatga ccaagaacca ggtcagcctg   1140
acctgcctgg tcaaaggctt ctatcccagc gacatcgccg tggagtggga gagcaatggc   1200
cagcccgaga caactacaa gaccacccct cccgtgctgg actccgacgg ctccttcttc   1260
ctctacagca agctcaccgt ggacaagagc aggtggcagc agggcaacgt cttctcatgc   1320
tccgtgatgc atgaggctct gcacaaccac tacacccaga gagcctctc cctgtctccc   1380
ggcaaa                                                             1386
```

<210> SEQ ID NO 150
<211> LENGTH: 462
<212> TYPE: PRT
<213> ORGANISM: Artificial
<220> FEATURE:
<223> OTHER INFORMATION: h#11B7-T11H heavy chain
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 150

```
Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Thr Val Ser Gly Tyr Ser Ile
        35                  40                  45

Thr Ser Asn Tyr Trp Gly Trp Ile Arg Gln Pro Pro Gly Lys Gly Leu
    50                  55                  60

Glu Trp Met Gly Tyr Ile Thr Tyr Ser Gly Ser Thr Ser Tyr Asn Pro
65                  70                  75                  80

Ser Leu Lys Ser Arg Ile Thr Ile Ser Arg Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Ile Thr Thr Phe Tyr Tyr Trp Gly Gln Gly Thr Thr Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
```

```
                    180                 185                 190
Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
        210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
        450                 455                 460

<210> SEQ ID NO 151
<211> LENGTH: 462
<212> TYPE: PRT
<213> ORGANISM: Artificial
<220> FEATURE:
<223> OTHER INFORMATION: h#11B7-T12H heavy chain
<220> FEATURE:
<221> NAME/KEY: SIGNAL
<222> LOCATION: (1)..(19)
<220> FEATURE:
<221> NAME/KEY: SITE
<222> LOCATION: (20)..(132)
<223> OTHER INFORMATION: variable region
<220> FEATURE:
<221> NAME/KEY: SITE
<222> LOCATION: (133)..(462)
<223> OTHER INFORMATION: constant region

<400> SEQUENCE: 151

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30
```

```
Pro Ser Glu Thr Leu Ser Leu Thr Cys Thr Val Ser Gly Tyr Ser Ile
         35                  40                  45

Thr Ser Asn Tyr Trp Gly Trp Ile Arg Gln Pro Pro Gly Lys Gly Leu
     50                  55                  60

Glu Trp Ile Gly Tyr Ile Thr Tyr Ser Gly Ser Thr Ser Tyr Asn Pro
 65                  70                  75                  80

Ser Leu Lys Ser Arg Val Thr Ile Ser Arg Asp Thr Ser Lys Asn Gln
                 85                  90                  95

Phe Ser Leu Lys Leu Ser Ser Val Thr Ala Ala Asp Thr Ala Val Tyr
                100                 105                 110

Tyr Cys Ala Ile Thr Thr Phe Tyr Tyr Trp Gly Gln Gly Thr Thr Val
                115                 120                 125

Thr Val Ser Ser Ala Ser Thr Lys Gly Pro Ser Val Phe Pro Leu Ala
        130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
        210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445
```

Asn His Tyr Thr Gln Lys Ser Leu Ser Leu Ser Pro Gly Lys
    450                 455                 460

<210> SEQ ID NO 152
<211> LENGTH: 20
<212> TYPE: DNA
<213> ORGANISM: Artificial
<220> FEATURE:
<223> OTHER INFORMATION: Primer kappa_GSP1

<400> SEQUENCE: 152
gatggatgca ttggtgcagc                                              20

<210> SEQ ID NO 153
<211> LENGTH: 20
<212> TYPE: DNA
<213> ORGANISM: Artificial
<220> FEATURE:
<223> OTHER INFORMATION: Primer new_kappa_GSP1

<400> SEQUENCE: 153
atagatacag ttggtgcagc                                              20

<210> SEQ ID NO 154
<211> LENGTH: 19
<212> TYPE: DNA
<213> ORGANISM: Artificial
<220> FEATURE:
<223> OTHER INFORMATION: Primer heavy_GSP1

<400> SEQUENCE: 154
cagggtcacc atggagtta                                               19

<210> SEQ ID NO 155
<211> LENGTH: 32
<212> TYPE: DNA
<213> ORGANISM: Artificial
<220> FEATURE:
<223> OTHER INFORMATION: Primer XhoI-hGSP2

<400> SEQUENCE: 155
ccgctcgagc gggccagtgg atagacagat gg                                32

<210> SEQ ID NO 156
<211> LENGTH: 32
<212> TYPE: DNA
<213> ORGANISM: Artificial
<220> FEATURE:
<223> OTHER INFORMATION: Primer XhoI-kGSP2

<400> SEQUENCE: 156
ccgctcgagc ggccgtttca gctccagctt gg                                32

<210> SEQ ID NO 157
<211> LENGTH: 21
<212> TYPE: DNA
<213> ORGANISM: Artificial
<220> FEATURE:
<223> OTHER INFORMATION: Primer RT-gamma

<400> SEQUENCE: 157
gcgtgtagtg gttgtgcaga g                                            21

<210> SEQ ID NO 158
<211> LENGTH: 16
<212> TYPE: DNA

```
<213> ORGANISM: Artificial
<220> FEATURE:
<223> OTHER INFORMATION: Primer RT-gamma2

<400> SEQUENCE: 158
gggcttgccg gccgtg                                                        16

<210> SEQ ID NO 159
<211> LENGTH: 20
<212> TYPE: DNA
<213> ORGANISM: Artificial
<220> FEATURE:
<223> OTHER INFORMATION: Primer RT-kappa

<400> SEQUENCE: 159
tggaactgag gagcaggtgg                                                    20

<210> SEQ ID NO 160
<211> LENGTH: 39
<212> TYPE: DNA
<213> ORGANISM: Artificial
<220> FEATURE:
<223> OTHER INFORMATION: Primer 5'Blp

<400> SEQUENCE: 160
agataagctt tgctcagcgt ccaccaaggg cccatcggt                               39

<210> SEQ ID NO 161
<211> LENGTH: 34
<212> TYPE: DNA
<213> ORGANISM: Artificial
<220> FEATURE:
<223> OTHER INFORMATION: Primer 3'Bam(GAG)

<400> SEQUENCE: 161
agatggatcc tcatttaccc ggagacaggg agag                                    34

<210> SEQ ID NO 162
<211> LENGTH: 39
<212> TYPE: DNA
<213> ORGANISM: Artificial
<220> FEATURE:
<223> OTHER INFORMATION: Primer 5'Bsi

<400> SEQUENCE: 162
agataagctt cgtacggtgg ctgcaccatc tgtcttcat                               39

<210> SEQ ID NO 163
<211> LENGTH: 36
<212> TYPE: DNA
<213> ORGANISM: Artificial
<220> FEATURE:
<223> OTHER INFORMATION: Primer 3'Bam (CTT)

<400> SEQUENCE: 163
agatggatcc ctaacactct cccctgttga agctct                                  36

<210> SEQ ID NO 164
<211> LENGTH: 42
<212> TYPE: DNA
<213> ORGANISM: Artificial
<220> FEATURE:
<223> OTHER INFORMATION: Primer VL-11B7-5'

<400> SEQUENCE: 164
agataagctt gtgcattccg acatccagat gacccaggct cc                           42
```

```
<210> SEQ ID NO 165
<211> LENGTH: 33
<212> TYPE: DNA
<213> ORGANISM: Artificial
<220> FEATURE:
<223> OTHER INFORMATION: Primer VL-11B7-3'

<400> SEQUENCE: 165
agatcgtacg tttcagctcc agcttggtgc ctc                             33

<210> SEQ ID NO 166
<211> LENGTH: 45
<212> TYPE: DNA
<213> ORGANISM: Artificial
<220> FEATURE:
<223> OTHER INFORMATION: Primer VL-11D5-5'

<400> SEQUENCE: 166
agataagctt gtgcattccg acatccagat gacccagtct ccatc                45

<210> SEQ ID NO 167
<211> LENGTH: 27
<212> TYPE: DNA
<213> ORGANISM: Artificial
<220> FEATURE:
<223> OTHER INFORMATION: Primer VL-11D5-3'

<400> SEQUENCE: 167
agatcgtacg tttcagcttg gtcccag                                    27

<210> SEQ ID NO 168
<211> LENGTH: 42
<212> TYPE: DNA
<213> ORGANISM: Artificial
<220> FEATURE:
<223> OTHER INFORMATION: Primer VH-11b7/11D5-5'

<400> SEQUENCE: 168
agataagctt gtgcattccg aggtgcagct tcaggagtca gg                   42

<210> SEQ ID NO 169
<211> LENGTH: 36
<212> TYPE: DNA
<213> ORGANISM: Artificial
<220> FEATURE:
<223> OTHER INFORMATION: Primer VH-11B7/11D5-3'

<400> SEQUENCE: 169
agatgctgag ctgacagtga ccatgactcc ttggcc                          36
```